US009499842B2

(12) United States Patent
Hendrickson et al.

(10) Patent No.: US 9,499,842 B2
(45) Date of Patent: *Nov. 22, 2016

(54) ALTERING THE INTERFACE OF HYDROCARBON-COATED SURFACES

(71) Applicant: E I DU PONT DE NEMOURS AND COMPANY, Wilmington, DE (US)

(72) Inventors: Edwin R Hendrickson, Hockessin, DE (US); Abigail K Luckring, West Chester, PA (US); Michael P Perry, Downingtown, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 74 days.

This patent is subject to a terminal disclaimer.

(21) Appl. No.: 14/532,086

(22) Filed: Nov. 4, 2014

(65) Prior Publication Data

US 2016/0017386 A1    Jan. 21, 2016

Related U.S. Application Data

(60) Division of application No. 13/226,817, filed on Sep. 7, 2011, now Pat. No. 9,029,123, which is a continuation-in-part of application No. 12/784,518, filed on May 21, 2010, now Pat. No. 8,658,412.

(60) Provisional application No. 61/180,529, filed on May 22, 2009, provisional application No. 61/180,445, filed on May 22, 2009.

(51) Int. Cl.
| | |
|---|---|
| C09K 9/02 | (2006.01) |
| C12P 7/64 | (2006.01) |
| C09K 8/582 | (2006.01) |
| C09K 8/60 | (2006.01) |
| C12N 1/20 | (2006.01) |
| C12R 1/01 | (2006.01) |
| E21B 43/16 | (2006.01) |

(52) U.S. Cl.
CPC ............. *C12P 7/64* (2013.01); *C09K 8/582* (2013.01); *C09K 8/60* (2013.01); *C12N 1/20* (2013.01); *C12R 1/01* (2013.01); *E21B 43/16* (2013.01)

(58) Field of Classification Search
None
See application file for complete search history.

(56) References Cited

U.S. PATENT DOCUMENTS

| | | | |
|---|---|---|---|
| 4,717,653 A | 1/1988 | Webster, Jr. | |
| 5,877,014 A | 3/1999 | Shetty et al. | |
| 6,087,155 A | 7/2000 | York et al. | |
| 6,110,372 A | 8/2000 | Perriello | |
| 6,150,155 A | 11/2000 | Wildung et al. | |
| 6,244,346 B1 | 6/2001 | Perriello | |
| 6,245,235 B1 | 6/2001 | Perriello | |
| 6,350,605 B1 | 2/2002 | Mita et al. | |
| 6,573,087 B2 | 6/2003 | Lehr | |
| 6,719,902 B1 | 4/2004 | Alvarez et al. | |
| 6,923,914 B2 | 8/2005 | Perriello | |
| 7,708,065 B2 | 5/2010 | Hendrickson et al. | |
| 7,740,063 B2 | 6/2010 | Fallon et al. | |
| 7,776,795 B2 | 8/2010 | Keeler et al. | |
| 2006/0216811 A1 | 9/2006 | Cunningham et al. | |
| 2007/0092930 A1 | 4/2007 | Lal et al. | |
| 2009/0082227 A1 | 3/2009 | Hnatow et al. | |
| 2009/0260803 A1 | 10/2009 | Keeler et al. | |
| 2009/0263887 A1 | 10/2009 | Keeler et al. | |
| 2011/0030956 A1 | 2/2011 | Choban et al. | |

FOREIGN PATENT DOCUMENTS

| | | | |
|---|---|---|---|
| EP | 1189843 A | | 3/2002 |
| EP | 1873234 A1 | * | 2/2008 |
| WO | 0056668 A1 | | 9/2000 |
| WO | 2006115199 A1 | | 2/2006 |
| WO | 2009029502 A1 | | 3/2009 |

OTHER PUBLICATIONS

Bagge, Dorthe et al., Shewanella putrefaciens Adhesion and Biofilm Formation on Food Processing Surfaces, Applied and Environmental Microbiology, May 2001, pp. 2319-2325, vol. 67, No. 5, American Society for Microbiology.

Banat, I. M., Biosurfactants Production and Possible Uses in Microbial Enhanced Oil Recovery and Oil Pollution Remediation: A Review, Bioresource Technology, 1995, pp. 1-12, vol. 51, Elsevier Science Limited.

Desai, Jitendra D. et al., Microbial Production of Surfactants and Their Commerical Potential, Microbiology and Molecular Biology Reviews, Mar. 1997, pp. 47-64, vol. 61, No. 1, American Society for Microbiology.

Doong, Ruey-An et al., Solubilization and mineralization of polycyclic aromatic hydrocarbons by Pseudomonas putida in the presence of surfactant, Journal of Hazardous Materials, 2003, pp. 15-27, vol. B96, Elsevier Science B.V.

McInerney, M. J. et al., Development of microorganisms with improved transport and biosurfactant activity for enhanced oil recovery, Annual Report DE-FC-02NT15321, DOE, Jun. 26, 2003.

Bico, Jose et al., Wetting of textured surfaces, Colloids and Surfaces, 2002, pp. 41-46, vol. 206, Elsevier Science B.V.

Kuyukina, Maria S. et al., Effect of biosurfactants on crude oil desorption and mobilization in a soil system, Environment International, 2005, pp. 155-161, vol. 31, Elsevier Ltd.

Mulligan, Catherine N., Environmental applications for biosurfactants, Environmental Pollution, 2005, pp. 183-198, vol. 133, Elsevier Ltd.

Hau, Heidi H. et al., Ecology and Biotechnology of the Genus *Shewanella*, Annual Review of Microbiology, 2007, pp. 237-258, vol. 61, Annual Reviews.

Martin-Gil, J. et al., Shewanella putrefaciens in a fuel-in-water emulsion from the Prestige oil spill, Antonie van Leeuwenhoek, 2004, pp. 283-285, vol. 86, Kluwer Academic Publishers.

(Continued)

*Primary Examiner* — Richard Hutson

(57) ABSTRACT

Methods and compositions are provided wherein microorganisms are used to alter the interface of hydrocarbons and hydrocarbon-coated surfaces to increase oil recovery, for improved bioremediation and/or to benefit pipeline maintenance.

5 Claims, 25 Drawing Sheets

(56) References Cited

OTHER PUBLICATIONS

Altschul, Stephen F. et al., Bacic Local Alignment Search Tool, Journal of Molecular Biology, 1990, pp. 403-410, vol. 215, Academie Press Limited.

Barbeau, C. et al., Bioremediation of pentachlorophenol-contaminated soil by bioaugmentation using activated soil, Applied Microbiology Biotechnology, 1997, pp. 745-752, vol. 48, Springer-Verlag.

Berry, J. F. et al., In-Situ Saturation Measurements Improve Analysis and Interpretation of Laboratory Miscible and Immiscible Displacement Processes, SPE Reservoir Engineering, Nov. 1991, pp. 429-436, Society of Petroleum Engineers.

Moreno-Vivan, Conrado et al., Prokaryotic Nitrate Reduction: Molecular Properties and Functional Distinction among Bacterial Nitrate Reductases, Journal of Bacteriology, Nov. 1999, pp. 6573-6584, vol. 181, No. 21.

Bruce, James, Automated System Rapidly Identifies and Characterizes Microorganisms in Food, Food Technology, Jan. 1996, pp. 77-81.

Burgos, William D. et al., Soil Humic Acid Decreases Biological Uranium(VI) Reduction by Shewanella putrefaciens CN32, Environmental Enginerring Science, 2007, pp. 755-761, vol. 24, No. 6.

Fallon, R. D. et al., Anaerobic Biodegradation of Cyanide under Methanogenic Conditions, Applied and Environmental Microbiology, Jun. 1991, pp. 1656-1662, vol. 57, No. 6, American Society for Microbiology.

Validation of the Publication of New Names and New Combinations Previously Effectively Published Outside the IJSB, International Journal of Systematic Bacterilogy, Apr. 1986, pp. 354-356, vol. 36, No. 2, Intl. Union of Microbiological Societies.

Levi, J. D. et al., Meor Strategy and Screening Methods for Anaerobic Oil-Mobilizing Bacteria, Microbes and Oil Recovery (vol. 1), International Bioresources Journal, Edited by Zajic and Donaldson, 1985, pp. 336-344.

Picardal, Flynn W. et al., Involvement of Cytochromes in the Anaerobic Biotransformation of Tetrachloromethane by Shewanella putrefaciens 200, Applied and Environmental Microbiology, Nov. 1993, pp. 3763-3770, vol. 59, No. 11.

Liu, Chongxuan et al., Reduction Kinetics of Fe(III), Co(III), U(VI), Cr(VI), and Tc(VII) in Cultures of Dissimilatory Metal-Reducing Bacterial, Biotechnology and Bioengineering, Dec. 20, 2002, pp. 637-649, vol. 80, No. 6.

Maudgalya, Saikrishna et al., Development of Bio-surfactant Based Microbial Enhanced Oil Recovery Procedure, SPE 89473, SPE International, 2004, pp. 1-6, Society of Petroleum Engineers.

Sethi, Manju, Fully automated microbial characterization and identification for industrial microbiologists, American Laboratory, May 1997, pp. 31-35.

Stapleton, Jr., Raymond D. et al, Metal reduction at cold temperatures by Shewanella isolates from various marine environments, Aquatic Microbial Ecology, Jan. 21, 2005, pp. 81-91, vol. 38.

Brown, L. R. et al., Slowing Production Decline and Extending the Economic Life of an Oil Field: New MEOR Technology, SPE/DOE Improved Oil Recovery Symposium, SPE 59306, Apr. 3-5, 2000, Tulsa, OK, pp. 1-16.

Sunde, Egil et al., Aerobic Microbial Enhanced Oil Recovery for Offshore Use, SPE/DOE Symposium on Enhanced Oil Recovery, SPE/DOE 24204, Apr. 22-24, 1992, Tulska, OK, pp. 497-502.

Office Action mailed Nov. 19, 2009, in co-pending U.S. Pat. No. 7,776,795.

Office Action mailed Jan. 13, 2010, in co-pending U.S. Pat. No. 7,776,795.

Notice of Allowance mailed May 20, 2010, in co-pending U.S. Pat. No. 7,776,795.

Brosius et al., Gene Organization and Primary Structure of a Ribosomal RNA Operon from *Escherichia coli*, Journal of Microbiology, 1981, 148, 107-127, Academic Press Inc., London.

Morris et al., Purification and properties of a novel cytochrome: flavocytochrome c from Shewanella putrefaciens, Biochemical Jouranl, 1994, 302, 587-593, Great Britain.

Pham et al., Characterizing microbial diversity in production water from an alaskan mesothermic petroleum reservoir with two independent molecular methods, Environmental Microbiology, 2009, 11(1), 176-187, Society for Applied Microbiology and Blackwell Publishing Ltd.

Woese et al, Bacterial Evolution, Microbiological Reviews, 1987, 51(2), 221-271.

Chenna et al., Multiple sequence alignment with the clustal series of programs, Nucleic Acids Research, 2003, 31(13), 3497-3500, Oxford University Press, 2003.

Venkateswaran et al., Polyphasic taxonomy of the genus *Shewanella* and description of *Shewanella oneidensis* sp. nov., Inter. J. of systematic Bacteriology, 1999, 49, 705-724, Great Britain.

Bennasar et al., 16S rRNA Gene sequence analysis relative to genomovars of pseudomonas stutzeri and proposal of *pseudomonas balearica* sp. nov., Inter. J. of Systematic Bacteriology, 1996, 46(1), 200-205, International Union of Microbiological Societies.

Saitou et al., The neighbor joining method: A new method for Reconstructing phylogenetic tress, Molecular Biology and Evolution, 1987, 4(4), 406-425.

Sucharita et al., *Shewanella chilikensis* sp. nov. a moderately alkaliphilic gammaproteobacterium isolated from a lagoon, Inter. J. systematic and Evolutionary Microbiology, 2009, 59, 3111-3115.

Tindall et al., Notes on the characterization of prokaryote strains for taxonomic purposes, Inter. J. systematic and Evolutionary Microbiology, 2010, 60, 249-266.

International Search Report, PCT/US2010/035784, mailed Jul. 20, 2010.

Computational Molecular Biology, Lesk, A. M., ed. Oxford University Press, NY, 1988.

Biocomputing: Informatics and Genome Projects, Smith, D. W., ed., Academic Press, NY, 1993.

Computer Analysis of Sequence Data, Part I, Griffin, A. M., and Griffin, H. G., 25 eds., Humana Press, NJ, 1994.

Sequence Analysis in Molecular Biology, von Heinje, G., ed., Academic Press, 1987.

Sequence Analysis Primer, Gribskov, M. And Devereux, J., eds., Stockton Press, NY, 1991.

Pearson, W. R., Comput. Methods 5 Genome Res., Proc. Int. Symp, Meeting Date 1992, 111-120, Eds: Suhai, Sandor, Plenum Publishing, New York, NY, 1994.

Nontechnical guide to petroleum geology, exploration, drilling, and production, 2nd edition. N. J. Hyne, PennWell Corp. Tulsa, OK, USA, Freethey, G.W., Naftz, D.L., Rowland, R.C., &Davis, J.A. (2002).

Deep aquifer remediation tools: Theory, design, and performance modeling, In: D.L. Naftz, S.J. 30 Morrison, J.A. Davis, & C.C. Fuller (Eds.).

Handbook of groundwater remediation using permeable reactive barriers (pp. 133-161), Amsterdam: Academic Press.

Higgins and Sharp, Fast and sensative multiple sequence alignments on a microcomputer, CABIOS, 1989, . 5:151-153.

Higgins et al., Clustal V: improved software for multiple sequence alignment, Comput. Appl. Biosci., 1992 8:189-191.

Isolation of Biotechnological Organisms from Nature, (Labeda, D. P. ed. 117-140, McGraw-Hill Publishers, 1990.

Saikrishna et al. 2004, SPE paper No. 89473, 2004.

Abhijit, Petroleum Reservoir Rock and Fluid Properties, CRC Press (2006).

* cited by examiner

* SEQ ID NO preceeds Shewanella

* SEQ ID NO preceeds Shewanella

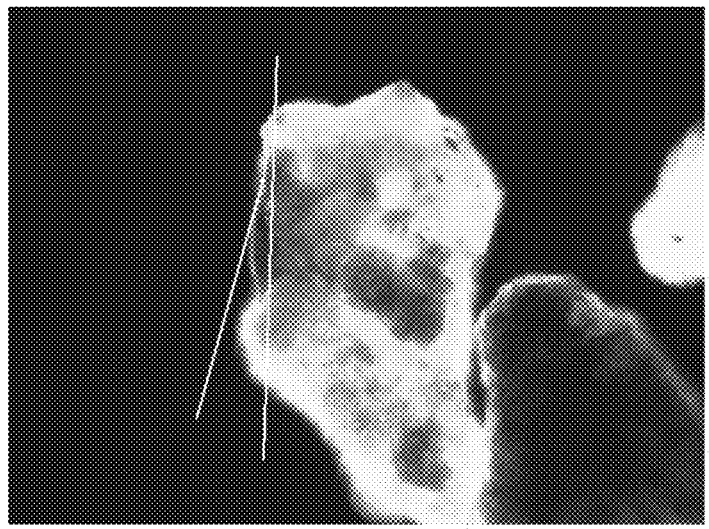 
FIG. 17A  FIG. 17B
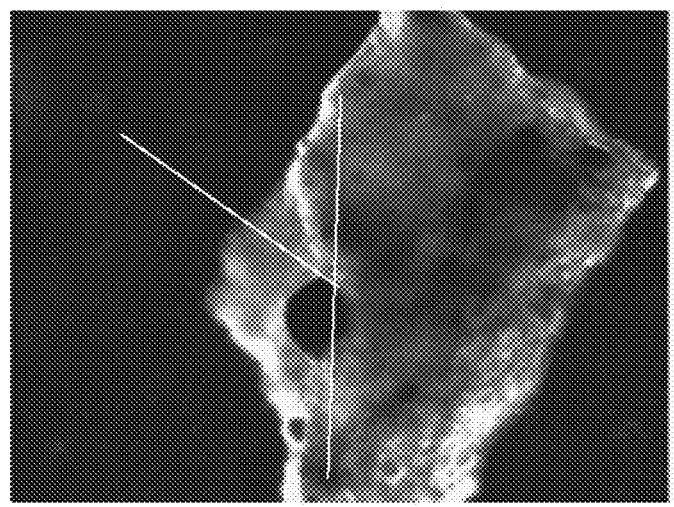 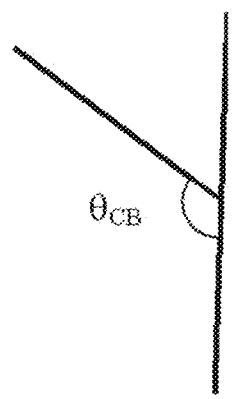
FIG. 17C  FIG. 17D

FIG. 25

ALTERING THE INTERFACE OF HYDROCARBON-COATED SURFACES

This is a divisional application claiming the benefit U.S. application Ser. No. 13/226,817 filed on Sep. 7, 2011, and U.S. Divisional application Ser. No. 14/467,082 filed on Aug. 25, 2014, and U.S. Divisional application Ser. No. 14/083,688 filed on Nov. 19, 2013, and U.S. application Ser. No. 12/784,518 filed May 21, 2010, now granted U.S. Pat. No. 8,658,412B2, and U.S. Provisional Applications 61/180,529 and 61/180,445, each filed on May 22, 2009.

FIELD OF INVENTION

This invention relates to the field of environmental microbiology and modification of heavy crude oil properties using microorganisms. More specifically, microorganisms are used to alter the interface between hydrocarbons and a surface to increase oil recovery from hydrocarbon coated surfaces.

BACKGROUND OF THE INVENTION

Hydrocarbons in the form of petroleum deposits and oil reservoirs are distributed worldwide. These oil reservoirs are measured in the hundreds of billions of recoverable barrels. Because heavy crude oil has a relatively high viscosity and may adhere to surfaces, it is essentially immobile and cannot be easily recovered by conventional primary and secondary means.

Microbial Enhanced Oil Recovery (MEOR) is a methodology for increasing oil recovery by the action of microorganisms (Brown, L. R., Vadie, A. A, Stephen, O. J. SPE 59306, SPE/DOE Improved Oil Recovery Symposium, Oklahoma, Apr. 3-5, 2000). MEOR research and development is an ongoing effort directed at discovering techniques to use microorganisms to benefit oil recovery (Sunde. E., Beeder, J., Nilsen, R. K. Torsvik, T., SPE 24204, SPE/DOE 8th Symposium on enhanced Oil Recovery, Tulsa, Okla., USA, Apr. 22-24, 1992). An effective MEOR treatment for crude oil desorption and mobilization could utilize microbially derived surface active agents (McInerney, M. J., et al., Development of microorganisms with improved transport and biosurfactant activity for enhanced oil recovery. DE-FE-02NT15321. DOE, 2003). Few have been identified that have been shown to alter the surface interaction between hydrocarbons and rocks, soil, brine, sand or clay to which the hydrocarbons are adhered.

Use of surface active agents or surfactants to increase solubility of oil through reduction in surface and interfacial tensions is another technique for increasing oil recovery. A wide variety of surfactants identified thus far are able to significantly reduce surface and interfacial tensions at the oil/water and air/water interfaces. Because surfactants partition at oil/water interfaces, they are capable of increasing the solubility and bioavailability of hydrocarbons (Desai, J. D. and I. M. Banat. Microbial production of surfactants and their commercial potential. Microbiol. Mol. Biol. Rev., 47-64, 1997 and Banat, I. M. Bioresource Technol. 51: 1-12, 1995 and Kukukina, M. S., et al. Environment International. 31: 155-161, 2005 and Mulligan, C., Environmental Pollution. 133: 183-198, 2005). Doong and Lei (J. Hazardous Materials. B96: 15-27, 2003), for example, found that the addition of surfactants to soil environments contaminated with polyaromatic hydrocarbons increased the mineralization rate of some hydrocarbons (Doong, R and W. Lei, supra). Such surfactants are expensive and may pose environmental or other equipment issues.

Biosurfactants, (biologically produced surfactants), have helped to substantially increase oil recovery from sandstone deposits by increasing solubility and decreasing viscosity of the oil (Mulligan, C., supra). Depending on the application, biosurfactants may be preferred since they are generally more biodegradable and less toxic than synthetically produced surfactants, and are effective under a broad range of oil and reservoir conditions. Examples of biosurfactants include glycolipids, lipopeptides and lipoproteins, fatty acids and phospholipids, polymeric compounds, and particulate biosurfactants (Desai, J. D. supra). However, further characterization of production and use of biosurfactants is needed. Further, there is a need to identify microorganisms that are able to produce these biosurfactants under reservoir conditions or other relevant environmental conditions.

Certain microorganisms have been described as having properties that may benefit MEOR processes. Certain *Shewanella* species have been disclosed as useful for remediation of metal contamination (U.S. Pat. No. 6,923,914B2), iron containing mixed waste (U.S. Pat. No. 6,719,902B1), manganese contamination (U.S. Pat. No. 6,350,605B1), and other pollutants with the aid of butane (U.S. Pat. No. 6,245,235B1). In EP1189843, certain *Shewanella* species were described as being useful for bioremediation of petroleum contaminants aerobically. In addition, *Shewanella* supplemented with butane was used for reduction of fouling in injection and recovery wells under aerobic conditions (U.S. Pat. No. 6,244,346B1). Other *Shewanella* species have been described as having the ability to produce biofilms (D. Bagge, et al., Appl. Environ. Microbiol. 67, 2319-2325. 2001); to sequester gases, in particular $CO_2$, in underground geological formations and prevent their release into the atmosphere (see US20060216811A1); and to enhance oil recovery (commonly owned and co-pending US 2009-0260803 A1). The activity reported by these microorganisms is related to the degradation and transformation of hydrocarbons and other pollutants and not related to altering the interfacial boundaries between hydrocarbons and the surfaces to which they are bound.

The problem to be solved therefore, relates to the identification of microorganisms that: 1) have the ability to alter the interface between hydrocarbons and rock or other surfaces subject to coating by oil; 2) can be inoculated under suitable conditions which effect these alterations in surface properties; and 3) can be used in a cost-efficient way, to improve oil recovery, and benefit bioremediation.

SUMMARY OF THE INVENTION

In one aspect, the invention relates to a method of oil recovery comprising:
  a) providing an oil reservoir;
  b) injecting the oil reservoir with a medium selected from the group consisting of:
    i) a cell-containing medium comprising one or more *Shewanella* sp.; and
    ii) a conditioned medium which is substantially cell free and which has been in contact with one or more *Shewanella* sp.; wherein the *Shewanella* sp. comprises a 16S rDNA comprising SEQ ID NO:21, SEQ ID NO:23 and SEQ ID NO:28; and
  c) recovering oil from the oil reservoir;
wherein the medium enhances oil recovery.

BRIEF DESCRIPTION OF FIGURES AND SEQUENCES

The invention can be more fully understood from the following detailed description, the Figures, and the accompanying sequence descriptions, which form a part of this application.

FIG. 1 shows the relative sand release by strain LH4:18 cultures over a period of three weeks. After about 6 days, a 6 mm zone of released sand was observed in the bottom of the wells for the week old (week 1—solid line) culture and a 3 mm zone was observed for the day-old sample (Day 1—dotted line).

FIG. 2 depicts sand/oil release using either an aerobic or an anaerobic culture. PPGAS medium samples (PPGAS), with and without supplements, were used as controls in both aerobic and anaerobic experiments. The *Shewanella* strain (LH4:18) was used in the experiment. Experiments were performed in the absence of lactate and nitrate (L/N) or in their presence in both anaerobic and aerobic experiments.

FIG. 3 depicts a comparison of CFU/mL in various samples, expressed as Log 10 (MPN), on the day of the LOOS test set up (Day 3) and the relative sand release for each sample. The symbols designate presence of the following ingredients in the growth medium: fumarate (F); nitrate (N); and lactate and nitrate (L/N).

FIG. 4 depicts sand/oil release by *Shewanella* strain (LH4:18) in the presence or absence of glucose. One week old cultures were used and the experiment was continued for 20 days. One set of cultures did not receive any glucose and another set received 0.5% glucose. The experiment was performed for one week in the absence of any heat.

FIG. 5 depicts oil release over time with strain LH4:18 grown in different media and supplements for 21 days. Where indicated, supplements were 1° A) peptone, 1.6 mM $MgSO_4$, 20 mM KCl, 20 mM $NH_4Cl$, and 20 mM tris base.

FIG. 6 shows the ability of *Shewanella* strain (LH4:18) to release oil in sand/oil release. The strain was tested for 13 days using the SIB medium either with peptone or YE added. The controls contained medium but no microbes.

Figure 9:
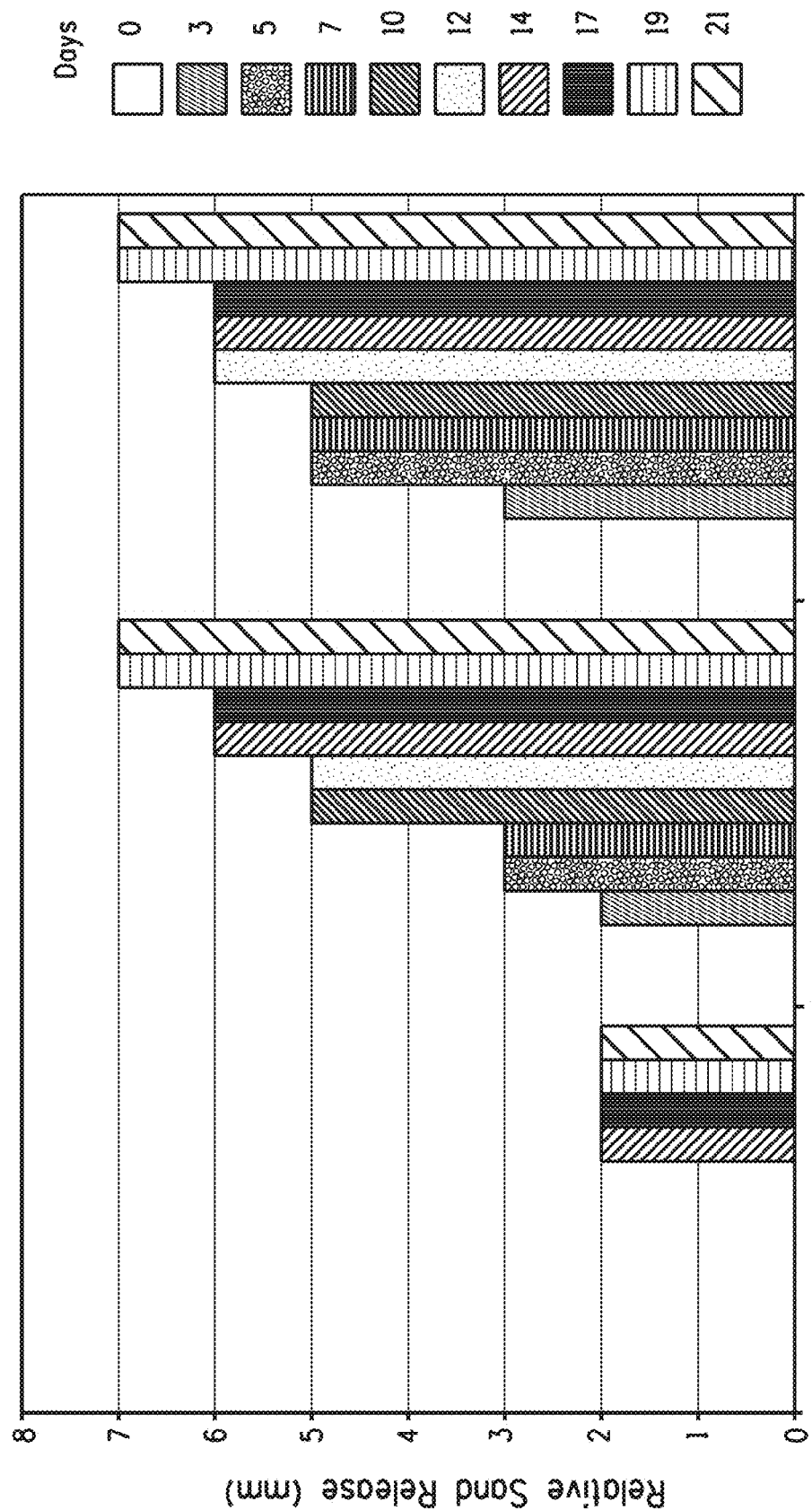

FIG. 9 depicts the results of the ability of strain LH4:18 to release sand/oil in the presence of other organisms such as *Pseudomonas stutzeri* strain LH4:15. One set of the experiment was performed measuring sand/oil release by LH4:15, another set used strain LH4:18 and the third set used a mixture of both LH4:15 and LH4:18. The experiment was performed for 21 days.

Figure 10:
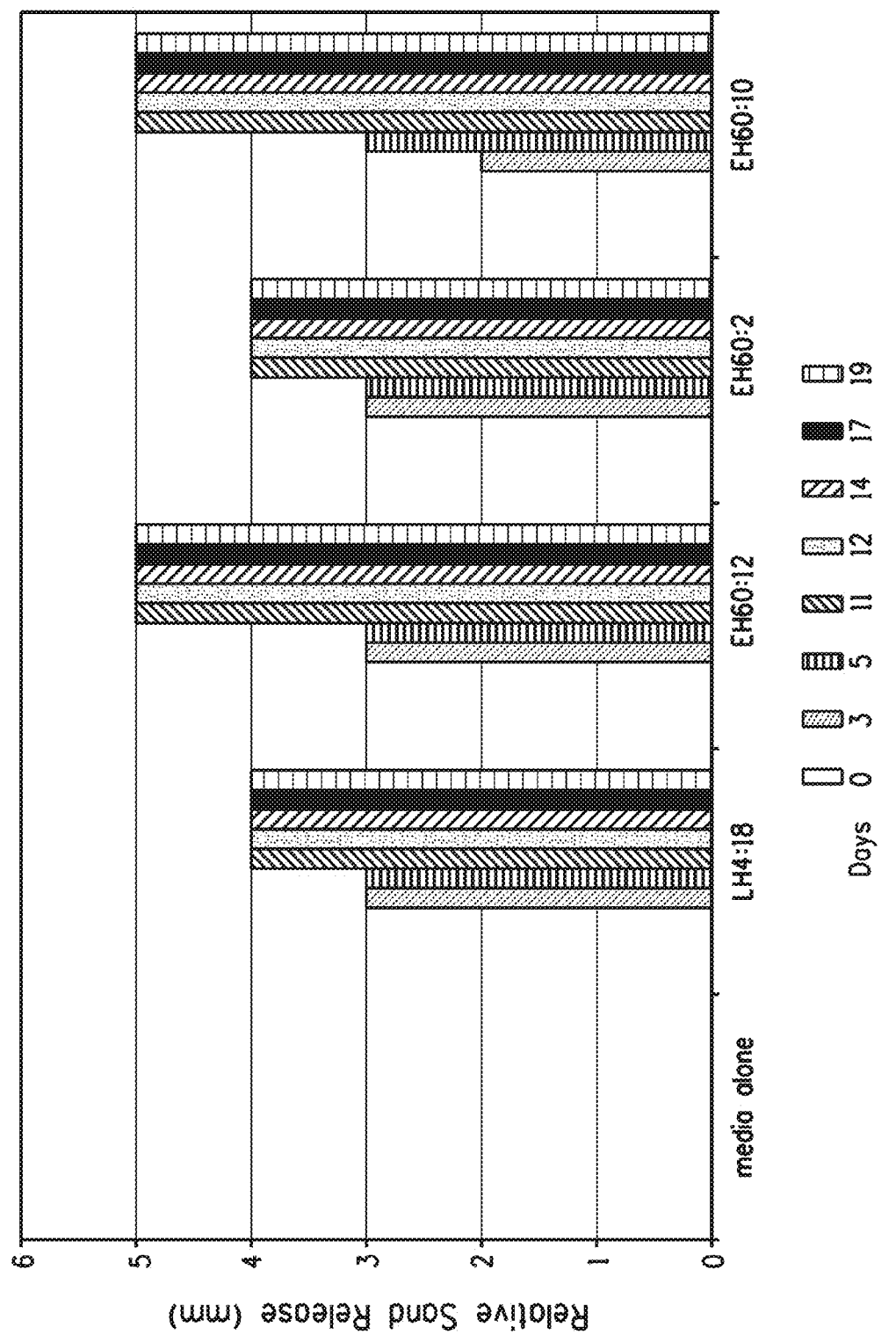

FIG. 10 depicts oil release over time with LH4:18 and other *Shewanella* species (strains EH60:12, EH60:2, and EH60:10). The experiment was performed for 19 days.

Figure 11:
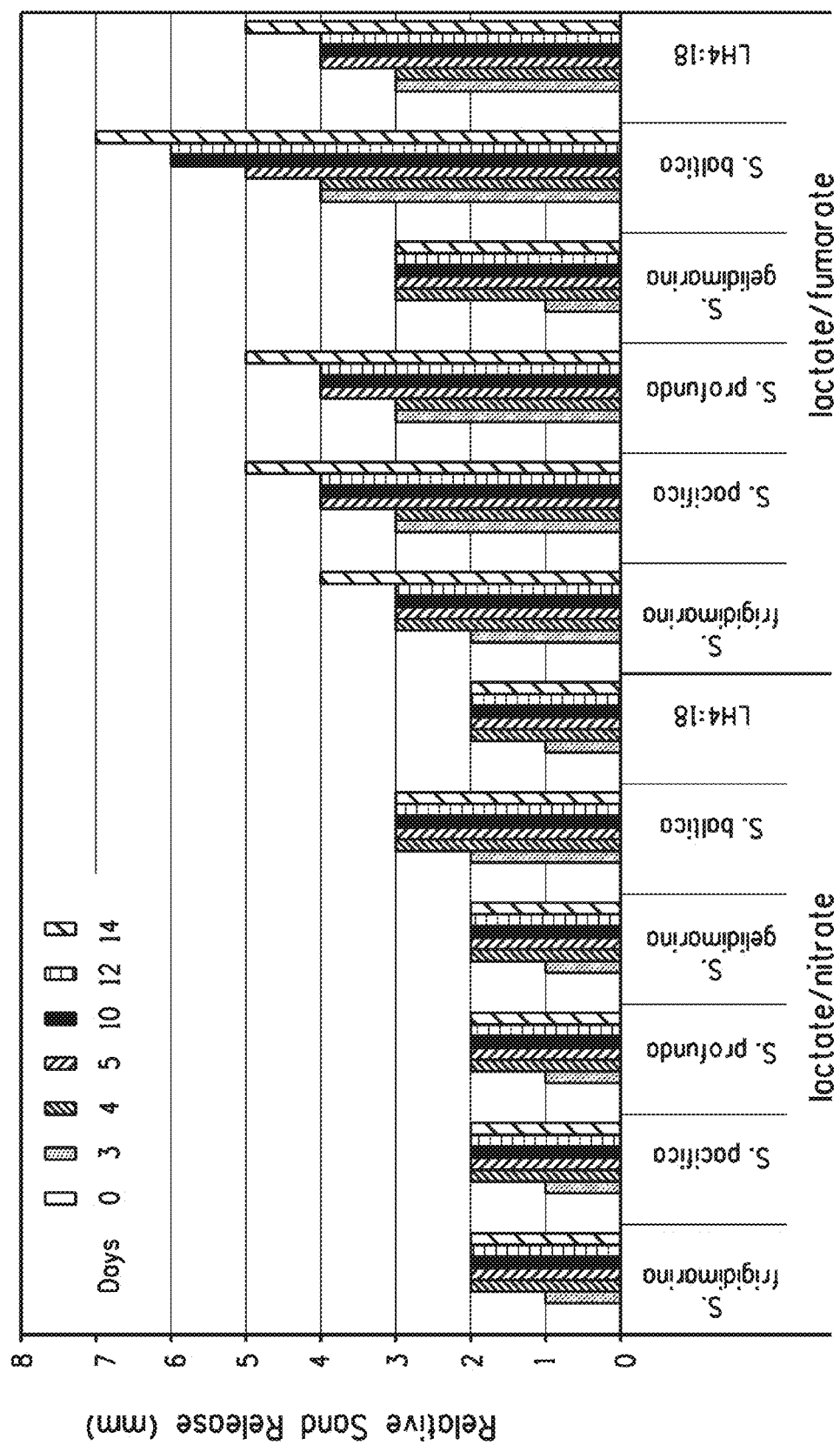

FIG. 11 depicts oil release over time in a LOOS test in the presence of fumarate or nitrate as the electron acceptors. The experiment was performed for 14 days with LH4:18 and other *Shewanella* species purchased through DSMZ (Deutsche Sammlung von Mikrorganismen and Zellkulturen, German Collection of Microorganisms and Cell Cultures).

Figure 12A:
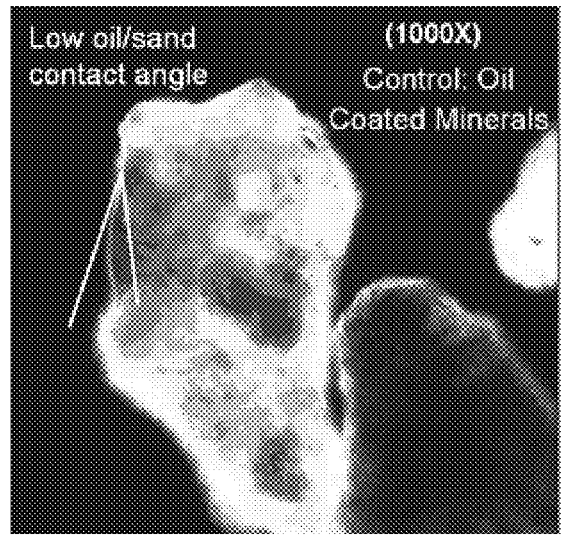

FIG. 12(A) shows a photomicrograph of untreated oil coated sand.

Figure 12B:
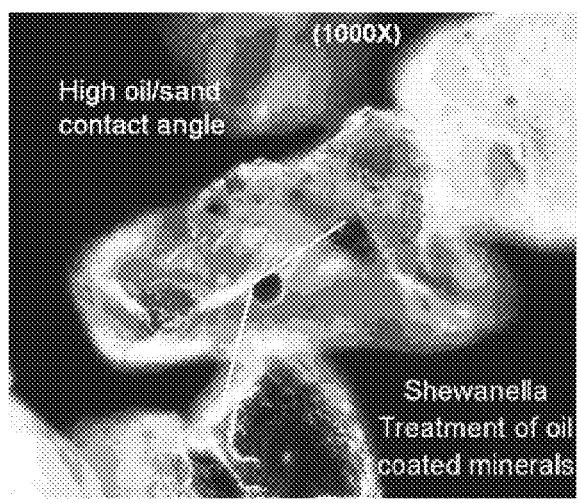

FIG. 12(B) shows a photomicrograph of oil coated sand treated with *Shewanella* LH4:18. The lines drawn on the picture depict the contact angle between the hydrocarbon and the sand through the oil.

Figure 13:
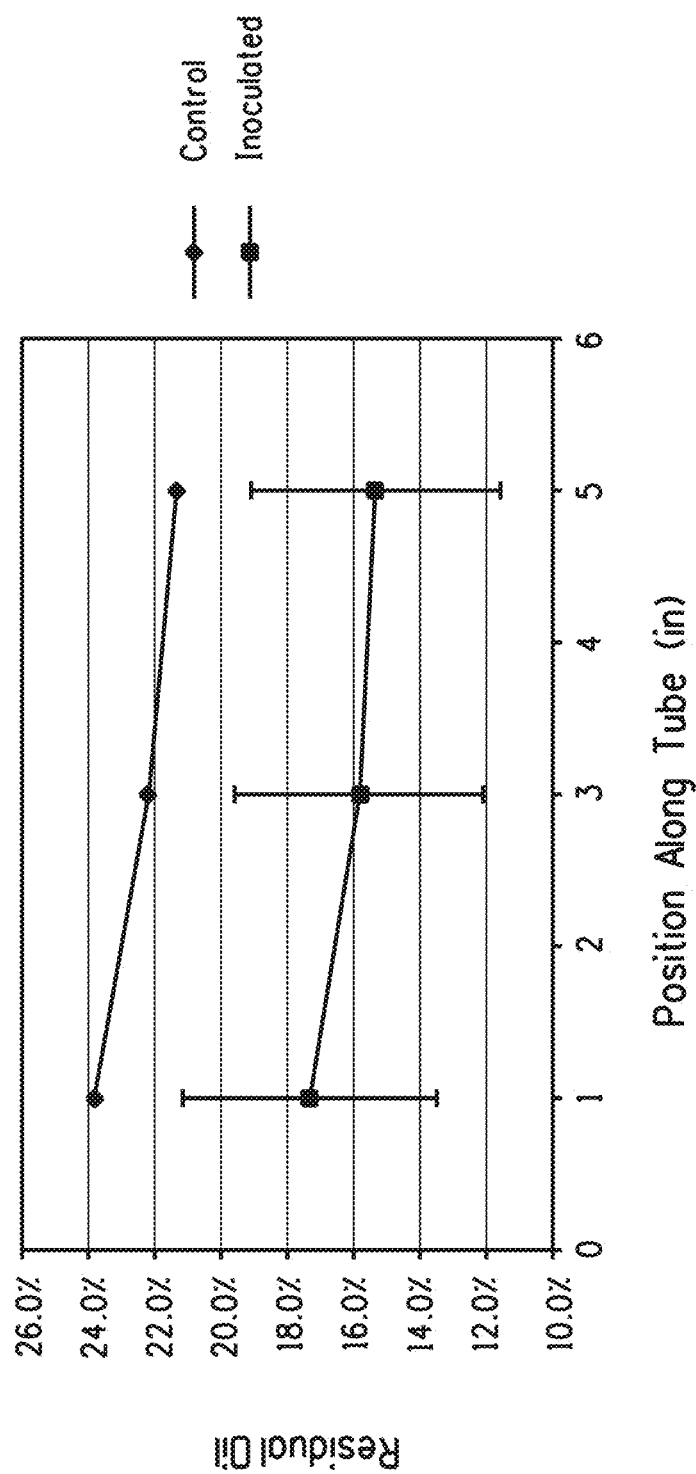

FIG. 13 depicts the level of average residual oil saturation along the sand pack column. The results with control are shown with diamonds and the results with the inoculated (strain LH4:18) are shown with squares. The amount of residual oil saturation in the control column was 22.5% whereas the residual oil saturation for strain LH4:18 inoculated columns was 16.1%, indicating that strain LH4:18 was able to reduce residual oil saturation by approximately 6.5%.

Figure 14:
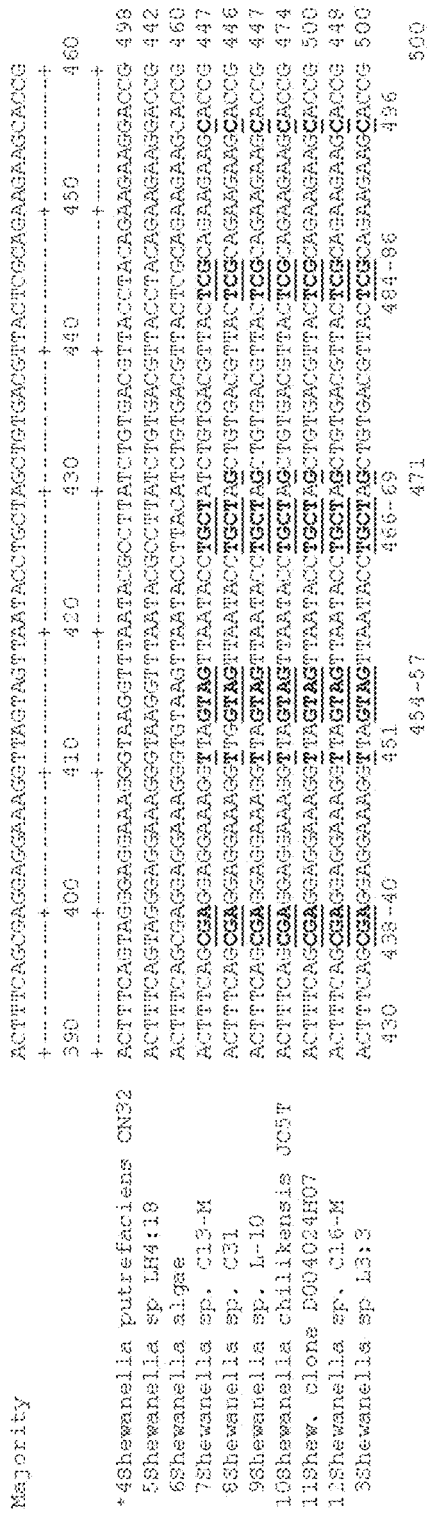

FIG. 14 shows strain and species-specific signature base variations that occur in strain L3:3 in the 16S rRNA variable region 3 and SEQ ID NO: 13 (bp coordinates 430 to 500) at specific coordinate positions: 438-40, 451, 454-57, 466-69, 471, 484-86 and 496.

Figure 15:
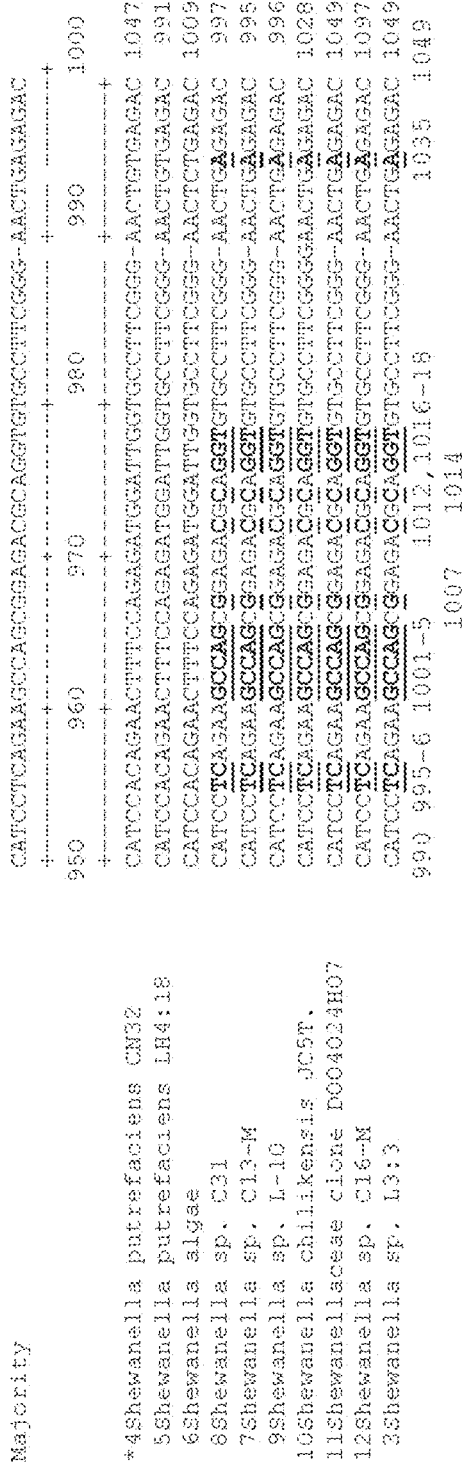

FIG. 15 shows strain and species-specific signature base variations for bacterial variable region 6 for sequences closely related to *Shewanella* sp L3:3, e.g., sequences similar to that defined by SEQ ID NO: 14. Strain and species-specific variations occur between base coordinates 990 and 1049, specifically at positions: 995-6, 1001-5, 1007, 1012, 1014, 1016-18 and 1035.

Figure 16:
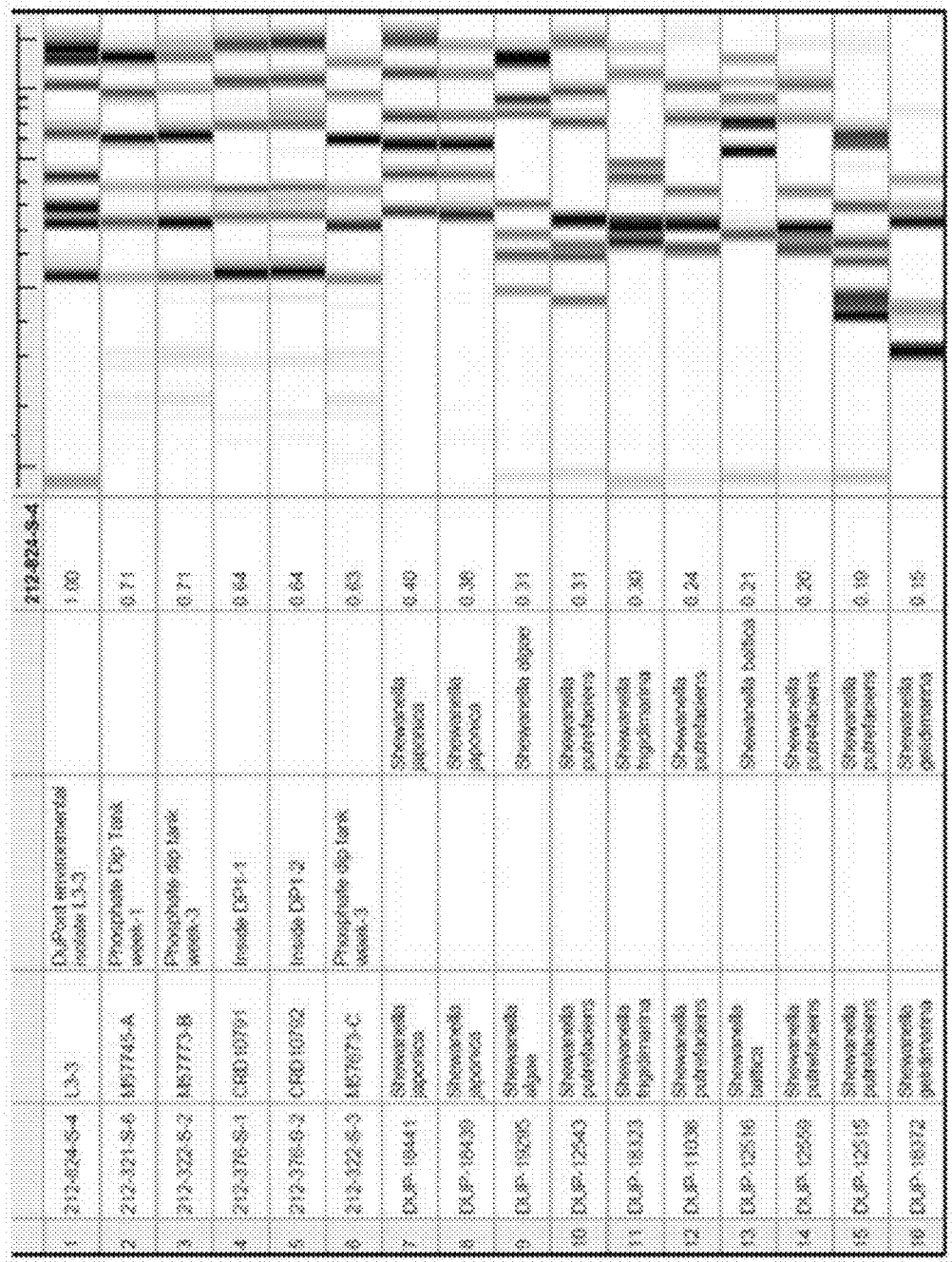

FIG. 16 shows the Riboprint batch report, 052009, used for comparisons of *Shewanella* sp. L3:3 designated riboprint #212-824-S-4 to other *Shewanella* riboprints available in the Qualicon and DuPont Environmental Sciences Riboprint Databases.

FIG. 17(A) shows a photomicrograph of untreated oil coated sand.

FIG. 17(B) shows that the untreated oil coated sand has a low contact angle (qCA).

FIG. 17(C) shows a photomicrograph of oil coated sand following exposure to strain L3:3.

FIG. 17(D) shows a significant increase in the contact angle of the oil coated sand (qCB) following exposure to strain L3:3.

Figure 18:
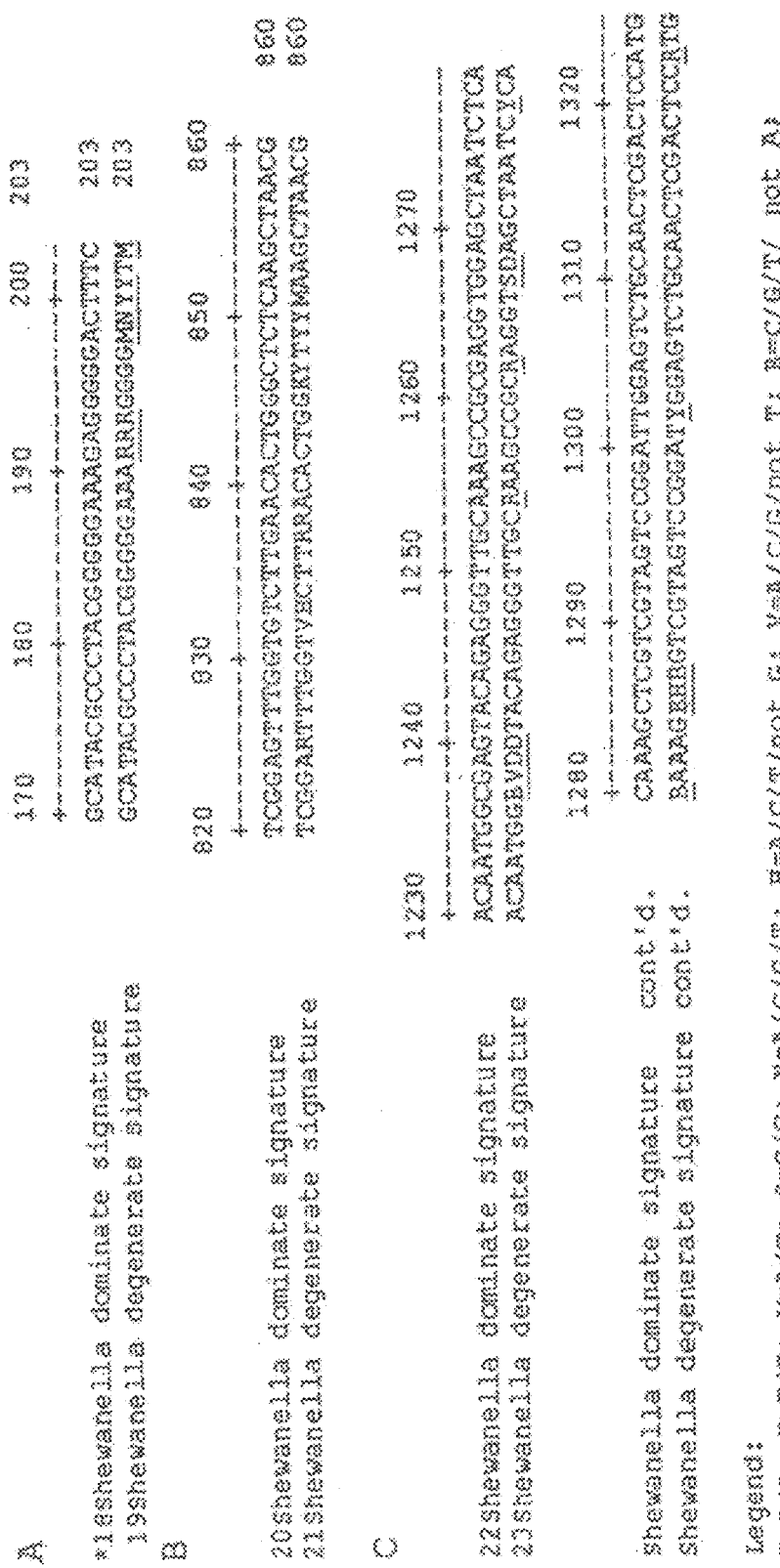

FIG. 18 shows dominant and degenerate signature sequences for *Shewanella* species in rDNA variable regions 2 (A), 5 (B), and 8 (C). The variable positions are underlined. Alternative nucleotides for each variable position designation are given in the legend. *Shewanella oneidensis* MR-1 is representative of *Shewanella* having the dominant signature sequences.

Figure 19:
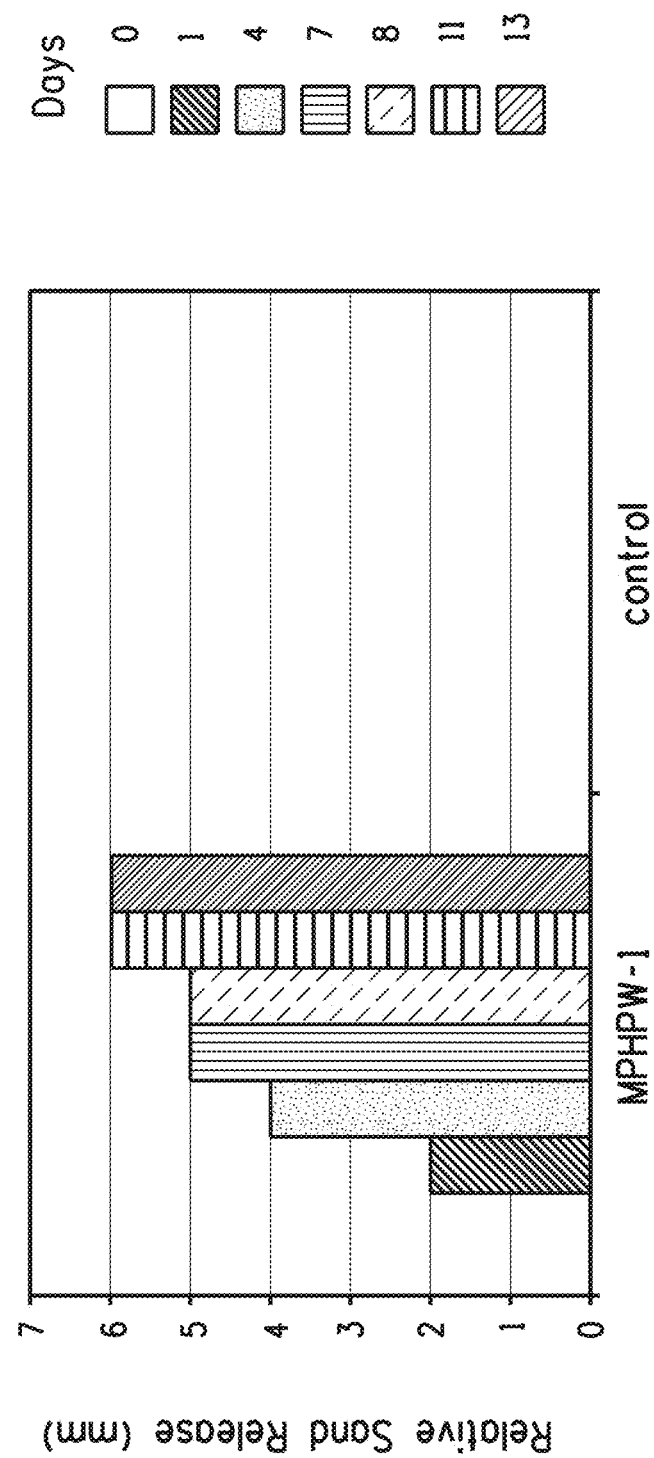

FIG. 19 is a graph of oil release over time in a LOOS test using strain MPHPW-1 as compared to a medium alone control. The experiment was performed for 13 days.

Figure 20:
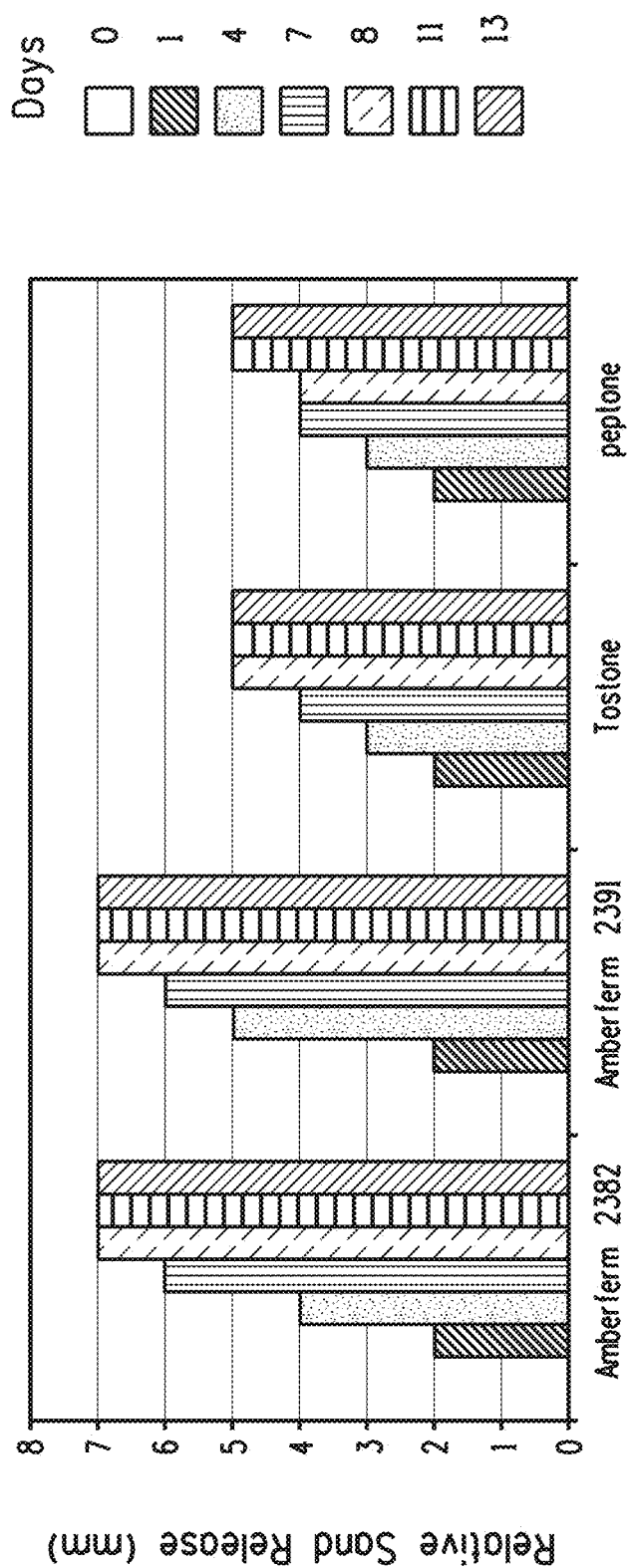

FIG. 20 depicts oil release over time in a LOOS test using strain MPHPW-1 grown with different nutrients added to growth medium. The nutrients tested were Amberferm 2832, Amberferm 2391, Tastone, and Peptone. The experiment was performed for 13 days.

Figure 21:
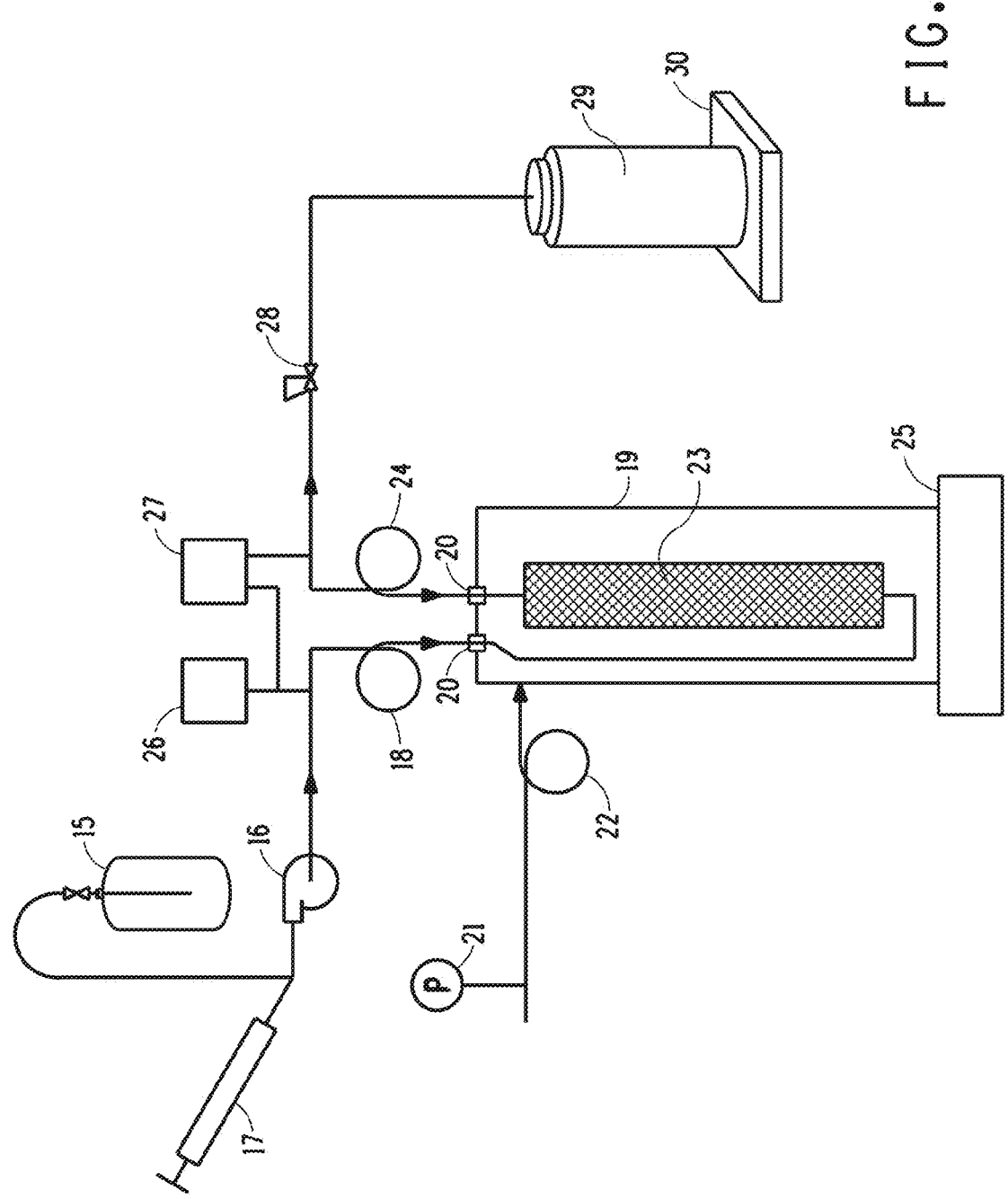

FIG. 21 shows a schematic diagram of the sandpack apparatus experimental set-up used to demonstrate oil release. Apparatus parts correspond to designated numbers as follows: injection brine reservoir (15), pressure pump (16), syringe pump (17), inlet tubing (18), pressure vessel (19), bulkhead pressure fittings (20), pressure gauge (21), flexible tubing (22), sandpack (23), outlet tubing (24), weigh scale (25), absolute pressure gauge (26), differential pressure transducer (27), back pressure regulator (28), jug (29), and weigh scale (30).

Figure 22:
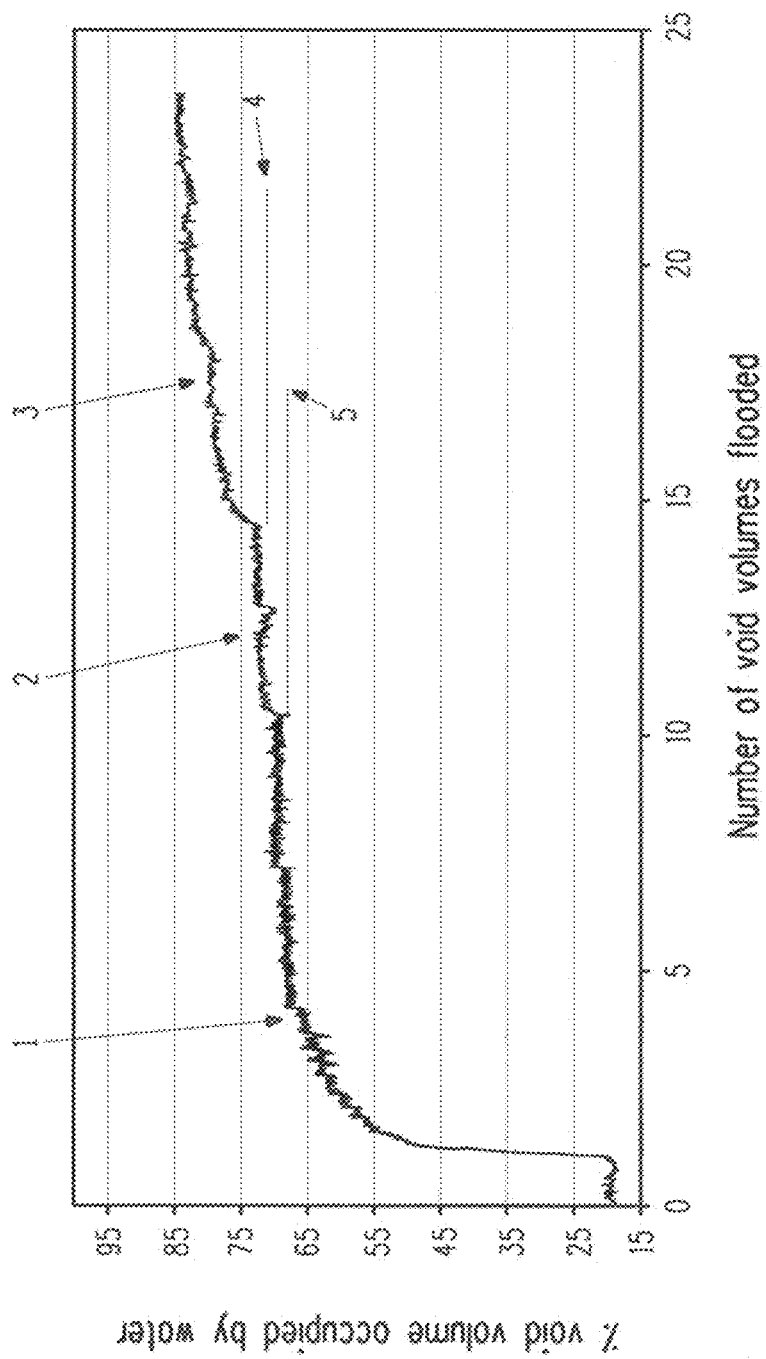

FIG. 22 depicts water saturation before and after treatment with strain MPHPW-1. The first part of the curve, labeled 1, is the deoiling curve using injection brine alone. The second part of the curve, labeled 2, is the deoiling curve using medium alone without any microorganisms added. The third part of the curve, labeled 3, is the deoiling curve using medium plus MPHPW-1. The extrapolated deoiling line from the medium alone treatment is labeled 4. The extrapolated deoiling line from injection brine alone treatment is labeled 5.

Figure 23:
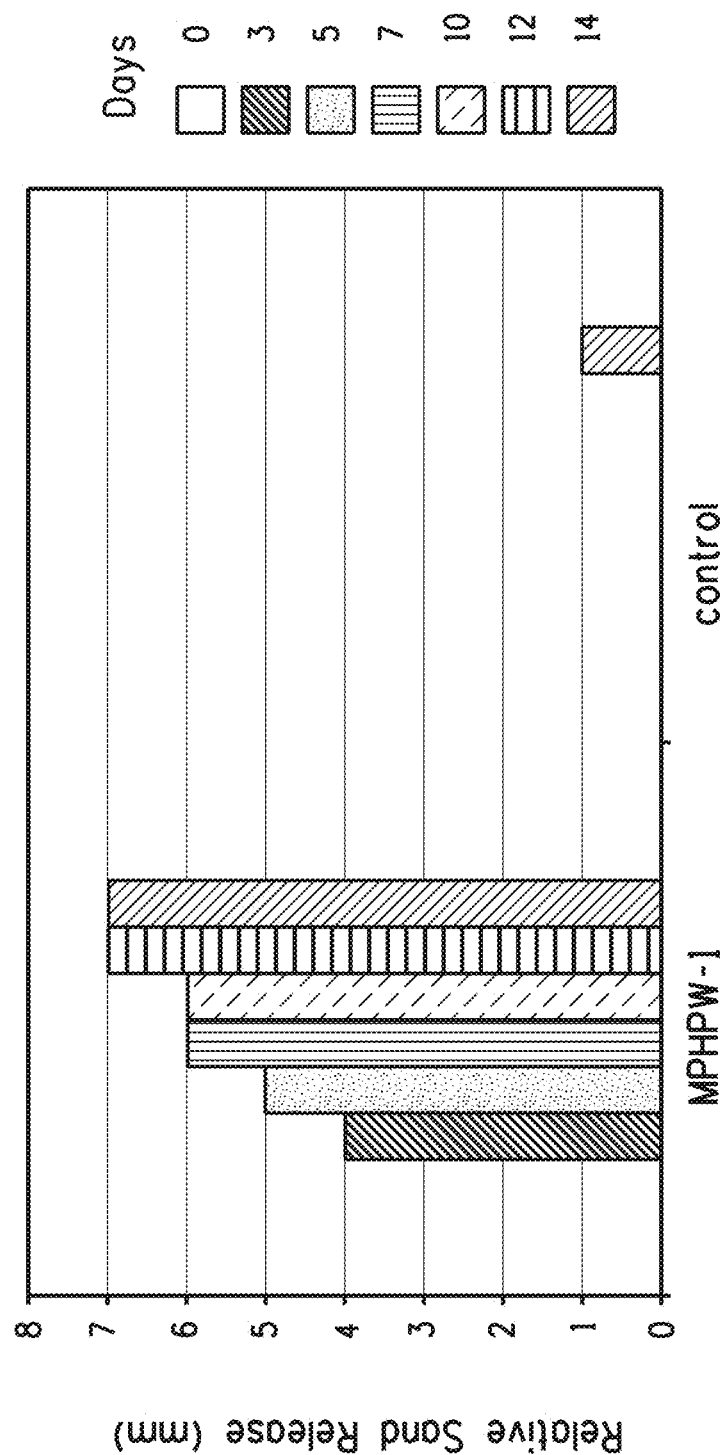

FIG. 23 depicts sand release over time in a LOOS test using the MPHPW-1 inoculum that was used in the sandpack experiment compared to a medium alone control.

Figure 24:
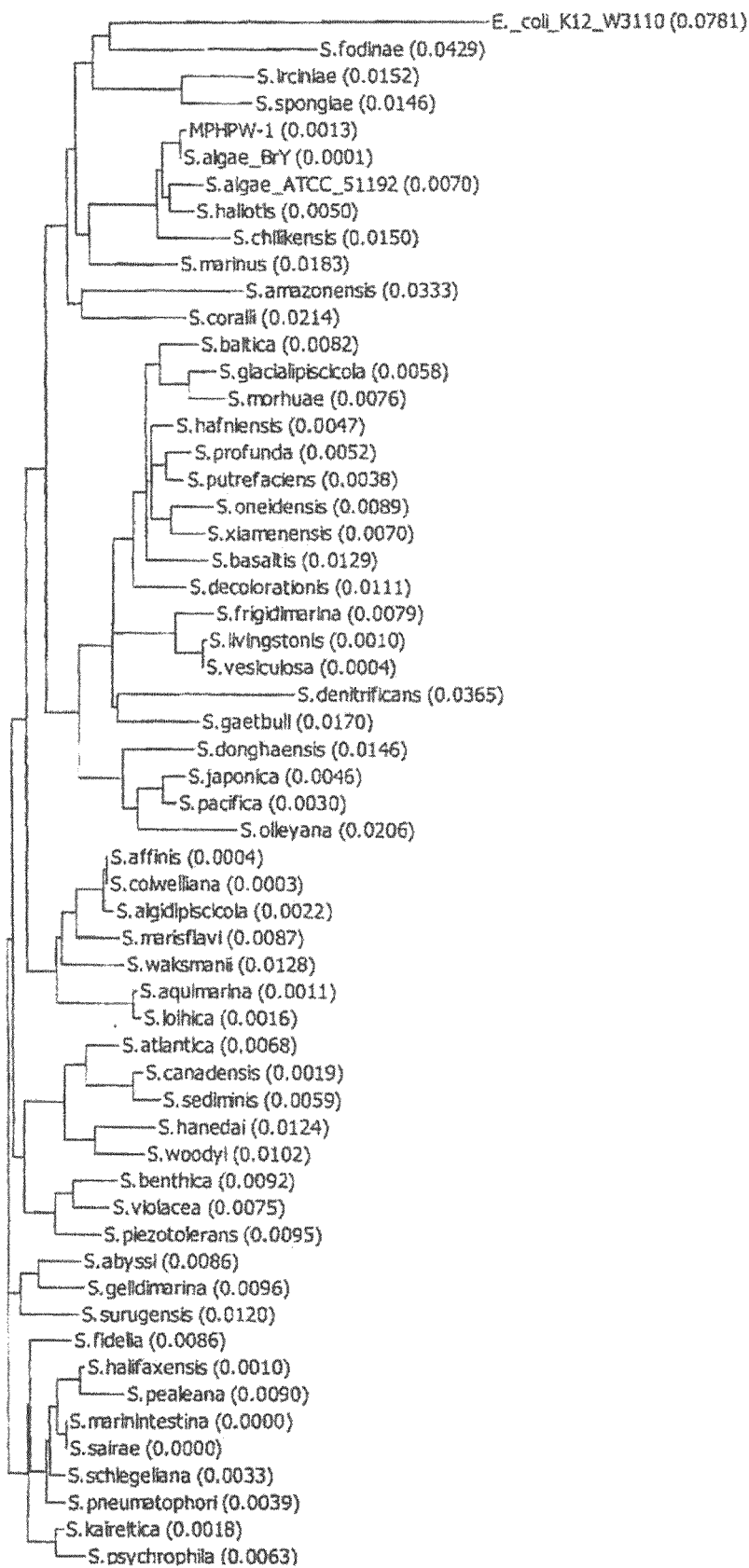

FIG. 24 is Guide Tree, resembling a phylogenetic tree, showing the genus *Shewanella* type strains, *Shewanella algae* strain BrY, and strain MPHPW-1. The tree was prepared based on a sequence distance method and utilizes Neighbor Joining algorithm of Saitou and Nei from 1987 (infra).

Figure 25:
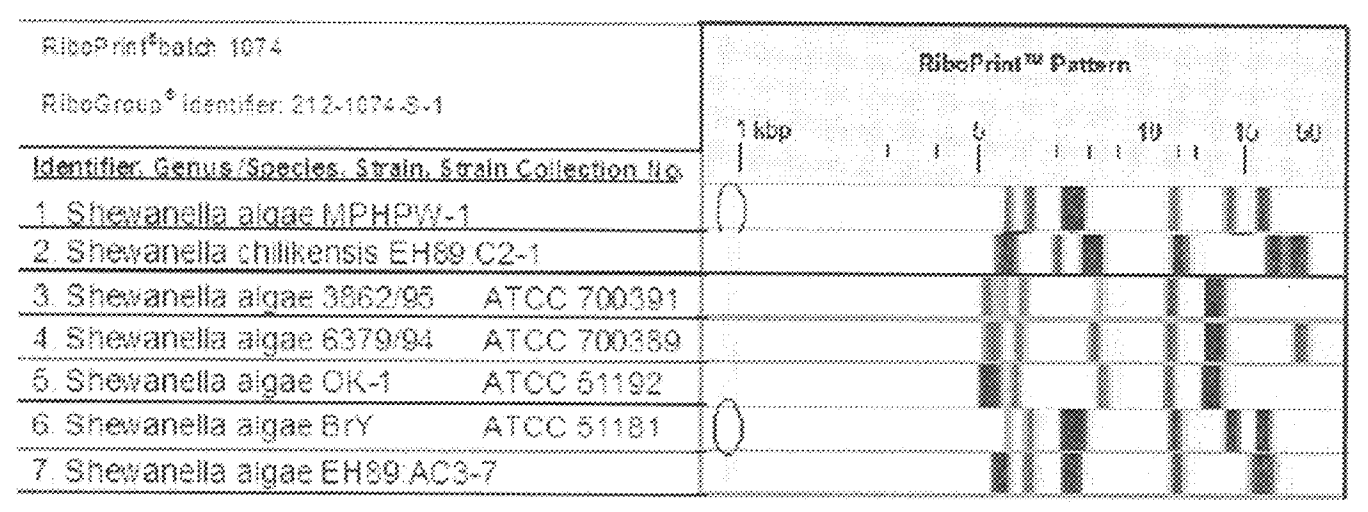

FIG. 25 shows a Riboprint® batch report, 1074, used for comparisons of strain *Shewanella algae* MPHPW-1 to other *Shewanella* riboprints available in the Qualicon and DuPont Environmental Sciences Riboprint Databases.

The following DNA sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST. 25 (2009) and the sequence listing requirements of the EPO and PCT (Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO:1 is oligonucleotide primer 1492R.

SEQ ID NO:2 is oligonucleotide primer 8F.

SEQ ID NO:3 is 16S rDNA from *Shewanella* sp. L3:3

SEQ ID NO:4 is 16S rDNA from CP000681 *Shewanella putrefaciens* CN-32.

SEQ ID NO:5 is 16S rDNA from *Shewanella putrefaciens* LH4:18.

SEQ ID NO:6 is 16S rDNA FJ210800 from *Shewanella algae*.

SEQ ID NO:7 is 16S rDNA EU563337.1 from *Shewanella* sp. C13-M.

SEQ ID NO:8 is 16S rDNA EU563345.1 from *Shewanella* sp. C31.

SEQ ID NO:9 is 16S rDNA DQ164801.1 from *Shewanella* sp. L-10.

SEQ ID NO:10 is 16S rDNA FM210033.2 from *Shewanella chilikensis* JC5T.

SEQ ID NO:11 is 16S rDNA EU721813 from *Shewanella* uncultured clone D004024H07.

SEQ ID NO:12 is 16S rDNA EU563338.1 from *Shewanella* sp. C16-M.

SEQ ID NO:13 is the DNA sequence corresponding to prokaryote 16S rRNA variable region 3 that is signature to *Shewanella* sp. L3:3 and related strains.

SEQ ID NO:14 is the DNA sequence corresponding to prokaryote 16S rRNA variable region 6 that is signature to *Shewanella* sp. L3:3 and related strains.

SEQ ID NO:15 is a partial sequence of the 16S rDNA of *Shewanella* sp. strain EH60:12.

SEQ ID NO:16 is a partial sequence of the 16S rDNA of *Shewanella* sp. strain EH60:10.

SEQ ID NO:17 is a partial sequence of the 16S rDNA of *Shewanella* sp. strain EH60:2.

SEQ ID NO:18 is the *Shewanella* dominant signature sequence for the 16S rDNA variable region 2.

SEQ ID NO:19 is the *Shewanella* degenerate signature sequence for the 16S rDNA variable region 2.

SEQ ID NO:20 is the *Shewanella* dominant signature sequence for the 16S rDNA variable region 5.

SEQ ID NO:21 is the *Shewanella* degenerate signature sequence for the 16S rDNA variable region 5.

SEQ ID NO:22 is the *Shewanella* dominant signature sequence for the 16S rDNA variable region 8.

SEQ ID NO:23 is the *Shewanella* degenerate signature sequence for the 16S rDNA variable region 8.

SEQ ID NO:24 is 16S rDNA from *Shewanella algae* MPHPW-1 SEQ ID NO:25 is the *Shewanella* degenerate signature sequence for the 16S rDNA variable region 2 adjusted at position 23 to include the MPHPW-1 16S rDNA sequence.

SEQ ID NO:26 is 16S rDNA from strain IBI-6P, which is SEQ ID 3 from US20100044304.

SEQ ID NO:27 is 16S rDNA from X81621 *Shewanella algae* BrY.

SEQ ID NO:28 is the *Shewanella* degenerate signature sequence for the 16S rDNA variable region 2 containing the MPHPW-1 distinguishing C at position 23.

SEQ ID NO:29 is the DNA sequence corresponding to prokaryote 16S rRNA variable region 3 that is signature to *Shewanella* sp. MPHPW-1.

SEQ ID NO:30 is Genbank Accession No. X82131 *Shewanella benthica* 16S rRNA gene (ATCC 43992) type strain.

SEQ ID NO:31 is Genbank Accession No. X82132 *Shewanella hanedai* 16S rRNA gene (CIP 103207T) type strain.

SEQ ID NO:32 is Genbank Accession No. X81623 *Shewanella putrefaciens* 16S rRNA gene type strain.

SEQ ID NO:33 is Genbank Accession No. EF178282 *Shewanella haliotis* strain DW01 16S ribosomal RNA gene, partial sequence type strain.

SEQ ID NO:34 is Genbank Accession No. AJ311964 *Shewanella denitrificans* partial 16S rRNA gene, strain OS-217 type strain.

SEQ ID NO:35 is Genbank Accession No. EU143361 *Shewanella* sp. J83 16S ribosomal RNA gene, partial sequence type strain.

SEQ ID NO:36 is Genbank Accession No. AF420312 *Shewanella fidelia* strain KMM3582T 16S ribosomal RNA gene, partial sequence type strain.

SEQ ID NO:37 is Genbank Accession No. EU290154 *Shewanella marinus* strain C4 16S ribosomal RNA gene, partial sequence type strain.

SEQ ID NO:38 is Genbank Accession No. U85903 SFU85903 *Shewanella frigidimarina* ACAM 591T 16S ribosomal RNA gene, partial sequence type strain.

SEQ ID NO:39 is Genbank Accession No. U85907 SGU85907 *Shewanella gelidimarina* ACAM456 16S ribosomal RNA gene, partial sequence type strain.

SEQ ID NO:40 is Genbank Accession No. AJ300834 *Shewanella livingstonis* 16S rRNA gene, strain LMG19866T type strain.

SEQ ID NO:41 is Genbank Accession No. AM980877 *Shewanella vesiculosa* partial 16S rRNA gene, type strain M7T type strain.

SEQ ID NO:42 is Genbank Accession No. D21225 VIB16SRRF *Shewanella violacea* gene for 16S rRNA, partial sequence type strain. SEQ ID NO:43 is Genbank Accession No. FJ589031 *Shewanella* sp. S4 16S ribosomal RNA gene, partial sequence type strain.

SEQ ID NO:44 is Genbank Accession No. AF005248 *Shewanella amazonensis* 16S ribosomal RNA gene, partial sequence type strain.

SEQ ID NO:45 is Genbank Accession No. AF005249 *Shewanella algae* strain ATCC 51192 16S ribosomal RNA gene, partial sequence type strain.

SEQ ID NO:46 is Genbank Accession No. AF005251 *Shewanella oneidensis* MR-1 16S ribosomal RNA gene, partial sequence type strain.

SEQ ID NO:47 is Genbank Accession No. AB081757 *Shewanella marinintestina* gene for 16S rRNA, partial sequence type strain.

SEQ ID NO:48 is Genbank Accession No. AB081760 *Shewanella schlegeliana* gene for 16S rRNA, partial sequence type strain.

SEQ ID NO:49 is Genbank Accession No. AB081762 *Shewanella sairae* gene for 16S rRNA, partial sequence type strain.

SEQ ID NO:50 is Genbank Accession No. FM203122 *Shewanella* sp. JC15 partial 16S rRNA gene, strain JC15 type strain.

SEQ ID NO:51 is Genbank Accession No. AJ874353 *Vibrio natriegens* partial 16S rRNA gene, strain 01/252.

SEQ ID NO:52 is Genbank Accession No. AF011335 *Shewanella pealeana* 16S ribosomal RNA gene, complete sequence type strain.

SEQ ID NO:53 is Genbank Accession No. FJ041083 *Alteromonadales bacterium* fav-2-10-05 16S ribosomal RNA gene, partial sequence type strain.

SEQ ID NO:54 is Genbank Accession No. AY170366 *Shewanella waksmanii* 16S ribosomal RNA gene, partial sequence type strain.

SEQ ID NO:55 is Genbank Accession No. AJ000214 *Shewanella baltica* NCTC10735 16S rRNA gene type strain.

SEQ ID NO:56 is Genbank Accession No. AY190533 *Shewanella gaetbuli* 16S ribosomal RNA gene, partial sequence type strain.

SEQ ID NO:57 is Genbank Accession No. AB094597 *Shewanella surugensis* gene for 16S rRNA, partial sequence, strain: c959 type strain.

SEQ ID NO:58 is Genbank Accession No. AB094598 *Shewanella kaireitica* gene for 16S rRNA, partial sequence, strain: c931 type strain.

SEQ ID NO:59 is Genbank Accession No. AF500075 *Shewanella pacifica* KMM 3597 16S ribosomal RNA gene, partial sequence type strain.

SEQ ID NO:60 is Genbank Accession No. AY326275 *Shewanella donghaensis* strain LT17 16S ribosomal RNA gene, partial sequence type strain.

SEQ ID NO:61 is Genbank Accession No. AY351983 *Shewanella affinis* 16S ribosomal RNA gene, partial sequence type strain.

SEQ ID NO:62 is Genbank Accession No. AJ551089 *Shewanella psychrophila* partial 16S rRNA gene, type strain WP2T.

SEQ ID NO:63 is Genbank Accession No. AJ551090 *Shewanella piezotolerans* WP3 partial 16S rRNA gene, type strain WP3T.

SEQ ID NO:64 is Genbank Accession No. AY445591 *Shewanella profunda* strain LT13a 16S ribosomal RNA gene, partial sequence type strain.

SEQ ID NO:65 is Genbank Accession No. AJ609571 *Shewanella decolorationis* partial 16S rRNA gene, type strain CCTCC M 203093T.

SEQ ID NO:66 is Genbank Accession No. AY485224 *Shewanella marisflavi* 16S ribosomal RNA gene, partial sequence type strain.

SEQ ID NO:67 is Genbank Accession No. AY485225 *Shewanella aquimarina* 16S ribosomal RNA gene, partial sequence type strain.

SEQ ID NO:68 is Genbank Accession No. AY579749 *Shewanella canadensis* strain HAW-EB2 16S ribosomal RNA gene, partial sequence type strain.

SEQ ID NO:69 is Genbank Accession No. AY579750 *Shewanella sediminis* strain HAW-EB3 16S ribosomal RNA gene, partial sequence type strain.

SEQ ID NO:70 is Genbank Accession No. AY579751 *Shewanella halifaxensis* strain HAW-EB4 16S ribosomal RNA gene, partial sequence type strain.

SEQ ID NO:71 is Genbank Accession No. AY579752 *Shewanella atlantica* strain HAW-EB5 16S ribosomal RNA gene, partial sequence type strain.

SEQ ID NO:72 is Genbank Accession No. AF145921 *Shewanella* sp. KMM3299 16S ribosomal RNA gene, partial sequence type strain.

SEQ ID NO:73 is Genbank Accession No. AY653177 *Shewanella colwelliana* 16S ribosomal RNA gene, partial sequence type strain.

SEQ ID NO:74 is Genbank Accession No. AB201475 *Shewanella abyssi* gene for 16S rRNA, partial sequence, strain: c941 type strain.

SEQ ID NO:75 is Genbank Accession No. AB205566 *Shewanella hafniensis* gene for 16S rRNA, partial sequence, strain: P010 type strain.

SEQ ID NO:76 is Genbank Accession No. AB205570 *Shewanella algidipiscicola* gene for 16S rRNA, partial sequence, strain: S13 type strain.

SEQ ID NO:77 is Genbank Accession No. AB205571 *Shewanella glacialipiscicola* gene for 16S rRNA, partial sequence, strain: T147 type strain.

SEQ ID NO:78 is Genbank Accession No. AB205576 *Shewanella morhuae* gene for 16S rRNA, partial sequence, strain: U1417 type strain.

SEQ ID NO:79 is Genbank Accession No. AB204519 *Shewanella pneumatophori* gene for 16S rRNA, partial sequence type strain.

SEQ ID NO:80 is Genbank Accession No. DQ167234 *Shewanella spongiae* strain HJ039 16S ribosomal RNA gene, partial sequence type strain.

SEQ ID NO:81 is Genbank Accession No. DQ180743 *Shewanella irciniae* strain UST040317-058 16S ribosomal RNA gene, partial sequence type strain.

SEQ ID NO:82 is Genbank Accession No. DQ286387 *Shewanella loihica* strain PV-4 16S ribosomal RNA gene, partial sequence type strain.

SEQ ID NO:83 is Genbank Accession No. AF295592 *Shewanella* sp. ACEM-9 16S ribosomal RNA gene, partial sequence type strain.

SEQ ID NO:84 is Genbank Accession No. CP000961 *Shewanella woodyi* strain MS32=ATCC 51908 REGION: 53358 . . . 54894 type strain.

SEQ ID NO:85 is Genbank Accession No. AP009048 *E. coli* str. K12 substr. W3110 DNA, complete genome, REGION: 3468481 . . . 3470022.

SEQ ID NO:86 is Genbank Accession No. AE014299 *Shewanella oneidensis* MR-1 REGION: 46116 . . . 47644.

SEQ ID NO:87 is Genbank Accession No. NC_009438 *Shewanella putrefaciens* CN-32 REGION: 38741 . . . 40295.

SEQ ID NO:88 is Genbank Accession No. NC_009052 *Shewanella baltica* OS155 chromosome, complete genome REGION: 44440 . . . 45976.

SEQ ID NO:89 is Genbank Accession No. CP000821 *Shewanella sediminis* HAW-EB3, complete genome region 51967-53501.

SEQ ID NO:90 is Genbank Accession No. X81622 *Shewanella algae* 16S rRNA gene (FeRed).

SEQ ID NO:91 is Genbank Accession No. FJ866783 *Shewanella algae* strain PSB-05 16S ribosomal RNA gene, partial sequence.

SEQ ID NO:92 is Genbank Accession No. HQ851081 *Rhodobacter capsulatus* strain NBY31 16S ribosomal RNA gene, partial sequence.

SEQ ID NO:93 is Genbank Accession No. FJ866781 *Shewanella algae* strain PSB-04 16S ribosomal RNA gene, partial sequence.

SEQ ID NO:94 is Genbank Accession No. GU223381 *Shewanella* sp. EM0501 16S ribosomal RNA gene, partial sequence.

SEQ ID NO:95 is Genbank Accession No. HM016084 *Shewanella* sp. KJW27 16S ribosomal RNA gene, partial sequence.

SEQ ID NO:96 is Genbank Accession No. EU817498 *Alishewanella jeotgali* strain MS1 16S ribosomal RNA gene, partial sequence.

SEQ ID NO:97 is Genbank Accession No. X82147 *A. rubra* 16S rRNA gene (ATCC 29570T).

Applicants have made the following biological deposits under the terms of the Budapest Treaty on the International Recognition of the Deposit of Microorganisms for the Purposes of Patent Procedure:

TABLE 1

INFORMATION ON DEPOSITED STRAINS

| Depositor Identification Reference | International Depository Designation | Date of Deposit |
|---|---|---|
| *Shewanella* sp L3:3 | ATCC No. PTA-10980 | May 19, 2010 |
| *Shewanella putrefaciens* LH4:18 | ATCC No. PTA-8822 | Dec. 4, 2007 |
| *Shewanella algae* MPHPW-1 | ATCC No. PTA-11920 | Jun. 3, 2011 |

DETAILED DESCRIPTION

Applicants specifically incorporate the entire content of all cited references in this disclosure. Unless stated otherwise, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The invention relates to identification of a new strain of *Shewanella* isolated from production water samples obtained from an oil reservoir and to methods for altering the interfacial properties of hydrocarbon coated surfaces by contacting these surfaces with these *Shewanella* microorganisms that have the ability to alter the interface between the hydrocarbons and such surfaces. These alterations result in substantial oil liberation from the hydrocarbon-coated surfaces.

The following definitions are provided for the special terms and abbreviations used in this application:

The abbreviation "dNTPs" refers to Deoxyribonucleotide triphosphates.

The abbreviation "ATCC" refers to American Type Culture Collection International Depository, Manassas, Va., USA. "ATCC No." refers to the accession number to cultures on deposit with ATCC.

The abbreviation "ASTM" refers to the American Society for Testing and Materials.

The term "terrestrial subsurface formation" or "subsurface formation" refers to in ground or under ground geological formations and may comprise elements such as rock, soil, brine, sand, shale, clays and mixtures thereof.

The term "terrestrial surface formation" or "surface formation" refers to above ground geological formations and may comprise elements such as rock, soil, brine, sand, shale, clays and mixtures thereof.

The term "environmental sample" means any sample exposed to hydrocarbons, including a mixture of water and oil. As used herein environmental samples include water and oil samples that comprise indigenous microorganisms useful for phylogenetic mapping of genera present in a given sampling area.

The term "environmental site" means a site that has been contaminated with hydrocarbons and/or other persistent environmental pollutants. Environmental sites may be in surface or subsurface locations.

"Production wells" are wells through which oil is withdrawn from an oil reservoir. An oil reservoir or oil formation is a subsurface body of rock having sufficient porosity and permeability to store and transmit oil. Production fluid containing a mixture of water and oil is also recovered from a production well.

The term "sweep efficiency" refers to the fraction of an oil-bearing stratum that has seen fluid or water passing through it to move oil to production wells. One problem that can be encountered with waterflooding operations is the relatively poor sweep efficiency of the water, i.e., the water can channel through certain portions of the reservoir as it travels from the injection well(s) to the production well(s), thereby bypassing other portions of the reservoir. Poor sweep efficiency may be due, for example, to differences in the mobility of the water versus that of the oil, and permeability variations within the reservoir which encourage flow through some portions of the reservoir and not others.

The term "injection water" refers to fluid injected into oil reservoirs for secondary oil recovery. Injection water may be supplied from any suitable source, and may include, for example, sea water, brine, production water, water recovered from an underground aquifer, including those aquifers in contact with the oil, or surface water from a stream, river, pond or lake. As is known in the art, it may be necessary to remove particulate matter including dust, bits of rock or sand and corrosion by-products such as rust from the water prior to injection into the one or more well bores. Methods to remove such particulate matter include filtration, sedimentation and centrifugation.

The term "irreducible water saturation" is the minimal water saturation that can be achieved in a porous core plug when flooding with oil to saturation. It represents the interstitial water content of the matrix where the water is never completely displaced by the oil because a minimal amount of water must be retained to satisfy capillary forces.

The term "growing on oil" means the microbial species are capable of metabolizing hydrocarbons or other organic components of crude petroleum as a nutrient to support growth.

The term "remediation" refers to the process used to remove hydrocarbon contaminants from an environmental site containing hydrocarbons and/or other persistent environmental pollutants.

The term "bioremediation" refers to the use of microorganisms to remediate or detoxify contaminants form a contaminant-altered environment "Petroleum" or "oil" is a naturally occurring, flammable liquid found in rock and sand formations in the Earth, which consisting of a complex mixture of hydrocarbons and polycyclic aromatic hydrocarbon of various molecular weights, plus other organic compounds.

"Crude oil" refers to the unrefined oil taken from a petroleum reservoir.

"Oil well" and "oil reservoir" may be used herein interchangeably and refer to a subsurface formation from which oil may be recovered.

"Interface" as used herein refers to the surface of contact or boundary between immiscible materials, such as oil and water or a liquid and a solid. As used herein "interfaces" may be between a water layer and an oil layer, a water layer and a solid surface layer, or an oil layer and a solid surface layer.

"Hydrocarbon-coated" as used herein refers to a coating of a hydrocarbon to a solid surface of at least 10% areal coverage.

The term "components of a subsurface formation" refers to rock, soil, brine, sand, shale, clay or mixtures thereof of either subterranean or seabed formations, that have come in contact with one or more hydrocarbon. These components may be part of an oil well or reservoir. At least a portion of the components include some hydrocarbon-coated surfaces, including particles with coated surfaces.

"Adhered to" refers to coating or adsorption of a liquid to a solid surface of at least 10% areal coverage.

"*Shewanella* species" or "*Shewanella* sp." is a bacterial genus that has been established, in part through phylogenetic classification by rDNA. There is at least about 89% sequence identity of 16S rDNA sequences among *Shewanella* species. The 16S rDNA sequences of *Shewanella* species have at least about 89% sequence identity to any of SEQ ID NOs:3-12. *Shewanella* species have 16S rDNA which has the dominant and degenerate signature sequences listed respectively of regions 2 (SEQ ID NO:18, 19), 5, (SEQ ID NO:20,21) and 8 (SEQ ID NO: 22,23) as shown in FIG. 18. The degenerate signature sequence for each region gives the sequence that defines *Shewanella* species, including some position variations as shown in FIG. 18. The dominant signature sequences in FIG. 18 are those with the variable positions designated as the most frequently found nucleotides in *Shewanella* species. Additional *Shewanella* species have the degenerate signature sequence for region 2 of SEQ ID NO:28, replacing SEQ ID NO:19. This sequence has a C in position 23 in the region 2 sequence.

*Shewanella* are gram negative, gamma-proteobacteria, which have the ability to reduce metals and are capable of additionally reducing a wide range of terminal electron acceptors. These microorganisms gain energy to support anaerobic growth by coupling the oxidation of $H_2$ or organic matter to the redox transformation of a variety of multivalent metals, which leads to the precipitation, transformation, or dissolution of minerals.

The abbreviation "rDNA" refers to ribosomal deoxyribonucleic acid gene sequence.

The term "rDNA typing" means the process of using the sequence of the 16S rDNA gene to obtain the "closest relative" microbial species by homology to rDNA sequences maintained in several international databases.

The term "percent identity", as known in the art, is a relationship between two or more polypeptide sequences or two or more polynucleotide sequences, as determined by sequence comparisons. In the art, "identity" also means the degree of sequence relatedness or homology between polynucleotide sequences, as determined by the match between strings of such sequences and their degree of invariance. The term "similarity" refers to how related one nucleotide or protein sequence is to another. The extent of similarity between two sequences is based on the percent of sequence identity and/or conservation. "identity" and "similarity" can be readily calculated by known methods, including but not limited to those described in "Computational Molecular Biology, Lesk, A. M., ed. Oxford University Press, NY, 1988"; and "Biocomputing: Informatics and Genome Projects, Smith, D. W., ed., Academic Press, NY, 1993"; and "Computer Analysis of Sequence Data, Part I, Griffin, A. M., and Griffin, H. G., eds., Humana Press, NJ, 1994"; and "Sequence Analysis in Molecular Biology, von Heinje, G., ed., Academic Press, 1987"; and "Sequence Analysis Primer, Gribskov, M. and Devereux, J., eds., Stockton Press, NY, 1991". Preferred methods to determine identity are designed to give the best match between the sequences tested. Methods to determine identity and similarity are codified in publicly available computer programs such as sequence analysis software. Typical sequence analysis software includes, but is not limited to: the GCG suite of programs (Wisconsin Package Version 9.0, Genetics Computer Group (GCG), Madison, Wis.), BLASTP, BLASTN, BLASTX (Altschul et al., *J. Mol. Biol.* 215, 403-410, 1990), DNASTAR (DNASTAR, Inc., Madison, Wis.), and the FASTA program incorporating the Smith-Waterman algorithm (Pearson, W. R., *Comput. Methods Genome Res.*, Proc. Int. Symp, Meeting Date 1992, 111-120, Eds: Suhai, Sandor, Plenum Publishing, New York, N. Y., 1994). Within the context of this application, it will be understood that, where sequence analysis software is used for analysis, the results of the analysis will be based on the "default values" of the program used, unless otherwise specified. As used herein "default values" will mean any set of values or parameters which originally load with the software when first initialized.

The term "wetting" refers to the ability of a liquid to maintain contact with a solid surface, resulting from intermolecular interactions when the two are brought together. The degree of wetting (expressed as "wettability") is determined by a force balance between adhesive and cohesive forces.

"Wetting agent" refers to a chemical such as a surfactant that increases the water wettability of a solid or porous surface by changing the hydrophobic surface into one that is more hydrophilic. Wetting agents help spread the wetting phase (e.g., water) onto the surface thereby making the surface more water wet.

"Wettability" refers to the preference of a solid to contact one liquid, known as the wetting phase, rather than another. Solid surfaces can be water wet, oil wet or intermediate wet. "Water wettability" pertains to the adhesion of water to the surface of a solid. In water-wet conditions, a thin film of water coats the solid surface, a condition that is desirable for efficient oil transport.

The term "adhesive forces" refers to the forces between a liquid and solid that cause a liquid drop to spread across the surface.

The term "cohesive forces" refers to forces within the liquid that cause the drop to ball up and avoid contact with the surface.

The term "contact angle" is the angle at which a liquid (oil or water) interface meets a solid surface, such as sand or clay. Contact angle is a quantitative measurement of the wetting of a solid by a liquid and is specific for any given system, and is determined by interactions across three interfaces. The concept is illustrated with a small liquid droplet resting on a flat horizontal solid surface. The shape of the droplet is determined by the "Young Relation" (Bico et al., Colloids and Surfaces A: Physicochemical and Engineering Aspects 206 (2002) 41-46). The theoretical description of contact arises from the consideration of a thermodynamic equilibrium between the three phases: the liquid phase of the droplet (L), the solid phase of the substrate (S), and the gas/vapor phase of the ambient (V) (which will be a mixture of ambient atmosphere and an equilibrium concentration of the liquid vapor). The V phase could also be another (immiscible) liquid phase. At equilibrium, the chemical potential in the three phases should be equal. It is convenient to frame the discussion in terms of interfacial energies. The solid-vapor interfacial energy (see surface energy) is $\gamma_{SV}$, the solid-liquid interfacial energy is $\gamma_{SL}$ and the liquid-vapor energy (i.e. the surface tension) is simply $\gamma$. The Young equation: $0=\gamma_{SV}-\gamma_{SL}-\cos\theta$ is written such that describes an equilibrium where $e_c$ is the equilibrium contact angle.

"Microbial populations" means one or more populations of microorganisms present, either in samples obtained from oil wells or in an inoculum for injection into an oil well or subsurface formation.

"Medium" as used herein means an aqueous milieu which supports the growth of organisms. Medium containing *Shewanella* sp. cells is referred to herein as "cell containing" medium and medium that has been in contact with one or more *Shewanella* sp. but is a cell free supernatant is referred to herein as "conditioned" medium. Medium will be aqueous based and may contain various nutrients, buffers, salts, vitamins, co-factors and the like and carbon sources useful for microbial growth.

An "electron acceptor" is a molecular compound that receives or accepts an electron during cellular respiration. Microorganisms obtain energy to grow by transferring electrons from an "electron donor" to an electron acceptor. During this process, the electron acceptor is reduced and the electron donor is oxidized. Examples of acceptors include oxygen, nitrate, fumarate, iron (III), manganese (IV), sulfate or carbon dioxide. Sugars, low molecular weight organic acids, carbohydrates, fatty acids, hydrogen and crude oil or its components such as petroleum hydrocarbons or polycyclic aromatic hydrocarbons are examples of compounds that can act as electron donors.

"Denitrifying" and "denitrification" mean reducing nitrate for use as an electron acceptor in respiratory energy generation. "Denitrifying conditions" means conditions where denitrification occurs.

"Inoculating an oil well" means injecting one or more microorganisms or microbial populations or a consortium into an oil well or oil reservoir such that microorganisms are delivered to the well or reservoir without loss of total viability.

The term "simple nitrates" and "simple nitrites" refer to nitrite ($NO_2$) and nitrate ($NO_3$).

The term "nutrient supplementation" refers to the addition of nutrients that benefit the growth of microorganisms that are capable of using crude oil as their main carbon source but grow optimally with other non-hydrocarbon nutrients, i.e., yeast extract, peptone, succinate, lactate, formate, acetate, propionate, glutamate, glycine, lysine, citrate, glucose, pyruvate and vitamin solutions.

The term "biofilm" means a film or "biomass layer" made up of a matrix of a compact mass of microorganisms consisting of structural heterogeneity, genetic diversity, complex community interactions, and an extracellular matrix of polymeric substances. Biofilms are often embedded in these extracellular polymers, which adhere to surfaces submerged in, or subjected to, aquatic environment The term "bacterial" means belonging to the bacteria. Bacteria are an evolutionary domain or kingdom of microbial species separate from other prokaryotes based on their physiology, morphology and 16S rDNA sequence homologies.

"Microbial species" means distinct microorganisms identified based on their physiology, morphology and phylogenetic characteristics using 16S rDNA sequences. The closest relative microbial species may also be referred to as a "homolog".

The term "pure culture" means a culture derived from a single cell isolate of a microbial species. The pure cultures specifically referred to herein include those that are publicly available in a depository. Additional pure cultures are identifiable by the methods described herein.

The term "simulated injection brine" or "SIB" is a medium composition containing 198 mM NaCl, 1 mM $MgCl_2$, 1.8 mM $CaCl_2$, 1.2 mM KCl, 16 mM $NaHCO_3$, 0.05 mM $SrCl_2$, 0.13 mM $BaCl_2$, 0.14 mM LiCl.

The abbreviation "NCBI" refers to the National Center for Biotechnology Information.

A spectrophotometer is a device for measuring light intensity that can measure intensity as a function of the color, or more specifically, the wavelength of light. In microbiology, the term "optical density" is a unit-less measure of the transmittance of light at a given wavelength that uses an empirical relationship that relates the absorption of light to the properties of the material through which the light is traveling.

The term "MPN" or "most probable number" is a quantitative measurement of the concentration of microbes in a given medium. It is expressed as CFU/ml (colony forming units/ml), log 10 (CFU/ml) or log 10 (MPN).

The term "hypervariable regions" as used herein refers to sequence regions in the 16S rRNA gene where the nucleotide sequence is highly variable. In most microbes the 16S rDNA sequence consists of nine hypervariable regions that demonstrate considerable sequence diversity among different bacterial genera and species and can be used for genus and species identification The term "signature sequences" as used herein refers to specific nucleotides at specific 16S rRNA encoding gene (rDNA) positions (signature positions), which usually occur within the hypervariable regions, that are distinguishing for microorganisms at different levels. At the signature positions, nucleotides that distinguish between species may be one or more specific base substitutions, insertions or deletions. When taken together, the signature sequences of 16S rDNA are useful for describing microbes at the species, strain or isolate level and can be used in the identification of a microbe.

The term "degenerate base position" refers herein to a position in a nucleotide sequence that may be more than one choice of nucleotide. A position is a "two-fold degenerate" site if only two of four possible nucleotides may be at that position. A position is a "three-fold degenerate" site if three of four possible nucleotides may be at that position. A position is a "four-fold degenerate" site if all four nucleotides may be at that position. "Degeneracy" refers to the existence of more than one nucleotide in at least one position in a specified population of sequences having high identity.

The term "degenerate signature sequence" refers to a signature sequence that has one or more variable position(s) that may include the occurrence of different bases, base insertions and/or base deletions in different individual sequences.

The term "phylogenetic typing" "phylogenetic mapping" or "phylogenetic classification" may be used interchangeably herein and refer to a form of classification in which microorganisms are grouped according to their ancestral lineage. The methods herein are specifically directed to phylogenetic typing on environmental samples based on 16S Ribosomal DNA (rDNA) sequencing. In this context, approximately 1400 base pair (bp) length of the 16S rDNA gene sequence is generated using 16S rDNA universal primers identified herein and compared by sequence homology to a database of microbial rDNA sequences. This comparison is then used to help taxonomically classify pure cultures for use in enhanced oil recovery.

The term "phylogenetics" refers to the field of biology that deals with identifying and understanding evolutionary relationships between organisms, and in particular molecular phylogenetics uses DNA sequence homologies in this analysis. In particular, similarities or differences in 16S rDNA sequences, including signature sequences, identified using similarity algorithms serves to define phylogenetic relationships.

The term "phylogenetic tree" refers to a branched diagram depicting evolutionary relationships among organisms. The phylogenetic tree herein is based on DNA sequence homologies of 16S rDNAs, including of signature sequences in the 16S rDNA, and shows relationships of the present strains to related reference strains and species.

The term "Glade" or "phylogenetic Glade" refers to a branch in a phylogenetic tree. A Glade includes all of the related organisms that are located on the branch, based on the chosen branch point. A Glade is defined by a change in one or more signature sequences.

The term "genomovar" is used to describe a sub-species classification which is used when a group of strains of a species are differentiable by DNA sequence, but are phenotypically indistinguishable. Genomovars are defined and identified by DNA-DNA hybridization and/or by 16S rDNA signature sequences. This terminology has been used to describe *Pseudomonas stutzeri* by Bennasar et al. ((1996) Int. J. of Syst. Bacteriol. 46:200-205).

The term "Ribotyping®" refers to fingerprinting of genomic DNA restriction fragments that contain all or part of the rRNA operon encoding for the 5S, 16S and 23S rRNA genes (Webster, John A, 1988. U.S. Pat. No. 4,717,653; Bruce, J. L., Food Techno., (1996), 50: 77-81; and Sethi, M. R., Am. Lab. (1997), 5: 31-35). Ribotyping® involves generation of restriction fragments, from microbial chromosomal DNA, which are then separated by electrophoresis, and transferred to a filter membrane and finally probed with labeled rDNA operon probes. Restriction fragments that hybridize to the labeled probe produce a distinct labeled pattern or fingerprint/barcode that is unique to a specific microbial strain. Ribotyping® is performed using the DuPont RIBOPRINTER® system.

The term "Riboprint®" refers to the unique genomic fingerprint of a specific microbial isolate or strain, generated using the DuPont RIBOPRINTER® system that can be given a unique "Riboprint® identifier" (alphanumeric characters) and stored electronically to be used to identify the isolate when compared to the database at a later date. The Ribotyping® procedure can be entirely performed on the Riboprinter® instrument (DuPont Qualicon, Wilmington, Del.).

The term "Riboprint® batch" refers to comparison alignment of two or more Riboprints® and is depicted in a report as a pictograph.

The term "type strain" refers to the reference strain recognized in the International Journal of Systematic and Evolutionary Microbiology for a particular species, whose description is used to define and characterize that species. It is one of the first strains of a species studied and is usually more fully characterized than other strains; however, it does not have to be the most representative member. Type strains are usually deposited in a national strain collection, such as the ATCC (USA) or DSMZ (German).

The term "reference strain or species" refers to any strain or species in the public domain.

The term "standard strain" means a strain which matches the type strain in character and sequence. These strains were used as sequence standards in defining signature sequences because their genomes have been completely sequenced and these sequences scrutinized for accuracy The abbreviation "LPNSN" refers to the List of Prokaryotic names with Standing in Nomenclature (LPNSN), the official database of accepted prokaryote names that have conformity within the rules of the International Code of Nomenclature of Bacteria and have been validated by the International Journal of Systematic and Evolutionary Microbiology.

The acronym "IPOD" refers to International Patent Organism Depositary, Independent Administrative Agency National Institute of Advanced Industrial Science and Technology (AIST Tsukuba Central 6,1-1, Higashi 1-chrome, Tsukuba-shi, Ibaraki-ken, Japan), which is a collection of microorganisms.

The acronym "CCUG" refers to the Culture Collection of the University of Göteborg, Sweden, which is a collection of microorganisms.

The terms "water saturation" and "oil saturation" refer to, respectively, the percentage of void volume occupied by water or oil.

"Void volume" is a measure of empty space in a material that is accessible by fluids flowing through that material.

Altering Hydrocarbon-Surface Interface

Provided herein are methods for oil recovery and remediation which rely on altering the wettability of hydrocarbon-coated surfaces. Through altering wettability, the characteristics of the interface between hydrocarbons and a hydrocarbon-coated surface are changed, thereby releasing the hydrocarbons from the surface. For example, this alteration may result in the surface having a preference for binding water as opposed to oil thereby providing for recovery of the oil more readily. Changes in the wettability may be monitored by measuring changes in the contact angle between a hydrocarbon and the surface to which it is adhered. For example, an increase in the contact angle is an indication of a reduction in the surface energy required to bind the oil to the surface (see Example 8). Thus, an aspect of the present invention is the discovery that contact between *Shewanella* sp. or biomolecules produced by *Shewanella* sp., and hydrocarbon coated surfaces produces alterations in the wettability properties of the hydrocarbon coated surface such that the surface energy binding the hydrocarbon to the surface is decreased, (as measured by an increase in the contact angle) resulting in the subsequent release of oil.

Hydrocarbon-coated surfaces may be any hard surface (including one or more particles) that is coated or contaminated with hydrocarbons with at least 10% areal coverage by said hydrocarbons. The hydrocarbons may be adhered to said surfaces. Hydrocarbon-coated surfaces may be in subsurface formations, for example in oil reservoirs, and may include rock, soil, brine, sand, clays, shale, and mixtures thereof. In addition, hydrocarbon-coated surfaces may include materials that are not subsurface including rock, clay, soil, sediments, sand, sludge, harbor dredge spoils, sediments, refinery wastes, wastewater, sea water, and mixtures thereof. In addition, hydrocarbon-coated surfaces may include equipment such as pipelines, oil tanks and tankers, and other machinery that may be contaminated with hydrocarbons.

In the present methods, *Shewanella* sp. alter the wettability of hydrocarbon-coated surfaces. Alteration may be by contact with said microbes or by contact with extracellular molecules produced by said microbes, which may include one or more wetting agents. The *Shewanella* sp. under certain conditions undergo modifications in surface-bound or extracellular molecules. Modifications include changes in the composition and/or ratio of the molecules which include but are not limited to cytochromes, flavins, siderophores, membrane vesicles, glycoproteins, glycolipids, lipoproteins, fimbriae, extracellular polymeric substances, polysaccharides, monosaccharides, and lipopolysaccharides. These modifications, in turn, alter the water wettability of a hydrocarbon-coated surface contacted by the altered *Shewanella* microbe.

Conditions for growth that are suitable for *Shewanella* species to be used in the present methods are determined by the environment of the target hydrocarbon-coated surface, and the conditions for growth of said species in a given environment. Suitable conditions include those that are favorable to producing changes in the wettability of the hydrocarbon-coated surface. Such suitable conditions may include growth and medium compositions that are beneficial for the production and/or modification of surface bound or extracellular molecules, especially those molecules related to stress, oxygen limitation, redox, and/or electron transfer which may be wetting agents. Typical growth media compositions include enriched media containing diverse nutrient sources such as peptone, yeast extract, or casamino acids, for example. In some aspects the media may be a minimal media such as SL10 or simulated injection brine supplemented with an electron donor and electron acceptor. Examples of electron donors include, but are not limited to, lactate and/or acetate. Examples of electron acceptors include but are not limited to, nitrate, fumarate, pyruvate, ferric ion (Fe (III)) and/or manganese ion (Mn (IV)). Additional carbon sources may include but are not limited to yeast extract, peptone, pyruvate, glucose, succinate, formate, propionate, glutamate, glycine lysine, oil, and oil components. Oil components may be any of the many components that are present in crude oil. Cultures may be grown aerobically or anaerobically, and may be grown at a temperature that is similar to that of a target reservoir, typically about 30° C., or in the range of room temperature, +/−5° C. In addition, stress conditions may be suitable for growth of the present strains. Growth under stress inducing conditions includes, but is not limited to, switching growth from oxic to anoxic conditions, growth under population pressure or high density growth, switching electron acceptors, growth at low temperatures, and growth under osmotic stress (such as in high salt).

Cultures of *Shewanella* species may be used to contact hydrocarbon-coated surfaces in the present methods. Alternatively, cells may be removed from the cultures and the remaining medium, which has been conditioned by growth of *Shewanella* species cells, may be used to contact hydrocarbon-coated surfaces in the present methods. It is likely that conditioned medium contains biosurfactants or other biomolecules that act as wetting agents and contribute to the alterations in the wettability hydrocarbon coated surfaces.

Multiple cultures of different strains of *Shewanella* species may be used in the present methods. Alternatively, multiple strains may be grown in the same culture that is used in the present methods.

Treating Surface and Subsurface Formations

In the present methods, hydrocarbon-coated surfaces in surface and subsurface formations are contacted with a *Shewanella* species culture as a cell containing medium or a conditioned medium. Typically the subsurface formations will be contained within an oil well site, often comprising an injection well site and a production well site.

Application of the medium may include processes such as waterflooding, or the use of a fluid such as an aqueous solution or gas (such as $CO_2$) or a solvent or a polymer that is injected into the subsurface formation. Injection methods are common and well known in the art and any suitable method may be used. For example, *Nontechnical guide to petroleum geology, exploration, drilling, and production*, $2^{nd}$ edition. N. J. Hyne, PennWell Corp. Tulsa, Okla., USA, Freethey, G. W., Naftz, D. L., Rowland, R. C., & Davis, J. A. (2002); *Deep aquifer remediation tools*: Theory, design, and performance modeling, In: D. L. Naftz, S. J. Morrison, J. A. Davis, & C. C. Fuller (Eds.); and *Handbook of groundwater remediation using permeable reactive barriers* (pp. 133-161), Amsterdam: Academic Press.

Typically the injection site or well will communicate with the production well where oil is recovered. The application of the medium (either cell containing or cell free, conditioned) may follow any number of sequences for the effective production of oil and the various options will be readily apparent to the one skilled in the art of oil recovery.

For example treatment of the subsurface formations may include pumping or adding water containing *Shewanella* microbes via an injection well into an area comprising hydrocarbons ("treatment zone") and allowing that water to be produced along with the recovered hydrocarbon at the production well. Treatment may also involve pumping water with cell-free medium produced by conditioning with *Shewanella* into a treatment zone. Treatment of an oil reservoir also may include pumping water with medium down the producer well and into the formation and then back-flowing oil and water out of the producer well (huff and puff). Additionally reservoir treatment may also include inoculating an injector well that is in communication with one or more producer wells, and then subsequently adding an injection water that has been augmented with nutrients either continuously or periodically to promote growth of the *Shewanella* microbes, where oil is recovered at the producer well. Other treatments may include pumping water containing conditioned medium onto an environmental site comprising elements as a pile of oil sand or oil shale, collecting the water and released oil, and separating the oil from the water. The water may optionally be recycled back to be treated with *Shewanella* sp.

Hydrocarbon-coated surfaces may be contacted with cell containing *Shewanella* sp. medium or conditioned medium alone or with additional components. Additional components may be provided separately or in compositions with the medium. Components other than cultures may be injected, pumped, or otherwise applied to an area with hydrocarbon-coated surfaces prior to, together with, or following contact with cultures or conditioned medium.

Mixtures of the present one or more *Shewanella* species and at least one electron acceptors provide compositions for use in any oil recovery or clean-up site as listed above. Electron acceptors may include, but are not limited to, nitrate, fumarate, pyruvate, ferric ion (Fe (III)) or manganese ion (Mn (IV)). Mixtures of one or more electron acceptor may be used.

Additional components of the compositions may include at least one carbon sources, such as but not limited to, lactate, yeast extract, peptone, pyruvate, glucose, succinate, formate, acetate, propionate, glutamate, glycine lysine, oil, and oil components. Oil components may be any of the many components that are present in crude oil.

The compositions may include other agents or components such as one or more additional microorganisms, such as bacteria, yeast, or fungus. Particularly useful additional microorganisms are capable of growing on oil under denitrifying conditions. In some embodiments, the additional agents may be the microorganisms *Pseudomonas stutzeri* strain LH4:15 (ATCC No. PTA-8823), and/or *Thauera* sp AL9:8, (ATCC No. PTA-9497), which are described in commonly owned and co-pending US 20090263887 A1, and U.S. Pat. No. 7,708,065. Other agents may also include one or more chemical compounds that are not lethal to microorganisms, but are effective at degrading or partially degrading hydrocarbons and/or other contaminants.

Enhanced Oil Recovery from a Reservoir or Oil Well

Enhanced oil recovery in this context may include secondary or tertiary oil recovery of hydrocarbons from subsurface formations by techniques that alter the original properties of hydrocarbon-coated surface interface. Specifically, hydrocarbons that are adhered to surfaces within subsurface formations may be substantially liberated by contact with *Shewanella* sp. or biomolecules produced by these microorganisms. Typically oil is liberated on an order of about 5, 10, 15, 20, 25, 30, to about 35% of the areal coverage. These methods permit the release of oil that could not normally be recovered by waterflooding or other traditional oil recovery techniques.

Bioremediation.

In addition to applications in oil recovery the present *Shewanella* sp may be useful in effecting the remediation of environmental sites contaminated with hydrocarbons and other pollutants. Bioremediation strategies for hydrocarbons depend on their locations in the environment. Contamination by hydrocarbon spills can be costly to remediate and cause toxicity to environmental inhabitants. Use of microbial action as described here may provide cost-effective mechanisms for remediating hydrocarbon contamination especially under circumstances in which contamination results in hydrocarbon-coated surfaces. For example, use of *Shewanella* sp. and their surface active agents (such as wetting agents) help to increase wettability of soil and solubility of soil contaminants through reduction in surface and interfacial tensions. This action liberates the hydrocarbons from the surface of soils and renders them available for other remediating action, including degradation by other microbes. In this context bioremediation may be accomplished by a combination of microbes including *Shewanella* sp. in addition to oil-degrading microorganisms.

*Shewanella* Species

It has been discovered that the presence of *Shewanella* species, or materials or biomolecules produced by *Shewanella*, has the effect of altering the wettability of a hydrocarbon coated surface. Any and all members of the genus *Shewanella* have this utility.

*Shewanella* is a bacterial genus that has been established, in part through phylogenetic classification by rDNA and is fully described in the literature (see for example Fredrickson et al., *Towards Environmental Systems Biology Of Shewanella*, Nature Reviews Microbiology (2008), 6(8), 592-603; Hau et al., *Ecology And Biotechnology Of The Genus Shewanella*, Annual Review of Microbiology (2007), 61, 237-258).

It is within the scope of the present invention to classify relevant *Shewanella* on the basis of conserved regions contained in the 16S rDNA. Analysis of the 16 S rDNA from 50 different *Shewanella* strains revealed three conserved signature regions each having dominant and degenerate sequences listed respectively: 2 (SEQ ID NO:18, 19), 5, (SEQ ID NO:20, 21) and 8 (SEQ ID NO:22, 23) as shown in FIG. 18.

To identify the *Shewanella* signature sequences, 50 different 16S rDNA sequences of *Shewanella* strains that are available in the NCBI database were aligned. The sequences are from strains that have been classified as *Shewanella* in the International Journal of Systematic and Evolutionary Microbiology. The sequences were aligned using the MegAlign program of the LASERGENE bioinformatics computing suite (DNASTAR Inc., Madison, Wis.). Multiple alignment of the sequences was performed using the "Clustal method of alignment" (described by Higgins and Sharp, *CABIOS.* 5:151-153 (1989); Higgins, D. G. et al., *Comput. Appl. Biosci.,* 8:189-191 (1992)). For multiple alignments, the default values correspond to GAP PENALTY=10 and GAP LENGTH PENALTY=10. In addition to the *Shewanella* rDNA sequences, the alignment included 16S rDNA sequences of *E. coli* (SEQ ID NO:85), and of microbes closely related to *Shewanella: Alishewanella jeotgali*(SEQ ID NO:96), *Pseudoalteromonas rubra* (SEQ ID NO:97), and *Vibrio natriegenas* (SEQ ID NO:51). Through visual analysis of the 16S rDNA variable regions 2, 5, and 8, signature sequences for *Shewanella* species were identified and are given in FIG. 18.

In further analysis of the 16S rDNA sequences of 55 recognized species of *Shewanella* from the List of Prokaryotic names with Standing in Nomenclature (LPNSN), as described in Example 26 herein, an additional base variation was identified for *Shewanella* strains that is in position 23 of region 2. The sequence for region 2 with the new base variation of C at position 23 and degeneracy at other positions that are in SEQ ID NO:19 is SEQ ID NO:28, and the degenerate sequence for region 2 that includes this variation in position 23 by placing V at this position (V=A/C/G) is SEQ ID NO:25. Thus *Shewanella* sp. useful in the present invention are those that comprise within the 16s rDNA the dominant or degenerate signature sequences for each of regions 2, 5, and 8 as set forth in SEQ ID NOs:18-23, as well as those with SEQ ID NO:25 and 28 for region 2 instead of SEQ ID NO:18 or 19. Specifically, *Shewanella* sp. comprising 16S rDNA comprising SEQ ID NOs:21, 23, and 28 may be used in the present invention.

Specific strains of *Shewanella* are disclosed herein that are useful in the methods of the invention. One such strain is *Shewanella putrefaciens* strain LH4:18 which was isolated, identified, and deposited to the ATCC under the Budapest Treaty as #PTA-8822, as described in commonly owned and co-pending U.S. Pat. No. 7,776,795. Strain LH4:18 has the 16S rDNA sequence of SEQ ID NO:5.

Examples of additional *Shewanella* species that may be used include but are not limited to *Shewanella frigidimarina* (DSM 12253), *Shewanella pacifica* (DSM 15445), *Shewanella profunda* (DSM 15900), *Shewanella gelidimarina* (DSM 12621), and *Shewanella baltica* (DSM 9439). These strains may be purchased through the German Collection of Microorganisms and Cell Cultures (DSMZ). These and other strains that may be used have at least about 94%, 95%, 96%, 97%, 98%, or 99% identity to SEQ ID NO:5 of strain LH4:18.

Additionally useful strains are *Shewanella* strains EH60: 12, EH60:2, and EH60:10, which were identified herein and characterized with partial 16S rDNA sequences of SEQ ID NOs:15, 16, and 17, respectively. *Shewanella* species include microorganisms having a 16S rDNA sequence with at least about 95%, 96%, 97%, 98%, or 99% identity to any one or all of SEQ ID NOs:15-17.

In addition to the known *Shewanella* sp. described above, a newly identified *Shewanella* sp. which is useful in the present methods was disclosed in US Pat. Appl. Pub. #2011-0030956 A1. This new strain is identified as *Shewanella* sp. strain L3:3 which has been deposited with the ATCC under the Budapest Treaty as #PTA-10980. *Shewanella* sp. strain L3:3 was isolated from an injection water sample obtained from the Alaskan North Slope and has the 16S rDNA sequence of SEQ ID NO:3. Within the 16S rDNA sequence are signature sequences that were identified in variable regions 3 and 6 of prokaryote rDNA that have nucleotide sequences of SEQ ID NOs: 13 and 14, respectively. As shown in FIG. 14, the nucleotides at specific positions (with respect to the first nucleotide of SEQ ID NO:3) 438-40, 451, 454-57, 466-69, 471, 484-86 and 496 within SEQ ID NO:13 are different in strain L3:3 from the nucleotides present in the 16S rDNA of *Shewanella putrefaciens, Shewanella* sp. LH4:18 and *Shewanella algae*. As shown in FIG. 15, the nucleotides at specific positions (with respect to the first nucleotide of SEQ ID NO:3) 995-6, 1001-05, 1007, 1012, 1014, 1016-1018 and 1035 within SEQ ID NO:14 are also different in strain L3:3 from the nucleotides present in the 16S rDNA of *Shewanella putrefaciens, Shewanella* sp. LH4: 18 and *Shewanella algae*. *Shewanella* strains found herein to have the same nucleotides at all of these positions are *Shewanella* sp. C31 (SEQ ID:8), *Shewanella* sp. L-10 (SEQ ID:9), *Shewanella chilikensis* JC5T (SEQ ID:10), *Shewanella* sp. C16-M (SEQ ID:12), and a *Shewanella* clone identified as D00402024H07 (SEQ ID:11). While having the signature sequences of SEQ ID NOs:13 and 14, the present *Shewanella* species that are closely related to the newly identified strain L3:3 have at least about 97%, 98% or 99% sequence identity to the DNA sequences for 16S ribosomal RNA of SEQ ID NO:3. In addition, strains closely related to strain L3:3 have a Riboprint® pattern identifier of 212-824-S-4 as demonstrated in FIG. 16. This Riboprint® pattern was identified herein for *Shewanella* sp. strain L3:3.

Within the 16S rDNA sequence are signature sequences that were identified in variable regions 3 and 6 of prokaryote rDNA that have nucleotide sequences of SEQ ID NOs: 13 and 14, respectively. As shown in FIG. 14, the nucleotides at specific positions (with respect to the first nucleotide of SEQ ID NO:3) 438-40, 451, 454-57, 466-69, 471, 484-86 and 496 within SEQ ID NO:13 are different in strain L3:3 from the nucleotides present in the 16S rDNA of *Shewanella putrefaciens, Shewanella* sp. LH4:18 and *Shewanella algae*. As shown in FIG. 15, the nucleotides at specific positions (with respect to the first nucleotide of SEQ ID NO:3) 995-6, 1001-05, 1007, 1012, 1014, 1016-1018 and 1035 within SEQ ID NO:14 are also different in strain L3:3 from the nucleotides present in the 16S rDNA of *Shewanella putrefaciens, Shewanella* sp. LH4:18 and *Shewanella algae*. *Shewanella* strains found herein to have the same nucleotides at all of these positions are *Shewanella* sp. C31, *Shewanella* sp. L-10, *Shewanella chilikensis* JC5T, *Shewanella* sp. C16-M, and a *Shewanella* clone identified as D00402024H07. While having the signature sequences of SEQ ID NOs:13 and 14, the present *Shewanella* species that are closely related to the newly identified strain L3:3 have at least about 97%, 98% or 99% sequence identity to the DNA sequences for 16S ribosomal RNA of SEQ ID NO:3.

The present invention provides a newly identified strain of *Shewanella* which is useful in the present methods. This new strain is identified as *Shewanella algae* strain MPHPW-1 which was isolated, identified, and deposited to the ATCC under the Budapest Treaty as # PTA-11920. The new strain named MPHPW-1 was isolated from oil well production water collected from an oil reservoir near Wainwright, Alberta Canada. The 16S rDNA sequence of MPHPW-1 was determined to be SEQ ID NO:24.

Strain MPHPW-1 was identified as a *Shewanella* strain by using 16S rDNA sequence analysis consistent with the criteria set forth in the International Journal of Systematic and Evolutionary Microbiology (B. J. Tindall, R. Rosselló-Mora, H.-J. Busse, W. Ludwig and P. Kämpfer, *Int. J. Syst. Evol. Microbiol.* 60 (2010), pp. 249-266). A multiple sequence alignment was performed of the MPHPW-1 16S rDNA sequence and the 16S rDNA sequences of the type strains of 55 recognized species of *Shewanella* from the List of Prokaryotic names with Standing in Nomenclature (LPNSN), as well as a few additional representative strains that are listed in Table 13. This multiple sequence alignment showed that among all pairs of the aligned *Shewanella* type species sequences there was at least 90% identity with the MPHPW-1 sequence confirming that MPHPW-1 is a *Shewanella*.

Of the strains in this alignment, MPHPW-1 is most closely related to the the BrY strain that is classified as a *Shewanella algae* (Venkateswaran, K, et al. International Journal of Systematic Bacteriology (1999) pp. 705-724). This relationship is shown in the phylogenetic tree diagram in FIG. 24, which is described in Example 26 herein. Based on this relationship, the MPHPW-1 strain was identified as *Shewanella algae* MPHPW-1.

To further characterize strain MPHPW-1, the MPHPW-1 16S rDNA sequence was aligned with all sequences retrieved in a BLAST search having at least as high percent identity as the BrY sequence. Each of these sequences had at least four position differences with the sequence of MPHPW-1, including nucleotide changes, insertions, and deletions. Thus, based on the 16S rDNA sequence analysis, MPHPW-1 was identified as a new strain of *Shewanella algae*. RiboPrint® analysis confirmed that the genomic sequences surrounding the rDNA operons in strain MPHPW-1 have different genomic structure than those of any strain represented in the RiboPrint® database (7525 patterns contained within DuPont Environmental Services and Qualicon libraries compiled from samples taken from DuPont as well as another 6950 patterns that DuPont Qualicon has supplied from standard identified organisms). *Shewanella algae* strain BrY, whose sequence identity to strain MPHPW-1 is 99.8%, has a RiboPrint® pattern that is similar to that of MPHPW-1, but its pattern is missing the 1 kb band (fragment). Therefore strain MPHPW-1's Ribo-Print® is a unique genomic identifier of the new *Shewanella* strain MPHPW-1.

EXAMPLES

The present invention is further defined in the following Examples. It should be understood that these Examples, while indicating preferred embodiments of the invention, are given by way of illustration only. From the above discussion and these Examples, one skilled in the art may ascertain the essential characteristics of this invention, and without departing from the spirit and scope thereof, may make various changes and modifications of the invention to adapt it to various usages and conditions.

Additional Abbreviations Used in the Examples

The meaning of abbreviations is as follows: "hr" means hour(s); "mL" or :ml" means milliliter; "° C." means degrees Celsius; "mg" means milligram(s); "mm" means millimeter; "g" means gram(s); "GC" means gas chromatography; "g of oil/g of total fluid" means gram of oil per gram of total fluid; "ppm" means part per million; "mM" means millimolar; "%" means percent; "CFU/mL" means colony forming unit per milliliter; "LB" means Luria broth medium; "min" means minute(s); "mL/min means milliliter per minute; "NIC" means non-inoculated control (negative controls in microbial culture experiments); "µg/L" means microgram per liter; "nM" means nanomolar; "µM" means micromolar, "PSIG" means pounds-force per square inch gauge.

General Methods

Growth of Microorganisms

Techniques for growth and maintenance of anaerobic cultures are described in "Isolation of Biotechnological Organisms from Nature", (Labeda, D. P. ed. 117-140, McGraw-Hill Publishers, 1990). When using nitrate as an electron acceptor in anaerobic cultures, growth is measured by nitrate depletion from the growth medium over time. Nitrate is utilized as one of the primary electron acceptors under the growth conditions used herein. The reduction of nitrate to nitrogen has been previously described (Moreno-Vivian, C., et al., J. Bacteriol., 181, 6573-6584, 1999). In some cases nitrate reduction processes lead to nitrite accumulation, which is subsequently further reduced to nitrogen. Accumulation of nitrite is therefore also considered evidence for active growth and metabolism by microorganisms.
Determination of Viable Cell Titer (Most Probable Number: MPN)

In order to determine viable cell titer, samples from cultures or sand packs were diluted by 1:10 serial dilution in 8 rows per sample of a 96 well plate using standard Miller's Luria Broth or Luria Broth with 3.5% NaCl added. Titration was done using an automated Biomek200 robotic pipettor. Growth was determined by visual turbidity and recorded for each of 8 rows. The most probable number algorithm of Cochran (Biometrics (1950) 6:105-116) was used to determine the viable cells/ml and the 95% confidence limits for this number in the original sample.

The serial dilution method plating was used to determine the bacterial titer of such cultures. A series of 1:10 dilutions of such samples was plated and the resulting colonies were counted. The number of colonies on a plate was then multiplied by the dilution factor (the number of times that the 1:10 dilution was done) for that plate to obtain the bacterial count in the original sample as CFU/mL.

Ion Chromatography

An ICS2000 chromatography unit (Dionex, Banockburn, Ill.) was used to quantitate nitrate and nitrite ions in growth medium. Ion exchange was accomplished on an AS15 anion exchange column using a gradient of 2 to 50 mM potassium hydroxide. Standard curves were generated and used for calibrating nitrate and nitrite concentrations.

Genomic DNA Extractions from Bacterial Cultures

To extract genomic DNA from liquid bacterial cultures, cells were harvested by centrifugation (10,000 rpm, at room temperature) and resuspended in lysis buffer (100 mM Tris-HCL, 50 mM NaCl, 50 mM EDTA, pH8.0) followed by agitation using a Vortex mixer. Reagents were then added to a final concentration of 2.0 mg/mL lysozyme, 10 mg/mL SDS, and 10 mg/mL Sarkosyl to lyse the cells. After further mixing with a Vortex mixer, 0.1 mg/mL RNAse and 0.1 mg/mL Proteinase K were added to remove RNA and protein contaminants, and the samples were incubated at 37° C. for 1.0-2.0 hr. Post incubation, the samples were extracted twice with an equal volume of a phenol:chloroform:isoamyl alcohol (25:24:1, v/v/v) and once with chloroform:isoamyl alcohol (24:1). One-tenth volume of 5.0 M NaCl and two volumes of 100% ethanol were added to the aqueous layer, and mixed. The tubes were frozen at −20° C. overnight and then centrifuged at 15,000×g for 30 min at room temperature to pellet chromosomal DNA. The pellets were washed once with 70% ethanol, centrifuged at 15,000×g for 10 min, dried, resuspended in 100 µL of de-ionized water and stored at −20° C. An aliquot of the extracted DNA was visualized on an agarose gel to ascertain the quantity and quality of the extracted DNA.

Direct Colony rDNA Sequence Analysis

Genomic DNA from bacterial colonies was isolated by diluting bacterial colonies in 50 µL of water or Tris-HCL buffer pH7-8. Diluted colony DNAs were amplified with Phi 29 DNA polymerase prior to sequencing (GenomiPHI Amplification Kit GE Life Sciences, New Brunswick, N.J.). An aliquot (1.0 µL) of a diluted colony was added to 9.0 µL of the Lysis Reagent (from the GenomiPHI Amplification Kit) and heated to 95° C. for 3 min followed by immediate cooling to 4° C. 9.0 µL of Enzyme Buffer and 1.0 µL of Phi 29 enzyme were added to each lysed sample followed by incubation at 30° C. for 18 hr. The polymerase was inactivated by heating to 65° C. for 10 min followed by cooling to 4° C.

DNA sequencing reactions were set up as follows: 8.0 µL of GenomiPHI amplified sample were added to 8.0 µL of BigDye v3.1 Sequencing reagent (Applied Biosystems, Foster City, Calif.) followed by 3.0 µL of 10 µM primers SEQ ID NO: 1 in combination with SEQ ID NO: 2 (prepared by Sigma Genosys, Woodlands, Tex.), 4.0 µL of 5× BigDye Dilution buffer (Applied Biosystems) and 17 µL Molecular Biology Grade water (Mediatech, Inc., Herndon, Va.). Sequencing reactions were heated for 3 min at 96° C. followed by 200 thermocycles of (95° C. for 30 sec; 55° C. for 20 sec; 60° C. for 2 min) and stored at 4° C. Unincorporated fluorescently labeled ddNTPs were removed using Edge Biosystems (Gaithersburg, Md.) clean-up plates. Amplified reactions were pipetted into wells of a pre-spun 96 well clean up plate. The plate was centrifuged for 5 min at 5,000×g in a Sorvall RT-7 (Sorvall, Newtown, Conn.) at 25° C. The cleaned up reactions were placed directly onto an Applied Biosystems 3730 DNA sequencer and sequenced with automatic base-calling. Each of the assembled rDNA sequences was compared to the NCBI rDNA database (~260,000 rDNA sequences) using the BLAST algorithm (Altschul et al., supra). The primary hit was used as an identifier of the most closely related known species identification. The initial screen using the rDNA colony direct sequencing reduced the number of colonies to be carried through further screening by 20 fold.

Automated Ribotyping

Automated ribotyping was used for identification of selected strains with similar 16S rDNA sequence phylogenetic characteristics (Webster, John A, 1988. U.S. Pat. No. 4,717,653; Bruce, J. L., Food Techno., (1996), 50: 77-81; and Sethi, M. R., Am. Lab. (1997), 5: 31-35). Ribotyping was performed as recommended by the manufacturer (DuPont Qualicon Inc., Wilmington, Del.). For these analyses, one fresh colony was picked, resuspended in the sample buffer and added to the processing module for the heat treatment step at 80° C. for 10 min to inhibit endogenous DNA-degrading enzymes. The temperature was then reduced and lytic enzymes lysostaphin and N-acetyl-muramidase, provided by the manufacturer, were added to the sample. The sample carrier was then loaded onto the Riboprinter® system with other commercial reagents. Restriction enzyme digestion using EcoRI enzyme, gel electrophoresis and blotting steps were completely automated. Briefly, bacterial DNA was digested with the EcoRI restriction enzyme and loaded onto an agarose gel, restriction fragments were separated by electrophoresis and then transferred to a nylon membrane. After a denaturation step, the nucleic acids were hybridized with a sulfonated DNA probe containing the genes for the small and large rRNA subunits of $E.$ $coli$, the 5S, 16S, and 23S ribosomal rRNAs. The hybridized labeled-probe was detected by capturing light emission from a chemiluminescent substrate with a charge-coupled device camera. The output consisted of a densitometry finger scan depicting the specific distribution of the EcoRI restriction fragments containing the genomic rDNA sequences and their molecular weights, which are particular to the genomic DNA sequence of a specific strain independent of the 16S rDNA sequence.

Measuring the Potential for Microbes to Release Oil from Sand Particles

In order to screen test cultures for the ability to release oil from a nonporous silica medium, a microtiter plate assay to measure the ability of the microbes to release oil/sand from oil-saturated North Slope sand was developed. The assay is referred to as the LOOS test (Less Oil On Sand). Autoclaved North Slope sand was dried under vacuum at 160° C. for 48 hr. Twenty grams of the dried sand was then mixed with 5 mL of autoclaved, degassed crude oil. The oil-coated sand was then allowed to age anaerobically at room temperature, in an anaerobic chamber, for at least a week. Microtiter plate assays were set up and analyzed in an anaerobic chamber. Specifically, 2 mL of test cultures were added into the wells of a 12-well microtiter plate (Falcon Multiwell 12 well plates, #353225, Becton Dickinson, Franklin Lakes, N.J.). The control wells contained 2 mL of the medium alone. Approximately 40 mg of oil-coated sand was then added to the center of each well. Samples were then monitored over time for release and accumulation of "free" sand that collected in the bottom of the wells. Approximate diameters (in millimeters) of the accumulated total sand released were measured. A score of 2 mm and above indicates the microbes' potential to release oil from the nonporous silica medium.

Gas Chromatography for Determining Residual Oil on Sand

A gas chromatography (GC) method was developed to analyze the sand from sandpacks for residual oil. An empirical relationship was determined based on the North Slope sand and the intrinsic pore volume of packed sand, e.g., for 240 g of packed sand there is a pore volume of about 64 mL. Weights of the individual sand samples were obtained and the oil on the sand was extracted with a known amount of toluene. A sample of this toluene with extracted oil was then analyzed by GC. A calibration curve was generated and used to determine the amount of oil in toluene on a weight percent basis. This was then multiplied by the total amount of toluene used to extract the oil resulting in the total amount of oil on the sand. This value was then divided by the total sample weight to yield the percent of oil with respect to the total sample weight. The weight percent of oil of the sample was multiplied by the ratio of the empirically derived characteristic of packed North Slope sand (total weight of sample after being flooded with brine divided by total sand weight, 1.27). This relationship was equal to the amount of oil on dry sand. This value was then multiplied by the ratio of the weight of North Slope sand to the weight of fluid trapped in the pore space of the sand, 3.75. This resulting value was the residual oil left on the sand in units of g of oil/g of total fluid in the pore space.

Growth Medium and Growth Protocol

PPGAS medium was used in the following Examples unless stated otherwise. The medium contained: 1.6 mM $MgSO_4$, 20 mM KCl, 20 mM $NH_4Cl$, 120 mM Tris base 0.5% glucose and 1')/0 Bacto peptone. The initial culture was grown aerobically in the medium at 25° C.

Sterile injection brine (SIB) contained: 198 mM NaCl, 1 mM $MgCl_2$, 1.8 mM $CaCl_2$, 1.2 mM KCl, 16 mM $NaHCO_3$, 0.05 mM $SrCl_2$, 0.13 mM $BaCl_2$, 0.14 mM LiCl) plus 1% peptone.

The SL10 medium had the following composition summarized in Table 2 below:

TABLE 2

Composition of the SL10 Medium

| Growth component | Final Concentration | Chemical Source |
|---|---|---|
| Nitrogen | 18.7 mM | $NH_4Cl$ |
| Phosphorus | 3.7 mM | $KH_2PO_4$ |
| Magnesium | 984 µM | $MgCl_2 \cdot 6H_2O$ |
| Calcium | 680 µM | $CaCL_2 \cdot 2H_2O$ |
| Sodium chloride | 172 mM | NaCl |
| Trace metals | 7.5 µM | $FeCl_2 \cdot 4H_2O$ |
| | 12 nM | $CuCl_2 \cdot 2H_2O$ |
| | 500 nM | $MnCL_2 \cdot 4H_2O$ |
| | 800 nM | $CoCl_2 \cdot 6H_2O$ |
| | 500 nM | $ZnCl_2$ |
| | 97 nM | $H_3BO_3$ |
| | 149 nM | $Na_2MoO_4 \cdot 2H_2O$ |
| | 100 nM | $NiCl_2 \cdot 6H_2O$ |
| Selenium-tungstate | 22.8 nM | $Na_2SeO_3 \cdot 5H_2O$ |
| | 24.3 nM | $Na_2WO_4 \cdot 2H_2O$ |
| pH buffer/Bicarbonate | 29.7 mM | $NaHCO_3$ |
| Vitamins | 100 µg/L | vitamin B12 |
| | 80 µg/L | p-aminobenzoic acid |
| | 20 µg/L | D(+)-Biotin |
| | 200 µg/L | nicotinic acid |
| | 100 µg/L | calcium pantothenate |
| | 300 µg/L | pyridoxine hydrochloride |
| | 200 µg/L | thiamine-HCL$\cdot 2H_2O$ |
| | 50 µg/L | Alpha-lipoic acid |

The pH of the medium was adjusted to between 7.4-7.8.

Example 1

Comparison of the Ability of Early and Late Stage Microbial Cultures to Release Oil from Sand Particles To determine whether late stationary phase growth enhances oil release, the oil release activity of an anaerobic overnight culture of strain LH4:18 was compared to that of a one week old culture of the same strain. A culture was grown initially as described above in PPGAS medium. It was then moved into an anaerobic chamber, was supplemented with 500 ppm sodium lactate and 1000 ppm sodium nitrate, and divided in half. One half was used immediately in an anaerobic LOOS test, described in General Methods. The other half (Week1 culture) was aged (left for a week in the anaerobic chamber) and then the LOOS test was performed using this culture.

Figure 1:
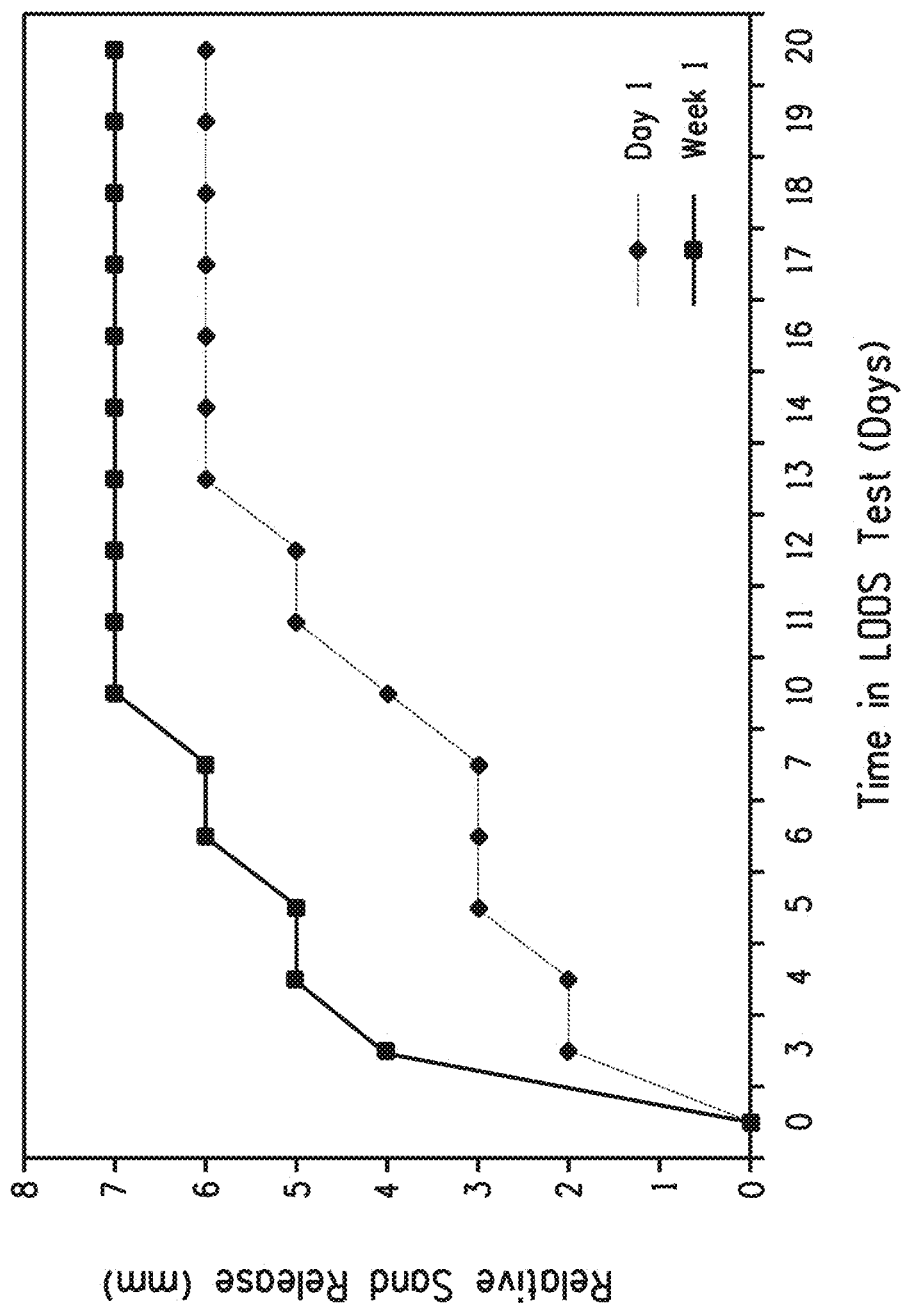

FIG. 1 shows the relative sand release by strain LH4:18 cultures over a period of three weeks. After about 6 days, a 6 mm zone of released sand was observed in the bottom of the wells for the week old (week 1) culture and a 3 mm zone was observed for the day-old sample (Day 1). Thus these results indicate that late stationary phase growth cultures may be more effective in expression of wetting agent molecules in that the rate of the sand/oil release was higher for the week old sample and continued to increase with time.

Example 2

Demonstration of Oil Release During Both Aerobic and Anaerobic Growth

To ascertain whether oil release occurs when the assay is performed aerobically versus anaerobically, and whether the addition of lactate and nitrate are beneficial, the following experiment was performed. A LOOS test was set up as described above. A culture of strain LH4:18 was grown aerobically overnight at 25° C. in the PPGAS medium. It was then divided in half. One half was supplemented with 1000 ppm sodium lactate and 2000 ppm sodium nitrate. The other half received no further supplements. Each of these cultures was then divided into an aerobic set and an anaerobic set. LOOS tests were set up to compare the samples. PPGAS medium alone samples, with and without the respective supplements, were used as controls.

Figure 2:
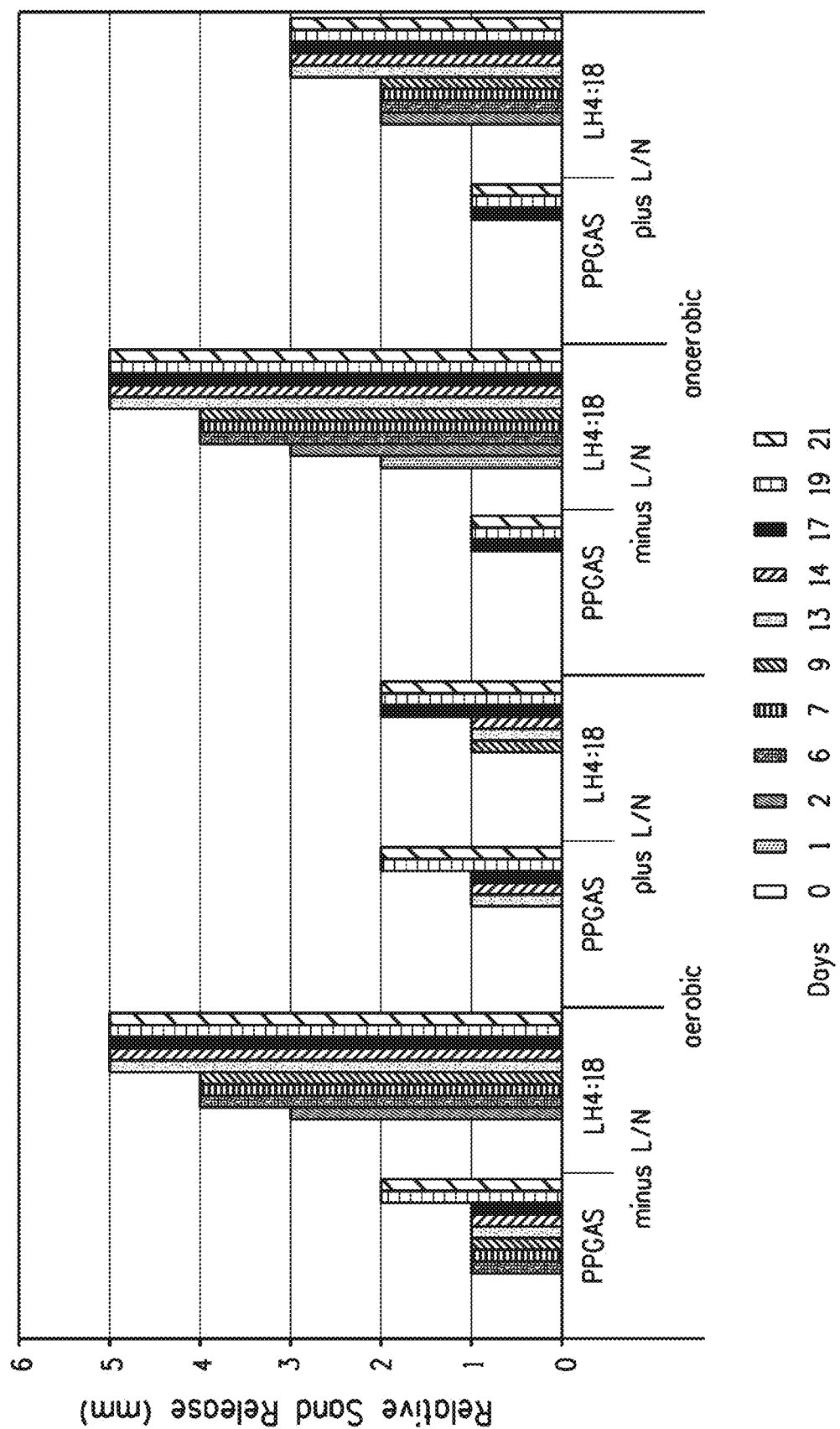

The results showed that the sand/oil release was relatively the same irrespective of whether the assay was performed aerobically or anaerobically (FIG. 2). Interestingly, the addition of lactate and nitrate had a detrimental effect on both aerobic and anaerobic cultures. It should be noted, however, that even with the aerobic cultures, oxygen could still be limiting due to the high cell density.

Example 3

Comparison of Electron Acceptors and their Effect on Oil Release by Strain LH4:18

A survey of the literature shows that fumarate may act as an efficient terminal electron acceptor (Morris, C. J., et al., Biochem. J., 302: 587-593, 1994). In addition, in *Shewanella* species, certain cell surface and respiratory molecules are more abundant in cells grown with fumarate, rather than nitrate or iron citrate, as the terminal electron acceptor (Morris et al., supra). In Example 2, it was demonstrated that nitrate addition was detrimental in oil/sand release. Fumarate was therefore tested as an acceptable and possibly more advantageous replacement in this assay.

A frozen stock culture of strain LH4:18 was diluted 1:100 in SIB plus 1% peptone and placed into an anaerobic chamber. The culture was then split and sodium nitrate (2000 ppm), both sodium lactate (1000 ppm) and sodium nitrate (2000 ppm), sodium fumarate (2000 ppm), or both sodium lactate and sodium fumarate supplements were added to different samples. The control sample contained no additional supplements. Samples were grown anaerobically for 3 days. On the second day, samples were fed again with their respective supplements. MPNs were monitored at Day 1 and again after 3 days of anaerobic growth. On Day 3, a LOOS test was set up and sand/oil release was compared across all samples over time.

Figure 3:
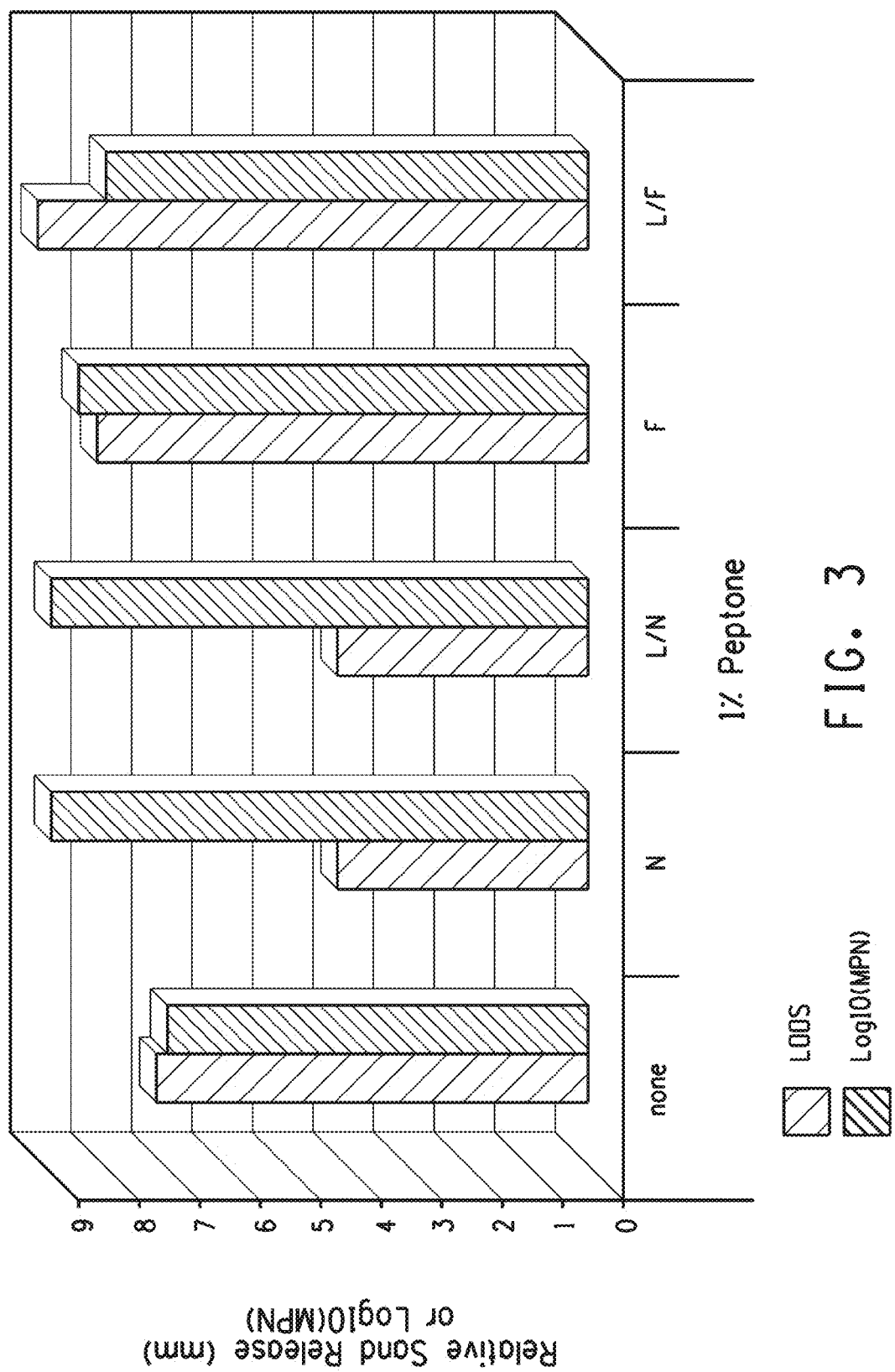

FIG. 3 shows a comparison of CFU/mL, expressed as Log 10 (MPN), on the day of the LOOS test set up (Day 3) and the relative sand release for each sample. The results show that even though growth was relatively the same across all conditions, the sand/oil release was better for samples containing fumarate instead of nitrate as the terminal electron acceptor.

Example 4

Demonstration of the Effect of Various Media Formulations on Oil Release by Strain LH4:18

For certain bacterial species, glucose is necessary for the expression of some surface molecules and surfactants. To determine whether glucose can improve oil release using strain LH4:18, a LOOS test with this strain grown aerobically overnight in PPGAS medium with and without glucose was performed. The samples were then placed into an anaerobic chamber and the LOOS test was performed anaerobically as described above.

Figure 4:
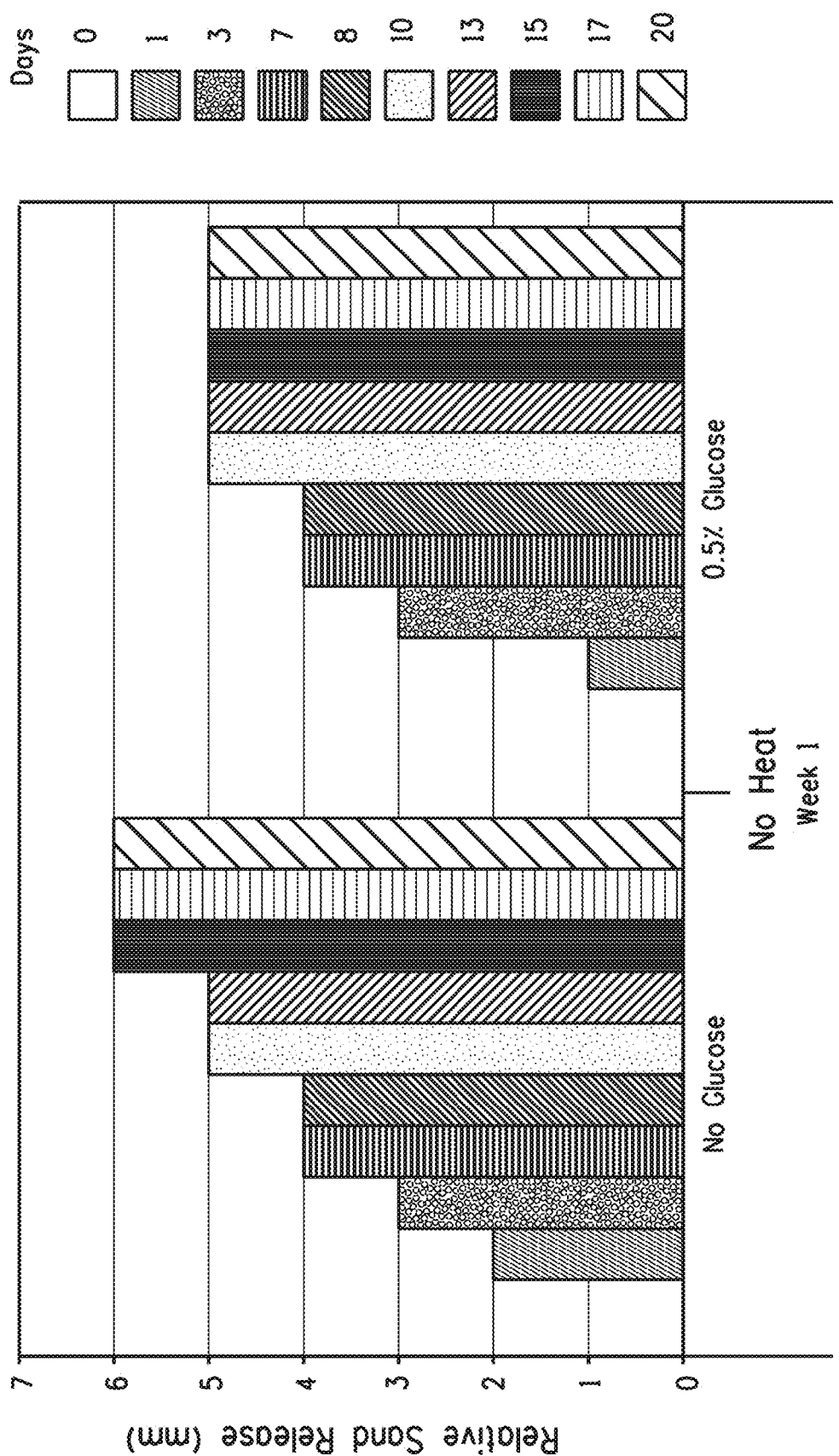

FIG. 4 shows that the sand/oil release response was relatively the same whether glucose was present or not In order to determine if the effect of strain LH4:18 on oil release was limited to a rich medium, the LOOS test response was measured using different media. Media tested were PPGAS, LB, and supplemented simulated injection brine (SIB). SIB was supplemented with 1% peptone and either $MgSO_4$ and KCl, $NH_4CL$, or Tris. Cultures of strain LH4:18 were grown aerobically overnight. Samples were then placed into an anaerobic chamber and the LOOS test was performed anaerobically.

Figure 5:
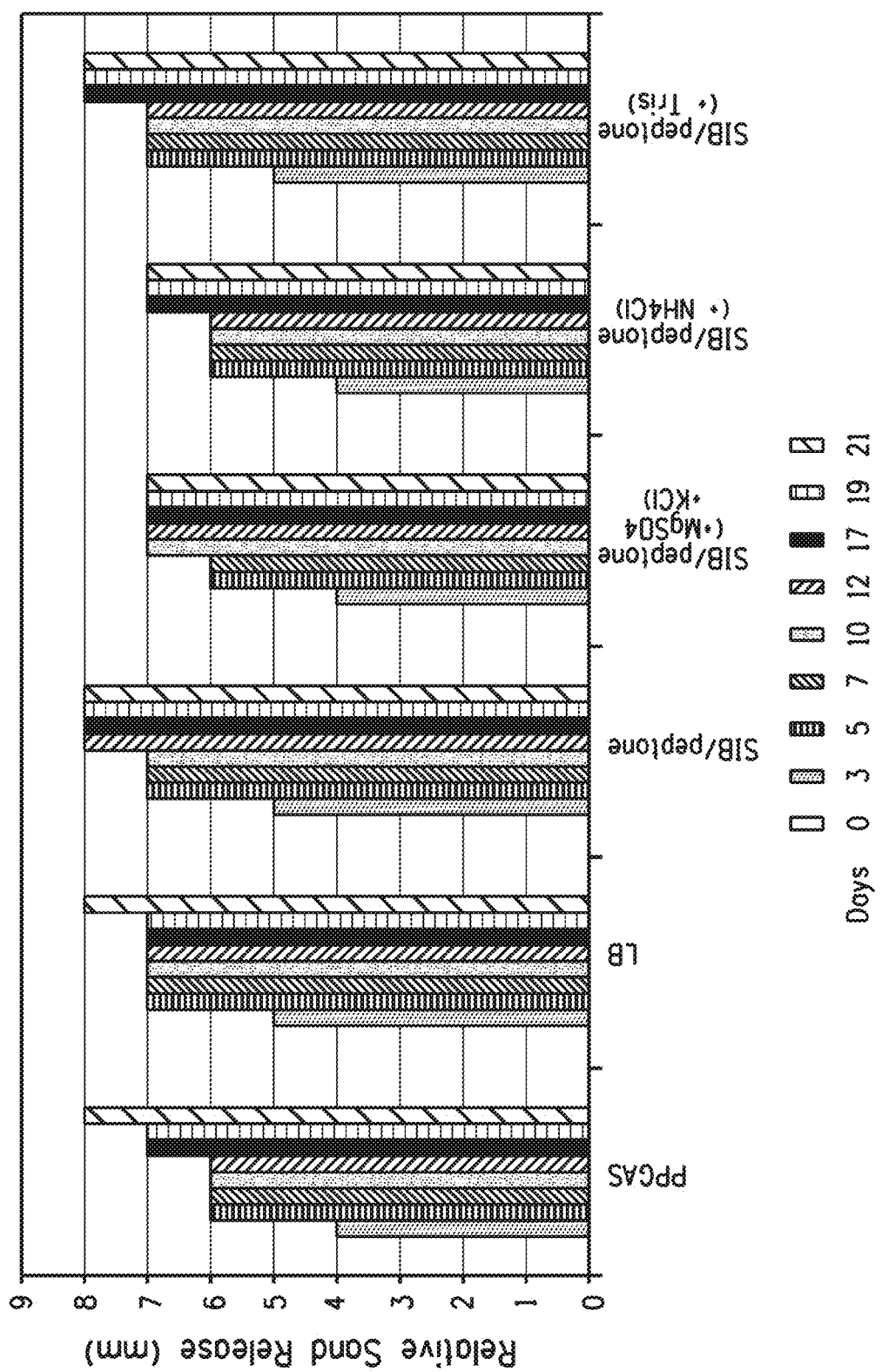

The simulated injection brine with 1')/0 peptone added worked as well as the other rich medium formulations as shown in FIG. 5. Strain LH4:18 grew relatively the same in each of the media. All cultures exhibited about the same sand/oil release response in the LOOS test.

To determine whether yeast extract worked as well as peptone in the simulated injection brine, these supplements were compared directly in a LOOS assay. Strain LH4:18 was grown aerobically overnight at 25° C. in SIB supplemented with 1')/0 peptone or 1')/0 yeast extract (YE). After 20 hr, the SIB/peptone culture had approximately 4.27E+09 CFU/mL and the SIB/YE culture contained about 9.33E+09 CFU/mL. The samples were then placed into the anaerobic chamber and the LOOS test was performed anaerobically.

Figure 6:
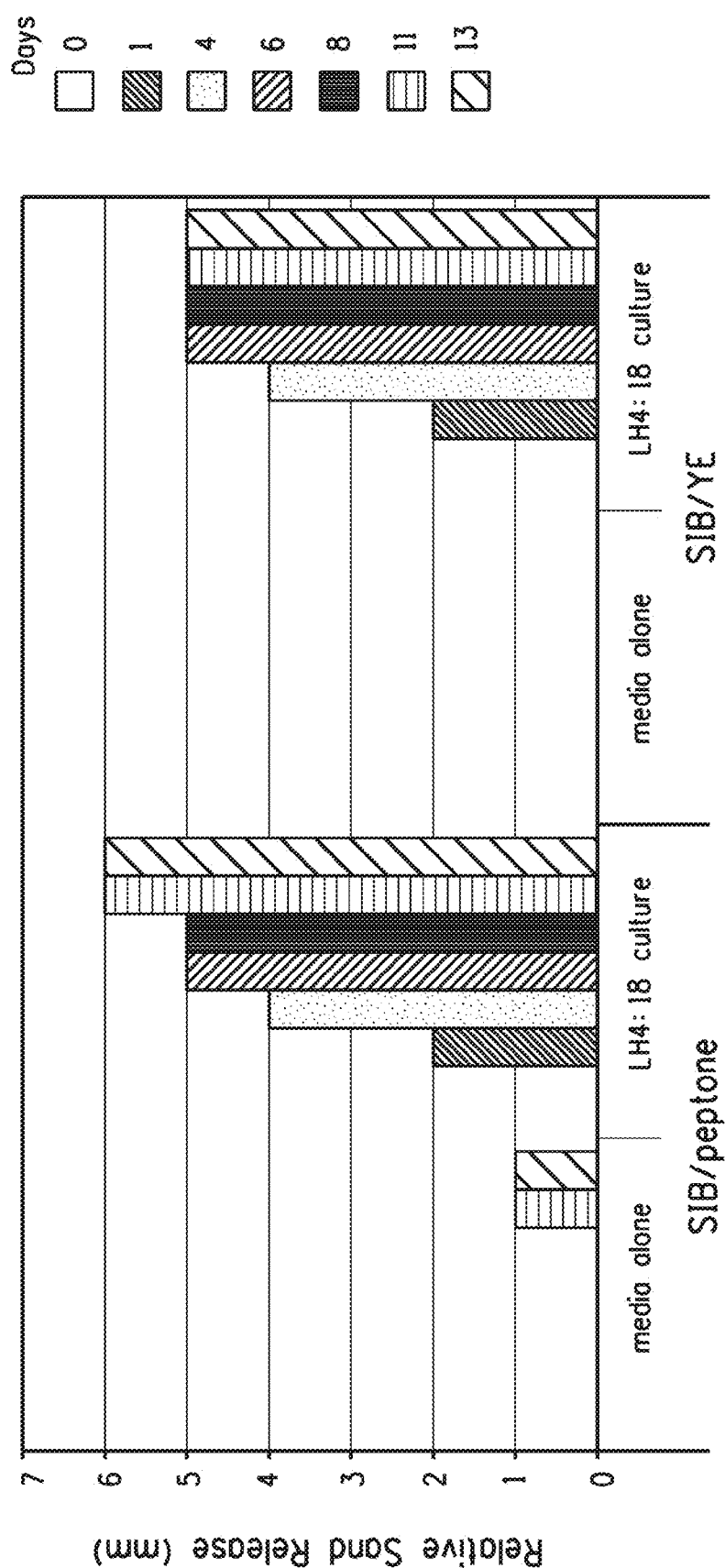

The data in FIG. 6 shows that YE may be substituted for peptone with no detrimental effect on the oil release response.

Example 5

Demonstration of Oil Release by Culture Supernatant

A number of microbial species release surfactants in their surrounding media. To determine whether a wetting agent from strain LH4:18 might be released into the surrounding medium, a LOOS test was performed using both a whole LH4:18 culture and also the supernatant alone of an LH4:18 culture. Strain LH4:18 was grown aerobically overnight at 25° C. in SIB supplemented with 1% peptone. After 20 hr, the culture contained approximately 1.49E+09 CFU/mL. The culture was then divided into two aliquots and one aliquot was centrifuged at 12000×g for 3 min to remove the cells. The supernatant was collected from the centrifuged sample and transferred into a new tube. Both samples were then placed into an anaerobic chamber and the LOOS test was performed anaerobically as described above.

Figure 7:
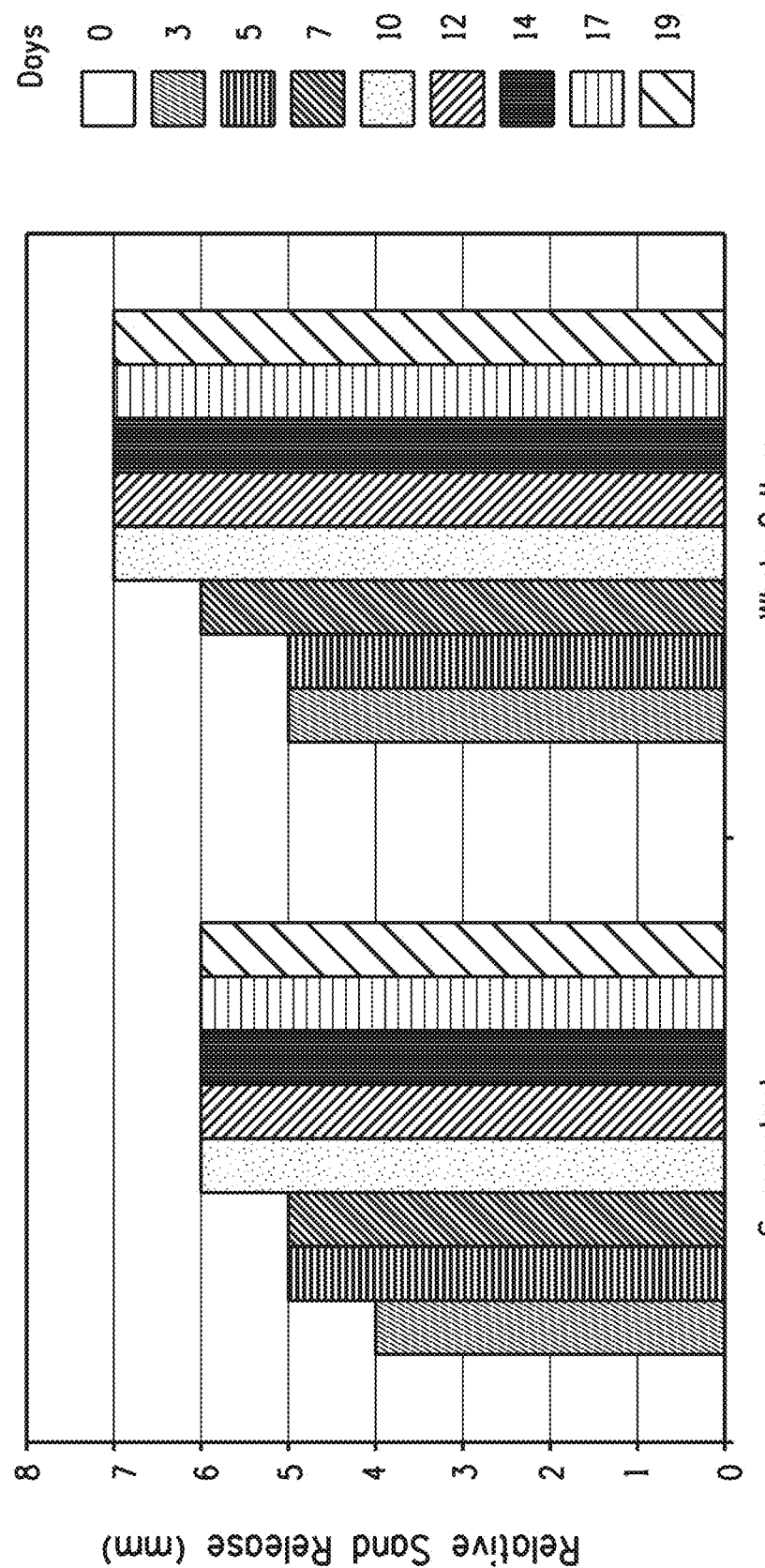
FIG. 7 shows sand/oil release using either cell free supernatants of the *Shewanella* strain (LH4:18) cultures or the whole culture. The experiment was performed for 19 days.

FIG. 7 shows that the supernatant alone released the sand/oil as effectively as the whole culture indicating that an agent affecting oil release was present in the medium.

Figure 8:
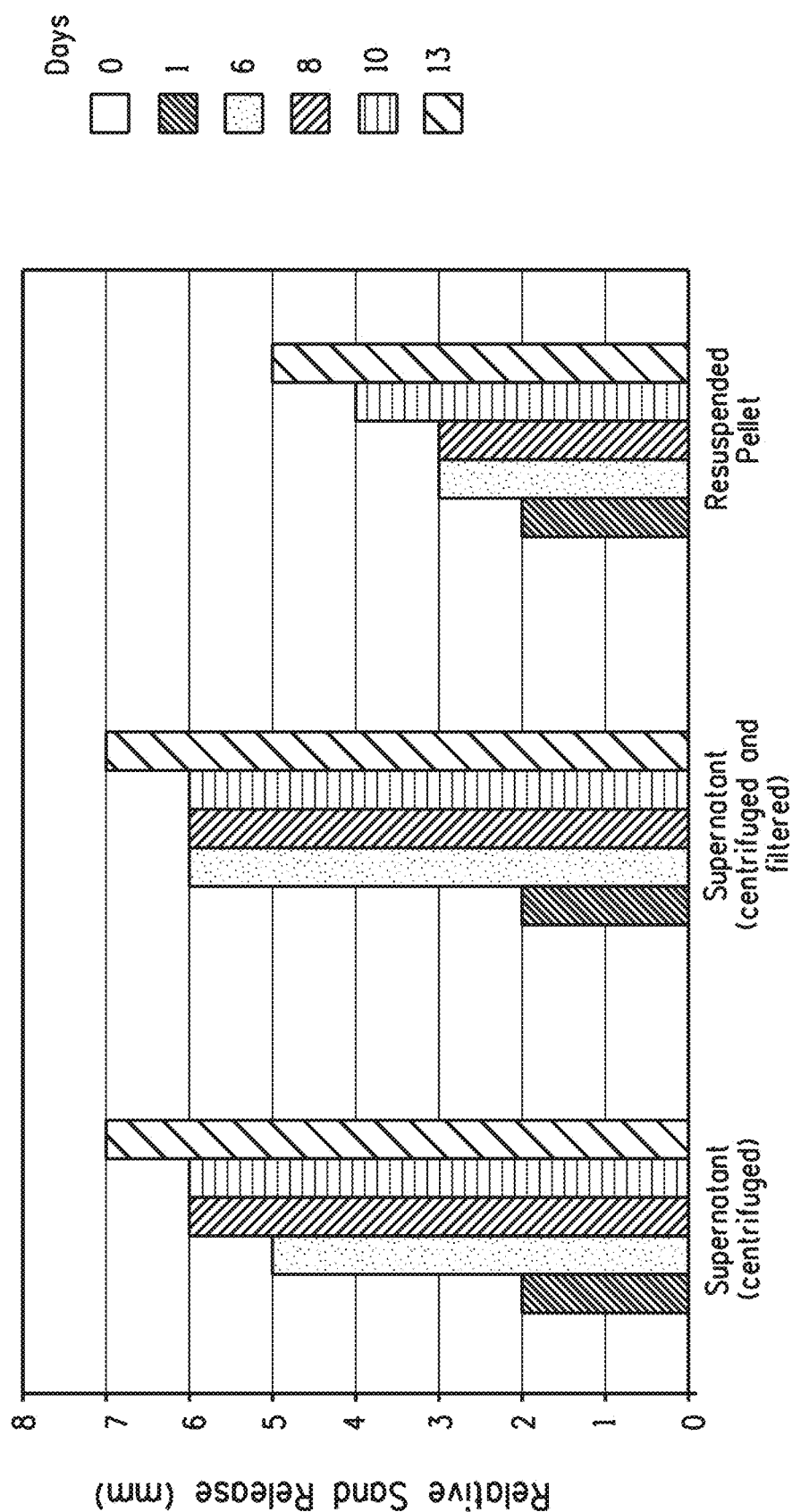
FIG. 8 depicts oil release over time with strain LH4:18 cell free supernatant (centrifuged compared with centrifuged and filtered) and strain LH4:18 cell pellet resuspended in fresh medium.

While the Example above showed that the supernatant alone released the sand/oil almost as effectively as the whole culture, an experiment was performed to determine if oil release ability remained surface bound. A culture of strain LH4:18 was grown overnight at 25° C. in SIB supplemented with 1% peptone. The culture was then divided into two aliquots and half was centrifuged at 12000×g for 3 min to remove the cells. The supernatant was collected from the centrifuged sample and transferred into a new tube. The pellet was then resuspended in fresh medium. The other half of the overnight culture was also centrifuged and the supernatant was filtered (Supor, 0.2 µm, Pall Corp., Ann Arbor, Mich.) to remove the microorganisms. The three samples (centrifuged supernatant, filtered supernatant, and resuspended cells) were then placed into the anaerobic chamber and the LOOS test was performed anaerobically. FIG. 8 shows that both supernatant samples released the oil/sand equally well, while oil release by the resuspended cells was less effective. However the resuspended cells were able to cause some oil release.

Example 6

Effect of Strain LH4:18 in Combination with Pseudomonas stutzeri Strain LH4:15 in Oil Release To determine whether the oil release effected by strain LH4:18 is compromised by the presence of other microbes, a LOOS test was performed on strain LH4:18 alone and also in the presence of Pseudomonas stutzeri LH4:15 (ATCC No. PTA-8823). Specifically, cultures of strains LH4:15 and LH4:18 were grown separately overnight in the PPGAS medium. Three LOOS tests were performed: 1) using strain LH4:15 alone; 2) using strain LH4:18 alone; and 3) using the combined cultures. The results shown in FIG. 9 indicate that the oil release ability of strain LH4:18 was not adversely affected by the presence of the other microorganism.

Example 7

Measuring the Effects of Other Shewanella Species in Oil Release

Additional Shewanella strains had been identified through anaerobic enrichments on oil production fluids, using SL10 medium and Fe(III) as the electron acceptor. Strains EH60:12, EH60:10, and EH60:2 were identified as Shewanella species by their 16S rDNA sequences (SEQ ID NOs:15, 16, and 17, respectively). These strains were grown aerobically overnight in the LB medium. A LOOS test was set up on 2 mL of the whole cultures as previously described.

The results in FIG. 10 demonstrate that other Shewanella species (e.g., strains EH60:12, EH60:2, and EH60:10) were also capable of releasing oil. Results were comparable to those of strain LH4:18.

Other known Shewanella species were purchased through the German Collection of Microorganisms and Cell Cultures (DSMZ): Shewanella frigidimarina (DSM 12253), S. pacifica (DSM 15445), S. profunda (DSM 15900), S. gelidimarina (DSM 12621), and S. baltica (DSM 9439). Cultures of each strain were grown aerobically overnight in SIB supplemented with 1% peptone. The cultures were then split and 1000 ppm sodium lactate and 2000 ppm sodium nitrate, or 1000 ppm sodium lactate and 3715 ppm sodium fumarate were added. A LOOS test was performed on 2 mL of the cultures as previously described. Samples were not adjusted for growth.

FIG. 11 shows that these known Shewanella species also released oil in the LOOS assay. As in Example 3, those samples grown in the presence of fumarate as the electron acceptor performed better than those grown in the presence of nitrate.

Example 8

Shewanella Increases the Contact Angle of Oil in Deep Sediment Sand

Strain LH4:18 was grown aerobically in PPGAS medium and added to a LOOS test as described above. After approximately two weeks, an aliquot of the sand was removed from the bottom of the strain LH4:18 well and was compared microscopically to oil coated sand from a medium alone control well. FIG. 12 shows photomicrographs for comparison. FIG. 12 A shows the untreated oil coated sand. As indicated by the lines drawn on the picture, the contact angle between the hydrocarbon and sand is low indicating that the surface energy encourages the hydrocarbon to coat the entire mineral grain. The right photomicrograph in FIG. 12B shows the effect of exposure to strain LH4:18. As indicated by the lines drawn on the picture, the contact angle has increased dramatically indicating a significant change in the surface energy between the hydrocarbon and the mineral, and showing substantial liberation of hydrocarbon from the surface of the sand particle. This is a visual demonstration of change in wettability.

Example 9

Measuring Oil Release from Sandpacks

Oil Release Sandpack or Core Flood Assay

The potential application of strain LH4:18 in MEOR treatment was evaluated using the sandpack technique. This was done with an in-house developed Teflon® shrink-wrapped sandpack apparatus. Using a 0.5 inches (1.27 cm) OD and 7 inches (17.78 cm) long Teflon® heat shrink tube, an aluminum inlet fitting with Viton® O-ring was attached to one end of the tube by heat with a heat gun. North Slope sand was added to the column which was vibrated with an engraver to pack down the sand and release trapped air. A second aluminum inlet fitting with Viton® O-ring was attached to the other end of the tube and sealed with heat a gun. The sandpack was then put in an oven at 275° C. for 7 min to evenly heat and shrink the wrap. The sandpack was removed and allowed to cool to room temperature. A second Teflon® heat shrink tube was installed over the original pack and heated in the oven as described above. After the column had cooled, a hose clamp was attached on the pack on the outer wrap over the O-ring and then tightened.

Four sandpack columns were flooded horizontally with three pore volumes of SIB1 low bicarbonate (same as SIB but with 1 mM bicarbonate) at 10 mL/min via a syringe pump and a 60 mL (Becton Dickinson, Franklin Lakes, N.J.) sterile plastic polypropylene syringe. All four sandpacks were then flooded with two pore volumes of anaerobic autoclaved crude oil at 0.5 mL/min to achieve irreducible water saturation. The crude oil was aged on the sand for three weeks before inoculating. For the inoculation culture, strain LH4:18 was grown aerobically overnight in PPGAS medium. The culture was then placed in an anaerobic environment where Na-Lactate was added to 1000 ppm and Na-Nitrate was added to 2000 ppm. This sample was anaerobically aged for 5 days before inoculating the sandpacks. Two columns were anaerobically inoculated with a sample of strain LH4:18 for one pore volume at 0.4 mL/hr. Two control sandpacks were flooded using anaerobic SIB1 low bicarbonate using the same inoculation procedure. The four sandpacks were then shut-in for incubation with the oil for five days. After the shut-in, the columns were produced by flushing with anaerobic sterile SIB low bicarbonate at 0.4 mL/hr for three pore volumes to prepare the production flood.

At the conclusion of the production flood, the 7 inches (17.78 cm) slim tubes were sacrificed into 5 one-inch sections labeled A-E. One inch was skipped at the beginning and at the exit of the slim tube to avoid edge effects during analysis. Sections A, C, and E were analyzed for residual oil saturation on the sand by the GC method described in General Methods.

The results in FIG. 13 show that average residual oil saturation in the uninoculated column was 22.5% whereas the residual oil saturation for strain LH4:18 inoculated columns was 16.1%, indicating that strain LH4:18 was able to reduce residual oil saturation by approximately 6.5%.

Example 10

Discovery of Oil Recovery Activity in Live Injection Water Sample

To screen enrichment cultures, environmental samples or isolated strains for the ability to release oil from a nonporous silica medium, a microtiter plate assay was developed to measure the ability of microbes to release oil/sand from oil-saturated North Slope sand. North Slope sand was autoclaved and then dried under vacuum at 160° C. for 48 hr and 20 g of this dried sand was then mixed with 5 mL of autoclaved, degassed crude oil obtained from Milne point, North Slope. The oil-coated sand was then allowed to adsorb to the sand and age anaerobically at room temperature for at least a week. Microtiter plate assays were set up in a Coy anaerobic chamber (Coy Laboratories Products, Inc., Grass Lake, Mich.). The assay is referred to as the LOOS test (Liberation of Oil Off Sand).

Water samples were obtained from production and injection well heads as mixed oil/water liquids in glass 1.0 L brown bottles, filled to the top, capped and sealed with tape to prevent gas leakage. Gas from inherent anaerobic processes sufficed to maintain anaerobic conditions during shipment. The bottles were shipped in large plastic coolers filled with ice blocks to the testing facilities within 48 hr of sampling.

A sample of non sterile (Live') injection water obtained from Alaskan North Slope was used in a LOOS test plus and minus *Shewanella putrefaciens* strain LH4:18 (ATCC No. PTA-8822) to determine the efficacy of the *Shewanella* LH4:18 surface active agent in a background microbial population simulated by the live injection water. Live water was included in the LOOS test as a control. A positive LOOS result was obtained for live injection +/−LH4:18 microbial treatments. The oil/sand release scores obtained from these LOOS tests are given in Table 3.

TABLE 3

Response of Live Injection Water vs. *Shewanella* LH4:18 in the Release of Oil from Sand in the LOOS Test

| Test Sample | Live Injection Water | LH4:18 | Nutrients[1] | Time in days |   |   |   |   |   |
|---|---|---|---|---|---|---|---|---|---|
|   |   |   |   | 0 | 3 | 7 | 10 | 18 | 26 |
|   |   |   |   | Response as diameter of sand released (mm) |   |   |   |   |   |
| L1 | + | − | none | 0 | 1 | 2 | 4 | 4 | 4 |
| L2 | + | − | N | 0 | 1 | 2 | 3 | 3 | 3 |
| L3 | + | − | L/N | 0 | 5 | 6 | 6 | 7 | 7 |
| L4 | + | − | F | 0 | 2 | 2 | 4 | 5 | 5 |
| L5 | + | − | L/N | 0 | 2 | 3 | 4 | 6 | 6 |
| L6 | + | + | none | 0 | 4 | 4 | 4 | 5 | 5 |
| L7 | + | + | N | 0 | 2 | 4 | 4 | 4 | 4 |
| L8 | + | + | L/N | 0 | 4 | 5 | 6 | 6 | 6 |
| L9 | + | + | F | 0 | 4 | 5 | 5 | 6 | 6 |
| L10 | + | + | L/N | 0 | 3 | 5 | 6 | 6 | 6 |

[1]N = Nitrate (2000 ppm); L/N = Lactate (1000 ppm) plus Nitrate (2000 ppm); F = Fumarate (2000 ppm)

The degree of oil release response is measured as the diameter of the sand released from oil. The data demonstrates that test sample L3 consisting of live injection water released oil faster than the other samples. This sample was not inoculated with *Shewanella* LH4:18. This test demonstrates that the live injection water contained an agent or agents that facilitated the release of oil from sand independent of *Shewanella* sp LH4:18.

Example 11

Isolation and Identification of *Shewanella* Species in Oil Reservoir Production Water Aliquots of the live injection water giving positive oil release results in the LOOS test were streaked on LB agar plates (Teknova, Hollister, Calif.) in order to isolate and identify those strain(s) present in live injection water capable of oil release. Representative colonies with unique morphologies were isolated from the live injection water test samples. Samples of these isolated colonies were screened by PCR amplification using direct colony rDNA analysis described in the General Methods using both the reverse PCR primer 1492r (SEQ ID NO:1) and forward PCR primer 8f (SEQ ID NO:2). The resultant rDNA sequence from each colony was aligned and matched with the GenBank sequence database for phylogenetic strain identification.

One isolate, named L3:3, was identified as having 16S rDNA homology to *Shewanella* sp C16-M. Both L3:3 and C16-M strains as well as four other reported *Shewanella* isolates (C31, L31, C13-M and JC5T) have 16S rDNA sequences that are similar to a newly proposed *Shewanella* species, *Sh. chilikensis* (K. Sucharita et al, (2009) *International Journal of Systematic and Evolutionary Microbiology* 59:3111-3115). The 16S rDNA sequence of L3:3 has 99.9% identity to three of the six rDNA gene sequences in the GenBank database that could be classified as *Shewanella chilikensis*: strain JC5T, strain C16-M, and sequence from a population study designated *Shewanella* clone D004024H07. *Shewanella chilikensis* JC5T was isolated from a lake mud environment, *Shewanella chilikensis* C16-M was isolated from a marine environment and *Shewanella* clone D004024H07 was isolated (by DuPont) from environmental samples taken from an Alaskan oil well (Pham, V. D, et al., Environ. Microbiol. 11:176-187 (2008)).

Strain L3:3 was identified to be *Shewanella* sp L3:3 and was further characterized by DNA sequence analysis to have signature sequences within *Shewanella* species rDNA sequences. Specifically, *Shewanella* sp L3:3 was found to have 16S rDNA sequence (SEQ ID NO: 3) and signature sequences within *Shewanella* 16S rRNA variable regions 3 and 6 that are defined in SEQ ID NO:13 (within the prokaryote 16S rRNA variable region 3) and SEQ ID NO: 14 (within the prokaryote 16S rRNA variable region 6). These signature sequence regions were discovered when the 16S rDNA sequence profile of *Shewanella* sp L3:3 was aligned with 42 published 16S rDNA sequences of *Shewanella* sp., which were pared down to the nine sequences (SEQ ID NO:4 through 12) in FIGS. 1 and 2 for demonstration of the variations. *Shewanella* sp L3:3 full 16S rDNA sequence (SEQ ID NO: 3) was used as the alignment anchor. FIG. 14 shows signature base variations that occur in L3:3 in the 16S rRNA variable region 3 and SEQ ID NO: 13 (bp coordinates 430 to 500) at specific coordinate positions: 438-40, 451, 454-57, 466-69, 471, 484-86 and 496 and are observed as signature in nature when compared across 16S rDNA of various *Shewanella* species. A similar observation was made for bacterial variable region 6 for sequences closely related to *Shewanella* sp L3:3, e.g., sequences similar to that defined by FIG. 15 and SEQ ID NO: 14 can be found in published sequences. Strain variations occur between base coordinates 990 and 1049, specifically at positions: 995-6, 1001-5, 1007, 1012, 1014, 1016-18 and 1035 as shown in FIG. 2.

In addition to strain L3:3, there are six *Shewanella* 16S rDNA-like sequences, which were found in sequence databases, that contain the diagnostic signature sequences within variable regions 3 and 6 that are similar to those defined by SEQ ID NO: 13 and SEQ ID NO: 14. This *Shewanella* group includes: uncultured bacterium clone D004024H07 (NCBI GenBank accession No. gb|EU721813|), *Shewanella* sp C16-M (gb|EU563338.1|), *Shewanella* sp. L-10 (gb|DQ164801.1|), *Shewanella* sp. C31 (gb|EU563345.1|) and *Shewanella* Sp. JC5T (sp.=*chilikensis*) (gb|FM210033.2|). *Shewanella* sp. C13-M (gb|EU563337.1|) does not have the position 471 nucleotide of the L3:3 diagnostic signature.

All strains were isolated from marine environment, oil fields or the bottom of a lagoon. None of these strains at the time of this invention were available from the ATCC or DSMZ public depositories to allow for Ribotyping® comparisons.

Example 12

Riboprint® Analysis of Strain L3:3

To further characterize *Shewanella* strain L3:3, preparations of this strain were analyzed by Riboprinter® and compared to 7525 patterns contained within DuPont Environmental Services and Qualicon libraries compiled from samples taken all over DuPont as well as another 6950 patterns that DuPont Qualicon has supplied from standard identified organisms. Based on the analyses of Riboprint® batch 052009 (FIG. 16), which provides a chromosomal fingerprint of the tested strains, it is clear that the Riboprint® pattern for strain L3:3 (sample 1) constitutes a Riboprint® which is unique when compared against the available DuPont Riboprint® Libraries and is designated as Ribogroup® identifier 212-824-S-4. It is probable for various strains to share single similar Riboprint® bands generated by hybridizing the labeled *E. coli* rDNA operon probe to each strain's genomic Eco RI fragments, but it is the overall Riboprint® banding pattern that constitutes identification of a given strain in a specific Riboprint® or Ribogroup® identifier.

Example 13

Enhanced Oil Release by Strain L3:3

The purified strain L3:3 was tested in a LOOS test designed to identify the strains' efficacy in altering the surface tension of oil coated silica particles. Strain L3:3 clearly contributed to oil release from sand as compared to the efficiency of oil release by *Shewanella* strain LH4:18 (ATCC No. PTA-8822) as shown in Table 4. Both strains exhibited release of oil/sand from oil coated particles. The ability to release oil/sand was similar when fumarate was the electron acceptor for both *Shewanella* strains tested (LH4:18 and L3:3), but L3:3 appeared to have greater release as compared to LH4:18 when nitrate was used as the electron acceptor.

TABLE 4

LOOS test: Oil/sand Release Response for Purified Cultures of *Shewanella* strains L3:3 and LH4:18

| | | | Time in Days | | | | | | |
|---|---|---|---|---|---|---|---|---|---|
| | | | 0 | 2 | 5 | 7 | 9 | 12 | 14 |
| Test | Strain | Electron receptor | Response as diameter of sand released (mm) | | | | | | |
| 1 | L3:3 | none | 0 | 4 | 6 | 7 | 7 | 8 | 8 |
| 2 | L3:3 | L/N[1] | 0 | 2 | 5 | 5 | 7 | 7 | 8 |
| 3 | L3:3 | L/F[2] | 0 | 3 | 7 | 7 | 7 | 8 | 8 |
| 4 | LH4:18 | none | 0 | 2 | 6 | 7 | 7 | 7 | 7 |
| 5 | LH4:18 | L/N | 0 | 0 | 3 | 3 | 3 | 4 | 4 |
| L6 | LH4:18 | L/F | 0 | 3 | 6 | 7 | 7 | 7 | 7 |

[1]lactate plus nitrate
[2]lactate plus fumarate

Example 14

Prophetic

Anaerobic Growth of Strain L3:3 on Oil as the Sole Carbon Source

To study growth of strain L3:3 as compared to *Shewanella* LH4:18, purified isolates are inoculated into 20 mL serum vials containing ~10 mL minimal salts medium (Table 5), 1.6 g/l sodium nitrate and 5.0 mL of autoclaved crude oil. The medium is deoxygenated by sparging the filled vials with a mixture of nitrogen and carbon dioxide followed by autoclaving. All manipulations of bacteria are done in an anaerobic chamber (Coy Laboratories Products, Inc., Grass Lake, Mich.). The cultures are incubated at ambient temperatures with moderate shaking (100 rpm) for several weeks to several months and monitored for nitrate, nitrite, visible turbidity and visible oil modifications. When the nitrate is depleted in any culture, sodium nitrate at 50 g/l is added to bring its concentration in the medium up to 0.4 g/l sodium nitrate.

TABLE 5

Minimal salts medium

| Growth component | Final concentration | Chemical Source |
|---|---|---|
| Nitrogen | 18.7 µM | $NH_4Cl$ |
| Phosphorus | 3.7 µM | $KH_2PO_4$ |
| Magnesium | 984 µM | $MgCl_2 \cdot 6H_2O$ |
| Calcium | 680 µM | $CaCL_2 \cdot 2H_2O$ |
| Sodium chloride | 172 mM | NaCl |
| Trace metals | 670 µM | nitrilotriacetic acid |
| | 15.1 µM | $FeCl_2 \cdot 4H_2O$ |
| | 1.2 µM | $CuCl_2 \cdot 2H_2O$ |
| | 5.1 µM | $MnCL_2 \cdot 4H_2O$ |
| | 12.6 µM | $CoCl_2 \cdot 6H_2O$ |
| | 7.3 µM | $ZnCl_2$ |
| | 1.6 µM | $H_3BO_3$ |
| | 0.4 µM | $Na_2MoO_4 \cdot 2H_2O$ |
| | 7.6 µM | $NiCl_2 \cdot 6H_2O$ |
| pH buffer (7.5 final) | 10 mM | Hepes |
| Selenium-tungstate | 22.8 nM | $Na_2SeO_3 \cdot 5H_2O$ |
| | 24.3 nM | $Na_2WO_4 \cdot 2H_2O$ |
| Bicarbonate | 23.8 nM | $NaHCO_3$ |
| vitamins | 100 µg/L | vitamin B12 |
| | 80 µg/L | p-aminobenzoic acid |
| | 20 µg/L | nicotinic acid |
| | 100 µg/L | calcium pantothenate |
| | 300 µg/L | pyridoxine hydrochloride |
| | 200 µg/L | thiamine-HCl·$2H_2O$ |
| | 50 µg/L | alpha-lipoic acid |
| Electron acceptor | 1.0. g/L | $NaNO_3$, $Na_2$ fumarate or Fe(III) Na EDTA |

The pH of the medium is adjusted to 7.5.

Strain L3:3 is expected to show growth via nitrate reduction and turbidity increase under denitrifying conditions as does LH4:18.

Example 15

Anaerobic Growth of Strain L3:3 on Oil as the Sole Carbon Source

Strain L3:3 and *Shewanella* strain LH4:18 were studied and compared in their abilities for anaerobic growth on oil as the sole carbon source using different electron acceptors. *Shewanella* strain LH4:18 has been show to grow using nitrate as the electron acceptor in commonly owned and co-pending US 2009-0260803 A1. *Shewanella* strains L3:3 and LH4:18 were inoculated into 20 mL serum vials containing ~10 mL SL10 minimal salts medium (Table 2), supplemented with one of the following electron acceptors: $NaNO_3$ (2000 ppm), $Na_2$ fumarate (3500 ppm), or Fe(III) Na EDTA (5000 ppm), and overlayed with 5.0 mL of autoclaved crude oil. LH4-18 samples were excluded from $NaNO_3$ test vials. The medium and crude oil had been deoxygenated by sparging these reagents with a mixture of carbon dioxide and nitrogen (20% and 80%, respectively) followed by autoclaving. All manipulations of bacteria were done in an anaerobic chamber (Coy Laboratories Products, Inc., Grass Lake, Mich.) (gas mixture: 5% hydrogen, 10% carbon dioxide and 85% nitrogen). Replicate test vials were set up per electron acceptor treatment by L3-3 inoculum. The cultures were incubated at ambient temperature for two weeks. Cell growth/titer of the test cultures were analyzed by MPNs.

L3:3 grew anaerobically in oil enrichments where crude oil was provided as the sole carbon source when either $NaNO_3$, $Na_2$ fumarate, or Fe (III) Na EDTA was provided as the electron acceptor. A table of growth results as analyzed by cell titers recorded as MPN log 10 is listed below in Table. 6. Strain L3:3 grew anaerobically 3 logs to cell titers of ~$10^5$-$10^7$ cells per mL from starting titers of ~$10^3$ cells per mL after two weeks incubation time. The change in cell numbers as a result of anaerobic growth on oil are listed as the $log_{10}$ of the MPN recorded for growth ±0.5 log. The growth of *Shewanella* strain L3:3 on the different electron acceptors was comparable to that of *Shewanella* strain LH4:18. Strain L3:3 grew anaerobically on oil using either $NaNO_3$, $Na_2$ fumarate, or Fe (III) Na EDTA as the electron acceptor. Cell titers are presented as the average of replicate test vials. *Shewanella* strain LH4:18 also grew on oil using fumarate or Fe (III) Na EDTA as electron acceptor. Its growth on oil using nitrate as an electron acceptor had been previously demonstrated in commonly owned and co-pending US 2009-0260803 A1. Both L3:3 and *Shewanella* strain LH4:18 grew ~3 logs to titers of ~$10^5$-$10^7$ cells per mL from starting titers of $10^3$ cells per mL anaerobically after two weeks incubation time.

TABLE 6

Anaerobic Growth on oil

| | Delta MPN log10 Electron Acceptor | | |
|---|---|---|---|
| Strain | $NaNO_3$ | $Na_2$ fumarate | Fe(III) Na EDTA |
| *Shewanella* strain L3:3 | 3.0 | 3.2 | 2.7 |
| *Shewanella* strain LH4:18 | n.t. | 4.7 | 2.2 |

.n.t. = not tested

Example 16

Determining the Temperature Limits for Growth of Strain L3:3

To determine the optimal temperature range as well as tolerances for *Shewanella putrefaciens* LH4:18 and *Shewanella* sp L3:3, these strains were grown at different test temperatures as given in Table 7.

Inoculums of *Shewanella* strains LH4:18 and L3:3 were grown overnight (16 to 18 hours) aerobically in LB medium with shaking at 30-35° C. These overnight cultures were grown to visible turbidity and relatively high levels of cell counts as measured by optical density. Aliquots from these starter cultures were then used to seed flasks of 10 mL sterile LB media that had been pre-incubated at a specific test temperature over night. Temperature test cultures were seeded at an optical density of approximately 0.1 as measured using a spectrophotometer and visible light, wavelength of 600 nm. This constituted a dilution of starter cultures approximating between a 1:50 and 1:100 dilution. Growth was then measured by tracking the turbidity or optical density of cultures over time. The resulting growth rates determined for strains LH4:18 and L3:3 obtained for the different test temperatures is expressed as doubling time, the time to double cell number, in units of hours; the smaller the number the faster the growth rate. At doubling times of <2 h these strains are presumed to compete successfully with background microbial populations in situ. Table 7 shows the results for growth rates at the recorded temperatures. Both *Shewanella* strains were shown to grow at a rate that would allow them to compete with microbial populations in situ for a relatively broad range of environmental temperatures.

TABLE 7

Average Recorded Doubling Time for selected temperatures ° C.

| | Doubling times (in hours) Temperature | | | | | | | | |
|---|---|---|---|---|---|---|---|---|---|
| strain | 10° C. | 16° C. | 22° C. | 27° C. | 30° C. | 32° C. | 35° C. | 37° C. | 41° C. |
| LH4:18 | 3.18 | 1.71 | 1.02 | 0.95 | 0.87 | 0.79* | 0.97 | 1.45 | No growth |
| L3:3 | n.t. | n.t. | n.t. | n.t. | n.t. | n.t. | n.t. | 0.98 | 0.63 | n.t. = not tested

Example 17

Anaerobic Growth of Strain L3:3 in the Presence of Oil Under Denitrifying Conditions To demonstrate the ability to grow anaerobically in the presence of oil under denitrifying conditions, an aliquot ($10^4$-$10^5$ cells) of each of *Shewanella* strains LH4:18 and L3:3 was inoculated under anaerobic conditions into 20 mL serum vials containing a 1:2 ratio of minimal salts medium supplemented with sodium lactate. The media formulation used was designed to promote growth and propagation of *Shewanella* strain L3:3 as well as the oil release mechanism within a reservoir environment. The medium composition for anaerobic growth was as follows: 10 mL minimal salts medium (Table 4 minimal salts medium), 1000 ppm sodium lactate and ~2000 ppm sodium nitrate with 5.0 mL of autoclaved crude oil. Strain LH4:18 acted as a positive control for anaerobic growth under denitrifying conditions containing surface active agent(s). Both the medium and crude oil were deoxygenated by sparging the filled vials with a mixture of nitrogen and carbon dioxide followed by autoclaving. All manipulations of bacteria were done in an anaerobic chamber (Coy Laboratories Products, Inc., Grass Lake, Mich.). These cultures were incubated at ambient temperatures for several days and monitored for nitrate and nitrite levels, for visible turbidity, and for visible changes to the integrity of the oil phase.

Table 8 shows the results of this growth study in the presence of oil. A pure culture of strain L3:3 showed growth through a reduction in lactate and nitrate levels when grown in the presence of oil. These strains also showed ~two to three logs growth as indicated by MPN data (Table 8).

TABLE 8

Nitrate Reduction as a Measure of Anaerobic Growth In the presence of Oil with lactate as the primary carbon source

| Bacteria isolate | 16S Genus ID | % nitrate reduction in oil | % Lactate reduction in oil | MPN log10 | time (days) |
|---|---|---|---|---|---|
| NIC[1] | n.a. | 8% | 0% | n.t.[2] | 14 |
| L3:3 | *Shewanella chilikensis*, JC5T | 58% | 44% | 7.0 | 14 |
| LH4:18 | *Shewanella putrefaciens* | 51% | 35% | 6.4 | 14 |

[1]NIC: Non inoculated control
[2]n.t.: not tested

Example 18

Identification of Electron Acceptors which Promote Oil Release by Strain L3:3

Different terminal electron acceptors (shown in Table 9) were tested in anaerobic growth of strain L3:3 to determine its ability to grow on a range of terminal electron acceptors including fumarate as well as various metal oxides. A mixed culture of LH4:18 and L3:3 was also tested with nitrate and fumarate. Anaerobic test growths were set up using minimal salts media (Table 4). 20 mL of minimal salts medium was supplemented with 1000 ppm sodium lactate, where 2000 ppm sodium nitrate was used as the electron acceptor control. The milli-equivalents of the following electron acceptors were each applied in their respective electron assay sample: fumarate, pyruvate, Fe (III) sodium EDTA, manganese dioxide, and vanadium dioxide. The minimal salts base medium, lactate, and terminal electron acceptor preparations were all deoxygenated by sparging with a mixture of nitrogen and carbon dioxide followed by autoclaving. All manipulations of bacteria were done in an anaerobic chamber (Coy Laboratories Products, Inc., Grass Lake, Mich.). These cultures were incubated at ambient temperature for several days and monitored for growth by increases in visible turbidity as measured by OD/MPN or by lactate depletion as measured by IC. Results are shown in Table 9.

TABLE 9

Relative Growth obtained for Strains L3:3 and LH4:18 on different electron acceptors using Lactate as supplemental Carbon Source

| | Nitrate | Fumarate | Iron (Fe(III)) EDTA | Manganese Dioxide | Vanadium Dioxide | Pyruvate |
|---|---|---|---|---|---|---|
| L3:3 | + | ++ | ++ | ++ | + | ++ |
| L3:3 + LH4:18 | + | ++ | n.t.[1] | n.t. | n.t. | n.t. |

[1]n.t. not tested

Example 19

Strain L3:3 Increases the Contact Angle of Oil on Deep Sediment Sand

Strain L3:3 was grown aerobically overnight in SIB (Synthetic Injection Brine; Table 10) plus 1% peptone. Samples were then added into an anaerobic LOOS test, described above, and were supplemented with 1000 ppm sodium lactate and 2000 ppm sodium nitrate. After approximately one week, an aliquot of the sand was removed from the bottom of the strain L3:3 well and was visualized microscopically. FIG. 17(A) is a typical image of untreated oil coated sand. As indicated, the contact angle (qCA) between the hydrocarbon and sand is low—the surface energy encourages the hydrocarbon to coat the entire mineral grain. FIG. 17(B) shows the effect of exposure of oil coated sand to strain L3:3. The contact angle (qCB) is increased dramatically indicating a significant change in the surface energy between the hydrocarbon and the mineral

TABLE 10

Components of SIB1 Minimal Medium (per Liter) and added electron acceptor and electron donor

| | |
|---|---|
| NaHCO3 | 0.138 g |
| CaCl2*6H$_2$O | 0.39 g |
| MgCl2*6H$_2$O | 0.220 g |
| KCl | 0.090 g |
| NaCl | 11.60 g |
| Trace metals (Table 4) | 1 mL |
| Vitamins (Table 4) | 1 mL |
| Na$_2$HPO$_4$ | 0.015 g (10 ppm PO$_4$) |
| NH$_4$Cl | 0.029 g (10 ppm NH$_4$) |
| Electron donor added | |
| Na-Lactate | 0.124 g (124 ppm Na-Lactate) |
| Electron acceptor added | |
| Na$_2$nitrate | 0.4 g/400 ppm |

Adjust pH with HCl or NaOH
Filter sterilize

Example 20

Demonstration of Strain L3:3 Oil Release Sandpack or Core Flood Assay

To test the amount of residual oil left in a sandpack after the oil soaked sandpack was flooded with a water solution that simulated the injection brine used in flooding an underground oil reservoir, the sandpack was fabricated as per standard methods described by Petroleum Reservoir Rock and Fluid Properties, Abhijit Y. Dandehar, CRC Press (2006). A similar core flood/sandpack apparatus and techniques used to operate it are also described by Berry et al. (SPE paper number 200056, SPE Reservoir Engineering, November 1991, p 429). The use of a similar apparatus and techniques for testing microbial treatments in a sandpack is described by Saikrishna et al. (SPE paper number 89473, (2004)).

To demonstrate that strain L3:3 is capable of oil release, a L3:3 culture was applied to a sandpack saturated with oil in an in-house developed Teflon® shrink-wrapped sandpack apparatus that simulates packed sand of sandstone. The process described herein was used for making two column sets, a "control" set and a "test" set, which was inoculated with L3:3 to test its efficacy to release oil from the sand column. Using a 1.1 inches (2.8 cm) diameter, and 7 inches (17.8 cm) long Teflon heat shrink tube, an aluminum inlet fitting with Viton® 0-ring was attached to one end of the tube using a heat gun. Alaskan North Slope sand was added to the column which was vibrated with an engraver to pack down the sand and release trapped air. A second aluminum inlet fitting with Viton® O-ring was attached to the other end of the tube and sealed with heat a gun. The sandpack was then put in an oven at 275° C. for 7 min to evenly heat and shrink the wrap. The sandpack was removed and allowed to cool to room temperature. A second Teflon® heat shrink tube was installed over the original pack and heated in the oven as described above. After the column had cooled, a hose clamp was attached on the pack on the outer wrap over the O-ring and then tightened. For this demonstration there were four sandpack columns assembled.

The four sandpack columns were flooded horizontally with three pore volumes of SIB1 Synthetic Injection Brine (Table 10) at 10 mL/min via a syringe pump and a 60 mL (BD) sterile plastic polypropylene syringe. All four sandpacks were then flooded with two pore volumes of anaerobic autoclaved crude oil at 0.5 mL/min to achieve irreducible water saturation. The crude oil was aged on the sand for three weeks prior to being inoculated with strain L3:3.

For inoculation, the culture was grown aerobically overnight in PPGAS media (Table 11). The culture was then placed in an anaerobic environment where sodium lactate was added to SIB1 minimal brine solution to a concentration of 1000 ppm and sodium nitrate was added to a concentration of 2000 ppm. The inoculation sample was then anaerobically aged in an anaerobic chamber (Coy Laboratories Products, Inc., Grass Lake, Mich.) for 5 days before inoculating the sandpacks. After the aging period, two columns were anaerobically inoculated with a sample of Shewanella sp L3:3 for one pore volume at 0.4 mL/hr. Two control sandpacks were flooded using anaerobic SIB1, using the same inoculation procedure. The four sandpacks were then shut-in for incubation with the oil for five days. After the shut-in, the columns were then produced for three pore volumes with anaerobic sterile SIB1 low bicarbonate at 0.4 mL/hr.

TABLE 11

Components for PPGAS Growth Medium (per Liter)

| | |
|---|---|
| Peptone | 10 g |
| Mg SO$_4$ | 0.2 g |
| KCl | 1.5 g |
| NH$_4$ CL | 1.07 g |
| Tris HCL Buffer, pH 7.5 | 120 mL |

At the conclusion of the production flood, the 7 inches long slim tubes were sacrificed into three 1.9-inch sections labeled A-C. One inch was skipped at the beginning and at the exit of the slim tube to avoid edge effects during analysis. Section "A" came from the front end of the column. Sections A, B and C were analyzed for residual oil saturation on the sand. The amount of oil on the wet sand from the sacrificed slim tubes for residual oil was measured by GC as described above. This value was multiplied by the total amount of toluene used to extract the oil resulting in the total amount of oil on the sand. The value obtained was then divided by the total sample weight to yield the percent of oil with respect to the total sample weight. The weight percent of oil of the sample was then multiplied by the ratio of the empirically derived characteristic of packed North Slope sand (total weight of sample after being flooded with brine divided by total sand weight, 1.27). This relationship is equal to the amount of oil on dry sand. This value was then multiplied by the ratio of the weight of the North Slope sand to the weight of the fluid trapped in the pore space of the sand, 3.75. The resulting value reflected the residual oil left on the sand in units of g of oil/g of total fluid in the pore space. As shown in Table 12, residual oil left on the column, in fractions A and C of the test column, were less than the controls confirming that the columns inoculated with the Shewanella sp. L3:3 released more oil than uninoculated control columns, with an average of 4.1% decrease in residual oil remaining on the columns when L3:3 was inoculated on the columns.

TABLE 12

Residual oil left on sand along the tube length after flooding with anaerobic sterile "Brine"

| Assay Column | Average Percent Residual Oil on Sand Column Fraction | | |
|---|---|---|---|
| | A | C | Average. |
| Test columns | 12.6% | 15.3% | 13.9% |
| Control columns | 18.9% | 17.1% | 18.0% |

Example 21

Isolation of Strain MPHPW-1

Oil well production water collected from an oil reservoir near Wainwright, Alberta Canada was enriched by supplementing with 1% Bacto Peptone (Becton Dickinson, Franklin Lakes, N.J.) and cultured by incubating aerobically overnight at room temperature (21-24° C.) with shaking at 220 rpm. This culture was further enriched during an anaerobic LOOS oil release assay that was run as described in General Methods. An aliquot of the overnight culture received 1000 ppm sodium lactate and 2000 ppm sodium nitrate. Samples were then run in the anaerobic oil release test for approximately two weeks. Samples from microtiter plate wells in which oil was released were then plated onto LB agar plates (Teknova, Hollister, Calif., USA) to obtain pure isolates. Representative colonies with unique morphologies were streaked again onto LB plates and one strain was selected for further testing, which was named MPHPW-1.

Example 22

Demonstration of Oil Release Potential of Strain MPHPW-1

To further assess the ability of strain MPHPW-1 to release oil from oil saturated sand, an oil release test was performed. Briefly, a small volume of MPHPW-1 frozen stock was plated onto an LB agar plate and allowed to grow at room temperature. Simulated injection brine plus 1% peptone was inoculated with an individual colony from the plate. The culture was incubated aerobically overnight at room temperature (21-24° C.) with shaking at 220 rpm and grown to a cell density of approximately $1 \times 10^9$ CFU/ml, as determined using the MPN assay described in General Methods. An anaerobic LOOS test was performed as described in General Methods. A control sample contained medium (simulated injection brine plus 1% peptone) alone. Sand/oil release was compared in the MPHPW-1 and control samples over time. The oil release results were that strain MPHPW-1 released oil from a sample of oil soaked sand while the medium alone control released no oil (FIG. 19).

Example 23

Demonstration of Oil Release by Strain MPHPW-1 Grown in the Presence of Different Nutrients Strain MPHPW-1 was grown in the presence of different media supplements. MPHPW-1 was inoculated into SHS-10 medium (171 mM NaCl, 0.98 mM $MgCl_2$, 1.4 mM $CaCl_2$, 0.1 mM KCl, 0.16 mM $Na_2SO_4$, 16.4 mM $NaHCO_3$) supplemented with 1% of Amberferm 2382 (Sensient Flavors, Inc., Harbor Beach, Mich.), Amberferm 2391 (Sensient Flavors, Inc), Tastone (Sensient Flavors, Inc.), or Bacto peptone. These supplements are different sources of small peptides and free amino acids. The cultures were incubated aerobically overnight at room temperature (21-24° C.) with shaking at 220 rpm. An anaerobic LOOS test was performed as described in General Methods. Sand/oil release was compared across all samples over time. The results in FIG. 20 showed that strain MPHPW-1 released oil when grown in the presence of the different supplements.

Example 24

Measuring Oil Release by MPHPW-1 from Sandpacks

The potential application of strain MPHPW-1 in MEOR treatment was evaluated using a sandpack assay. This was done with an in-house sandpack. A schematic diagram of the sandpack experimental set-up is shown in FIG. 21. All numbers below in bold refer to FIG. 21.

A sample of produced sand that was obtained from the Schrader Bluff formation at the Milne Point Unit of the Alaska North Slope was cleaned by washing with a solvent made up of a 50/50 (volume/volume) mixture of methanol and toluene. The solvent was subsequently drained and then evaporated off the sand to produce clean, dry, flowable sand. This sand was sieved to remove particles less than one micrometer in size. The sand was packed tightly into a 20 cm long and 3 cm inner diameter, flexible heat shrinkable tubing (23) and compacted by vibration using a laboratory engraver.

Both ends of the sandpack were capped with compression type fittings to retain the sand mix. Flexible ⅛ inch (0.32 cm) tubing capable of sustaining the pressures used in the test was attached to the fittings. The sandpack was mounted into a pressure vessel (19) with the tubing (18 and 24) passing through the ends of the pressure vessel using commonly available bulkhead pressure fittings (20). Additional fittings and tubing were used to connect the inlet of the sandpack to a pressure pump (16), and an injection brine reservoir (15). Low flow rate of a concentrated solution of nutrients could be pumped using a common syringe pump (17) and diluted into the brine being fed from the brine reservoir (15). Other common compression fittings, including elbow unions and tees, and tubing connected the inlet of the sandpack to a transducer that measured the pressure above atmospheric pressure (absolute pressure gauge) (26). The inlet of the sandpack was also connected using the same types of tubing and fittings to the high pressure side of a commonly available differential pressure transducer (27). Fittings and tubing connected the outlet of the sandpack to the low pressure side of the differential pressure transducer (27) and to a back pressure regulator (28). The produced fluid was collected in a jug (29) and periodically weighed using a weigh scale (30) in order to confirm the flow rate of the feed pump (16). The pressure vessel (19), the sandpack (23) and the bulkhead fittings (20) were weighed as well, as a means to help determine the amount of oil left in the sandpack. The signals from the weigh scales (25, 30), and the differential pressure and the absolute pressure transducers (26, 27) were ported to a computer and these signals were monitored and periodically recorded. The pressure vessel (19) around the sandpack was pressurized using nitrogen ported into the pressure vessel through flexible tubing (22). The nitrogen pressure was monitored using a pressure gauge (21). The nitrogen was at a pressure of about 110 pounds per square inch (psi) (0.74 mega Pascal) while Brine from the feed reservoir (15) flowed through the sandpack and came out through the back pressure regulator (28). This operation was performed such that the pressure in the sandpack (23) was always 5 to 20 psi (0.034-0.137 mega Pascal) below the pressure in the pressure vessel (19).

Throughout the following experimental protocol, the sandpack was operated under pressure between 85 to 90 psig so any gas would remain dissolved, thus avoiding air or gas occupying the void volume. Before beginning the experiment, the sandpack was conditioned by flowing brine through the pack at 4 mL/hour for more than two months.

The sandpack was flooded vertically with three pore volumes of sterile simulated injection brine containing 40 ppt NaCl at 4 mL/min. The sandpack was then flooded with two pore volumes of anaerobic autoclaved crude oil at 4.0 mL/min to achieve irreducible water saturation. The crude oil was aged on the sand for one week and then flooded off using the same brine as above. This process was repeated three more times to insure that all hysteresis had been removed from the system and that a reproducible level of oil saturation could be regenerated with each oiling and de-oiling of the system.

When this was accomplished the system was ready for inoculation. For the inoculation culture one pore volume of strain MPHPW-1 was grown aerobically overnight in SHS-10 medium (171 mM NaCl, 0.98 mM $MgCl_2$, 1.4 mM $CaCl_2$, 0.1 mM KCl, 0.16 mM $Na_2SO_4$, 16.4 mM $NaHCO_3$) plus 1% Amberferm 2391. Just before inoculation of the sandpack, 1000 ppm Na-Lactate and 3715 ppm Na-Fumarate were added to the inoculum. The sandpack column was inoculated with this MPHPW-1 culture at 4.0 mL/min and was shut-in for 5 days. After the shut-in, the column was produced by flushing using the simulated injection brine with 40 ppt NaCl at 4.0 mL/hr for three pore volumes.

The percent of volume occupied by water, also called water saturation, was calculated during the experiment from the monitored weight of the sandpack. The water saturation calculation was performed as follows: The difference in oil and water densities along with the void volume of the sandpack together determine the difference in weight of the sandpack if the void volume were all oil or all water. The measured density of the oil used in the experiment was 0.91 g/ml and the density of water is 1.0 g/ml.
Water saturation calculations used for FIG. 22:
First the theoretical weight swing on column from 100% water to 100% oil was calculated as follows:
30% void fraction (estimated)
0.09 g/cc density difference (1 g/cc water, 0.91 g/cc oil)
116 total volume of sandpack in cc (measured ~1.1 inches in diameter×7.4 to 7.5 inches in length; used 1.1 inches diameter, 7.45 inches length for calculation)
3.1 theoretical weight swing from 100% oil to 100% water
0.30×(0.09×116)=3.1 g. (theoretical weight swing)
Oil density was measured; water density is known in the art; 30% void fraction is known in the art.

Next, Column was flooded with oil to the point at which the weight of the apparatus did not change. This corresponded to its irreducible water saturation; the column weight was measured as −2.702 grams and this weight was used in subsequent calculations as corresponding to 19% water content.

The art and prior work with these types of sand packs has shown us that the irreducible water saturation or residual water saturation will be around 10 to 30%. We chose 19% to use in these calculations. It is not the absolute value that is important; it is the change in the water saturation units or % void volume that is important.

Next, the amount of oil on column after SIB treatment was determined (baseline to determine effectiveness of subsequent medium-alone and MPHPW-1 treatments). Calculation: (measured weight after oil-saturated column washed with SIB)−(Weight with 100% SIB)=−1.134 g. Increased water saturation=(−1.134−(−2.702))/3.1× 100%=50% increase in water saturation.
Since the starting water saturation was 19%, then the new water saturation is 50+19=69%.

The amount of oil on column after medium treatment was determined, and then medium plus MPHPW-1 (referenced in calculation as test solution, meant to denote separate washes, first with just medium, and then with MPHPW-1 plus medium).
Calculation:

(observed weight of column−(−2.702)/3.1×100%+ 19%=the water saturation units plotted in FIG. 22.

This calculated water saturation was graphed in FIG. 22, with the Y axis, labeled "% void volume occupied by water" corresponding to % water saturation, and the X axis corresponding to the number of void volumes flooded by each solution. The water saturation percentage is a measurement of effectiveness of oil removal or recovery.

The results showed that MPHPW-1 treatment increased the average water saturation by about 15%. In FIG. 22, the first part of the curve, labeled 1, is the deoiling curve using injection brine alone. It shows that after the column has been saturated with oil and flushed with water, the water saturation is 69%. The second part of the curve, labeled 2 is the deoiling curve using medium alone without any microorganisms added. There appears to be an increased water saturation of about 2% (5) The third part of the curve, labeled 3 is the deoiling curve using medium plus MPHPW-1. There appears to be an increase in water saturation of about 15% (4).

Example 25

LOOS Test Confirmation of the Oil Release of the Sandpack Inoculum

To confirm that the MPHPW-1 inoculum used in the sandpack (Example 24 above) released oil from oil saturated sand, a standard LOOS test was performed as described in General Methods using SHS-10 plus 1% Amberferm medium. The effect on oil release of a sample of the inoculum used in Example 24 was compared to the effect of SHS-10 plus 1% Amberferm medium alone. Results are shown in FIG. 23. The MPHPW-1 sandpack inoculum released oil whereas the medium alone did not in the first 12 days of the assay.

Example 26

Identification of Strain MPHPW-1 as a New Strain of *Shewanella*

Strain MPHPW-1 was identified as a strain of *Shewanella*, most closely related to *S. algae* strain BrY, by using 16S rDNA sequence analysis consistent with the criteria set forth in the International Journal of Systematic and Evolutionary Microbiology (B. J. Tindall, R. Rosselló-Mora, H.-J. Busse, W. Ludwig and P. Kämpfer, Int. J. Syst. Evol. Microbiol. (2010), 60:249-266).

Genomic DNA was isolated from a pure single colony of this strain that was isolated as described in Example 21. The universal primers Reverse Primer 1492R (SEQ ID NO:1) and Forward Primer 8F (SEQ ID NO:2) were used to PCR-amplify a near full length 16S rDNA genomic DNA fragment of about 1450 bp from this isolate. This amplified fragment was cloned and then sequenced five times in each direction and the raw data was compiled to obtain the final sequence (SEQ ID NO: 24). The resulting consensus sequence (SEQ ID NO:24) was queried against the NCBI (The National Center for Biotechnology Information) nucleic acid database, using the BLAST (Basic Local Alignment Search Tool) algorithm. High identity sequence hits were sequences of 16S rDNA from strains of Shewanella species. There were no sequences found having 100% identity to SEQ ID NO:24.

The 16S rDNA sequences of the type strains of the 55 recognized species of Shewanella from the List of Prokaryotic names with Standing in Nomenclature (LPNSN), as well as a few additional representative strains that are listed in Table 13 were downloaded from the NCBI Genbank nucleic acid database. A multiple sequence alignment was performed anchored by the E. coli K12 16S rDNA B sequence, which is recognized as the standard 16S rDNA for base position assignment (Brosius, Jürge, et al., 1981, J. Mol. Biology 148:107; Woese, C. R. 1987. Bacterial Evolution. Microbial. Rev. 51:221), to provide base coordinate positions. The alignment was performed using the global multiple sequence alignment algorithm from the Clustal series of programs, Clustal W, DNAstar Lasergene Version 8.0.3 MegAlign package, Madison Wis. (Chenna, Ramu, et al., (2003) Nucl. Acids Res. 31:3497). Sequences were aligned across their entire length. All sequences used in the alignment were from near full length 16S rDNA sequence, which starts at E. coli coordinate base No. 61 and ends at base coordinate 1460. MPHPW-1 coordinates in SEQ ID NO:24 that correspond to the E. coli coordinates 61-1460 are MPHPW-1 base coordinates 17 (5'-GTCGA) through 1418 (GGGC-3'). Four exceptions with regard to sequence coverage from E. coli coordinates 61 to 1460 were the DNA sequences from the following type strains, which were not complete at the 5' or 3' termini
Shewanella atlantica strain HAW-EB5 (CCUG 54554; Genbank:AY579752, SEQ ID:71) sequence from positions 83 to 1376;
Shewanella canadensis strain HAW-EB2 (CCUG 54553: Genbank AY579749, SEQ ID:68) sequence from positions 83 to 1368;
Shewanella sediminis strain HAW-EB3 (DSM 17055: Genbank CP000821, SEQ ID:89) sequence from positions 83 to 1363;
Shewanella profunda strain LT13a (DSM 15900: Genbank AY445591, SEQ ID:64) sequence from positions 198 to 1531.

The multiple sequence alignment showed that among all pairs of the aligned Shewanella type species sequences, and representative species sequences that were included, there was at least 90% identity with MPHPW-1 confirming that MPHPW-1 is a strain of Shewanella.

The Guide Tree, which resembles a phylogenetic tree, in FIG. 24 is based on a sequence distance method and utilizes the Neighbor Joining (NJ) algorithm of Saitou and Nei (Saitou, N. and Nei, M. (1987), The neighbor-joining method: a new method for reconstructing Guide Trees. Mol. Biol. Evol. 4; 406-425). The NJ method works on a matrix of distances between all pairs of sequence to be analyzed. These distances are related to the degree of divergence between the sequences. The Guide Tree is calculated after the sequences are aligned. AlignX displays the calculated distance values in parenthesis following the molecule name displayed on the tree for genus Shewanella strains and strain MPHPW-1 based on similarity and differences in 16S rRNA gene sequences was generated from this alignment using bootstrap and Clustal W analysis (Vector NTI AlignX software package 10.3.1 Invitrogen, Carlsbad, Calif.). The software positioned strain MPHPW-1 in a phylogenetic Glade consisting of four species: Shewanella algae, Shewanella haliotis, Shewanella chilikensis and Shewanella marinus. Shewanella algae strain BrY and strain MPHPW-1 formed a sub-Glade within this Glade that was separate from the other Shewanella algae species of the Glade, represented by type strain Shewanella algae OK-1 (ATCC 51192). Based on the close relationship of MPHPW-1 and Shewanella. algae BrY, MPHPW-1 was determined to belong to the Shewanella algae species. Shewanella sp. strain KJW27 (16S rDNA Accession #HM016084) was also most closely related to S. algae BrY by 16S rDNA sequence analysis and has 2 position differences with the MPHPW-1 16S rDNA. The Shewanella sp. KJW27 strain is slated to be named a new species, Shewanella indica, by the International Journal of Systematic and Evolutionary Microbiology (personal communication). The naming of this new species and the relationships that it has with BrY and MPHPW-1 may indicate the assignment of MPHPW-1 as a Shewanella indica once the new naming is published.

By analyzing the ClustalW alignment, signature sequence positions in the 16S rDNA sequence were identified that could be used to distinguish different Shewanella species and also genomavars within the Shewanella algae species. These signature positions are listed in Table 14 with position coordinate numbers of the E. coli K12 W3110 rrnB allele for 16S rDNA sequence. Table 14 lists the hypervariable region of 16S RNA sequence, where each listed signature sequence position is located. Approximate positions of the hypervariable regions designated by nucleotides of the 16S rDNA sequence from E. coli are: hypervariable region 1 between positions 60 and 99;
hypervariable region 2 between positions 118 and 290;
hypervariable region 3 between positions 410 and 520;
hypervariable region 4 between positions 578 and 760;
hypervariable region 5 between positions 820 and 888;
hypervariable region 6 between positions 980 and 1048;
hypervariable region 7 between positions 1071 and 1179;
hypervariable region 8 between positions 1215 and 1335;
hypervariable region 9 between positions 1350 and 1480.

In Table 14, the sequences at the signature positions are given for Shewanella algae strains ATCC51192 (16S rDNA SEQ ID NO:45), FeRed (16S rDNA SEQ ID NO:90), and BrY (16S rDNA SEQ ID NO:27), and the closest strains on the phylogenetic tree (with >98% sequence identity): Shewanella haliotis (16S rDNA SEQ ID NO:33), and Shewanella chilikensis (16S rDNA SEQ ID NO:10). All of these strains have the same signature sequence at the positions shown in the boxed regions of the table, for example in hypervariable region 1 at positions 74-84 and 88-98. The signature sequences for less closely related strains Shewanella oneidensis (16S rDNA SEQ ID NO:86), Shewanella colwelliana (16S rDNA SEQ ID NO:73), and Shewanella amazonensis (16S rDNA SEQ ID NO:44), also shown in this table, differ at these positions.

A set of signature sequences that distinguished Shewanella algae BrY and strain MPHPW-1 from the other Shewanella strains occurred at 15 specific positions: two in variable region 2 (positions 264 and 278), two in variable region 3 (positions 456-463, 488-491), four in variable region 5 (positions 847, 853, 856 and 858), four in variable region 6 (positions 1000-1001, 1006-1012, 1017-1023 and 1039-1040) and three in variable region 8 (positions 1243-1245, 1283 and 1292-1294). The *Shewanella algae* BrY sequence differs from that of MPHPW-1 as follows: mismatches at positions 163 and 170 in the MPHPW-1 sequence (positions 203 and 213 using *E. coli* 16S rDNA position numbers as in Table 14 below), and deletions from MPHPW-1 following positions 16, 37, and 1421 of the MPHPW-1 sequence.

The sequences with closest identity to the MPHPW-1 16S rDNA sequence from the BLAST search, other than *S. algae* BrY, are listed in Table 15. Due to the sequence identities with other *Shewanella* strains, one of these sequences appear to be misclassified as belonging to a strain of *Rhodobacter capsulatus* rather than *Shewanella*. Each of these sequences had at least four position differences with the sequence of MPHPW-1, including nucleotide changes, insertions, and deletions. Thus, based on the 16S rDNA sequence analysis, MPHPW-1 was identified as a new strain of *Shewanella algae*.

The 16S rDNA sequence of MPHPW-1 fell within the *Shewanella* degenerate signature sequences shown in FIG. 18 with an exception at position 23 of SEQ ID NO:19. This position is number 199 with respect to the *E. coli* 16S rDNA positioning standard. In the MPHPW-1 sequence there is a C at this position. Thus to incorporate the MPHPW-1 sequence at this position into the *Shewanella* degenerate sequence, the degenerate designation was changed from R (which includes A or G) to V (which includes A, C, or G). The revised *Shewanella* degenerate signature sequence for the 16S variable region 2 is SEQ ID NO:25.

The *Shewanella* degenerate signature sequence for variable region 2 that specifies MPHPW-1 and the other members of the Glade to which it belongs (*Shewanella algae, Shewanella haliotis, Shewanella chilikensis* and *Shewanella marinus*) contains all of the degeneracy in SEQ ID NO:25 except C is specified at position 23 of region 2 (SEQ ID NO:28).

TABLE 13

Type strains and representative strains of *Shewanella* species, with GenBank accession numbers to reference rRNA encoding gene sequences used in alignment

| Genus and Species | Accession No. | Strain name and Deposit Identification | SEQ ID NO |
|---|---|---|---|
| *Shewanella putrefaciens* | X81623 | Hammer 95 = ATCC 8071. | 32 |
| *Shewanella hanedai* | X82132 | 281 = ATCC 33224 | 31 |
| *Shewanella benthica* | X82131 | W 145 = ATCC 43992 | 30 |
| *Shewanella colwelliana* | AY653177 | LST-W = ATCC 39565. | 73 |
| *Shewanella algae* | AF005249 | OK-1 = ATCC 51192 | 45 |
| *Shewanella frigidimarina* | U85903 | ACAM 591 = ATCC 700753 | 38 |
| *Shewanella gelidimarina* | U85907 | ACAM 456 = ATCC 700752 | 39 |
| *Shewanella woodyi* | CP000961 | MS32 = ATCC 51908 | 84 |
| *Shewanella amazonensis* | AF005248 | SB2B = ATCC 700329 | 44 |
| *Shewanella baltica* | AJ000214 | CCUG 39356 = DSM 9439 | 55 |
| *Shewanella oneidensis* | AF005251 | MR-1 = ATCC 700550. | 46 |
| *Shewanella pealeana* | AF011335 | ANG-SQ1 = ATCC 700345 | 52 |
| *Shewanella violacea* | D21225 | strain.DSS12 = CIP 106290 | 42 |
| *Shewanella japonica* | AF145921 | ATCC BAA-316 | 72 |
| *Shewanella denitrificans* | AJ311964 | OS217 = DSM 15013 | 34 |
| *Shewanella livingstonensis* | AJ300834 | NF22 = LMG 19866. | 40 |
| *Shewanella olleyana* | AF295592 | ACEM 9 = LMG 21437 | 83 |
| *Shewanella fidelis* | AF420312 | ATCC BAA-318 | 36 |
| *Shewanella marinintestina* | AB081757 | IK-1 = JCM 11558 | 47 |
| *Shewanella sairae* | AB081762 | SM2-1 = JCM 11563. | 49 |
| *Shewanella schlegeliana* | AB081760 | HRKA1 = JCM 11561 | 48 |
| *Shewanella waksmanii* | AY170366 | ATCC BAA-643 | 54 |
| *Shewanella affinis* | AY351983 | ATCC BAA-642 | 61 |
| *Shewanella aquimarina* | AY485225 | SW-120 = JCM 12193 | 67 |
| *Shewanella gaetbuli* | AY190533 | TF-27 = JCM 11814 | 56 |
| *Shewanella marisflavi* | AY485224 | SW-117 = JCM 12192 | 66 |
| *Shewanella pacifica* | AF500075 | R10SW1 = DSM 15445 | 59 |
| *Shewanella profunda* | AY445591 | LT13a = DSM 15900 | 64 |
| *Shewanella decolorationis* | AJ609571 | S12 = JCM 21555 | 65 |
| *Shewanella pneumatophori* | AB204519 | SCRC-2738 = JCM 13187. | 79 |
| *Shewanella sediminis* | CP000821 | HAW-EB3 = DSM 17055 | 89 |
| *Shewanella abyssi* | AB201475 | c941 = DSM 17171 | 74 |
| *Shewanella hafniensis* | AB205566 | P010 = ATCC BAA-1207 | 75 |
| *Shewanella halifaxensis* | AY579751 | HAW-EB4 = DSM 17350 | 70 |
| *Shewanella irciniae* | DQ180743 | UST040317-058 = JCM 13528 | 81 |
| *Shewanella kaireitica* | AB094598 | c931 = DSM 17170 | 58 |
| *Shewanella loihica* | DQ286387 | PV-4 = ATCC BAA-1088 | 82 |
| *Shewanella morhuae* | AB205576 | U1417 = ATCC BAA-1205 | 78 |
| *Shewanella spongiae* | DQ167234 | HJ039 = JCM 13830 | 80 |
| *Shewanella surugensis* | AB094597 | c959 = DSM 17177 | 57 |
| *Shewanella algidipiscicola* | AB205570 | S13 = LMG 23746 | 76 |
| *Shewanella atlantica* | AY579752 | HAW-EB5 = CCUG 54554 | 71 |
| *Shewanella canadensis* | AY579749 | HAW-EB2 = CCUG 54553 | 68 |
| *Shewanella donghaensis* | AY326275 | LT17 = JCM 12524 | 60 |
| *Shewanella glacialipiscicola* | AB205571 | T147 = LMG 23744 | 77 |
| *Shewanella haliotis* | EF178282 | DW01 = JCM 14758. | 33 |
| *Shewanella piezotolerans* | AJ551090 | WP3 = JCM 13877. | 63 |
| *Shewanella psychrophila* | AJ551089 | WP2 = JCM 13876. | 62 |

TABLE 13-continued

Type strains and representative strains of *Shewanella* species, with GenBank accession numbers to reference rRNA encoding gene sequences used in alignment

| Genus and Species | Accession No. | Strain name and Deposit Identification | SEQ ID NO |
|---|---|---|---|
| *Shewanella basaltis* | EU143361 | J83 = JCM 14937 | 35 |
| *Shewanella chilikensis* | FM210033 | JC5 = CCUG 57101 | 51 |
| *Shewanella marina* | EU290154 | C4 = JCM 15074 | 37 |
| *Shewanella vesiculosa* | AM980877 | M7 = CECT 7339 | 41 |
| *Shewanella corallii* | FJ041083 | fav-2-10-05 = DSM 21332 | 53 |
| *Shewanella fodinae* | FM203122 | JC15 = CCUG 57102 | 50 |
| *Shewanella xiamenensis* | FJ589031 | S4 = JCM 16212. | 43 |
| *Shewanella algae* | X81621 | BrY = ATCC 51181 | 27 |
| *Shewanella baltica* | NC_009052 | OS155 = ATCC BAA-1091 | 88 |
| *Shewanella putrefaciens* | NC_009438Error! Bookmark not defined. | CN-32 = ATCC BAA-453 or ATCC BA-1097 | 87 |

TABLE 14

Sequences that are underlined and bold are unique signatures different from the Shewanella consensus. Differences between MPHPW-1 and BrY are italicized for MPHPW-1. SEQ ID NOs are in parentheses.

| Bacterial Hyper-variable Regions | E. coli K12 rDNA coordinate No. | Shewanella haliotis DW01 (33) | Shewanella algae ATCC 51192 (45) | Shewanella algae FeRed (90) | Shewanella algae BrY (27) | Shewanella MPHPW-1 (24) | Shewanella chilikensis JC5 (10) | Shewanella oneidensis MR-1 (86) | Shewanella colwelliana LST-W (73) | Shewanella amazonensis SB2B (44) |
|---|---|---|---|---|---|---|---|---|---|---|
| 1 | 75-84 | _ATTTCAAA_ | _ATTTCAAA_ | _ATTTCAAA_ | _ATTTCAAA_ | _ATTTCAAA_ | _ATTTCAAA_ | ACACAAGT | AGGATT- | GGGAAGAT |
| | | _AG_ | _AG_ | _AG_ | _AG_ | _G_ | _AG_ | GA | TAG | AG |
| 1 | 88-98 | _TTTGAAGA_ | _TTTGAAGA_ | _TTTGAAGA_ | _TTTGAAGA_ | _TTTGAAGA_ | _TTTGAAGA_ | CATGACGT | AATTTGCT | ATCTTTGC |
| | | _TGA_ | _TGA_ | _TGA_ | _TGA_ | _TGA_ | _TGA_ | GGC | GAC | CGG |
| 2 | 206 | _A_ | C | C | C | _A_ | _A_ | C | C | T |
| 2 | 213 | _T_ | G | G | G | _T_ | _T_ | G | G | A |
| 2 | 223-225 | _TGA_ | _TGA_ | _TGA_ | _TGA_ | _TGA_ | _TGA_ | GAT | GAT | GAT |
| 2 | 230-232 | _AGG_ | _AGG_ | _AGG_ | _AGG_ | _AGG_ | _AGG_ | GAA | GTA | GAA |
| 2 | 253 | _A_ | _A_ | A | _A_ | _A_ | _A_ | T | T | _A_ |
| 2 | 264 | _T_ | G | A | _T_ | _T_ | _T_ | _T_ | _T_ | _T_ |
| 2 | 278 | _G_ | G | _G_ | _G_ | _G_ | _G_ | G | G | G |
| 2 | 293 | AT | AT | AT | AT | AT | AT | AT | AT | T |
| 2 | 306-307 | GGA | GGA | GGA | GGA | GGA | GGA | GGA | CGC | _GA_ |
| 2 | 379-381 | C | C | C | C | C | C | C | _CGC_ | _GGA_ |
| 2 | 384 | | | | | | | | _G_ | _A_ |
| 3 | 456-463 | _GTGTAAGT_ | _TTGTAAGT_ | _TTGTAAGT_ | _GTGTAAGT_ | _GTGTAAGT_ | _TTAGTAGT_ | _GTAAGTCC_ | _TTAAGTCG_ | _TTACTGGT_ |
| 3 | 473-477 | _TTACAT_ | _TTACAT_ | _TTACAT_ | _TTACAT_ | _TTACAT_ | _TGCTAG_ | _ACTTAT_ | _GTTTAG_ | _GTTTAT_ |
| 3 | 488-491 | _CTCG_ | _TTGG_ | _CTCG_ | _CTCG_ | _CTCG_ | _CTCG_ | _CCTA_ | _CGC_ | _CCCA_ |
| 3 | 513 | _C_ | _C_ | _C_ | _C_ | _C_ | _C_ | _C_ | _T_ | _C_ |
| 4 | 539 | GA | GA | GA | GA | GA | GA | GA | _AG_ | GA |
| 4 | 546 | G | G | G | G | G | G | G | _A_ | _A_ |
| 4 | 552 | T | T | T | T | T | T | T | _A_ | _G_ |
| 4 | 578 | G | T | G | G | G | G | T | _A_ | _G_ |
| 4 | 590 | T | T | T | T | T | T | T | _T_ | T |
| 4 | 632 | _C_ | _C_ | _C_ | _C_ | _C_ | _C_ | T | T | _C_ |
| 4 | 646-649 | _GCAA_ | _GCAA_ | _GCAA_ | _GCAA_ | _GCAA_ | _GCAA_ | ACCA | _GCAA_ | _GCAG_ |
| 4 | 679 | C | C | C | C | C | C | C | _T_ | C |
| 4 | 711 | _G_ | _G_ | _G_ | _G_ | _G_ | _G_ | _G_ | A | _G_ |
| 4 | 743-748 | ACAAAG | ACAAAG | ACAAAG | ACAAAG | ACAAAG | ACAAAG | ACAAAG | ACAAAG | ACAAAG |
| 4 | 760-763 | GGCA | GGCA | GGCA | GGCA | GGCA | GGCA | TGCA | TGTA | GGCA |
| 5 | 832 | G | G | G | G | G | G | G | _A_ | G |
| 5 | 847 | _C_ | G | _C_ | _C_ | _C_ | _C_ | | | |
| 5 | 853-858 | GCTCTC | _TCTTTA_ | GCTCTC | GCTCTC | GCTCTC | GCTCTC | GCTCTC | GTTCTC | GCTCTC |
| 6 | 1000-1001 | AGA | _ACA_ | _ACA_ | AGA | AGA | _TC_ | _ACG_ | AGA | AGA |
| 6 | 1006-1012 | _TCTGGTAG_ | _CTTTTCAG_ | _CTTTTCAG_ | _CTTTTCAG_ | _CTTTTCAG_ | _GCCAGCG_ | _GACTGCAG_ | _TTCGCTAG_ | _TTCGCTAG_ |
| 6 | 1017-1023 | _TACCTCA_ | TGAATTG | TGAATTG | TGAATTG | TGGATTG | _CGCAGGT_ | _TGCGGTT_ | _TAGCTTA_ | _TAGCTTA_ |
| 6 | 1038-40 | TGT | TGT | TGT | TGT | TCT | _TGA_ | _CGT_ | _TCT_ | _GCT_ |
| 6 | 1060-1063 | TGTC | TGTC | TGTC | TGTC | TGTC | TGTC | TGTC | TGTC | _-GTT_ |

TABLE 14-continued

| | | | | | | | | |
|---|---|---|---|---|---|---|---|---|
| 7 | 1115 | C | C | C | C | C | | T |
| 7 | 1124 | C | C | C | C | T | | T |
| 7 | 1133-34 | GG | GG | GG | GG | AC | | AC |
| 7 | 1138 | A | A | A | A | A | | G |
| 7 | 1140-1141 | CC | CC | CC | CC | GT | | CC |
| 7 | 1157-1160 | CTTT | CTTT | CTTT | CTTT | CTCT | CTTT | -TTT |
| 8 | 1243-1246 | TCAG | TCAG | TCGG | TCGG | CGAG | CAAG | CGAG |
| 8 | 1260 | G | G | G | G | A | G | G |
| 8 | 1273-74 | TG | TG | TG | TG | TG | TG | TG |
| 8 | 1283 | C | C | C | C | T | T | T |
| 8 | 1292-4 | TGG | TGG | CGG | CGG | TCG | TTG | TCG |
| 8 | 1308 | T | T | T | T | T | T | T |
| 8 | 1328 | A | A | A | A | A | A | A |
| 9 | 1354-1356 | TGG | TGG | TGG | TGG | TGG | TGG | TGG |
| 9 | 1366-1368 | CCA | CCA | CCA | CCA | CCA | CCA | CCA |
| 9 | 1401-1402 | CC | CC | CC | CC | CC | CC | CC |
| 9 | 1429-30 | GG | GG | GG | GG | AA | GG | GG |
| 9 | 1438-1440 | AGA | AGA | AGA | AGA | GGG | AGA | AGA |

TABLE 15

Listing of sequences with highest sequence identity to the 16S rDNA of MPHPW-1 identified in a BLAST search

| Accession (Seq ID) | Percent Identity | Alignment Length | Identified Organism |
| --- | --- | --- | --- |
| FJ866783(91) | 99.79 | 1423 | *Shewanella algae* strain PSB-05 |
| HQ851081(92) | 99.79 | 1423 | *Rhodobacter capsulatus*** strain NBY31 |
| US20100044304 SEQ ID 3 (26) | 99.79 | 1423 | *Shewanella algae* strain IBI-6P IPOD No. FERM BP-10568 |
| FJ866781(93) | 99.72 | 1423 | *Shewanella algae* strain PSB-04 |
| GU223381 (94) | 99.72 | 1423 | *Shewanella* sp EM0501 |
| HM016084 (95) | 99.72 | 1423 | *Shewanella* sp KJW27 |
| X81621(25) | 99.72 | 1423 | *Shewanella algae* BrY |

**Apparently misclassified as *Rhodobacter capsulatus*

Example 27

Riboprint® Analysis of MPHPW-1

To determine whether the 16S rDNA genomic region of *Shewanella algae* strain MPHPW-1 contained additional distinguishing elements from *Shewanella algae* BrY, other *Shewanella algae* strains and a *Shewanella chilikensis* strain, several genomic DNA preparations of this strain and six other *Shewanella algae* or algae-like strains were analyzed by Riboprinter® These Riboprints® were compared to 7525 patterns contained within DuPont Environmental Services and Qualicon libraries compiled from samples taken from DuPont as well as another 6950 patterns that DuPont Qualicon has supplied from standard identified organisms. Based on the analyses of Riboprint® Batch 1074 (FIG. 25), which provides a chromosomal fingerprint of 16S rDNA loci of the tested strains, it is clear that the Riboprint® pattern for strain MPHPW-1 (Sample 1) is unique when compared against the six other strains assayed. The MPHPW-1 Riboprint® pattern was also unique among the available DuPont Riboprint® Libraries. The MPHPW-1 pattern was designated as RiboGroup® Identifier 212-1074-S-1. It is probable for various strains to share single similar Riboprint® bands generated by hybridizing the labeled *E. coli* rDNA operon probe to each strain's genomic Eco RI fragments, but it is the overall Riboprint® banding pattern that constitutes identification of a given strain in a specific Riboprint® or Ribogroup® identifier.

This analysis confirmed that the genomic sequences surrounding the rDNA operons in strain MPHPW-1 have different genomic structure than those in the Riboprint® database. *Shewanella algae* strain BrY, whose sequence identity to strain MPHPW-1 is 99.72% has a Riboprint® pattern that is similar to that of MPHPW-1, but its pattern is missing the 1 kb band (fragment). The region for this band is circled in FIG. 25 to demonstrate its absence in row 6, which contains the Riboprint® pattern for *Shewanella algae* strain BrY. Therefore strain MPHPW-1's Riboprint® is a unique genomic identifier, indicating that MPHPW-1 is a newly identified strain.

What is claimed is:

1. A method of oil recovery comprising:
a) providing an oil reservoir;
b) injecting the oil reservoir with a conditioned medium which is substantially cell free and which has been in contact with one or more *Shewanella* sp.; wherein the *Shewanella* sp. comprises a 16S rDNA having at least 99% identity to SEQ ID NO:3 and further comprising SEQ ID NO:21, SEQ ID NO:23 and SEQ ID NO:28; and
c) recovering oil from the oil reservoir;
wherein the medium enhances oil recovery.

2. The method of claim 1, wherein injecting is into a production well or an injection well and recovery is from a production well.

3. The method of claim 1, wherein the medium comprises additional components selected from the group consisting of electron acceptor, at least one additional carbon source, and mixtures thereof.

4. The method of claim 1, wherein the medium comprises at least one additional microorganism.

5. The method of claim 1, wherein injection water or aqueous solution comprising components selected from the group consisting of electron acceptor, carbon source, and mixtures thereof is separately injected into the oil reservoir continuously or periodically following injection with the medium in (b).

* * * * *

```
                        SEQUENCE LISTING

<160> NUMBER OF SEQ ID NOS: 97

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
cggttacctt gttacgactt                                              20

<210> SEQ ID NO 2
<211> LENGTH: 20
<212> TYPE: DNA
<213> ORGANISM: artificial sequence
<220> FEATURE:
<223> OTHER INFORMATION: primer 8f

<400> SEQUENCE: 2
agagtttgat ymtggctcag                                              20

<210> SEQ ID NO 3
<211> LENGTH: 1456
<212> TYPE: DNA
<213> ORGANISM: unknown
<220> FEATURE:
<223> OTHER INFORMATION: Shewanella species L3:3

<400> SEQUENCE: 3
agagtttgat catggctcag attgaacgct ggcggcaggc ctaacacatg caagtcgagc      60
ggtaacattt caaaagcttg cttttgaaga tgacgagcgg cggacgggtg agtaatgcct     120
```

| | |
|---|---|
| gggaatttgc ccatttgtgg gggataacag ttggaaacga ctgctaatac cgcatacgcc | 180 |
| ctacggggga aagcagggga acttcggtcc ttgcgctgat ggataagccc aggtgggatt | 240 |
| agctagtagg tgaggtaatg gctcacctag gcaacgatcc ctagctggtc tgagaggatg | 300 |
| atcagccaca ctgggactga gacacggccc agactcctac gggaggcagc agtggggaat | 360 |
| attgcacaat gggggaaacc ctgatgcagc catgccgcgt gtgtgaagaa ggccttcggg | 420 |
| ttgtaaagca ctttcagcga ggaggaaagg ttagtagtta atacctgcta gctgtgacgt | 480 |
| tactcgcaga agaagcaccg gctaactccg tgccagcagc cgcggtaata cggagggtgc | 540 |
| gagcgttaat cggaattact gggcgtaaag cgtgcgcagg cggtttgtta agcgagatgt | 600 |
| gaaagccccg ggctcaacct gggaaccgca tttcgaactg caaactaga gtcttgtaga | 660 |
| ggggggtaga attccaggtg tagcggtgaa atgcgtagag atctggagga ataccggtgg | 720 |
| cgaaggcggc cccctggaca aagactgacg ctcaggcacg aaagcgtggg gagcaaacag | 780 |
| gattagatac cctggtagtc cacgccgtaa acgatgtcta ctcggagttt ggtgtcttga | 840 |
| acactgggct ctcaagctaa cgcattaagt agaccgcctg ggagtacgg ccgcaaggtt | 900 |
| aaaactcaaa tgaattgacg ggggcccgca caagcggtgg agcatgtggt ttaattcgat | 960 |
| gcaacgcgaa gaaccttacc tactcttgac atcctcagaa gccagcggag acgcaggtgt | 1020 |
| gccttcggga actgagagac aggtgctgca tggctgtcgt cagctcgtgt tgtgaaatgt | 1080 |
| tgggttaagt cccgcaacga gcgcaacccc tatccttact tgccagcggg taatgccggg | 1140 |
| aactttaggg agactgccgg tgataaaccg gaggaaggtg gggacgacgt caagtcatca | 1200 |
| tggcccttac gagtagggct acacacgtgc tacaatggtc ggtacagagg gttgcgaagc | 1260 |
| cgcgaggtgg agctaatctc ataaagccgg tcgtagtccg gattggagtc tgcaactcga | 1320 |
| ctccatgaag tcggaatcgc tagtaatcgt ggatcagaat gccacggtga atacgttccc | 1380 |
| gggccttgta cacaccgccc gtcacaccat gggagtgggc tgcaccagaa gtagatagct | 1440 |
| taaccttcgg gagggc | 1456 |

<210> SEQ ID NO 4
<211> LENGTH: 1535
<212> TYPE: DNA
<213> ORGANISM: Shewanella putrefaciens

<400> SEQUENCE: 4

| | |
|---|---|
| agagtttgat catggctcag attgaacgct ggcggcaggc ctaacacatg caagtcgagc | 60 |
| ggcagcacaa gggagtttac tcctgaggtg cgagcggcg gacgggtgag taatgcctag | 120 |
| ggatctgccc agtcgagggg gataacagtt ggaaacgact gctaataccg catacgccct | 180 |
| acggggaaa ggaggggacc ttcgggcctt ccgcgattgg atgaacctag gtggattag | 240 |
| ctagttggtg aggtaatggc tcaccaaggc gacgatccct agctgttctg agaggatgat | 300 |
| cagccacact gggactgaga cacggcccag actcctacgg gaggcagcag tgggaatat | 360 |
| tgcacaatgg gggaaaccct gatgcagcca tgccgcgtgt gtgaagaagg ccttcgggtt | 420 |
| gtaaagcact ttcagtaggg aggaaagggt aaggtttaat acgccttatc tgtgacgtta | 480 |
| cctacagaag aaggaccggc taactccgtg ccagcagccg cggtaatacg agggtccga | 540 |
| gcgttaatcg gaattactgg gcgtaaagcg tgcgcaggcg gtttgttaag cgagatgtga | 600 |
| aagccctggg ctcaacctag gaatagcatt tcgaactggc gaactagagt cttgtagagg | 660 |
| ggggtagaat tccaggtgta gcggtgaaat gcgtagagat ctgaggaat accggtggcg | 720 |
| aaggcggccc cctggacaaa gactgacgct catgcacgaa agcgtgggga gcaaacagga | 780 |

```
ttagatacccc tggtagtcca cgccgtaaac gatgtctact cggagtttgg tgtcttgaac      840
actgggctct caagctaacg cattaagtag accgcctggg gagtacggcc gcaaggttaa      900
aactcaaatg aattgacggg ggcccgcaca gcggtggag catgtggttt aattcgatgc       960
aacgcgaaga accttaccta ctcttgacat ccacagaact ttccagagat ggattggtgc     1020
cttcgggaac tgtgagacag gtgctgcatg gctgtcgtca gctcgtgttg tgaaatgttg     1080
ggttaagtcc cgcaacgagc gcaacccctc tccttatttg ccagcacgta atggtgggaa     1140
ctctagggag actgccggtg ataaaccgga ggaaggtggg gacgacgtca agtcatcatg     1200
gcccttacga gtagggctac acacgtgcta caatggcgag tacagagggt tgcaaagccg     1260
cgaggtggag ctaatctcac aaagctcgtc gtagtccgga ttggagtctg caactcgact     1320
ccatgaagtc ggaatcgcta gtaatcgtgg atcagaatgc cacggtgaat acgttcccgg     1380
gccttgtaca caccgcccgt cacaccatgg gagtgggctg caaaagaagt gggtagctta     1440
accttcgggg gggcgctcac cactttgtgg ttcatgactg gggtgaagtc gtaacaaggt     1500
agccctaggg gaacctgggg ctggatcacc tcctt                               1535

<210> SEQ ID NO 5
<211> LENGTH: 1407
<212> TYPE: DNA
<213> ORGANISM: unknown
<220> FEATURE:
<223> OTHER INFORMATION: Shewanella species strain LH:4:18

<400> SEQUENCE: 5
gagcggcagc acaagggagt ttactcctga ggtggcgagc ggcggacggg tgagtaatgc       60
ctagggatct gcccagtcga ggggggataac agttggaaac gactgctaat accgcatacg    120
ccctacgggg gaaaggaggg gaccttcggg ccttccgcga ttggatgaac ctaggtggga    180
ttagctagtt ggtgaggtaa tggctcacca aggcgacgat ccctagctgt tctgagagga    240
tgatcagcca cactgggact gagacacggc ccagactcct acgggaggca gcagtgggga    300
atattgcaca atgggggaaa ccctgatgca gccatgccgc gtgtgtgaag aaggccttcg    360
ggttgtaaag cactttcagt agggaggaaa gggtaaggtt tatacgcctt atctgtgacg    420
ttacctacag aagaaggacc ggctaactcc gtgccagcag ccgcggtaat acggagggtc    480
cgagcgttaa tcggaattac tgggcgtaaa gcgtgcgcag gcggtttgtt aagcgagatg    540
tgaaagccct gggctcaacc taggaatagc atttcgaact ggcgaactag agtcttgtag    600
aggggggtag aattccaggt gtagcggtga atgcgtaga gtctggagga ataccggtgg    660
cgaaggcggc cccctggaca agactgacg ctcatgcacg aaagcgtggg agcaaacag    720 gattagatac cctggtagtc cacgccgtaa acgatgtcta ctcggagttt ggtgtcttga    780
acactgggct ctcaagctaa cgcattaagt agaccgcctg gggagtacgg ccgcaaggtt    840
aaaactcaaa tgaattgacg ggggcccgca caagcggtgg agcatgtggt ttaattcgat    900
gcaacgcgaa gaaccttacc tactcttgac atccacagaa ctttccagag atggattggt    960
gccttcggga actgtgagac aggtgctgca tggctgtcgt cagctcgtgt tgtgaaatgt   1020
tgggttaagt cccgcaacga gcgcaacccc tatccttatt tgccagcacg taatggtggg   1080
aactctaggg agactgccgg tgataaaccg gaggaaggtg ggacgacgt caagtcatca   1140 tggcccttac gagtagggct acacacgtgc tacaatggcg agtacagagg ttgcaaagc   1200 cgcgaggtgg agctaatctc acaaagctcg tcgtagtccg gattggagtc tgcaactcga   1260
```
ctccatgaag tcggaatcgc tagtaatcgt ggatcagaat gccacggtga atacgttccc    1320
gggccttgta cacaccgccc gtcacaccat gggagtgggc tgcaaaagaa gtgggtagct    1380
taaccttcgg gggggcgctc accactt                                        1407

<210> SEQ ID NO 6
<211> LENGTH: 1425
<212> TYPE: DNA
<213> ORGANISM: Shewanella algae

<400> SEQUENCE: 6
gctacacatg caagtcgagc ggtaacattt caaaagcttg cttttgaaga tgacgagcgg     60
cggacgggtg agtaatgcct gggaatttgc ccatttgtgg gggataacag ttggaaacga    120
ctgctaatac cgcatacgcc ctacggggga aagcagggga acttcgggcc ttgcgctgat    180
ggataagccc aggtgggatt agctagtagg tgaggtaatg gctcacctag caacgatcc     240 ctagctggtc tgagaggatg atcagccaca ctgggactga gacacggccc agactcctac    300
gggaggcagc agtggggaat attgcacaat ggggaaacc tgatgcagc catgccgcgt      360 gtgtgaagaa ggccttcggg ttgtaaagca ctttcagcga ggaggaaagg gtgtaagtta    420
ataccttaca tctgtgacgt tactcgcaga agaagcaccg gctaactccg tgccagcagc    480
cgcggtaata cggagggtgc gagcgttaat cggaattact gggcgtaaag cgtgcgcagg    540
cggtttgtta agcagatgt gaaagccccg ggctcaacct gggaaccgca tttcgaactg     600
gcaaactaga gtcttgtaga gggggtaga attccaggtg tagcggtgaa atgcgtagag     660
atctggagga ataccggtgg cgaatgcggc ccctggaca aagactgacg ctcaagcacg     720
aaagcgtggg gagcaaacag gattagatac cctggtagtc cacgccgtaa acgatgtcta    780
ctcggagttt ggtgtcttga acactgggct ctcaagctaa cgcattaagt agaccgcctg    840
gggagtacgg ccgcaaggtt aaaactcaaa tgaattgacg ggggcccgca caagcggtgg    900
agcatgtggt ttaattcgat gcaacgcgaa gaaccttacc tactcttgac atccagagaa    960 cttt ccagag atggattggt gccttcggga actctgagac aggtgctgca tggctgtcgt   1020
cagctcgtgt tgtgaaatgt tgggttaagt cccgcaacga gcgcaacccc tatccttact   1080
tgccagcggg taatgccggg aactttaggg agactgccgg tgataaaccg gaggaaggtg   1140
gggacgacgt caagtcatca tggcccttac gagtagggct acacacgtgc tacaatggtc   1200
ggtacagagg gttgcgaagc cgcgaggtgg agctaatctc ataaagccgg tcgtagtccg    1260
gattggagtc tgcaactcga ctccatgaag tcggaatcgc tagtaatcgt ggatcagaat    1320
gccacggtga atacgttccc gggccttgta cacaccgccc gtcacaccat gggagtgggc    1380
tgcaccagaa gtagatagct taaccttcgg gagggcgtta ccacg                    1425

<210> SEQ ID NO 7
<211> LENGTH: 1401
<212> TYPE: DNA
<213> ORGANISM: unknown
<220> FEATURE:
<223> OTHER INFORMATION: Shewanella species strain C13-M

<400> SEQUENCE: 7
tcgagcggta acatttcaaa agcttgcttt tgaagatgac gagcggcgga cgggtgagta     60
atgcctggga atttgcccat ttgtggggga taacagttgg aaacgactgc taataccgca    120
tacgccctac gggggaaagc aggggaactt cggtccttgc gctgatggat aagcccaggt    180
gggattagct agtaggtgag gtaatggctc acctaggcga cgatccctag ctggtctgag    240

```
aggatgatca gccacactgg gactgagaca cggcccagac tcctacggga ggcagcagtg    300
gggaatattg cacaatgggg gaaaccctga tgcagccatg ccgcgtgtgt gaagaaggcc    360 ttcggggttgt aaagcacttt cagcgaggag gaaaggttag tagttaatac ctgctatctg    420
tgacgttact cgcagaagaa gcaccggcta actccgtgcc agcagccgcg gtaatacgga    480
gggtgcgagc gttaatcgga attactgggc gtaaagcgtg cgcaggcggt tgttaagcg    540 agatgtgaaa gccccgggct caacctggga accgcatttc gaactggcaa actagagtct    600
tgtagagggg ggtagaattc caggtgtagc ggtgaaatgc gtagagatct ggaggaatac    660
cggtggcgaa ggcggccccc tggacaaaga ctgacgctca ggcacgaaag cgtggggagc    720
aaacaggatt agatacccctg gtagtccacg ccgtaaacga tgtctactcg gagtttggtg    780
tcttgaacac tgggctctca agctaacgca ttaagtagac cgcctgggga gtacggccgc    840
aaggttaaaa ctcaaatgaa ttgacggggg cccgcacaag cggtggagca tgtggtttaa    900
ttcgatgcaa cgcgaagaac cttacctact cttgacatcc tcagaagcca gcggagacgc    960
aggtgtgcct tcgggaactg agagacaggt gctgcatggc tgtcgtcagc tcgtgttgtg    1020
aaatgttggg ttaagtcccg caacgagcgc aaccccctatc cttacttgcc agcgggtaat    1080
gccgggaact ttagggagac tgccggtgat aaaccggagg aaggtgggga cgacgtcaag    1140
tcatcatggc ccttacgagt agggctacac acgtgctaca atggtcggta cagagggttg    1200
cgaagccgcg aggtggagct aatctcataa agccggtcgt agtccggatt ggagtctgca    1260
actcgactcc atgaagtcgg aatcgctagt aatcgtggat cagaatgcca cggtgaatac    1320
gttcccgggc cttgtacaca ccgcccgtca caccatggga gtgggctgca ccagaagtag    1380
atagcttaac cttcgggagg g                                                1401

<210> SEQ ID NO 8
<211> LENGTH: 1410
<212> TYPE: DNA
<213> ORGANISM: unknown
<220> FEATURE:
<223> OTHER INFORMATION: Shewanella species C31

<400> SEQUENCE: 8
gtcgagcggt aacatttcaa aagcttgctt ttgaagatga cgagcggcgg acgggtgagt    60
aatgcctggg aatttgccca tttgtggggg ataacagttg gaaacgactg ctaataccgc    120
atacgcccta cggggaaag caggggaact tcggtccttg cgctgatgga taagcccagg    180
tgggattagc tagtaggtga ggtaatggct caccctaggcg acgatccccta gctggtctga    240 gaggatgatc agccacactg gactgagac acggcccaga ctcctacggg aggcagcagt    300
ggggaatatt gcacaatggg ggaaaccctg atgcagccat gccgcgtgtg tgaagaaggc    360 cttcggggttg taaagcactt tcagcgagga ggaaaggttg gtagttaata cctgctagct    420
gtgacgttac tcgcagaaga agcaccggct aactccgtgc cagcagccgc ggtaatacgg    480
agggtgcgag cgttaatcgg aattactggg cgtaaagcgt gcgcaggcgg tttgttaagc    540
gagatgtgaa agccccgggc tcaacctggg aaccgcatttt cgaactggca aactagagtc    600 ttgtagagggg ggtagaattt ccaggtgtag cggtgaaatg cgtagagatc tggaggaata    660
ccggtggcga aggcggcccc ctggacaaag actgacgctc aggcacgaaa gcgtggggag    720
caaacaggat tagatacccct ggtagtccac gccgtaaacg atgtctactc ggagtttggt    780
gtcttgaaca ctgggctctc aagctaacgc attaagtaga ccgcctgggg agtacggggcc    840
```

```
gcaaggttaa aactcaaatg aattgacggg ggcccgcaca agcggtggag catgtggttt      900
aattcgatgc aacgcgaaga accttaccta ctcttgacat cctcagaagc cagcggagac      960
gcaggtgtgc cttcgggaac tgagagacag gtgctgcatg gctgtcgtca gctcgtgttg     1020
tgaaatgttg ggttaagtcc cgcaacgagc gcaacccta tccttacttg ccagcgggta      1080
atgccgggaa ctttagggag actgccggtg ataaaccgga ggaaggtggg gacgacgtca     1140
agtcatcatg gcccttacga gtagggctac acacgtgcta caatggtcgg tacagagggt     1200
tgcgaagccg cgaggtggag ctaatctcat aaagccggtc gtagtccgga ttggagtctg     1260
caactcgact ccatgaagtc ggaatcgcta gtaatcgtgg atcagaatgc cacggtgaat     1320
acgttcccgg gccttgtaca caccgcccgt cacaccatgg gagtgggctg caccagaagt     1380
agatagctta accttcggga gggcgttacc                                      1410
```

<210> SEQ ID NO 9
<211> LENGTH: 1398
<212> TYPE: DNA
<213> ORGANISM: unknown
<220> FEATURE:
<223> OTHER INFORMATION: Shewanella species strain L-10

<400> SEQUENCE: 9

```
gtcgagcggt aacatttcaa aagcttgctt ttgaagatga cgagcggcgg acgggtgagt       60
aatgcctggg aatttgccca tttgtggggg ataacagttg gaaacgactg ctaataccgc      120
atacgcccta cggggaaag caggggaact tcggtccttg cgctgatgga taagcccagg       180
tgggattagc tagtaggtga ggtaatggct caccbaggcr acgatcccta gctggtctga     240
gaggatgatc agccacactg gactgagaca cggcccaga ctcctacggg aggcagcagt      300
ggggaatatt gcacaatggg ggaaaccctg atgcagccat gccgcgtgtg tgaagaaggc     360
cttcgggttg taaagcactt tcagcgagga ggaaaggtta gtagttaata cctgctagct     420
gtgacgttac tcgcagaaga agcaccggct aactccgtgc cagcagccgc ggtaatacgg     480
agggtgcgag cgttaatcgg aattactggg cgtaaagcgt gcgcaggcgg tttgttaagc     540
gagatgtgaa agccccgggc tcaacctggg aaccgcattt cgaactggca aactagagtc     600
ttgtagaggg gggtagaatt ccaggtgtag cggtgaaatg cgtagagatc tggaggaata     660
ccggtggcga aggcggcccc ctggacaaag actgacgctc aggcacgaaa gcgtggggag     720
caaacaggat tagataccct ggtagtccac gccgtaaacg atgtctactc ggagtttggt     780
gtcttgaaca ctgggctctc aagctaacgc attaagtaga ccgcctgggg agtacggccg     840
caaggttaaa actcaaatga attgacgggg gcccgcacaa gcggtggagc atgtggttta     900
attcgatgca acgcgaagaa ccttacctac tcttgacatc ctcagaagcc agcggagacg     960
caggtgtgcc ttcgggaact gagagacagg tgctgcatgg ctgtcgtcag ctcgtgttgt    1020
gaaatgttgg gttaagtccc gcaacgagcg caacccctat ccttacttgc cagcgggtaa    1080
tgccgggaac tttagggaga ctgccggtga taaaccggag gaaggtgggg acgacgtcaa    1140
gtcatcatgg cccttacgag tagggctaca cacgtgctac aatggtcggt acagagggtt    1200
gcgaagccgc gaggtggagc taatctcata aagccggtcg tagtccggat tggagtctgc    1260
aactcgactc catgaagtcg gaatcgctag taatcgtgga tcagaatgcc acggtgaata    1320
cgttcccggg ccttgtacac accgcccgtc acaccatggg agtgggctgc accagaagta    1380
gatagcttaa ccttcggg                                                  1398
```

```
<210> SEQ ID NO 10
<211> LENGTH: 1467
<212> TYPE: DNA
<213> ORGANISM: Shewanella chilikensis

<400> SEQUENCE: 10
gtaccttaca gcaaactaca catgcaagtc gagcggtaca tttcaaaagc ttgctttga      60 agatgacgag cggcggacgg gtgagtaatg cctgggaatt tgcccatttg tggggataa    120 cagttggaaa cgactgctaa taccgcatac gccctacggg ggaaagcagg ggaacttcgg   180
tccttgcgct gatggataag cccaggtggg attagctagt aggtgaggta atggctcacc   240
taggcaacga tccctagctg gtctgagagg atgatcagcc acactgggac tgagacacgg   300
cccagactcc tacgggaggc agcagtgggg aatattgcat caatggggga aaccctgatg   360
cagccatgcc gcgtgtgtga agaaggcctt cgggttgtaa agcactttca gcaggagga   420 aaggttagta gttaatacct gctagctgtg acgttactcg cagaagaagc accggctaac   480
tccgtgccag cagccgcggt aatacggagg gtgcgagcgt taatcggaat tactgggcgt   540
aaagcgtgcg caggcggttt gttaagcgag atgtgaaagc cccgggctca acctgggaac   600
cgcatttcga actggcaaac tagagtcttg tagaggggggg tagaattcca ggtgtagcgg   660
tgaaatgcgt agagatctgg aggaataccg gtggcgaagg cggccccctg gacaaagact   720
gacgctcagg cacgaaaagc gtgggggagc aaacaggtat tagatacct tggtagtcca   780 cgccgtaaac gatgtctact cggagtttgg tgtcttgaac actgggctct caagctaacg   840
cattaagtag accgcctggg gagtacggcc gcaaggttaa aactcaaatg aattgacggg   900
ggcccgcaca agcggtggag catgtggttt aattcgatgc aacgcgaaga accttaccta   960
ctcttgacat cctcagaagc cagcggagac gcaggtgtgc cttcggggaa ctgagagaca  1020
ggtgctgcat ggctgtcgtc agctcgtgtt gtgaaatgtt gggttaagtc cgcaacgag  1080 cgcaacccct atccttactt gccagcgggt aatgccggga actttaggga gactgccggt  1140
gataaaccgg aggaaggtgg ggacgacgtc aagtcatcat ggcccttacg agtagggcta  1200
cacacgtgct acaatggtcg gtacagaggg ttgcgaagcc gcgaggtgga gctaatctca  1260
taaagccggt cgtagtccgg attggagtct gcaactcgac tccatgaagt cggaatcgct  1320
agtaatcgtg gatcagaatg ccacggtgaa tacgttcccg ggccttgtac acaccgcccg  1380
tcacaccatg ggagtgggct gcaccagaag tagatagctt aaccttcggg agggcgttta  1440
ccacggtgtg gttcatgact ggggtga                                      1467

<210> SEQ ID NO 11
<211> LENGTH: 1402
<212> TYPE: DNA
<213> ORGANISM: unknown
<220> FEATURE:
<223> OTHER INFORMATION: Shewanella species clone D004024H07

<400> SEQUENCE: 11
agagtttgat tatggctcag attgaacgct ggcggcaggc ctaacacatg caagtcgagc      60
ggtaacattt caaaagcttg cttttgaaga tgacgagcgg cggacgggtg agtaatgcct    120
gggaatttgc ccatttgtgg gggataacag ttggaaacga ctgctaatac cgcatacgcc    180 ctacgggga aagcagggga acttaggtcc ttgcgctgat ggataagccc aggtgggatt    240
agctagtagg tgaggtaatg gctcacctag gcgacgatcc ctagctggtc tgagaggatg    300
atcagccaca ctgggactga gacacggccc agactcctac gggaggcagc agtggggaat    360
```

```
attgcacaat gggggaaacc ctgatgcagc catgccgcgt gtgtgaagaa ggccttcggg      420
ttgtaaagca ctttcagcga ggaggaaagg ttagtagtta atacctgcta gctgtgacgt      480
tactcgcaga agaagcaccg gctaactccg tgccagcagc cgcggtaata cggagggtgc      540
gagcgttaat cggaattact gggcgtaaag cgtgcgcagg cggtttgtta agcgagatgt      600 gaaagcccocg gctcaacct gggaaccgca tttcgaactg gcaaactaga gtcttgtaga      660 gggggggtaga attccaggtg tagcggtgaa atgcgtagag atctggagga ataccggtgg      720
cgaaggcggc ccctggaca aagactgacg ctcaggcacg aaagcgtggg gagcaaacag      780
gattagatac cctggtagtc cacgccgtaa acgatgtcta ctcggagttt ggtgtcttga      840
acactgggct ctcaagctaa cgcattaagt agaccgcctg gggagtacgg ccgcaaggtt      900
aaaactcaaa tgaattgacg ggggcccgca caagcggtgg agcatgtggt ttaattcgat      960
gcaacgcgaa gaaccttacc tactcttgac atcctcagaa gccagcggag acgcaggtgt     1020
gccttcggga actgagagac aggtgctgca tggctgtcgt cagctcgtgt tgtgaaatgt     1080
tgggttaagt cccgcaacga gcgcaacccc tatccttact gccagcggg taatgccggg     1140 aactttaggg agactgccgg tgataaaccg aggaaggtg gggacgacgt caagtcatca     1200
tggcccttac gagtagggct acacacgtgc tacaatggtc ggtacagagg ttgcgaagc     1260 cgcgaggtgg agctaatctc ataaagccgg tcgtagtccg gattggagtc tgcaactcga     1320
ctccatgaag tcggaatcgc tagtaatcgt ggatcagaat gccacggtga atacgttccc     1380
gggccttgca cacacccccg tc                                              1402

<210> SEQ ID NO 12
<211> LENGTH: 1404
<212> TYPE: DNA
<213> ORGANISM: unknown
<220> FEATURE:
<223> OTHER INFORMATION: Shewanella species strain C16-M

<400> SEQUENCE: 12
agtcgagcgg taacatttca aaagcttgct tttgaagatg acgagcggcg gacgggtgag      60
taatgcctgg gaatttgccc atttgtgggg gataacagtt ggaaacgact gctaataccg     120
catacgccct acggggaaa gcaggggaac ttcggtcctt gcgctgatgg ataagcccag     180
gtgggattag ctagtaggtg aggtaatggc tcacctaggc gacgatccct agctggtctg     240
agaggatgat cagccacact gggactgaga cacggcccag actcctacgg gaggcagcag     300 tgggaatat tgcacaatgg gggaaacct gatgcagcca tgccgcgtgt gtgaagaagg     360
ccttcgggtt gtaaagcact ttcagcgagg aggaaaggtt agtagttaat acctgctagc     420
tgtgacgtta ctcgcagaag aagcaccggc taactccgtg ccagcagccg cggtaatacg     480
gagggtgcga gcgttaatcg gaattactgg gcgtaaagcg tgcgcaggcg gtttgttaag     540
cgagatgtga aagccccggg ctcaacctgg gaaccgcatt tcgaactggc aaactagagt     600
cttgtagagg gggtagaat tccaggtgta gcggtgaaat gcgtagagat ctggaggaat     660
accggtggcg aaggcggccc cctggacaaa gactgacgct caggcacgaa agcgtgggga     720
gcaaacagga ttagataccc tggtagtcca cgccgtaaac gatgtctact cggagtttgg     780
tgtcttgaac actgggctct caagctaacg cattaagtag accgcctggg gagtacggcc     840
gcaaggttaa aactcaaatg aattgacggg ggcccgcaca agcggtggag catgtggttt     900
aattcgatgc aacgcgaaga accttaccta ctcttgacat cctcagaagc cagcggagac     960
gcaggtgtgc cttcgggaac tgagagacag gtgctgcatg gctgtcgtca gctcgtgttg    1020
```

| | |
|---|---|
| tgaaatgttg ggttaagtcc cgcaacgagc gcaaccccta tccttacttg ccagcgggta | 1080 |
| atgccgggaa ctttagggag actgccggtg ataaaccgga ggaaggtggg gacgacgtca | 1140 |
| agtcatcatg gcccttacga gtagggctac acacgtgcta caatggtcgg tacagagggt | 1200 |
| tgcgaagccg cgaggtggag ctaatctcat aaagccggtc gtagtccgga ttggagtctg | 1260 |
| caactcgact ccatgaagtc ggaatcgcta gtaatcgtgg atcagaatgc cacggtgaat | 1320 |
| acgttcccgg gccttgtaca caccgcccgt cacaccatgg gagtgggctg caccagaagt | 1380 |
| agatagctta accttcggga gggc | 1404 |

<210> SEQ ID NO 13
<211> LENGTH: 71
<212> TYPE: DNA
<213> ORGANISM: unknown
<220> FEATURE:
<223> OTHER INFORMATION: Shewanella species L3:3

<400> SEQUENCE: 13

| | |
|---|---|
| actttcagcg aggaggaaag gttagtagtt aatacctgct agctgtgacg ttactcgcag | 60 |
| aagaagcacc g | 71 |

<210> SEQ ID NO 14
<211> LENGTH: 51
<212> TYPE: DNA
<213> ORGANISM: unknown
<220> FEATURE:
<223> OTHER INFORMATION: Shewanella species L3:3

<400> SEQUENCE: 14

| | |
|---|---|
| catcctcaga agccagcgga gacgcaggtg tgccttcggg aactgagaga c | 51 |

<210> SEQ ID NO 15
<211> LENGTH: 931
<212> TYPE: DNA
<213> ORGANISM: unknown
<220> FEATURE:
<223> OTHER INFORMATION: Shewanella species EH60:12

<400> SEQUENCE: 15

| | |
|---|---|
| ggtaatacgg agggtgcgag cgttaatcgg aatactggcg taaagcgtgc gcaggcggtt | 60 |
| tgttaagcga gatgtgaaag ccccgggctc aacctgggaa ccgcatttcg aactggcaaa | 120 |
| ctagagtctt gtagaggggg gtagaattcc aggtgtagcg gtgaaatgcg tagagatctg | 180 |
| gaggaatacc ggtggcgaag gcggccccct ggacaaagac tgacgctcag gcacgaaagc | 240 |
| gtggggagca aacaggatta gataccctgg tagtccacgc cgtaaacgat gtctactcgg | 300 |
| agtttggtgt cttgaacact gggctctcaa gctaacgcat taagtagacc gcctgggag | 360 |
| tacggccgca aggttaaaac tcaaatgaat tgacggggc ccgcacaagc ggtggagcat | 420 |
| gtggtttaat tcgatgcaac gcgaagaacc ttacctactc ttgacatcct cagaagccag | 480 |
| cggagacgca ggtgtgcctt cgggaactga gagacaggtg ctgcatggct gtcgtcagct | 540 |
| cgtgttgtga atgttgggt taagtcccgc aacgagcgca accctatcc ttacttgcca | 600 |
| gcgggtaatg ccgggaactt tagggagact gccggtgata aaccgagga aggtggggac | 660 |
| gacgtcaagt catcatggcc cttacgagta gggctacaca cgtgctacaa tggtcggtac | 720 |
| agagggttgc gaagccgcga ggtggagcta atctcataaa gccggtcgta gtccggattg | 780 |
| gagtctgcaa ctcgactcca tgaagtcgga atcgctagta atcgtggatc agaatgccac | 840 |

```
ggtgaatacg ttcccgggcc ttgtacacac cgcccgtcac accatgggag tgggctgcac      900
cagaagtaga tagcttaacc ttcgggaggg c                                    931
```

<210> SEQ ID NO 16
<211> LENGTH: 928
<212> TYPE: DNA
<213> ORGANISM: unknown
<220> FEATURE:
<223> OTHER INFORMATION: Shewanella species EH60:10

<400> SEQUENCE: 16

```
ggttattcgg aggtgcgact ttatcgtaat tactgggcga aagcgtgcgc aggcgtttgt       60
ttagcgagat gtgaaagccc cgggctcaac ttgggaaccg catttcgaac tggcaaacta      120
gagtcttgta gaggggggta gaattccagg tgtagcggtg aaatgcgtag agatctggag      180
gaataccggt ggcgaaggcg ccccctggac aaagactga cgctcaggca cgaaagcgtg      240
gggagcaaac aggattagat accctggtag tccacgccgt aaacgatgtc tactcggagt      300
ttggtgtctt gaacactggg ctctcaagct aacgcattaa gtagaccgcc tggggagtac      360
ggccgcaagg ttaaaactca aatgaattga cggggcccg cacaagcggt ggagcatgtg      420
gtttaattcg atgcaacgcg aagaacctta cctactcttg acatcctcag aagccagcgg      480
agacgcaggt gtgccttcgg gaactgagag acaggtgctg catggctgtc gtcagctcgt      540
gttgtgaaat gttgggttaa gtcccgcaac gagcgcaacc cctatcctta cttgccagcg      600
ggtaatgccg ggaactttag ggagactgcc ggtgataaac cggaggaagg tggggacgac      660
gtcaagtcat catggccctt acgagtaggg ctacacacgt gctacaatgg tcggtacaga      720
gggttgcgaa gccgcgaggt ggagctaatc tcataaagcc ggtcgtagtc cggattggag      780
tctgcaactc gactccatga agtcggaatc gctagtaatc gtggatcaga atgccacggt      840
gaatacgttc ccgggccttg tacacaccgc ccgtcacacc atgggagtgg gctgcaccag      900
aagtagatag cttaacccttc ggagggc                                        928
```

<210> SEQ ID NO 17
<211> LENGTH: 929
<212> TYPE: DNA
<213> ORGANISM: unknown
<220> FEATURE:
<223> OTHER INFORMATION: Shewanella species EH60:2

<400> SEQUENCE: 17

```
ggtaatcgga gggtgcgagc gttaatcgga attacgggcg taaagcgtgc gcaggcggtt       60
tgttaagcga gatgtgaaag ccccgggctc aaccgggaac cgcattcgaa ctggcaaact      120
agagtcttgt agaggggggt agaattccag gtgtagcggt gaaatgcgta gagatctgga      180
ggaataccgg tggcgaaggc ggccccctgg acaaagactg acgctcaggc acgaaagcgt      240
ggggagcaaa caggattaga taccctggta gtccacgccg taaacgatgt ctactcggag      300
tttggtgtct tgaacactgg gctctcaagc taacgcatta agtagaccgc ctggggagta      360
cggccgcaag gttaaaactc aaatgaattg acggggccc gcacaagcgg tggagcatgt      420
ggtttaattc gatgcaacgc gaagaacctt acctactctt gacatcctca gaagccagcg      480
gagacgcagg tgtgccttcg ggaactgaga gacaggtgct gcatggctgt cgtcagctcg      540
tgttgtgaaa tgttgggtta agtcccgcaa cgagcgcaac ccctatcctt acttgccagc      600
gggtaatgcc gggaacttta gggagactgc cggtgataaa ccggaggaag gtggggacga      660
cgtcaagtca tcatggccct tacgagtagg gctacacacg tgctacaatg gtcggtacag      720
```
agggttgcga agccgcgagg tggagctaat ctcataaagc cggtcgtagt ccggattgga    780
gtctgcaact cgactccatg aagtcggaat cgctagtaat cgtggatcag aatgccacgg    840
tgaatacgtt cccgggcctt gtacacaccg cccgtcacac catgggagtg ggctgcacca    900
gaagtagata gcttaacctt cgggagggc                                      929

<210> SEQ ID NO 18
<211> LENGTH: 34
<212> TYPE: DNA
<213> ORGANISM: Shewanella oneidensis

<400> SEQUENCE: 18
gcatacgccc tacgggggaa agaggggac tttc                                  34

<210> SEQ ID NO 19
<211> LENGTH: 34
<212> TYPE: DNA
<213> ORGANISM: artificial sequence
<220> FEATURE:
<223> OTHER INFORMATION: Shewanella 16S rDNA degenerate signature
      sequence with variable positions in region 2
<220> FEATURE:
<221> NAME/KEY: misc_feature
<222> LOCATION: (22)..(24)
<223> OTHER INFORMATION: n=a or g
<220> FEATURE:
<221> NAME/KEY: misc_feature
<222> LOCATION: (29)..(29)
<223> OTHER INFORMATION: n=a or c
<220> FEATURE:
<221> NAME/KEY: misc_feature
<222> LOCATION: (30)..(30)
<223> OTHER INFORMATION: n=a,,c, g, or t
<220> FEATURE:
<221> NAME/KEY: misc_feature
<222> LOCATION: (30)..(30)
<223> OTHER INFORMATION: n=a, c, g, or t
<220> FEATURE:
<221> NAME/KEY: misc_feature
<222> LOCATION: (31)..(32)
<223> OTHER INFORMATION: n=t or c
<220> FEATURE:
<221> NAME/KEY: misc_feature
<222> LOCATION: (34)..(34)
<223> OTHER INFORMATION: n=a or c

<400> SEQUENCE: 19
gcatacgccc tacgggggaa annnggggnn nntn                                 34

<210> SEQ ID NO 20
<211> LENGTH: 41
<212> TYPE: DNA
<213> ORGANISM: Shewanella oneidensis

<400> SEQUENCE: 20
tcggagtttg gtgtcttgaa cactgggctc tcaagctaac g                         41

<210> SEQ ID NO 21
<211> LENGTH: 41
<212> TYPE: DNA
<213> ORGANISM: artificial sequence
<220> FEATURE:
<223> OTHER INFORMATION: Shewanella 16S rDNA degenerate signature
      sequence with variable positions in region 5
<220> FEATURE:
<221> NAME/KEY: misc_feature
<222> LOCATION: (6)..(6)
<223> OTHER INFORMATION: n=a or g
<220> FEATURE:

```
<221> NAME/KEY: misc_feature
<222> LOCATION: (13)..(13)
<223> OTHER INFORMATION: n=a , c or g
<220> FEATURE:
<221> NAME/KEY: misc_feature
<222> LOCATION: (14)..(14)
<223> OTHER INFORMATION: n=a , c or t
<220> FEATURE:
<221> NAME/KEY: misc_feature
<222> LOCATION: (18)..(19)
<223> OTHER INFORMATION: n=a or g
<220> FEATURE:
<221> NAME/KEY: misc_feature
<222> LOCATION: (27)..(27)
<223> OTHER INFORMATION: n=g or t
<220> FEATURE:
<221> NAME/KEY: misc_feature
<222> LOCATION: (28)..(28)
<223> OTHER INFORMATION: n=t or c
<220> FEATURE:
<221> NAME/KEY: misc_feature
<222> LOCATION: (30)..(31)
<223> OTHER INFORMATION: n=t or c
<220> FEATURE:
<221> NAME/KEY: misc_feature
<222> LOCATION: (32)..(32)
<223> OTHER INFORMATION: n=a or c

<400> SEQUENCE: 21 tcgganttg gtnncttnna cactggnntn nnaagctaac g                 41

<210> SEQ ID NO 22
<211> LENGTH: 96
<212> TYPE: DNA
<213> ORGANISM: Shewanella oneidensis

<400> SEQUENCE: 22
acaatggcga gtacagaggg ttgcaaagcc gcgaggtgga gctaatctca caaagctcgt      60
cgtagtccgg attggagtct gcaactcgac tccatg                               96

<210> SEQ ID NO 23
<211> LENGTH: 96
<212> TYPE: DNA
<213> ORGANISM: artificial sequence
<220> FEATURE:
<223> OTHER INFORMATION: Shewanella 16S rDNA degenerate signature
      sequence with variable positions in region 8
<220> FEATURE:
<221> NAME/KEY: misc_feature
<222> LOCATION: (8)..(8)
<223> OTHER INFORMATION: n=c, g, or t
<220> FEATURE:
<221> NAME/KEY: misc_feature
<222> LOCATION: (9)..(9)
<223> OTHER INFORMATION: n=a, c, or g
<220> FEATURE:
<221> NAME/KEY: misc_feature
<222> LOCATION: (10)..(11)
<223> OTHER INFORMATION: n=a, g, or t
<220> FEATURE:
<221> NAME/KEY: misc_feature
<222> LOCATION: (25)..(25)
<223> OTHER INFORMATION: n=a or g
<220> FEATURE:
<221> NAME/KEY: misc_feature
<222> LOCATION: (33)..(33)
<223> OTHER INFORMATION: n=a or g
<220> FEATURE:
<221> NAME/KEY: misc_feature
<222> LOCATION: (38)..(38)
<223> OTHER INFORMATION: n=g or c
<220> FEATURE:
<221> NAME/KEY: misc_feature
<222> LOCATION: (39)..(39)
```

```
<223> OTHER INFORMATION: n=a, g, or t
<220> FEATURE:
<221> NAME/KEY: misc_feature
<222> LOCATION: (48)..(48)
<223> OTHER INFORMATION: n=t or c
<220> FEATURE:
<221> NAME/KEY: misc_feature
<222> LOCATION: (51)..(51)
<223> OTHER INFORMATION: n=c, g, or t
<220> FEATURE:
<221> NAME/KEY: misc_feature
<222> LOCATION: (56)..(56)
<223> OTHER INFORMATION: n=c, g, or t
<220> FEATURE:
<221> NAME/KEY: misc_feature
<222> LOCATION: (57)..(57)
<223> OTHER INFORMATION: n=a, c, or t
<220> FEATURE:
<221> NAME/KEY: misc_feature
<222> LOCATION: (58)..(58)
<223> OTHER INFORMATION: n=c, g, or t
<220> FEATURE:
<221> NAME/KEY: misc_feature
<222> LOCATION: (73)..(73)
<223> OTHER INFORMATION: n=t or c
<220> FEATURE:
<221> NAME/KEY: misc_feature
<222> LOCATION: (94)..(94)
<223> OTHER INFORMATION: n=a or g

<400> SEQUENCE: 23
acaatggnnn ntacagaggg ttgcnaagcc gcnaggtnna gctaatcnca naaagnnngt    60
cgtagtccgg atnggagtct gcaactcgac tccntg                             96

<210> SEQ ID NO 24
<211> LENGTH: 1426
<212> TYPE: DNA
<213> ORGANISM: Shewanella algae

<400> SEQUENCE: 24
aggcctaaca catgcagtcg agcggtaaca tttcaaagct tgcttttgaa gatgacgagc    60
ggcggacggg tgagtaatgc ctgggaattt gcccatttgt gggggataac agttggaaac   120
gactgctaat accgcatacg ccctacgggg aaagcaggg gaacttcggt ccttgcgctg    180
atggataagc ccaggtggga ttagctagta ggtgaggtaa tggctcacct aggcaacgat   240
ccctagctgg tctgagagga tgatcagcca cactgggact gagacacggc ccagactcct   300
acgggaggca gcagtgggga atattgcaca atgggggaaa ccctgatgca gccatgccgc   360
gtgtgtgaag aaggccttcg ggttgtaaag cactttcagc gaggaggaaa gggtgtaagt   420 taataccta catctgtgac gttactcgca gaagaagcac cggctaactc cgtgccagca   480
gccgcggtaa tacggagggt gcgagcgtta atcggaatta ctgggcgtaa agcgtgcgca   540 ggcggttgt taagcgagat gtgaaagccc cgggctcaac ctgggaaccg catttcgaac   600
tggcaaacta gagtcttgta gagggggta gaattccagg tgtagcggtg aaatgcgtag   660
agatctggag gaataccggt ggcgaaggcg ccccctgga caaagactga cgctcaggca   720
cgaaagcgtg gggagcaaac aggattagat accctggtag tccacgccgt aaacgatgtc   780
tactcggagt ttggtgtctt gaacactggg ctctcaagct aacgcattaa gtagaccgcc   840
tggggagtac ggccgcaagg ttaaaactca atgaattga cggggcccg cacaagcggt    900 ggagcatgtg gtttaattcg atgcaacgcg aagaacctta cctactcttg acatccagag   960
aactttccag agatggattg gtgccttcgg gaactctgag acaggtgctg catggctgtc  1020
gtcagctcgt gttgtgaaat gttgggttaa gtcccgcaac gagcgcaacc cctatcctta  1080
```

-continued

```
cttgccagcg ggtaatgccg ggaactttag ggagactgcc ggtgataaac cggaggaagg    1140
tggggacgac gtcaagtcat catggccctt acgagtaggg ctacacacgt gctacaatgg    1200
tcggtacaga gggttgcgaa gccgcgaggt ggagctaatc tcataaagcc ggtcgtagtc    1260
cggattggag tctgcaactc gactccatga agtcggaatc gctagtaatc gtggatcaga    1320
atgccacggt gaatacgttc ccgggccttg tacacaccgc ccgtcacacc atgggagtgg    1380
gctgcaccag aagtagatag cttaaccttc gggagggcgt taccac                  1426
```

<210> SEQ ID NO 25
<211> LENGTH: 34
<212> TYPE: DNA
<213> ORGANISM: artificial sequence
<220> FEATURE:
<223> OTHER INFORMATION: Shewanella 16S rDNA degenerate signature
      sequence with variable positions in region 2
<220> FEATURE:
<221> NAME/KEY: misc_feature
<222> LOCATION: (22)..(22)
<223> OTHER INFORMATION: n=a or g
<220> FEATURE:
<221> NAME/KEY: misc_feature
<222> LOCATION: (23)..(23)
<223> OTHER INFORMATION: n=a or g or c
<220> FEATURE:
<221> NAME/KEY: misc_feature
<222> LOCATION: (24)..(24)
<223> OTHER INFORMATION: n=a or g
<220> FEATURE:
<221> NAME/KEY: misc_feature
<222> LOCATION: (29)..(29)
<223> OTHER INFORMATION: n=a or c
<220> FEATURE:
<221> NAME/KEY: misc_feature
<222> LOCATION: (30)..(30)
<223> OTHER INFORMATION: n=a,,c, g, or t
<220> FEATURE:
<221> NAME/KEY: misc_feature
<222> LOCATION: (30)..(30)
<223> OTHER INFORMATION: n=a, c, g, or t
<220> FEATURE:
<221> NAME/KEY: misc_feature
<222> LOCATION: (31)..(32)
<223> OTHER INFORMATION: n=t or c
<220> FEATURE:
<221> NAME/KEY: misc_feature
<222> LOCATION: (34)..(34)
<223> OTHER INFORMATION: n=a or c

<400> SEQUENCE: 25

```
gcatacgccc tacgggggaa annnggggnn nntn                                34
```

<210> SEQ ID NO 26
<211> LENGTH: 1513
<212> TYPE: DNA
<213> ORGANISM: Shewenella algae

<400> SEQUENCE: 26

```
cagccccagg ttcccctagg gctaccttgt atacgacttc accccagtca tgaaccacac     60
cgtggtaaac gccctcccga aggttaagct atctacttct ggtgcagccc actcccatgg    120
tgtgacgggc ggtgtgtaca aggcccggga acgtattcac cgtggcattc tgatccacga    180
ttactagcga ttccgacttc atggagtcga gttgcagact ccaatccgga ctacgaccgg    240
ctttatgaga ttagctccac ctcgcggctt cgcaaccctc tgtaccgacc attgtagcac    300
gtgtgtagcc ctactcgtaa gggccatgat gacttgacgt cgtccccacc ttcctccggt    360
ttatcaccgg cagtctccct aaagttcccg gcattacccg ctggcaagta aggataggg    420
```

```
ttgcgctcgt tgcgggactt aacccaacat ttcacaacac gagctgacga cagccatgca        480
gcacctgtct cagagttccc gaaggcacca atccatctct ggaaagttct ctggatgtca        540
agagtaggta aggttcttcg cgttgcatcg aattaaacca catgctccac cgcttgtgcg        600
ggcccccgtc aattcatttg agttttaacc ttgcggccgt actccccagg cggtctactt        660
aatgcgttag cttgagagcc cagtgttcaa gacaccaaac tccgagtaga catcgtttac        720
ggcgtggact accagggtat ctaatcctgt ttgctcccca cgctttcgtg cctgagcgtc        780
agtctttgtc caggggggccg ccttcgccac cggtattcct ccagatctct acgcatttca        840
ccgctacacc tggaattcta ccccctcta caagactcta gtttgccagt tcgaaatgcg        900
gttcccaggt tgagcccggg gctttcacat ctcgcttaac aaaccgcctg cgcacgcttt        960
acgcccagta attccgatta acgctcgcac cctccgtatt accgcggctg ctggcacgga       1020
gttagccggt gcttcttctg cgagtaacgt cacagatgta aggtattaac ttacacccctt      1080 tcctcctcgc tgaaagtgct ttacaacccg aaggccttct tcacacacgc ggcatggctg       1140
catcagggtt tcccccattg tgcaatattc cccactgctg cctcccgtag gagtctgggc       1200
cgtgtctcag tcccagtgtg gctgatcatc ctctcagacc agctagggat cgttgcctag       1260
gtgagccatt acctcaccta ctagctaatc ccacctgggc ttatccatca gcgcaaggac       1320
cgaaggtccc ctgctttccc ccgtagggcg tatgcggtat tagcagtcgt ttccaactgt       1380
tatcccccac aaatgggcaa attcccaggc attactcacc cgtccgccgc tcgtcatctt       1440
caaaagcaag cttttgaaat gttaccgctc gacttgcatg tgttaggcct gccgccagcg       1500
ttcaatctga gca                                                          1513

<210> SEQ ID NO 27
<211> LENGTH: 1538
<212> TYPE: DNA
<213> ORGANISM: Shewenella algae
<220> FEATURE:
<221> NAME/KEY: misc_feature
<222> LOCATION: (11)..(12)
<223> OTHER INFORMATION: n is a, c, g, or t

<400> SEQUENCE: 27
agagtttgat nntggctcag attgaacgct ggcggcaggc ctaacacatg caagtcgagc         60
ggtaacattt caaaagcttg cttttgaaga tgacgagcgg cggacgggtg agtaatgcct        120
gggaatttgc ccatttgtgg gggataacag ttggaaacga ctgctaatac cgcatacgcc        180
ctacggggga aagcagggga ccttcgggcc ttgcgctgat ggataagccc aggtgggatt        240
agctagtagg tgaggtaatg gctcacctag gcaacgatcc ctagctggtc tgagaggatg        300
atcagccaca ctgggactga gacacggccc agactcctac gggaggcagc agtgggaat        360 attgcacaat gggggaaacc ctgatgcagc catgccgcgt gtgtgaagaa ggccttcggg        420
ttgtaaagca ctttcagcga ggaggaaagg gtgtaagtta atccttacac tctgtgacgt        480
tactcgcaga agaagcaccg gctaactccg tgccagcagc cgcggtaata cggagggtgc        540
gagcgttaat cggaattact gggcgtaaag cgtgcgcagg cggtttgtta agcgagatgt        600
gaaagccccg ggctcaacct gggaaccgca tttcgaactg gcaaactaga gtcttgtaga        660 gggggtaga attccaggtg tagcggtgaa atgcgtagag atctggagga ataccggtgg        720
cgaaggcggc cccctggaca agactgacg ctcaggcacg aaagcgtggg agcaaacag         780 gattagatac cctggtagtc cacgccgtaa acgatgtcta ctcggagttt ggtgtcttga        840
```

```
acactgggct ctcaagctaa cgcattaagt agaccgcctg gggagtacgg ccgcaaggtt    900
aaaactcaaa tgaattgacg ggggcccgca caagcggtgg agcatgtggt ttaattcgat    960
gcaacgcgaa gaaccttacc tactcttgac atccagagaa ctttccagag atggattggt   1020
gccttcggga actctgagac aggtgctgca tggctgtcgt cagctcgtgt tgtgaaatgt   1080
tgggttaagt cccgcaacga gcgcaacccc tatccttact tgccagcggg taatgccggg   1140
aactttaggg agactgccgg tgataaaccg gaggaaggtg gggacgacgt caagtcatca   1200
tggcccttac gagtagggct acacacgtgc tacaatggtc ggtacagagg gttgcgaagc   1260
cgcgaggtgg agctaatctc ataaagccgg tcgtagtccg gattggagtc tgcaactcga   1320
ctccatgaag tcggaatcgc tagtaatcgt ggatcagaat gccacggtga atacgttccc   1380
gggccttgta cacaccgccc gtcacaccat gggagtgggc tgcaccagaa gtagatagct   1440
taaccttcgg gagggcgttt accacggtgt ggttcatgac tggggtgaag tcgtaacaag   1500
gtagccctag gggaacctgg ggctggatca cctccttt                            1538
```

<210> SEQ ID NO 28
<211> LENGTH: 34
<212> TYPE: DNA
<213> ORGANISM: artificial sequence
<220> FEATURE:
<223> OTHER INFORMATION: Shewanella 16S rDNA degenerate signature
      sequence with variable positions in region 2
<220> FEATURE:
<221> NAME/KEY: misc_feature
<222> LOCATION: (22)..(22)
<223> OTHER INFORMATION: n=a or g
<220> FEATURE:
<221> NAME/KEY: misc_feature
<222> LOCATION: (24)..(24)
<223> OTHER INFORMATION: n=a or g
<220> FEATURE:
<221> NAME/KEY: misc_feature
<222> LOCATION: (29)..(29)
<223> OTHER INFORMATION: n=a or c
<220> FEATURE:
<221> NAME/KEY: misc_feature
<222> LOCATION: (30)..(30)
<223> OTHER INFORMATION: n=a,,c, g, or t
<220> FEATURE:
<221> NAME/KEY: misc_feature
<222> LOCATION: (30)..(30)
<223> OTHER INFORMATION: n=a, c, g, or t
<220> FEATURE:
<221> NAME/KEY: misc_feature
<222> LOCATION: (31)..(32)
<223> OTHER INFORMATION: n=t or c
<220> FEATURE:
<221> NAME/KEY: misc_feature
<222> LOCATION: (34)..(34)
<223> OTHER INFORMATION: n=a or c

<400> SEQUENCE: 28

```
gcatacgccc tacgggggaa ancnggggnn nntn                                  34
```

<210> SEQ ID NO 29
<211> LENGTH: 71
<212> TYPE: DNA
<213> ORGANISM: Shewanella alga

<400> SEQUENCE: 29

```
gcatacgccc tacgggggaa agcagtggaa cttcggtcct tgcgctgatg gataagccca      60
ggtgggatta g                                                           71
```

<210> SEQ ID NO 30

<211> LENGTH: 1438
<212> TYPE: DNA
<213> ORGANISM: Shewanella benthica
<220> FEATURE:
<221> NAME/KEY: misc_feature
<222> LOCATION: (610)..(611)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (816)..(818)
<223> OTHER INFORMATION: n is a, c, g, or t
<220> FEATURE:
<221> NAME/KEY: misc_feature
<222> LOCATION: (1421)..(1421)
<223> OTHER INFORMATION: n is a, c, g, or t

<400> SEQUENCE: 30

| | | | | | |
|---|---|---|---|---|---|
| ttgaacgctg | gcggcaggcc | taacacatgc | aagtcgagcg | gaaacagaaa | gtagcttgct | 60 |
| actttgctgt | cgagcggcgg | acgggtgagt | aatgcctagg | gaactgccca | gtcgagggg | 120 |
| ataacagttg | gaaacgactg | ctaataccgc | atacgcccta | cggggaaag | gagggacct | 180 |
| tcgggccttt | cgcgattgga | tgtacctagg | tgggattagc | tagttggtaa | ggtaatagct | 240 |
| taccaaggcg | acgatcccta | gctggtctga | gaggatgatc | agccacactg | gaactgagac | 300 |
| acggtccaga | ctcctacggg | aggcagcagt | ggggaatatt | gcacaatggg | cgaaagcctg | 360 |
| atgcagccat | gccgcgtgtg | tgaagaaggc | cttcgggttg | taaagcactt | tcagcgagga | 420 |
| ggaaaggttg | tagtttaata | aactgcagct | gtgacgttac | tcgcagaaga | agcaccggct | 480 |
| aacttcgtgc | cagcagccgc | ggtaatacga | ggggtgcaag | cgttaatcgg | aattactggg | 540 |
| cgtaaagcgt | acgcaggcgg | tttgttaagc | aagatgtgaa | agccccgggc | tcaacctggg | 600 |
| aattgcattn | ngaactggca | aactagagtc | ttgtagaggg | gggtagaatt | ccaggtgtag | 660 |
| cggtgaaatg | cgtagagatc | tgaaggaata | ccggtggcga | aggcggcccc | ctggacaaag | 720 |
| actgacgctc | aggtacgaaa | gcgtggggag | caaacaggat | tagataccct | ggtagtccac | 780 |
| gccgtaaacg | atgtctactc | gnantttggt | gtcttnnnca | ctgggttctc | aagctaacgc | 840 |
| attaagtaga | ccgcctgggg | agtacggccg | caaggttaaa | actcaaatga | attgacgggg | 900 |
| gccgcacaag | cggtggagca | tgtggtttaa | ttcgatgcaa | cgcgaagaac | cttacctact | 960 |
| cttgacatcc | acagaactcg | ctagagatag | cttggtgcct | tcgggaactg | tgagacaggt | 1020 |
| gctgcatggc | tgtcgtcagc | tcgtgttgtg | aaatgttggg | ttaagtcccg | caacgagcgc | 1080 |
| aacccttatc | cttatttgcc | agcacgtaat | ggtgggaact | ttagggagac | tgccggtgat | 1140 |
| aaaccggagg | aaggtgggga | cgacgtcaag | tcatcatggc | ccttacgagt | agggctacac | 1200 |
| acgtgctaca | atggtcggta | cagagggtcg | caaagccgcg | aggtctagct | aatcccacaa | 1260 |
| agccggtcgt | agtccggatc | ggagtctgca | actcgactcc | gtgaagtcgg | aatcgctagt | 1320 |
| aatcgtgaat | cagaatgtca | cggtgaatac | gttcccgggc | cttgtacaca | ccgcccgtca | 1380 |
| caccatggga | gtgggctgca | ccagaagtag | atagcttaac | ntcggggagg | gcgtttac | 1438 |

<210> SEQ ID NO 31
<211> LENGTH: 1442
<212> TYPE: DNA
<213> ORGANISM: Shewanella hanedai
<220> FEATURE:
<221> NAME/KEY: misc_feature
<222> LOCATION: (488)..(488)
<223> OTHER INFORMATION: n is a, c, g, or t

<400> SEQUENCE: 31

```
ttgaacgctg gcggcaggcc taacacatgc aagtcgagcg gaaacaggaa rgtagcttgc    60
tactttccgg ctgtcgagcg gcggacgggt gagtaatgcc tagatatctg cctagtcgtg   120
ggggataaca gttggaaacg actgctaata ccgcatacgc cctacggggg aaaggagggg   180
accttcgggc ctttcgcgat tagatgagtc taggtgggat tagctagtag gtgaggtaat   240
ggctcaccta ggcgacgatc cctagctggt ctgagaggat gatcagccac actggaactg   300
agacacggtc cagactccta cgggaggcag cagtggggaa tattgcacaa tgggcgaaag   360
cctgatgcag ccatgccgcg tgtgtgaaga aggccttcgg gttgtaaagc actttcagcg   420
aggaggaaag gtaggtagtt aataactgct tactgtgacg ttactcgcag aagaagcacc   480
ggctaacntc gtgccagcag ccgcggtaat acgaggggtg caagcgttaa tcggaattac   540
tgggcgtaaa gcgtacgcag gcggtttgtt aagccagatg tgaaagccct gggctcaacc   600
taggaattgc atttggaact gacagactag agtcttgtag aggggggtag aatttcaggt   660
gtagcggtga aatgcgtaga gatctgaagg aataccggtg gcgaaggcgg cccctggac   720 aaagactgac gctcatgtac gaaagcgtgg ggagcaaaca ggattagata ccctggtagt   780
ccacgccgta acgatgtct actcggagtt tggtaactta gttactgggc tcccaagcta   840
acgcattaag tagaccgcct ggggagtacg gccgcaaggt taaaactcaa atgaattgac   900
gggggccgca caagcggtgg agcatgtggt ttaattcgat gcaacgcgaa gaaccttacc   960
tactcttgac atccacagaa cttaccagag atggtttggt gccttcggga actgtgagac  1020
aggtgctgca tggctgtcgt cagctcgtgt tgtgaaatgt tgggttaagt cccgcaacga  1080
gcgcaaccct tatccttatt tgccagcgag ttatgtcggg aactttaggg agactgccgg  1140
tgataaaccg gaggaaggtg gggacgacgt caagtcatca tggcccttac gagtagggct  1200
acacacgtgc tacaatggtc ggtacagagg gtcgcaaagc cgcgaggtgg agctaatccc  1260
acaaagccgg tcgtagtccg gatcggagtc tgcaactcga ctccgtgaag tcggaatcgc  1320
tagtaatcgt ggatcagaat gccacggtga atacgttccc gggccttgta cacaccgccc  1380
gtcacaccat gggagtgggc tgcaccagaa gtagatagct taacctttcg gggagggcgt  1440
tt                                                                 1442
```

<210> SEQ ID NO 32
<211> LENGTH: 1536
<212> TYPE: DNA
<213> ORGANISM: Shewanella putrefaciens
<220> FEATURE:
<221> NAME/KEY: misc_feature
<222> LOCATION: (11)..(12)
<223> OTHER INFORMATION: n is a, c, g, or t

<400> SEQUENCE: 32

```
agagtttgat nntggctcag attgaacgct ggcggcaggc ctaacacatg caagtcgagc    60
ggcagcacaa gggagtttac ttctgaggtg gcgagcggcg gacgggtgag taatgcctag   120
ggatctgccc agtcgagggg gataacagtt ggaaacgact gctaataccg catacgccct   180 acggggaaa ggaggggacc ttcgggcctt ccgcgattgg atgaacctag gtgggattag   240
ctagttggtg aggtaatggc tcaccaaggc gacgatccct agctgttctg agaggatgat   300
```

| | |
|---|---:|
| cagccacact gggactgaga cacggcccag actcctacgg gaggcagcag tggggaatat | 360 |
| tgcacaatgg gggaaaccct gatgcagcca tgccgcgtgt gtgaagaagg ccttcgggtt | 420 |
| gtaaagcact ttcagtaggg aggaaagggt gtagcttaat acgctatatc tgtgacgtta | 480 |
| cctacagaag aaggaccggc taactccgtg ccagcagccg cggtaatacg agggtccga | 540 |
| gcgttaatcg gaattactgg gcgtaaagcg tgcgcaggcg gtttgttaag cgagatgtga | 600 |
| aagccctggg ctcaacctag aatagcatt tcgaactggc gaactagagt cttgtagagg | 660 |
| ggggtagaat tccaggtgta gcggtgaaat gcgtagagat ctggaggaat accggtggcg | 720 |
| aaggcggccc cctggacaaa gactgacgct catgcacgaa agcgtgggga gcaaacagga | 780 |
| ttagataccc tggtagtcca cgccgtaaac gatgtctact cggagtttgg tgtcttgaac | 840 |
| actgggctct caagctaacg cattaagtag accgcctggg gagtacggcc gcaaggttaa | 900 |
| aactcaaatg aattgacggg ggcccgcaca agcggtggag catgtggttt aattcgatgc | 960 |
| aacgcgaaga accttaccta ctcttgacat ccacagaact cgccagagat ggcttggtgc | 1020 |
| cttcgggaac tgtgagacag gtgctgcatg gctgtcgtca gctcgtgttg tgaaatgttg | 1080 |
| ggttaagtcc cgcaacgagc gcaacccta tccttatttg ccagcacgta atggtgggaa | 1140 |
| ctctaggag actgccggtg ataaaccgga ggaaggtggg gacgacgtca agtcatcatg | 1200 |
| gcccttacga gtagggctac acacgtgcta caatgcgag tacagagggt tgcaaagccg | 1260 |
| cgaggtggag ctaatctcac aaagctcgtc gtagtccgga ttggagtctg caactcgact | 1320 |
| ccatgaagtc ggaatcgcta gtaatcgtgg atcagaatgc cacggtgaat acgttcccgg | 1380 |
| gccttgtaca caccgcccgt cacaccatgg gagtgggctg caaaagaagt gggtagctta | 1440 |
| accttcgggg gggcgctcac cactttgtgg ttcatgactg gggtgaagtc gtaacaaggt | 1500 |
| agccctaggg gaacctgggg ctggatcacc tcctt | 1536 |

<210> SEQ ID NO 33
<211> LENGTH: 1420
<212> TYPE: DNA
<213> ORGANISM: Shewanella haliotis

<400> SEQUENCE: 33

| | |
|---|---:|
| cctaacacat gcaagtcgag cggtaacatt tcaaaagctt gcttttgaag atgacgagcg | 60 |
| gcggacgggt gagtaatgcc tgggaatttg cccatttgtg ggggataaca gttggaaacg | 120 |
| actgctaata ccgcatacgc cctacggggg aaagcagggg accttcgggc cttgcgctga | 180 |
| tgataagcc caggtgggat tagctagtag gtgaggtaaa ggctcaccta ggcgacgatc | 240 |
| cctagctggt ctgagaggat gatcagccac actgggactg agacacggcc cagactccta | 300 |
| cgggaggcag cagtggggaa tattgcacaa tggggggaaac cctgatgcag ccatgccgcg | 360 |
| tgtgtgaaga aggccttcgg gttgtaaagc actttcagcg aggaggaaag ggtgtaagtt | 420 |
| aataccttac atctgtgacg ttactcgcag aagaagcacc ggctaactcc gtgccagcag | 480 |
| ccgcggtaat acgagggtg cgagcgttaa tcggaattac tgggcgtaaa gcgtgcgcag | 540 |
| gcggttttgtt aagcgagatg tgaaagcccc gggctcaacc tgggaaccgc atttcgaact | 600 |
| ggcaaactag agtcttgtag aggggggtag aattccaggt gtagcggtga atgcgtaga | 660 |
| gatctggagg aataccggtg gcgaaggcgg cccctggac aaagactgac gctcaggcac | 720 |
| gaaagcgtgg ggagcaaaca ggattagata ccctggtagt ccacgccgta acgatgtct | 780 |
| actcggagtt tggtgtcttg aacactgggc tctcaagcta acgcattaag tagaccgcct | 840 |
| ggggagtacg gccgcaaggt taaaactcaa atgaattgac ggggggcccgc acaagcggtg | 900 |

-continued

```
gagcatgtgg tttaattcga tgcaacgcga agaaccttac ctactcttga catccacaga    960
atctggtaga gatacctcag tgccttcggg aactgtgaga caggtgctgc atggctgtcg   1020
tcagctcgtg ttgtgaaatg ttgggttaag tcccgcaacg agcgcaaccc ctatccttac   1080
ttgccagcgg gtaatgccgg gaactttagg gagactgccg gtgataaacc ggaggaaggt   1140
ggggacgacg tcaagtcatc atggccctta cgagtagggc tacacacgtg ctacaatggt   1200
cagtacagag ggttgcgaag ccgcgaggtg gagctaatcc cataaagctg gtcgtagtcc   1260
ggattggagt ctgcaactcg actccatgaa gtcggaatcg ctagtaatcg tggatcagaa   1320
tgccacggtg aatacgttcc cgggccttgt acacaccgcc cgtcacacca tgggagtggg   1380
ctgcaccaga gtagatagc ttaaccttcg ggagggcgtt    1420
```

<210> SEQ ID NO 34
<211> LENGTH: 1500
<212> TYPE: DNA
<213> ORGANISM: Shewanella denitrificans
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t

<400> SEQUENCE: 34

```
aktkaacrct ggnggcaggc cyaanacatg caagtygagc ggcrgcgggr agrtagattr     60
ntanntttgc cggcgagcgg cggacgggtg agtaatgcct agggatytgc ccagtygtgg    120
gggataacag ttggaaacga ctgctaatac cgcatacgcc ctacggggga aggaggggga    180
ccttcgggcc tttcgcgatt ggatgaacct aggtgggatt agctagttgg tgaggtaatg    240
gctcaccaag scgacgatcc ctagytggty tgagaggatg atcagccaca ctggaactga    300
gacacggtcc agacwcctac ggaggcagc agtggggaat attgcacaat ggggaaacc     360 ctgatgcagc catgccgcrt gtgtgaagaa ggccttcggg ttgtaaagca ctttcagtca    420
ggaggaaagg tagcgtgtta atagcaygtt rctgtgacgt tactgacaga agaaggaccg    480
gctaactccg tgccagcagc cgcggtaata cggagggtcc gagcgttaat cggaattact    540
gggcgtaaag cgtgcgcagg cggtttgtta agccagatgt gaaagcccg ggctcaacct    600 gggaattgca tttggaactg gcgaactaga gtcttgtaga gggaggtaga atttcaggtg    660
tagcggtgaa atgcgtarat atctgaagga ataccgtgg cgaaggcggc ctcctggaca    720
aagactgacg ctcatgcacg aaagcgtggg gagcaaacag gattagatac cctggtagtc    780
cacgccgtaa acgatgtcta ctcggagttt ggtgccttga gcactgggct cccaagctaa    840
cgcattaagt araccgcctg gggagtacgg ccgcaaggtt aaaactcaaa tgaattgacg    900
ggggcccgca caagcggtgg agcatgtggt ttaattcgat gcaacgcgaa gaaccttacc    960
tactcttgac atccacagaa gccagcagag atgcaggtgt gccttcggga actgtgagac   1020
aggtgctgca tggctgtcgt cagctcgtgt tgtgaaatgt tgggttaagt cccgcaacga   1080
```

```
gcgcaacccc tatccttatt tgccascacg taatggtggg aactctaggg agactgccgg   1140
tgataaaccg gaggaaggtg gggacgacgt caagtcatca tggcccttac gagtagggct   1200
acacacgtgc tacaatggcg agtacagagg gttgcaaagc cgcgaggtgg agctaatctc   1260
acaaagctcg tcgtagtccg gatcggagtc tgcaactcga ctccgtgaag tcggaatcgc   1320
tagtaatcgt gaatcagaat gtcacggtga atacgttccc gggccttgta cacaccgccc   1380
gtcacaccat gggagtgggy tgcaaaagaa gtgggtagtc taaccttcgg gaggacgctc   1440
accactttgt ggttmatgwc tggggtgaag tcgtaacaag gtagccctag ggaacctgg    1500

<210> SEQ ID NO 35
<211> LENGTH: 1415
<212> TYPE: DNA
<213> ORGANISM: Shewanella basaltis

<400> SEQUENCE: 35
catgcaagtc gagcggcagc acaagggagt ttactcctga ggtggcgagc ggcggacggg     60
tgagtaatgc ctagggatct gcccagtcga ggggataaac agttggaaac gactgctaat    120
accgcatacg ccctacgggg gaaaggaggg gaccttcggg ccttccgcga ttggatgaac    180
ctaggtggga ttagctagtt ggtgaggtaa tggctcacca aggcgacgat ccctagctgt    240
tctgagagga tgatcagcca cactgggact gagacacggc ccagactcct acggggaggca   300 gcagtgggga atattgcaca atgggcgaaa gcctgatgca gccatgccgc gtgtgtgaag    360
aaggccttcg ggttgtaaag cactttcagt agggaggaaa gggtattact taatacgtaa    420
tacctgtgac gttacctaca gaagaaggac cggctaactc cgtgccagca gccgcggtaa    480
tacggagggt ccgagcgtta atcggaatta ctgggcgtaa agcgtgcgca ggcggtttgt    540
taagccagat gtgaaatccc cgggctcaac ctgggaattg catttggaac tggcgaacta    600
gagtcttgta gagggggggta gaattccagg tgtagcggtg aaatgcgtag agatctggag    660
gaataccggt ggcgaaggcg gccccctgga caaagactga cgctcatgca cgaaagcgtg    720
gggagcaaac aggattagat accctggtag tccacgccgt aaacgatgtc tactcggagt    780
ttggtgtctt gaacactggg ctctcaagct aacgcattaa gtagaccgcc tggggagtac    840
ggccgcaagg ttaaaactca aatgaattga cgggggcccg cacaagcggt ggagcatgtg    900
gtttaattcg atgcaacgcg aagaacctta cctactcttg acatccacag aagattgcar    960
agatgcgatt gtgccttcgg gaactggtga gacaggtgct gcatggctgt cgtcagctcg   1020
tgttgtgaaa tgttgggtta agtcccgcaa cgagcgcaac ccctatcctt atttgccagc   1080
acgtaatggt gggaactcta gggagactgc cggtgataaa ccggaggaag gtggggacga   1140
cgtcaagtca tcatggccct tacgagtagg gctacacacg tgctacaatg gcagtacag    1200 agggttgcaa agccgcgagg tggagctaat ctcacaaagc tcgtcgtagt ccggattgga   1260
gtctgcaact cgactccatg aagtcggaat cgctagtaat cgtgaatcag aatgtcacgg   1320
tgaatacgtt cccgggcctt gtacacaccg cccgtcacac catgggagtg ggctgcaaaa   1380
gaagtgggta gtttaacctt cgggagaacg ctcac                              1415

<210> SEQ ID NO 36
<211> LENGTH: 1500
<212> TYPE: DNA
<213> ORGANISM: Shewanella fidelia

<400> SEQUENCE: 36
ttgaacgctg gcggcaggcc taacacatgc aagtcgagcg gtaacacaag ggagcttgct     60
```

```
cctgaggtga cgagcggcgg acgggtgagt aatgcctagg tatctgccca gtcgaggggg      120
ataacagttg gaaacgactg ctaataccgc atacgcccta cggggaaaag gaggggacct      180
tcgggccttc cgcgattgga tgagtctagg tgggattagc tagttggtga ggtaatggct      240
caccaaggcg acgatcccta gctggtctga gaggatgatc agccacactg gaactgagac      300
acggtccaga ctcctacggg aggcagcagt ggggaatatt gcacaatggg cgaaagcctg      360
atgcagccat gccgcgtgtg tgaagaaggc cttcgggttg taaagcactt tcagcgagga      420
ggaaaggtta ctggctaata tccagtagct gtgacgttac tcgcagaaga agcaccggct      480
aacttcgtgc cagcagccgc ggtaatacga gggtgcaag cgttaatcgg aattactggg      540
cgtaaagcgt acgcaggcgg tttgttaagc gagatgtgaa agccccgggc tcaacctggg      600
aactgcattt cgaactggca aactagagtc ttgtagaggg gggtagaatt tcaggtgtag      660
cggtgaaatg cgtagagatc tgaaggaata ccggtggcga aggcggcccc ctggacaaag      720
actgacgctc aggtacgaaa gcgtggggag caaacaggat tagataccct ggtagtccac      780
gccgtaaacg atgtctactc ggagtttggt gtcttgaaca ctgggctctc aagctaacgc      840
attaagtaga ccgcctgggg agtacggccg caaggttaaa actcaaatga attgacgggg      900
gcccgcacaa gcggtggagc atgtggttta attcgatgca acgcgaagaa ccttacctac      960
tcttgacatc ctcagaactt tccagagatg gattggtgcc ttcgggaact gagagacagg     1020
tgctgcatgg ctgtcgtcag ctcgtgttgt gaaatgttgg gttaagtccc gcaacgagcg     1080
caacccttat ccttatttgc cagcacgtaa tggtgggaac tttagggaga ctgccggtga     1140
taaaccggag gaaggtgggg acgacgtcaa gtcatcatgg cccttacgag tagggctaca     1200
cacgtgctac aatggtcggt acagagggtt gcgaagccgc gaggtggagc taatctcaca     1260
aagccggtcg tagtccggat tggagtctgc aactcgactc catgaagtcg gaatcgctag     1320
taatcgtaga tcagaatgct acggtgaata cgttcccggg ccttgtacac accgcccgtc     1380
acaccatggg agtgggctgc accagaagta gatagcttaa ccttcgggag ggcgtttacc     1440
acggtgtggt tcatgactgg ggtgaagtcg taacaaggta gccctagggg aacctgcggc     1500
```

<210> SEQ ID NO 37
<211> LENGTH: 1443
<212> TYPE: DNA
<213> ORGANISM: Shewanella marinus

<400> SEQUENCE: 37

```
tggcggcagg cctaacacat gcaagtcgag cggtaacagg aaagtagctt gctactttg       60 ctgacgagcg gcggacgggt gagtaatgcc tgggaatttg cccatttgtg gggataact      120 actggaaacg gtagctaata ccgcatacgc cctacggggg aaagcagggg agccttykgg     180
tccttgcgct gatggataag cccaggtggg attagctagt tggtgaggta agagctcacc     240
aaggcgacga tccctagctg ttctgagagg atgatcagcc acactgggac tgagacacgg     300
cccagactcc tacgggaggc agcagtgggg aatattgcac aatggggggaa accctgatgc     360 agccatgccg cgtgtgtgaa gaaggccttc gggttgtaaa gcactttcag cgaggaggaa     420
aggttaacgt taatacccg ttagctgtga cgttactcgc agaagaagca ccggctaact     480
ccgtgccagc agccgcggta atacggaggg tgcgagcgtt aatcggaatt actgggcgta     540
aagcgtgcgc aggcggttgg ttaagcgaga tgtgaaagcc ccgggctcaa cctgggaact     600
gcatttcgaa ctggcaaact agagtcttgt agagggggt agaatttcag gtgtagcggt     660
```

```
gaaatgcgta gagatctgaa ggaataccgg tggcgaaggc ggccccctgg acaaagactg    720
acgctcaggc acgaaagcgt ggggagcaaa caggattaga taccctggta gtccacgccg    780
taaacgatgt ctactcggag tttggtgcct tgagcactgg gctctcaagc taacgcatta    840
agtagaccgc ctgggagta cggccgcaag gttaaaactc aaatgaattg acggggggccc    900 gcacaagcgg tggagcatgt ggtttaattc gatgcaacgc gaagaacctt acctactctt    960
gacatccaga gaagttacca gagatggttt cgtgccttcg ggaactctga dacaggtgct   1020
gcatggctgt cgtcagctcg tgttgtgaaa tgttgggtta agtcccgcaa cgagcgcaac   1080
ccttatcctt atttgccagc acgtaatggt gggaactcta gggagactgc cggtgataaa   1140
ccggaggaag gtgggacga cgtcaagtca tcatggccct tacgagtagg gctacacacg   1200
tgctacaatg gtcggtacag agggttgcaa agccgcgagg tggagctaat ctcacaaagc   1260
cggtcgtagt ccggattgga gtctgcaact cgactccatg aagtcggaat cgctagtaat   1320
cgtggatcag aatgccacgg tgaatacgtt cccgggcctt gtacacaccg cccgtcacac   1380
catgggagtg ggctgcacca gaagtagata gcttaacctt cgggagggcg tttaccacgg   1440
tgt                                                                1443
```

```
<210> SEQ ID NO 38
<211> LENGTH: 1505
<212> TYPE: DNA
<213> ORGANISM: Shewanella frigidimarina
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1277)..(1277)
<223> OTHER INFORMATION: n is a, c, g, or t

<400> SEQUENCE: 38
agagtttgat catggctcag attgaacgct ggcggcaggc ctaacacatg caagtcgagc     60
ggtaacacna gggagcttgc tcctgaggtg acgagcggcg gacgggtgag taatgcctag    120
ggatctgccc agtcgagggg gataacagtt ggaaacgact gctaataccg catacgccct    180 acggggaaa ggagggggacc ttcgggcctt ccgcgattgg atgaacctag gtgggattag    240
ctagttggtg aggtaatggc tcaccaaggc gacgatccct agctgttctg agaggatgat    300
cagccacact gggactgaga cacggcccag actcctacgg gaggcagcag tggggaatat    360
tgcacaatgg gggaaaccct gatgcagcca tgccgcgtgt gtgaagaagg ccttcgggtt    420
gtaaagcact ttcagtaggg aggaaaggta atagtttaat aaaatattgc tgtgacgtta    480
cctacagaag aagcaccggc taacttcgtg ccagcagccg cggtaatacg aggggtgcaa    540
gcgttaatcg gaattactgg gcgtaaagcg tgcgcaggcg gtttgttaag ccagatgtga    600
aatccccggg ctcaacctgg gaattgcatt tggaactggc aactagagt cttgtagagg    660 ggggtagaat tccaggtgta gcggtgaaat gcgtagatat ctggaggaat accggtggcg    720
```

-continued

```
aaggcggccc cctggacaaa gactgacgct catgcacgaa agcgtgggga gcaaacagga       780
ttagataccc tggtagtcca cgccgtaaac gatgtctact cggagtttgg tgacttngtc       840
actgggttnc caagctaacg cattaagtag accgcctggg gagtacggcc gcaaggttaa       900
aactcaaatg aattgacggg ggcccgcaca agcggtggag catgtggttt aattcgatgc       960
aacgcgaaga accttaccta ctcttgacat ccacagaaga gaccagagat ggacttgtgc      1020
cttcgggaac tgtgagacag gtgctgcatg gctgtcgtca gctcgtgttg tgaaatgttg      1080
ggttaagtcc cgcaacgagc gcaacccta tccttatttg ccagcacgta atggtgggaa       1140 ctntaggag actgccggtg ataaaccgga ggaaggtggg gacgacgtca agtcatcatg       1200
gcccttacga gtagggctac acacgtgcta caatggcgta tacagagggt tgcaaagccg      1260
cgaggtggag ctaatcncac aaagtacgtc gtagtccgga tcggagtctg caactcgact      1320
ccgtgaagtc ggaatcgcta gtaatcgtgg atcagaatgc cacggtgaat acgttcccgg      1380
gccttgtaca caccgcccgt cacaccatgg gagtgggctg caaaagaagt gggtagttta      1440
acttcgggag aacgctcacc actttgtggt tcatgactgg ggtgaagtcg taacaaggta      1500
gccgt                                                                  1505
```

<210> SEQ ID NO 39
<211> LENGTH: 1507
<212> TYPE: DNA
<213> ORGANISM: Shewanella gelidimarina

<400> SEQUENCE: 39

```
agagtttgat catggctcag attgaacgct ggcggcaggc ctaacacatg caagtcgagc        60
ggtaacacaa gggagcttgc tcctgaggtg acgagcggcg gacgggtgag taataccta       120 gtatctgccc aatcgagggg gataacagtt ggaaacgact gctaataccg catacgccct      180 acggggggaaa ggagggggacc ttcgggcctt ccgcgattgg atgaacctag gcgggattag     240
ctagttggtg aggtaatggc tcaccaaggc gacgatccct agctggtctg agaggatgat      300
cagccacact ggaactgaga cacggtccag actcctacgg gaggcagcag tgggaatat       360 tgcacaatgg gcgaaagcct gatgcagcca tgccgcgtgt atgaagaagg ccttcgggtt      420
gtaaagtact ttcagcgagg aggaaagctc aagcgttaat agcgcttggg tgtgacgtta      480
ctcgcagaag aagcaccggc taacttcgtg ccagcagccg cggtaatacg aggggtgcaa      540
gcgttaatcg gaattactgg gcgtaaagcg tacgcaggcg gtttgttaag cgagatgtga      600
aagccccggg ctcaacctgg gaactgcatt tcgaactggc aaactagagt cttgtagagg      660
ggggtagaat ttcaggtgta gcggtgaaat gcgtagagat ctgaaggaat accggtggcg      720
aaggcggccc cctggacaaa gactgacgct catgtacgaa agcgtgggga gcaaacagga      780
ttagataccc tggtagtcca cccctaaac gatgtctact cggagtttgg tgtcttgaac       840
actgggttct caagctaacg cattaagtag accgcctggg gagtacggcc gcaaggttaa      900
aactcaaatg aattgacggg ggcccgcaca agcggtggag catgtggttt aattcgatgc      960
aacgcgaaga accttaccta ctcttgacat ccacagaatt ttccagagat ggattagtgc      1020
cttcgggaac tgtgagacag gtgctgcatg gctgtcgtca gctcgtgttg tgaaatgttg      1080
ggttaagtcc cgcaacgagc gcaaccctta tccttatttg ccagcacgta atggtgggaa      1140 ctttaggag actgccggtg ataaaccgga ggaaggtggg gacgacgtca agtcatcatg       1200
gcccttacga gtagggctac acacgtgcta caatggtcgg tacagagggt cgcaaagccg      1260
```

```
cgaggtgtag ctaatcccac aaagccggtc gtagtccgga tcggagtctg caactcgact    1320
ccgtgaagtc ggaatcgcta gtaatcgtga atcagaatgt cacggtgaat acgttcccgg    1380
gccttgtaca caccgcccgt cacaccatgg gagtgggctg caccagaagt agatagctta    1440
accttcgggg agggcgttta ccacggtgtg gttcatgact ggggtgaagt cgtaacaagg    1500
tagccgt                                                              1507

<210> SEQ ID NO 40
<211> LENGTH: 1495
<212> TYPE: DNA
<213> ORGANISM: Shewanella livingstonis

<400> SEQUENCE: 40
attgaacgct ggcggcaggc ctaacacatg caagtcgagc ggtaacacaa gggagcttgc      60
ttctgaggtg acgagcggcg gacgggtgag taatgcctag ggatctgccc agtcgagggg    120
gataacagtt ggaaacgact gctaataccg catacgccct acgggggaaa ggaggggacc    180
ttcgggcctt ccgcgattgg atgaacctag gtggattag ctagttggtg aggtaatggc     240
tcaccaaggc gacgatccct agctgttctg agaggatgat cagccasact gggactgaga    300
cacggcccag actcctacgg gaggcagcag tggggaatat tgcacaatgg ggaaaccct     360 gatgcagcca tgccgcgtgt gtgaagaagg ccttcgggtt gtaaagcact ttcagtaggg    420
aggaaaggtg atgtgttaat agcacattgc tgtgacgtta cctacagaag aaggaccggc    480
taactccgtg ccagcagccg cggtaatacg agggtccga gcgttaatcg aattactgg     540 gcgtaaagcg tgcgcaggcg gtttgttaag ccagatgtga atccccggg ctcaacctgg     600 gaattgcatt tggaactggc gaactagagt cttgtagagg gggtagaat tccaggtgta     660 gcggtgaaat gcgtagatat ctggaggaat accggtggcg aaggcggccc cctggacaaa    720
gactgacgct catgcacgaa agcgtgggga gcaaacagga ttagatacc c tggtagtcca    780 cgccgtaaac gatgtctact cggagtttgg tgacttagtc actgggctcc caagctaacg    840
cattaagtag accgcctggg gagtacggcc gcaaggttaa aactcaaatg aattgacggg    900
ggcccgcaca gcggtggag catgtggttt aattcgatgc aacgcgaaga accttaccta    960
ctcttgacat ccacagaaga gaccagagat ggacttgtgc cttcgggaac tgtgagacag    1020
gtgctgcatg gctgtcgtca gctcgtgttg tgaaatgttg ggttaagtcc cgcaacgagc    1080
gcaaccccta tccttatttg ccagcacgta atggtgggaa ctctagggag actgccggtg    1140
ataaaccgga ggaaggtggg gacgacgtca agtcatcatg gcccttacga gtagggctac    1200
acacgtgcta caatggcgta tacagagggt tgcaaagccg cgaggtggag ctaatctcac    1260
aaagtacgtc gtagtccgga tcggagtctg caactcgact ccgtgaagtc ggaatcgcta    1320
gtaatcgtgg atcagaatgc cacggtgaat acgttcccgg gccttgtaca caccgcccgt    1380
cacaccatgg gagtgggctg caaaagaagt gggtagttta accttcggga gaacgctcac    1440
cactttgtgg ttcatgactg gggtgaagtc gtaacaaggt agccctaggg gaacc         1495

<210> SEQ ID NO 41
<211> LENGTH: 1495
<212> TYPE: DNA
<213> ORGANISM: Shewanella vesiculosa

<400> SEQUENCE: 41
attgaacgct ggcggcaggc ctaacacatg caagtcgagc ggtaacacaa gggagcttgc      60
tyctgaggtg acgagcggcg gacgggtgag taatgcctag ggatctgccc agtcgagggg    120
```

```
gataacagtt ggaaacgact gctaataccg catacgccct acggggggaaa ggagggggacc      180 ttcgggcctt ccgcgattgg atgaacctag gtgggattag ctagttggtg aggtaatggc      240
tcaccaaggc gacgatccct agctgttctg agaggatgat cagccacact gggactgaga      300 cacgcccag actcctacgg gaggcagcag tggggaatat tgcacaatgg gggaaaccct      360
gatgcagcca tgccgcgtgt gtgaagaagg ccttcgggtt gtaaagcact ttcagtaggg      420
aggaaaggtg atgtgttaat agcacattgc tgtgacgtta cctacagaag aaggaccggc      480
taactccgtg ccagcagccg cggtaatacg gagggtccga gcgttaatcg gaattactgg      540
gcgtaaagcg tgcgcaggcg gtttgttaag ccagatgtga atccccggg ctcaacctgg      600 gaattgcatt tggaactggc gaactagagt cttgtagagg ggggtagaat tccaggtgta      660
gcggtgaaat gcgtagatat ctggaggaat accggtggcg aaggcggccc cctggacaaa      720
gactgacgct catgcacgaa agcgtgggga gcaaacagga ttagataccc tggtagtcca      780
cgccgtaaac gatgtctact cggagtttgg tgacttagtc actgggctcc caagctaacg      840
cattaagtag accgcctggg gagtacggcc gcaaggttaa aactcaaatg aattgacggg      900
ggcccgcaca agcggtggag catgtggttt aattcgatgc aacgcgaaga accttaccta      960
ctcttgacat ccacagaaga gaccagagat ggacttgtgc cttcgggaac tgtgagacag     1020
gtgctgcatg gctgtcgtca gctcgtgttg tgaaatgttg ggttaagtcc cgcaacgagc     1080 gcaacccta tccttatttg ccagcacgta atggtgggaa ctctagggag actgccggtg     1140
ataaaccgga ggaaggtggg gacgacgtca agtcatcatg gcccttacga gtagggctac     1200
acacgtgcta caatggcgta tacagagggt tgcaaagccg cgaggtggag ctaatctcac     1260
aaagtacgtc gtagtccgga tcggagtctg caactcgact ccgtgaagtc ggaatcgcta     1320
gtaatcgtgg atcagaatgc cacggtgaat acgttcccgg gccttgtaca caccgcccgt     1380
cacaccatgg gagtgggctg caaaagaagt gggtagttta accttcggga gaacgctcac     1440
cactttgtgg ttcatgactg gggtgaagtc gtaacaaggt agccctaggg gaacc          1495
```

<210> SEQ ID NO 42
<211> LENGTH: 1506
<212> TYPE: DNA
<213> ORGANISM: Shewanella violacea

<400> SEQUENCE: 42

```
agagtttgat cctggctcag attgaacgct ggcggcaggc ctaacacatg caagtcgagc       60
ggaaacagaa agtagcttgc tactttgctg tcgagcggcg gacgggtgag taatgcctag      120
ggaactgccc agtcgagggg gataacagtt ggaaacgact gctaataccg catacgccct      180 acggggggaaa ggagggggacc ttcgggcctt tcgcgattgg atgtacctag gtgggattag      240
ctacttggta aggtaatggc ttaccaaggc gacgatccct acctggtctg agaggatgat      300
cagccacact ggaactgaga cacggtccag actcctacgg gaggcagcag tggggaatat      360
tgcacaatgg gcgaaagcct gatgcagcca tgccgcgtgt gtgaagaagg ccttcgggtt      420
gtaaagcact ttcagcgagg aggaaaggta ggtagttaat aactgcttac tgtgacgtta      480
ctcgcagaag aagcaccggc taacttcgtg ccagcagccg cggtaatacg aggggtgcaa      540
gcgttaatcg gaattactgg gcgtaaagcg tacgcaggcg gtttgttaag caagatgtga      600 aagcccggg ctcaacctgg gaattgcatt ttgaactggc aaactagagt cttgtagagg      660
ggggtagaat ttcaggtgta gcggtgaaat gcgtagagat ctgaaggaat accggtggcg      720
```

```
aaggcggccc cctggacaaa gactgacgct caggtacgaa agcgtgggga gcaaacagga      780
ttagataccc tggtagtcca cgccgtaaac gatgtctact cggaatttgg tgtcttgaac      840
actgggttcc caagctaacg cattaagtag accgcctggg gagtacggcc gcaaggttaa      900
aactcaaatg aattgacggg ggcccgcaca agcggtggag catgtggttt aattcgatgc      960
aacgcgaaga accttaccta ctcttgacat ccatagaact cgctagagat agcttggtgc     1020
cttcgggaac tatgagacag gtgctgcatg gctgtcgtca gctcgtgttg tgaaatgttg     1080
ggttaagtcc cgcaacgagc gcaacccta tccttatttg ccagcacgta atggtgggaa      1140
ctttagggag actgccggtg ataaaccgga ggaaggtggg gacgacgtca agtcatcatg     1200
gcccttacga gtagggctac acacgtgcta caatggtcgg tacagagggt cgcaacgccg     1260
cgaggtcaag ctaatcccac aaagccggtc gtagtccgga tcggagtctg caactcgact     1320
ccgtgaagtc ggaatcgcta gtaatcgtga atcagaatgt cacggtgaat acgttcccgg     1380
gccttgtaca caccgcccgt cacaccatgg gagtgggctg caccagaagt agatagctta     1440
acccttcggg gagggcgttt accacggtgt ggttcatgac tggggtgaag tcgtaacaag     1500
gtaacc                                                                1506

<210> SEQ ID NO 43
<211> LENGTH: 1535
<212> TYPE: DNA
<213> ORGANISM: Shewanella xiamenensis

<400> SEQUENCE: 43
agagtttgat cctggctcag attgaacgct ggcggcaggc ctaacacatg caagtcgagc       60
ggcagcacaa gggagtttac tcctgaggtg gcgagcggcg gacgggtgag taatgcctag      120
ggatctgccc agtcgagggg gataacagtt ggaaacgact gctaataccg catacgccct      180 acggggaaa gagggggacc ttcgggcctc tcgcgattgg atgaacctag gtgggattag       240
ctagttggtg aggtaatggc tcaccaaggc gacgatccct agctgttctg agaggatgat      300
cagccacact gggactgaga cacggcccag actcctacgg gaggcagcag tggggaatat      360
tgcacaatgg gggaaaccct gatgcagcca tgccgcgtgt gtgaagaagg ccttcgggtt      420
gtaaagcact ttcagtaggg aggaaagggt gagtcttaat acggctcatc tgtgacgtta      480
cctacagaag aaggaccggc taactccgtg ccagcagccg cggtaatacg agggtccga      540 gcgttaatcg gaattactgg gcgtaaagcg tgcgcaggcg gtttgttaag cgagatgtga      600
aagccctggg ctcaacctag gaatagcatt tcgaactggc gaactagagt cttgtagagg      660
ggggtagaat tccaggtgta gcggtgaaat gcgtagagat ctggaggaat accggtggcg      720
aaggcggccc cctggacaaa gactgacgct catgcacgaa agcgtgggga gcaaacagga      780
ttagataccc tggtagtcca cgccgtaaac gatgtctact cggagtttgg tgtcttgaac      840
actgggctct caagctaacg cattaagtag accgcctggg gagtacggcc gcaaggttaa      900
aactcaaatg aattgacggg ggcccgcaca agcggtggag catgtggttt aattcgatgc      960
aacgcgaaga accttaccta ctcttgacat ccacagaaga gaccagagat ggacttgtgc     1020
cttcgggaac tgtgagacag gtgctgcatg gctgtcgtca gctcgtgttg tgaaatgttg     1080
ggttaagtcc cgcaacgagc gcaacccta tccttatttg ccagcacgta atggtgggaa      1140
ctctagggag actgccggtg ataaaccgga ggaaggtggg gacgacgtca agtcatcatg     1200
gcccttacga gtagggctac acacgtgcta caatggcgag tacagagggt tgcaaagccg     1260
cgaggtggag ctaatctcac aaagctcgtc gtagtccgga ttggagtctg caactcgact     1320
```

```
ccatgaagtc ggaatcgcta gtaatcgtgg atcagaatgc cacggtgaat acgttcccgg    1380
gccttgtaca caccgcccgt cacaccatgg gagtgggctg caaaagaagt gggtagctta    1440
accttcgggg gggcgctcac cactttgtgg ttcatgactg gggtgaagtc gtaacaaggt    1500
agccctaggg gaacctgggg ctggatcacc tcctt                               1535
```

<210> SEQ ID NO 44
<211> LENGTH: 1468
<212> TYPE: DNA
<213> ORGANISM: Shewanella amazonensis
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (1468)..(1468)
<223> OTHER INFORMATION: n is a, c, g, or t

<400> SEQUENCE: 44

```
tctnntganc ctggctncan gcctaacaca tgcaagtcga gcggcagcgg gaagatagct     60
tgctatcttt gccggcgagc ggcggacggg tgagtaatac ctgggatct gcccaatcga    120 gggggataac agttggaaac gactgctaat accgcatacg ccctacgggg gaaggagggg    180
gctcttcgga ccttccgcga ttggatgaac ccaggcggga ttagctagta ggtgaggtaa    240
tggctcacct aggcgacgat ccctagctgt tctgagaaga tggacagcca cactgggact    300
gagacacggc cagactccta cgggaagcag cagtggggaa tattggacaa tgggggaaaa    360
ccctngatcc anccatgccg cgtgtgtgaa gaaggccttc gggttgtaaa gcactttcaa    420
tggggaggaa aggttgtagg ttaatacct atagctgtga cgttacccac agaagaacac    480
cggctaactc cgtgccagca gccgcggtaa tacggagggt gcaagcgtga atcggaatta    540
ctgggcgtaa agcgtgcgca ggcggtctgt tnagcgagat gtgaaagccc cgggctcaac    600 ctggaactg catttcgaac tggcagacta gattcttgta gaggggggta gaattccagg    660
tgtagcggtg aaatgcgtag agatctggag gaataccggt ggcgaaggcg gccccntgga    720
caaagactga cgctcaggca cgaaagcgtg gggagcaaac aggattagat accctggtag    780
```

```
tccacgccgt aaacgatgtc tactcggagt ttggtgtctt gaacactggg ctctcaagct    840
aacgcattaa gtagaccgcc tggggagtac ggccgcaagg ttaaaactca aatgaattga    900
cgggggcccg cacaagcggt ggagcatgtg gtttaattcg atgcaacgcg aagaacctta    960
cctactcttg acatccagag aattcgctag agatagctta ggccttcggg aattctgaga   1020
caggtgctgc atggcgttgt cagctcgtgt tgtgaaatgt tgggttaagt cccgcaacga   1080
gcgcaaccct tatccttatt tgccagcggg tagtgccggg aatttaggga gactgccggt   1140
gataaaccgg aggaaggtgg ggacgacgtc aagtcatcat ggcccttacg agtagggcta   1200
cacacgtgct acaatggcga gtacagaggg ttgcgaagcc gcgaggtgga gctaatctca   1260
taaagctcgt cgtagtccgg attggagtct gcaactcgac tccatgaagt cggaatcgct   1320
agtaatcgtg gatcagaatg ccacggtgaa tacgtttccc gggccttgta cacaccgccc   1380
gtcacaccat gggagtgggc tgcaccagaa gtagatagct taaccttcgg gagggcgttt   1440
accacggtgt gatcatgact gggtgaan                                      1468
```

<210> SEQ ID NO 45
<211> LENGTH: 1538
<212> TYPE: DNA
<213> ORGANISM: Shewanella algae
<220> FEATURE:
<221> NAME/KEY: misc_feature
<222> LOCATION: (11)..(12)
<223> OTHER INFORMATION: n is a, c, g, or t

<400> SEQUENCE: 45

```
agagtttgat nntggctcag attgaacgct ggcggcaggc ctaacacatg caagtcgagc     60
ggtaacattt caaaagcttg cttttgaaga tgacgagcgg cggacgggtg agtaatgcct    120
gggaatttgc ccatttgtgg gggataacag ttggaaacga ctgctaatac cgcatacgcc    180
ctacggggga aagcagggga ccttcgggcc ttgcgctgat ggataagccc aggtgggatt    240
agctagtagg tgaggtaaag gctcacctag gcgacgatcc ctagctggtc tgagaggatg    300
atcagccaca ctgggactga gacacggccc agactcctac gggaggcagc agtggggaat    360
attgcacaat gggggaaacc ctgatgcagc catgccgcgt gtgtgaagaa ggccttcggg    420
ttgtaaagca ctttcagcga ggaggaaagg ttgtaagtta ataccttaca tctgtgacgt    480
tattggcaga agaagcaccg gctaactccg tgccagcagc cgcggtaata cggagggtgc    540
gagcgttaat cggaattact gggcgtaaag cgtgcgcagg cggtttgtta agcgagatgt    600
gaaagcgccg gctcaacct gggaaccgca tttcgaactg gcaaactaga gtcttgtaga    660 gggggtaga attccaggtg tagcggtgaa atgcgtagag atctggagga ataccggtgg    720
cgaaggcggc ccctggaca aagactgacg ctcaggcacg aaagcgtggg gagcaaacag    780
gattagatac cctggtagtc cacgccgtaa acgatgtcta ctcggagttt ggtgtcttga    840
agactggtct ttaaagctaa cgcattaagt agaccgcctg gggagtacgg ccgcaaggtt    900
aaaactcaaa tgaattgacg ggggcccgca caagcggtgg agcatgtggt ttaattcgat    960
gcaacgcgaa gaaccttacc tactcttgac atccacagaa cttttcagag atgaattggt   1020
gccttcggga actgtgagac aggtgctgca tggctgtcgt cagctcgtgt tgtgaaatgt   1080
tgggttaagt cccgcaacga gcgcaacccc tatccttact tgccagcggg taatgccggg   1140
aactttaggg agactgccgg tgataaaccg gaggaaggtg gggacgacgt caagtcatca   1200
tggcccttac gagtagggct acacacgtgc tacaatggtc agtacagagg ttgcgaagc    1260 cgcgaggtgg agctaatccc ataaagctgg tcgtagtccg gattggagtc tgcaactcga   1320
```

<210> SEQ ID NO 46
<211> LENGTH: 1389
<212> TYPE: DNA
<213> ORGANISM: Shewanella oneidensis
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t

<400> SEQUENCE: 46

```
ctccatgaag tcggaatcgc tagtaatcgt ggatcagaat gccacggtga atacgttccc   1380
gggccttgta cacaccgccc gtcacaccat gggagtgggc tgcaccagaa gtagatagct   1440
taaccttcgg gagggcgttt accacggtgt ggttcatgac tggggtgaag tcgtaacaag   1500
gtagccctag gggaacctgg ggctggatca cctcctttt                          1538
```

```
gatctgccca gtcgagggg ataacagttg gaaacgactg ctaataccgc atacgccta    60
cgggggaaag aggggggactt tcgggcctct cgcgattgga tgaacctagg tgggattagc  120
tagttggtga ggtaatggct caccaaggcg acgatcccta gctgttctga gaggatgatc  180
agccacactg gaactgagac acggcccaga ctcctacggg aggcagcagt ggggaatatt  240
gcacaatggg ggaaaccctg atgcagccat gccgcgtgtg tgaagaaggc cttcggttg   300
taaagcactt tcagtaggga ggaaagggta antcctaata cgncttatct gtgacgttac  360
ctacagaaga aggaccggct aactccgtgc cagcagccgc ggtaatacgg agggtccnag  420
cgttaatcgg aattactggg cgtaaagcgt gcgcaggcgg tttgttaagc gagatgtgaa  480
agccctgggc tcaacctagg aatcgcattt cgaactgacc aactagagtc ttgtagaggg  540
gggtagaatt ccaggtgtag cggtgaaatg cgtagagatc tggaggaata ccggtggcga  600
aggcggcccc ctgacaaag actgacgctc atgcacgaaa gcgtgggag caaacaggat    660
tagatacccct ggtagtccac gccgtaaacg atgtctactc ggagtttggt gtcttgaaca  720
ctgggctctc aagctaacgc attaagtaga ccgcctgggg agtacggccg caaggttaaa  780
actcaaatga attgacgggg gcccgcacaa gcggtggagc atgtggttta attcgatgca  840
acgcgaagaa ccttacctac tcttgacatc cacggaagac tgcagagatg cggttgtgcc  900
ttcgggaacc gtgagacagg tgctgcatgg ctgtcgtcag ctcgtgttgt gaaatgttgg  960
gttaagtccc gcaacgagcg caaccccat ccttatttgc cagcacgtaa tggtgggaac   1020
tctagggaga ctgccggtga taaaccggag gaaggtgggg acgacgtcaa gtcatcatgg  1080
cccttacgag tagggctaca cacgtgctac aatggcgagt acagagggtt gcaaagccgc  1140
gaggtggagc taatctcaca aagctcgtcg tagtccggat tggagtctgc aactcgactc  1200
catgaagtcg gaatcgctag taatcgtgga tcagaatgcc acggtgaata cgttcccggg  1260
ccttgtacac accgcccgtc acaccatggg agtgggctgc aaaagaagtg ggtagcttaa  1320
ccttcggggg ggcgctcacc actttgtggt tcatgactgg ggtgaagtcg taacaaggta  1380
gccgtaaat                                                          1389
```

<210> SEQ ID NO 47

<211> LENGTH: 1440
<212> TYPE: DNA
<213> ORGANISM: Shewanella marinintestina

<400> SEQUENCE: 47

| | | | | | |
|---|---|---|---|---|---|
| aggcctaaca | catgcaagtc | gagcggtaac | acaagggagc | ttgctcctga | ggtgacgagc | 60 |
| ggcggacggg | tgagtaatgc | ctaggtatct | gcccagtcga | gggggataac | agttggaaac | 120 |
| gactgctaat | accgcatacg | ccctacgggg | gaaaggaggg | gaccttcggg | ccttccgcga | 180 |
| ttggatgaac | ctaggtggga | ttagctagtt | ggtgaggtaa | tggctcacca | aggcgacgat | 240 |
| ccctagctgg | tctgagagga | tgatcagcca | cactggaact | gagacacggt | ccagactcct | 300 |
| acgggaggca | gcagtgggga | atattgcaca | atgggcgaaa | gcctgatgca | gccatgccgc | 360 |
| gtgtgtgaag | aaggccttcg | ggttgtaaag | cactttcagc | gaggaggaaa | ggttaagtct | 420 |
| taatacggct | tagctgtgac | gttactcgca | gaagaagcac | cggctaactt | cgtgccagca | 480 |
| gccgcggtaa | tacgagggt | gcaagcgtta | atcggaatta | ctgggcgtaa | agcgtacgca | 540 |
| ggcggtttgt | taagcaagat | gtgaaagccc | cgggctcaac | ctgggaactg | cattttgaac | 600 |
| tgcaaactga | gagtcttgta | gagggggta | gaatttcagg | tgtagcggtg | aaatgcgtag | 660 |
| agatctgaag | gaataccggt | ggcgaaggcg | gccccctgga | caaagactga | cgctcaggta | 720 |
| cgaaagcgtg | gggagcaaac | aggattagat | accctggtag | tccacgccgt | aaacgatgtc | 780 |
| tactcggagt | ttggtgtctt | gaacactggg | ctctcaagct | aacgcattaa | gtagaccgcc | 840 |
| tggggagtac | ggccgcaagg | ttaaaactca | aatgaattga | cggggcccg | cacaagcggt | 900 |
| ggagcatgtg | gtttaattcg | atgcaacgcg | aagaaccta | cctactcttg | acatccagag | 960 |
| aattcgctag | agatagctta | gtgccttcgg | gaactctgag | acaggtgctg | catggctgtc | 1020 |
| gtcagctcgt | gttgtgaaat | gttgggttaa | gtcccgcaac | gagcgcaacc | cttatcctta | 1080 |
| tttgccagca | cgtaatggtg | ggaactttag | ggagactgcc | ggtgataaac | cggaggaagg | 1140 |
| tggggacgac | gtcaagtcat | catggccctt | acgagtaggg | ctacacacgt | gctacaatgg | 1200 |
| tcggtacaga | gggttgcgaa | gccgcgaggt | ggagctaatc | tcacaaagcc | ggtcgtagtc | 1260 |
| cggatcggag | tctgcaactc | gactccgtga | agtcggaatc | gctagtaatc | gtagatcaga | 1320 |
| atgctacggt | gaatacgttc | ccgggccttg | tacaccgc | ccgtcacacc | atgggagtgg | 1380 |
| gctgcaccag | aagtagatag | cttaaccttc | gggagggcgt | ttaccacggt | gtggttcatg | 1440 |

<210> SEQ ID NO 48
<211> LENGTH: 1440
<212> TYPE: DNA
<213> ORGANISM: Shewanella schlegeliana
<220> FEATURE:
<221> NAME/KEY: misc_feature
<222> LOCATION: (416)..(416)
<223> OTHER INFORMATION: n is a, c, g, or t

<400> SEQUENCE: 48

| | | | | | |
|---|---|---|---|---|---|
| aggcctaaca | catgcaagtc | gagcggtaac | acaagggagc | ttgctcctga | ggtgacgagc | 60 |
| ggcggacggg | tgagtaatgc | ctaggtatct | gcccagtcga | gggggataac | agttggaaac | 120 |
| gactgctaat | accgcatacg | ccctacgggg | gaaaggaggg | gaccttcggg | ccttccgcga | 180 |
| ttggatgaac | ctaggtggga | ttagctagtt | ggtgaggtaa | tggctcacca | aggcgacgat | 240 |
| ccctagctgg | tctgagagga | tgatcagcca | cactggaact | gagacacggt | ccagactcct | 300 |
| acgggaggca | gcagtgggga | atattgcaca | atgggcgaaa | gcctgatgca | gccatgccgc | 360 |
| gtgtgtgaag | aaggccttcg | ggttgtaaag | cactttcagc | gaggaggaaa | ggttangtct | 420 |

```
taatacggct tagctgtgac gttactcgca gaagaagcac cggctaactt cgtgccagca      480
gccgcggtaa tacgaggggt gcaagcgtta atcggaatta ctgggcgtaa agcgtacgca      540
ggcggtttgt taagcgagat gtgaaagccc cgggctcaac ctgggaactg catttcgaac      600
tggcaaacta gagtcttgta gagggggta gaatttcagg tgtagcggtg aaatgcgtag       660
agatctgaag gaataccggt ggcgaaggcg ccccctgga caaagactga cgctcaggta       720
cgaaagcgtg gggagcaaac aggattagat accctggtag tccacgccgt aaacgatgtc      780
tactcggaat ttggtgtctt gaacactggg ttctcaagct aacgcattaa gtagaccgcc      840
tggggagtac ggccgcaagg ttaaaactca aatgaattga cggggcccg cacaagcggt       900 ggagcatgtg gtttaattcg atgcaacgcg aagaacctta cctactcttg acatccagag      960
aattcgctag agatagctta gtgccttcgg gaactctgag acaggtgctg catggctgtc     1020
gtcagctcgt gttgtgaaat gttgggttaa gtcccgcaac gagcgcaacc cttatcctta    1080
tttgccagca cgtaatggtg gaactttag ggagactgcc ggtgataaac cggaggaagg      1140
tggggacgac gtcaagtcat catggcccctt acgagtaggg ctacacacgt gctacaatgg   1200
tcggtacaga gggttgcgaa gccgcgaggt ggagctaatc tcacaaagcc ggtcgtagtc    1260
cggattggag tctgcaactc gactccatga agtcggaatc gctagtaatc gtagatcaga    1320
atgctacggt gaatacgttc ccgggccttg tacacaccgc ccgtcacacc atgggagtgg    1380
gctgcaccag aagtagatag cttaaccttc gggagggcgt ttaccacggt gtggttcatg    1440
```

<210> SEQ ID NO 49
<211> LENGTH: 1440
<212> TYPE: DNA
<213> ORGANISM: Shewanella sairae

<400> SEQUENCE: 49

```
aggcctaaca catgcaagtc gagcggtaac acaagggagc ttgctcctga ggtgacgagc       60
ggcggacggg tgagtaatgc ctaggtatct gcccagtcga gggggataac agttggaaac     120
gactgctaat accgcatacg ccctacgggg gaaaggaggg gaccttcggg ccttccgcga     180
ttggatgaac ctaggtggga ttagctagtt ggtgaggtaa tggctcacca aggcgacgat     240
ccctagctgg tctgagagga tgatcagcca cactggaact gagacacggt ccagactcct     300
acgggaggca gcagtgggga atattgcaca atgggcgaaa gcctgatgca gccatgccgc     360
gtgtgtgaag aaggccttcg ggttgtaaag cactttcagc gaggaggaaa ggttaagtct     420
taatacggct tagctgtgac gttactcgca gaagaagcac cggctaactt cgtgccagca    480
gccgcggtaa tacgaggggt gcaagcgtta atcggaatta ctgggcgtaa agcgtacgca    540
ggcggtttgt taagcaagat gtgaaagccc cgggctcaac ctgggaactg cattttgaac   600
tggcaaacta gagtcttgta gagggggta gaatttcagg tgtagcggtg aaatgcgtag    660
agatctgaag gaataccggt ggcgaaggcg ccccctgga caaagactga cgctcaggta    720
cgaaagcgtg gggagcaaac aggattagat accctggtag tccacgccgt aaacgatgtc   780
tactcggagt ttggtgtctt gaacactggg ctctcaagct aacgcattaa gtagaccgcc   840
tggggagtac ggccgcaagg ttaaaactca aatgaattga cggggcccg cacaagcggt    900 ggagcatgtg gtttaattcg atgcaacgcg aagaacctta cctactcttg acatccagag   960
aattcgctag agatagctta gtgccttcgg gaactctgag acaggtgctg catggctgtc  1020
gtcagctcgt gttgtgaaat gttgggttaa gtcccgcaac gagcgcaacc cttatcctta  1080
```

| | |
|---|---:|
| tttgccagca cgtaatggtg ggaactttag ggagactgcc ggtgataaac cggaggaagg | 1140 |
| tggggacgac gtcaagtcat catggcccct acgagtaggg ctacacacgt gctacaatgg | 1200 |
| tcggtacaga gggttgcgaa gccgcgaggt ggagctaatc tcacaaagcc ggtcgtagtc | 1260 |
| cggatcggag tctgcaactc gactccgtga agtcggaatc gctagtaatc gtagatcaga | 1320 |
| atgctacggt gaatacgttc ccgggccttg tacacaccgc ccgtcacacc atgggagtgg | 1380 |
| gctgcaccag aagtagatag cttaaccttc gggagggcgt ttaccacggt gtggttcatg | 1440 |

<210> SEQ ID NO 50
<211> LENGTH: 1458
<212> TYPE: DNA
<213> ORGANISM: Shewanella fodinae

<400> SEQUENCE: 50

| | |
|---|---:|
| accttaagct acctacacat gcaagtcgag cggcagcggg gagtagcttg ctactctgcc | 60 |
| ggcgagcggc ggacgggtga gtaatgcctg ggaatttgcc cattcgaggg ggataacagt | 120 |
| tggaaacgac tgctaatacc gcatacgccc taagggggaa agcaggggaa cttaggtcct | 180 |
| tgcgcgaatg gataagccca ggtgggatta gctagttggt gaggtaaggg ctcaccaagg | 240 |
| cgacgatctc tagctggtct gagaggatga tcagccacac tggaactgag acacggtcca | 300 |
| gactcctacg ggaggcagca gtggggaata ttgcacaatg ggggaaaccc tgatgcagcc | 360 |
| atgccgcgtg tgtgaagaag gccttcgggt tgtaaagcac tttcagtcag gaggaaggtg | 420 |
| gtgtagctaa tatctgcacc aattgacgtt actgacagaa gaagcaccgg ctaactccgt | 480 |
| gccagcagcc gcggtaatac ggagggtgcg agcgttaatc ggaattactg ggcgtaaagc | 540 |
| gtgcgcaggc ggtttgttaa gcgagatgtg aaagccccgg gctcaacctg gatggtcat | 600 |
| ttcgaactgg caagctagag tctcgtagag ggggtagaa ttccaggtgt agcggtgaaa | 660 |
| tgcgtagaga tctggaggaa taccggtggc gaaggcggcc ccctggacga agactgacgc | 720 |
| tcaggcacga aagcgtgggg gagcaaacag gattagatac cctggtagtc cacgccgtaa | 780 |
| acgatgtcta ctcggagttt ggcgtctaga acgctgggct ctcaagctaa cgcattaagt | 840 |
| agaccgcctg gggagtacgg ccgcaaggtt aaaactcaaa tgaattgacg ggggcccgca | 900 |
| caagcggtgg agcatgtggt ttaattcgat gcaacgcgaa gaaccttacc tactcttgac | 960 |
| atccagagaa cttggcagag atgccttggt gccttcggga actctgagac aggtgctgca | 1020 |
| tggctgtcgt cagctcgtgt tgtgaaatgt tgggttaagt cccgcaacga gcgcaaccct | 1080 |
| tatccttact tgccagcggg tgatgccggg aactgtaggg agactgccgg tgataaaccg | 1140 |
| gaggaaggtg gggacgacgt caagtcatca tggcccttac gagtagggct acacacgtgc | 1200 |
| tacaatggac agtacagagg gaagcaaagc ggcgacgtgg agcggaacca aaaagctgtt | 1260 |
| cgtagtccgg attggagtct gcaactcgac tccatgaagt cggaatcgct agtaatcgtg | 1320 |
| gatcagaatg ccacggtgaa tacgttcccg ggccttgtac acaccgcccg tcacaccatg | 1380 |
| ggagtggttt gcaaaagaag tagctagctt aaccttcggg gggcggtta ccactttgtg | 1440 |
| gatcatgact ggggtgag | 1458 |

<210> SEQ ID NO 51
<211> LENGTH: 1515
<212> TYPE: DNA
<213> ORGANISM: Vibrio natriegens

<400> SEQUENCE: 51

| | |
|---|---:|
| agagtttgat catggctcag attgaacgct ggcggcaggc ctaacacatg caagtcgagc | 60 |

```
ggaaacgagt tgtctgaacc ttcggggaac gataacggcg tcgagcggcg gacgggtgag      120
taatgcctag gaaattgccc tgatgtgggg gataaccatt ggaaacgatg gctaataccg      180
catgatgcct acgggccaaa gagggggacc ttcgggcctc ttgcgtcagg atatgcctag      240
gtgggattag ctagttggtg aggtaagggc tcaccaaggc aacgatccct agctggtctg      300
agaggatgat cagccacact ggaactgaga cacggtccag actcctacgg gaggcagcag      360
tggggaatat tgcacaatgg gcgcaagcct gatgcagcca tgccgcgtgt atgaagaagg      420
ccttcgggtt gtaaagtact ttcagtcgtg aggaaggcgt tgtagttaat agctgcatcg      480
tttgacgtta gcgacagaag aagcaccggc taactccgtg ccagcagccg cggtaatacg      540
gagggtgcga gcgttaatcg gaattactgg gcgtaaagcg catgcaggtg gtttgttaag      600
tcagatgtga aagcccgggg ctcaaccctc gaatagcatt tgaaactggc agactagagt      660
actgtagagg ggggtagaat ttcaggtgta gcggtgaaat gcgtagagat ctgaaggaat      720
accagtggcg aaggcggccc cctggacaga tactgacact cagatgcgaa agcgtgggga      780
gcaaacagga ttagataccc tggtagtcca cgccgtaaac gatgtctact ggaggttgt      840 ggccttgagc cgtggctttc ggagctaacg cgttaagtag accgcctggg gagtacggtc      900
gcaagattaa aactcaaatg aattgacggg ggcccgcaca agcggtggag catgtggttt      960
aattcgatgc aacgcgaaga accttaccta ctcttgacat ccagagaact ttccagagat     1020
ggattggtgc cttcgggaac tctgagacag gtgctgcatg gctgtcgtca gctcgtgttg     1080
tgaaatgttg ggttaagtcc cgcaacgagc gcaacccctta tccttgtttg ccagcgagta     1140
atgtcgggaa ctccagggag actgccggtg ataaaccgga ggaaggtggg gacgacgtca     1200
agtcatcatg gcccttacga gtagggctac acacgtgcta caatggcgca tacagagggc     1260
ggccaacttg cgagagtgag cgaatcccaa aaagtgcgtc gtagtccgga ttggagtctg     1320
caactcgact ccatgaagtc ggaatcgcta gtaatcgtgg atcagaatgc cacggtgaat     1380
acgttcccgg gccttgtaca caccgcccgt cacaccatgg gagtgggctg caaaagaagt     1440
aggtagttta accttcgggg ggacgcttac cactttgtgg ttcatgactg gggtgaagtc     1500
gtaacaaggt agccg                                                     1515
```

<210> SEQ ID NO 52
<211> LENGTH: 1492
<212> TYPE: DNA
<213> ORGANISM: Shewanella pealeana

<400> SEQUENCE: 52

```
gatcttggct cagattgaac gctggcggca ggcctaacac atgcaagtcg agcggttaca       60
caagggagct tgctcctgag gtgacgagcg cggacgggt gagtaatgcc taggtatctg      120
cccagtcgag ggggataaca gttggaaacg actgctaata ccgcatacgc cctacggggg      180
aaaggagggg accttcgggc cttccgcgat tggatgaacc taggtgggat tagctacttg      240
gtgaggtaat ggctcaccaa ggcgacgatc cctacctggt ctgagaggat gatcagccac      300
actggaactg agacacggtc cagactccta cggaggcag cagtggggaa tattgcacaa      360
tgggcgaaag cctgatgcag ccatgccgcg tgtgtgaaga aggccttcgg gttgtaaagc      420
actttcagcg aggaggaaag ctcaagcgtt aatagcgttt gggtgtgacg ttactcgcag      480
aagaagcacc ggctaacttc gtgccagcag ccgcggtaat acgaggggtg caagcgttaa      540
tcggaattac tgggcgtaaa gcgtacgcag gcggtttgtt aagcaagatg tgaaagcccc      600
```

```
gggctcaacc tgggaactgc attttgaact ggcaaactag agtcttgtag aggggggtag    660
aatttcaggt gtagcggtga aatgcgtaga gatctgaagg aataccggtg gcgaaggcgg    720 cccccctggac aaagactgac gctcaggtac gaaagcgtgg ggagcaaaca ggattagata    780
ccctggtagt ccacgccgta acgatgtct actcggagtt tggtgtcttg aacactgggc     840
tctcaagcta acgcattaag tagaccgcct ggggagtacg gccgcaaggt taaaactcaa    900
atgaattgac gggggcccgc acaagcggtg gagcatgtgg tttaattcga tgcaacgcga    960
agaaccttac ctactcttga catccagaga attcgctaga gatagcttag tgccttcggg   1020
aactctgaga caggtgctgc atggctgtcg tcagctcgtg ttgtgaaatg ttgggttaag   1080
tcccgcaacg agcgcaaccc ttatccttat tgccagcac gtaatggtgg gaactttgag    1140
gagatcgccg gtgataaacc ggaggaaggt ggggacgacg tcaagtcatc atggccctta   1200
cgagtagggc tacacacgtg ctacaatggt cggtacagag ggttgcgacg ccgcgaggtg   1260
gagctaatct cacaaagccg gtcgtagtcc ggatcggagt ctgcaactgg actccgtgaa   1320
gtcggaatcg gtggtaatcg tagatcagaa tgctacggta aatacgttcc cgggccttgt   1380
acacaccgcc cgtcacacca tggggggtggc ctgcaccaga agtagatagc ttaaccttcg   1440
ggagggcgtt taccacggtg tggttcatga ctggggtgaa tcctaaccag gg            1492
```

<210> SEQ ID NO 53
<211> LENGTH: 1481
<212> TYPE: DNA
<213> ORGANISM: Shewanella coralli
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t

<400> SEQUENCE: 53

```
ttcctaacac atgcaagtcg agcggtaaca gaaagtagct tgctactttg ctgacgagcg     60
gcggacgggt gagtaatgcc tgggaatttg cccattcgag ggggataaca gttggaaacg    120
actgctaata ccgcatacgc cctacggggg aaggaggggg accttcgggc cttccgcgaa    180
tggataagcc caggtgggat tagctagtag gtgaggtaat ggctcaccta ggcgacgatc    240
cctagctgtt ctgagaggat gatcagccac actgggactg agacacggcc cagactccta    300
cgggaggcag cagtggggaa tattgcacaa tgggcgaaag cctgatgcag ccatgccgcg    360
tgtgtgaaga aggccttcgg gttgtaaagc actttcagcg aggaggaaag gttactggct    420
aatatccagt agctgtgacg ttactcgcag aagaagcacc ggctaactcc gtgccagcag    480
ccgcggtaat acggagggtg cgagcgttaa tcggaattac tgggcgtaaa gcgtgcgcag    540
gcggtttgtt aagcgagatg tgaaagcccc gggctcaacc tgggaactgc attttgaact    600
ggcaaactag cagtcttgga gagggggta gaattccagg tgtagcggtg aaatgcgtan    660
agatctggag gaataccggt ggctaaggcn gcccctgga caaagactga cgctcatgca    720
cgaaagcgtg gggagcaaac aggattagat accctggtag tccacgccgt aaacgatgtc    780
tactcggagt ttggtgtctt gaacactggg ctctcaagct aacgcattaa gtagaccgcc    840
tggggagtac ggccgcaagg ttaaaactca aatgaattga cggggcccg cacaagcggt     900 ggagcatgtg gtttaattcg atgcaacgcg aagaaccttc ctactcttg acatccacgg    960 aatttggtag agatacctta gtgccttcgg gaaccgtgag acaggtgctg catggctgtc   1020
```

```
gtcagctcgt gttgtgaaat gttgggttaa gtcccgcaac gagcgcaacc cttatcctta    1080
cttgccagcg ggtcatgccg ggaactttag ggagactgcc ggtgataaac cggaggaagg    1140
tggggacgac gtcaagtcat catggcccct acgagtaggg ctacacacgt gctacaatgg    1200
cgtatacaga gggttgcgaa gccgcgaggt ggagctaatc tcacaaagta cgtcgtagtc    1260
cggatcggag tctgcaactc gactccgtga agtcggaatc gctagtaatc gtggatcaga    1320
atgccacggt gaatacgttc ccgggccttg tacacaccgc ccgtcacacc atgggagtgg    1380
gctgcaccag aagtagatag cttaaccttc ggagggcgt ttaccacggt gtggttcatg     1440
actggggtga agtcgtaaca agctatccgt aggccttcac a                         1481

<210> SEQ ID NO 54
<211> LENGTH: 1540
<212> TYPE: DNA
<213> ORGANISM: Shewanella waksmanii

<400> SEQUENCE: 54
tggagagttt gatcctggct cagattgaac gctggcggca ggcctaacac atgcaagtcg      60
agcggtaaca grragaaagc ttgctttctt tgctgacgag cggcggacgg gtgagtaatg     120
cctagggaac tgcccagtcg aggggggataa cagttggaaa cgactgctaa taccgcatac    180
gccctacggg ggaaaggagg ggctcttcgg acctttcgcg attggatgta cctaggtggg    240
attagcttgt tggtgaggta agagctcacc aaggcgacga tccctagctg ttctgagagg    300
atgatcagcc acactgggac tgagacacg cccagactcc tacgggaggc agcagtgggg     360
aatattgcac aatgggcgaa agcctgatgc agccatgccg cgtgtgtgaa gaaggccttc    420
gggttgtaaa gcactttcag cgaggaggaa aggttaacgg ttaatacccg ttagctgtga    480
cgttactcgc agaagaagca ccggctaact tcgtgccagc agccgcggta atacgagggg    540
tgcaagcgtt aatcggaatt actgggcgta aagcgtacgc aggcggtttg ttaagcgaga    600
tgtgaaagcc ccgggctcaa cctgggaact gcatttcgaa ctggcaaact agagtcttgt    660 agagggggggt agaatttcag gtgtagcggt gaaatgcgta gagatctgaa ggaataccgg    720
tggcgaaggc ggccccctgg acaaagactg acgctcaggt acgaaagcgt ggggagcaaa    780
caggattaga taccctggta gtccacgccg taaacgatgt ctactcggaa tttggtgtct    840
tgaacactgg gttctcaagc taacgcatta agtagaccgc ctgggagta cggccgcaag    900 gttaaaactc aaatgaattg acggggggccc gcacaagcgg tggagcatgt ggtttaattc    960
gatgcaacgc gaagaacctt acctactctt gacatccaga gaatttacca gagatggttt   1020
agtgccttcg ggaactctga gacaggtgct gcatggctgt cgtcagctcg tgttgtgaaa   1080
tgttgggtta agtcccgcaa cgagcgcaac ccttatcctt atttgccagc acgtaatggt   1140
gggaacttta gggagactgc cggtgataaa ccggaggaag gtggggacga cgtcaagtca   1200
tcatggccct acagtaggg ctacacacg gctacaatg gcgagtacag agggttgcga     1260
agccgcgagg tgaagctaat cccagaaagc tcgtcgtagt ccggattgga gtctgcaact   1320
cgactccatg aagtcggaat cgctagtaat cgtggatcag aatgccacgg tgaatacgtt   1380
cccgggcctt gtacacaccg cccgtcacac catgggagtg ggctgcacca gaagtagata   1440
gcttaacctt cggagggcg tttaccacgg tgtggttcat gactggggtg aagtcgtaac    1500
aaggtagccc taggggaacc tgcggytgga tcacctcctt                           1540

<210> SEQ ID NO 55
```

<211> LENGTH: 1531
<212> TYPE: DNA
<213> ORGANISM: Shewanella baltica

<400> SEQUENCE: 55

```
agtttgatca tggctcagat tgaacgctgg cggcaggcct aacacatgca agtcgagcgg      60
cagcgggaag atagtttact atctttgccg gcgagcggcg gacgggtgag taatgcctag     120
ggatctgccc agtcgagggg gataacagtt ggaaacgact gctaataccg catacgccct     180
acggggaaa ggagggacc ttcgggcctt ccgcgattgg atgaacctag gtgggattag      240
ctagttggtg aggtaatggc tcaccaaggc gacgatccct agctgttctg agaggatgat     300
cagccacact gggactgaga cacggcccag actcctacgg gaggcagcag tggggaatat     360
tgcacaatgg gggaaaccct gatgcagcca tgccgcgtgt gtgaagaagg ccttcgggtt     420
gtaaagcact ttcagtaggg aggaaaggta atagtttaat acgctattac tgtgacgtta     480
cctacagaag aaggaccggc taactccgtg ccagcagccg cggtaatacg agggtccga     540
gcgttaatcg gaattactgg gcgtaaagcg tgcgcaggcg gtttgttaag cgagatgtga     600
aagccccggg ctcaacctgg gaattgcatt tcgaactggc gaactagagt cttgtagagg     660
ggggtagaat tccaggtgta gcggtgaaat gcgtagagat ctggaggaat accggtggcg     720
aaggcggccc cctggacaaa gactgacgct caggcacgaa agcgtgggga gcaaacagga     780
ttagataccc tggtagtcca cgccgtaaac gatgtctact cggagtttgg tgtcttgaac     840
actgggctct caagctaacg cattaagtag accgcctggg gagtacggcc gcaaggttaa     900
aactcaaatg aattgacggg ggcccgcaca agcggtggag catgtggttt aattcgatgc     960
aacgcgaaga accttaccta ctcttgacat ccacagaagc cagtagagat acaggtgtgc    1020
cttcgggaac tgtgagacag gtgctgcatg gctgtcgtca gctcgtgttg tgaaatgttg    1080
ggttaagtcc cgcaacgagc gcaacccta tccttatttg ccagcacgta atggtgggaa    1140
ctctaggag actgccggtg ataaaccgga ggaaggtggg gacgacgtca agtcatcatg    1200
gcccttacga gtagggctac acacgtgcta caatggcgag tacagagggt tgcaaagccg    1260
cgaggtggag ctaatctcac aaagctcgtc gtagtccgga ttggagtctg caactcgact    1320
ccatgaagtc ggaatcgcta gtaatcgtgg atcagaatgc cacggtgaat acgttcccgg    1380
gccttgtaca caccgcccgt cacaccatgg gagtgggctg caaaagaagt gggtagctta    1440
accttcgggg gggcgctcac cactttgtgg ttcatgactg gggtgaagtc gtaacaaggt    1500
agccctaggg gaacctgggg ctggatcacc t                                  1531
```

<210> SEQ ID NO 56
<211> LENGTH: 1497
<212> TYPE: DNA
<213> ORGANISM: Shewanella gaetbuli

<400> SEQUENCE: 56

```
attaacgctg gcggcaggcc taacacatgc aagtcgagcg gtaacagaaa gtagcttgct      60
actttgctga cgagcggcgg acgggtgagt aatgcctagg gatctgccca gtcgagggg     120
ataacagttg gaaacgactg ctaataccgc atacgcccta cggggaaag gagggacct      180
tcgggccttt cgcgattgga tgaacctagg tgggattagc tagttggtga ggtaatggct     240
caccaaggcg acgatcccta gctgttctga gaggatgatc agccacactg ggactgagac     300
acggcccaga ctcctacggg aggcagcagt ggggaatatt gcacaatggg ggaaaccctg     360
atgcagccat gccgcgtgtg tgaagaaggc cttcggggttg taaagcactt tcagttgtga     420
```

```
ggaaagggtg ttgcttaata cgcaacatct gtgacgttag caacagaaga aggaccggct    480
aactccgtgc cagcagccgc ggtaatacgg agggtccgag cgttaatcgg aattactggg    540
cgtaaagcgt gcgcaggcgg tttgttaagc cagatgtgaa agccccgggc tcaacctggg    600
aattgcattt ggaactggcg aactagagtc ttgtagaggg aggtagaatt tcaggtgtag    660
cggtgaaatg cgtagatatc tgaaggaata ccggtggcga aggcggcctc ctggacaaag    720
actgacgctc atgcacgaaa gcgtggggag caaacaggat tagataccct ggtagtccac    780
gccgtaaacg atgtctactc ggagtttggt gccttgagca ctgggctctc aagctaacgc    840
attaagtaga ccgcctgggg agtacggccg caaggttaaa actcaaatga attgacgggg    900
gcccgcacaa gcggtggagc atgtggttta attcgatgca acgcgaagaa ccttacctac    960
tcttgacatc cagagaagtt accagagatg gtttcgtgcc ttcgggaact ctgagacagg   1020
tgctgcatgg ctgtcgtcag ctcgtgttgt gaaatgttgg gttaagtccc gcaacgagcg   1080
caacccctat ccttatttgc cagcacgtaa tggtgggaac tttagggaga ctgccggtga   1140
taaaccggag gaaggtgggg acgacgtcaa gtcatcatgg cccttacgag tagggctaca   1200
cacgtgctac aatggcaagt acagagggtt gcaaagccgc gaggtggagc taatctcaca   1260
aagcttgtcg tagtccggat tggagtctgc aactcgactc catgaagtcg gaatcgctag   1320
taatcgtaga tcagaatgct acggtgaata cgttcccggg ccttgtacac accgcccgtc   1380
acaccatggg agtgggctgc aaaagaagtg ggtagtttaa ccttcgggag aacgctcacc   1440
actttgtggt tcatgactgg ggtgaagtcg taacaaggta gccctagggg aacctgg      1497
```

<210> SEQ ID NO 57
<211> LENGTH: 1499
<212> TYPE: DNA
<213> ORGANISM: Shewanella surugensis

<400> SEQUENCE: 57

```
agagtttgat cctggctcag attgaacgct ggcggcaggc ctaacacatg caagtcgagc     60
ggtaacagga agtagcttgc tactttgctg acgagcggcg gacgggtgag taatgcctag    120
gtatctgccc agtcgagggg gataacagtt ggaaacgact gctaataccg catacgccct    180 acggggaaa ggaggggacc ttcgggcctt tcgcgattgg atgaacctag gtgggattag    240
ctagttggtg gggtaatggc tcaccaaggc gacgatccct agctggtctg agaggatgat    300
cagccacact ggaactgaga cacggtccag actcctacgg gaggcagcag tggggaatat    360
tgcacaatgg gggaaaccct gatgcagcca tgccgcgtgt atgaagaagg cttcggggtt    420
gtaaagtact ttcagcgagg aggaaaggtt gagtgttaat agcacttagc tgtgacgtta    480
ctcgcagaag aagcaccggc taacttcgtg ccagcagccg cggtaatacg aggggtgcaa    540
gcgttaatcg gaattactgg gcgtaaagcg tacgcaggcg gtttgttaag caagatgtga    600
aagccctggg ctcaacctag gaaccgcatt ttgaactggc agactagagt cttgtagagg    660
ggggtagaat tcaggtgtag cggtgaaatg cgtagagat ctgaaggaat accggtggcg    720
aaggcggccc cctggacaaa gactgacgct catgtacgaa agcgtgggga gcaaacagga    780
ttagataccc tggtagtcca cgccgtaaac gatgtctact cggaatttgg tgtcttgaac    840
actgggttct caagctaacg cattaagtag accgcctggg gagtacggcc gcaaggttaa    900
aactcaaatg aattgacggg ggcccgcaca agcggtggag catgtggttt aattcgatgc    960
aacgcgaaga accttaccta ctcttgacat ccacagaact tttcagagat gaattggtgc   1020
```

```
cttcgggaac tgtgagacag gtgctgcatg gctgtcgtca gctcgtgttg tgaaatgttg    1080
ggttaagtcc cgcaacgagc gcaacccctta tccttatttg ccagcacgta atggtgggaa    1140
ctttagggag actgccggtg ataaaccgga ggaaggtggg gacgacgtca agtcatcatg    1200
gcccttacga gtagggctac acacgtgcta caatggtcgg tacagagggt tgcaaagccg    1260
cgaggtggag ctaatctcac aaagccggtc gtagtccgga ttggagtctg caactcgact    1320
ccatgaagtc ggaatcgcta gtaatcgtgg atcagaatgc cacggtgaat acgttcccgg    1380
gccttgtaca caccgcccgt cacaccatgg gagtgggctg caccagaagt agatagctta    1440
accttcggga gggcgtttac cacggtgtgg ttcatgactg gggtgaagtc gtaacaagg     1499
```

<210> SEQ ID NO 58
<211> LENGTH: 1492
<212> TYPE: DNA
<213> ORGANISM: Shewanella kaireitica

<400> SEQUENCE: 58

```
tgatcctggc tcagattgaa cgctggcggc aggcctaaca catgcaagtc gagcggtaac      60
acaagggagc ttgctcctga ggtgacgagc ggcggacggg tgagtaatgc ctaggtatct    120
gcccagtcga gggggataac agttggaaac gactgctaat accgcatacg ccctacgggg    180
gaaaggaggg gaccttcggg cctttcgcga ttggatgaac ctaggtggga ttagctagta    240 ggtgggtaa tggctcacct aggcaacgat ccctagctgg tctgagagga tgatcagcca    300
cactggaact gagacacggt ccagactcct acgggaggca gcagtgggga atattgcaca    360
atgggcgaaa gcctgatgca gccatgccgc gtgtatgaag aaggccttcg ggttgtaaag    420
tactttcagc gaggaggaaa ggttgttggt taataaccaa cagctgtgac gttactcgca    480
gaagaagcac cggctaactt cgtgccagca gccgcggtaa tacgagggt gcaagcgtta    540 atcggaatta ctgggcgtaa agcgtacgca ggcggtttgt taagcgagat gtgaaagccc    600
cgggctcaac ctgggaactg catttcgaac tggcaaacta gagtcttgta gaggggggta    660
gaatttcagg tgtagcggtg aaatgcgtag agatctgaag gaataccggt ggcgaaggcg    720
gccccctgga caaagactga cgctcaggta cgaaagcgtg gggagcaaac aggattagat    780
accctggtag tccacgccgt aaacgatgtc tactcggaat ttggtgtctt gaacactggg    840
ttctcaagct aacgcattaa gtagaccgcc tgggagtac ggccgcaagg ttaaaactca    900
aatgaattga cggggggcccg cacaagcggt ggagcatgtg gtttaattcg atgcaacgcg    960 aagaaccttta cctactcttg acatccagag aattcgctag agatagctta gtgccttcgg   1020
gaactctgag acaggtgctg catggctgtc gtcagctcgt gttgtgaaat gttgggttaa   1080
gtcccgcaac gagcgcaacc cttatcctta tttgccagca cgtaatggtg ggaactttag   1140
ggagactgcc ggtgataaac cggaggaagg tggggacgac gtcaagtcat catggcccctt    1200 acgagtaggg ctacacacgt gctacaatgg tcggtacaga gggttgcgaa gccgcgaggt   1260
ggagctaatc tcacaaagcc ggtcgtagtc cggattggag tctgcaactc gactccatga   1320
agtcggaatc gctagtaatc gtagatcaga atgctacggt gaatacgttc ccgggccttg   1380
tacacaccgc ccgtcacacc atgggagtgg gctgcaccag aagtagatag cttaaccttc   1440
gggagggcgt ttaccacggt gtggttcatg actggggtga agtcgtaaca ag            1492
```

<210> SEQ ID NO 59
<211> LENGTH: 1485
<212> TYPE: DNA
<213> ORGANISM: Shewanella pacifica
<220> FEATURE:
<221> NAME/KEY: misc_feature
<222> LOCATION: (443)..(443)
<223> OTHER INFORMATION: n is a, c, g, or t

<400> SEQUENCE: 59

```
cgctggcggc aggcctaaca catgcaagtc gagcggtaac agaaagtagc ttgctacttt      60
gctgacgagc ggcggacggg tgagtaatgc ctagggatct gcccagtcga gggggataac     120
agttggaaac gactgctaat accgcatacg ccctacgggg gaaggagggg gaccttcggg     180
cctttcgcga ttggatgaac ctaggtggga ttagctagtt ggtaaggtaa tggcttacca     240
aggcgacgat ccctagctgt tctgagagga tgatcagcca cactgggact gagacacggc     300
ccagactcct acgggaggca gcagtgggga atattgcaca atgggggaaa ccctgatgca     360
gccatgccgc gtgtgtgaag aaggccttcg ggttgtaaag cactttcagt agggaggaaa     420
ggtagcagct taatacgttg ttnctgtgac gttacctaca gaagaaggac cggctaactt     480
cgtgccagca gccgcggtaa tacgaggggt ccaagcgtta atcggaatta ctgggcgtaa     540
agcgtacgca ggcggttcat aagccagatg tgaaatccc cgggctcaac ctgggaattg     600
catttggaac tggtgaacta gagtcttgta gagggggta gaatttcagg tgtagcggtg     660
aaatgcgtag agatctgaag gaataccggt ggcgaaggcg gcccctgga caaagactga     720
cgctcatgta cgaaagcgtg gggagcaaac aggattagat accctggtag tccacgccgt     780
aaacgatgtc tactcggagt ttggtgcctt gagcactggg ctcccaagct aacgcattaa     840
gtagaccgcc tggggagtac ggccgcaagg ttaaaactca aatgaattga cgggggcccg     900
cacaagcggt ggagcatgtg gtttaattcg atgcaacgcg aagaacctta cctactcttg     960
acatccagag aattcgctag agatagctta gtgccttcgg gaactctgag acaggtgctg    1020
catggctgtc gtcagctcgt gttgtgaaat gttgggttaa gtcccgcaac gagcgcaacc    1080
cctatcctta tttgccagcg cgtaatggcg ggaactctag ggagactgcc ggtgataaac    1140
cggaggaagg tggggacgac gtcaagtcat catggcccct acgagtaggg ctacacacgt    1200
gctacaatgg cgagtacaga ggttgcaaa gccgcaaggt ctagctaatc tcataaagct    1260
cgtcgtagtc cggattggag tctgcaactc gactccatga agtcggaatc gctagtaatc    1320
gtagatcaga atgctacggt gaatacgttc ccgggccttg tacacaccgc ccgtcacacc    1380
atgggagtgg gctgcaccag aagtagatag tctaaccttc ggaggacgt ttaccacggt     1440
gtggttcatg actggggtga agtcgtaaca aggtagccct agggg                    1485
```

<210> SEQ ID NO 60
<211> LENGTH: 1539
<212> TYPE: DNA
<213> ORGANISM: Shewanella donghaensis

<400> SEQUENCE: 60

```
agagtttgat cctgctcaga ttgaactgct ggcggcaggc ctaacacatg caagtcgagc      60
ggtaacacaa gggagcttgc tcctgaggtg acgagcggcg gacgggtgag taatgcctag     120
ggatctgccc agtcgagggg gataacagtt ggaaacgact gctaataccg catacgccct     180
acggggaaa ggaggggacc ttcgggcctt tcgcgattgg atgaacctag gtgggattag     240
ctagttggtg aggtaatggc tcaccaaggc gacgatccct agctgttctg agaggatgat     300
cagccacact gggactgaga cacggcccag actcctacgg gaggcagcag tggggaatat    360
tgcacaatgg gcgaaagcct gatgcagcca tgccgcgtgt gtgaagaagg ccttagggtt     420
```

```
gtaaagcact tcagtaggg aggaaaggtt aacggttaat aaccgttagc tgtgacgtta      480
cctacagaag aaggaccggc taacttcgtg ccagcagccg cggtaatacg aggggtccaa     540
gcgttaatcg gaattactgg gcgtaaagcg tacgcaggcg gttcattaag ctagatgtga    600
aatccccggg ctcaacctgg gaattgcatt tagaactggt gaactagagt cttgtagagg    660
ggggtagaat tcaggtgta gcggtgaaat gcgtagagat ctgaaggaat accggtggcg    720
aaggcggccc cctggacaaa gactgacgct catgtacgaa agcgtgggga gcaaacagga   780 ttagatacccc tggtagtcca cgccgtaagt acgatgtcta ctcggagttt ggtgccttga   840
gcactgggct cccaagctaa cgcattaagt agaccgcctg ggagtacgg ccgcaaggtt    900 aaaactcaaa tgaattgacg ggggcccgca caagcggtgg agcatgtggt ttaattcgat   960
gcaacgcgaa agaaccttac ctactcttga catccacaga acttaccaga gatggtttgg   1020
tgccttcggg aactgtgaga caggtgctgc atggctgtcg tcagctcgtg ttgtgaaatg  1080
ttgggttaag tcccgcaacg agcgcaaccc ctatccttat ttgccagcgc gtaatggcgg   1140
gaactctagg gagactgccg gtgataaacc ggaggaaggt ggggacgacg tcaagtcatc    1200
atggccctta cgagtagggc tacacacgtg ctacaatggc gtatacagag ggttgcaaag   1260
ccgcaaggtc tagctaatct cacaaagtac gtcgtagtcc ggatcggagt ctgcaactcg    1320
actccgtgaa gtcggaatcg ctagtaatcg tagatcagaa tgctacggtg aatacgttcc    1380
cgggccttgt acacaccgcc cgtcacacca tgggagtggg ctgcaccaga agtagatagt    1440
ctaaccttcg ggaggacgtt taccacggtg tggttcatga ctggggtgaa gtcgtaacaa   1500
ggtagcccta ggggaacctg cggctggatc acctcctta                          1539
```

<210> SEQ ID NO 61
<211> LENGTH: 1511
<212> TYPE: DNA
<213> ORGANISM: Shewanella affinis

<400> SEQUENCE: 61

```
ggctcagatt gaacgctggc ggcaggccta acacatgcaa gtcgagcggt aacaggaatt     60
agcttgctaa tttgctgacg gcggcggacg ggtgagtaat gcctagggaa ctgcccagtc    120 gaggggggata acagttggaa acgactgcta ataccgcata cgccctacgg ggaaaagag    180 gggaccttcg gccttctgc gattggatgt acctaggtgg gattagctag ttggtgaggt    240
aatggctcac caaggcgacg atccctagct gttctgagag gatgatcagc cacactggga    300
ctgagacacg gcccagactc ctacgggagg cagcagtggg gaatattgca caatgggcgc    360
aagcctgatg cagccatgcc gcgtgtgtga agaaggcctt cgggttgtaa agcactttca    420
gcgaggagga aagcttaagc gttaatagcg tttaggtgtg acgttactcg cagaagaagg    480
accggcttaa cttcgtgcca gcagccgcgg taatacgagg gtccaagcgt taatcggaat    540
tactgggcgt aaagcgtacg caggcggttt gttaagcgag atgtgaaagc cccgggctca    600
acctgggaac tgcatttcga actggcaaac tagagtcttg tagaggggg tagaatttca    660 ggtgtagcgg tgaaatgcgt agagatctga aggaataccg gtggcgaagg cggcccctg    720 gacaaagact gacgctcatg tacgaaagcg tgggagcaa acaggattag ataccctggt     780
agtccacgcc gtaacgatg tctactcgga atttggtgtc ttgaacactg gttctcaag    840 ctaacgcatt aagtagaccg cctggggagt acgccgcaa ggttaaaact caaatgaatt    900 gacggggggcc cgcacaagcg gtggagcatg tgggtttaatt cgatgcaacg cgaagaacct   960
tacctactct tgacatccag agaattcgct agagatagct tagtgccttc gggaactctg   1020
```

```
agacaggtgc tgcatggctg tcgtcagctc gtgttgtgaa atgttgggtt aagtcccgca   1080
acgagcgcaa cccttatcct tatttgccag cacgtaatgg tgggaacttt agggagactg   1140
ccggtgataa accggaggaa ggtggggacg acgtcaagtc atcatggccc ttacgagtag   1200
ggctacacac gtgctacaat ggcaagtaca gagggttgcg aagccgcgag gtggagctaa   1260
tctcacaaag cttgtcgtag tccggattgg agtctgcaac tcgactccat gaagtcggaa   1320
tcgctagtaa tcgtggatca gaatgccacg gtgaatacgt tcccgggcct tgtacacacc   1380
gcccgtcaca ccatgggagt gggctgcacc agaagtagat agcttaacct tcgggagggc   1440
gtttaccacg gtgtggttca tgactggggt gaagtcgtaa caaggtagcc taggggaacc   1500
tgcggctgga t                                                        1511

<210> SEQ ID NO 62
<211> LENGTH: 1486
<212> TYPE: DNA
<213> ORGANISM: Shewanella psychrophila

<400> SEQUENCE: 62
agagtttgat cctggctcag attgaacgct ggcggcaggc ctaacacatg caagtcgagc     60
ggtaacacaa gggagcttgc tcctgaggtg acgagcggcg gacgggtgag taatgcctag    120
gtatctgccc agtcgagggg gataacagtt ggaaacgact gctaataccg catacgccct    180 acggggaaa ggagggacc ttcgggcctt tcgcgattgg atgaacctag gtgggattag    240
ctagtaggtg gggtaatggc tcacctaggc aacgatccct agctggtctg agaggatgat    300
cagccacact ggaactgaga cacggtccaa actcctacgg gaggcagcag tggggaatat    360
tgcacagtgg gcgaaagcct gatgcagcca tgccgcgtgt atgaagaagg ccttcgggtt    420
gtaaagtact tttcaagcga agaagaaaag gttgttggtt aataaccaac agcttgtgac    480
gttacttcgc agaagaagc accgggctaa cttttcgtgcc agcagccgcg gtaatacgag    540
gggtgcaagc gttaatcgga attactgggc gtaaagcgta cgcaggcggt ttgttaagcg    600
agatgtgaaa gccccgggct caacctggga actgcatttc gaactggcaa actagagtct    660
tgtagagggg ggtagaattt caggtgtagc ggtgaaatgc gtagagatct gaaggaatac    720
cggtggcgaa ggcggccccc tggacaaaga ctgacgctca ggtacgaaag cgtggggagc    780
aaacaggatt agatacctg gtagtccacg ccgtaaacga tgtctactcg gaatttggtg    840
tcttgacact gggttctcaa gctaacgcat taagtagacc gcctggggag tacggccgca    900
aggttaaaac tcaaatgaat tgacggggc ccgcacaagc ggtggagcat gtggtttaat    960
tcgatgcaac gcgaagaacc ttacctactc ttgacatcca gagaattttc cagagatgga   1020
ttagtgcctt cgggaactct gagacaggtg ctgcatggct gtcgtcagct cgtgttgtga   1080
aatgttgggt taagtcccgc aacgagcgca acccttatcc ttatttgcca gcacgtaatg   1140
gtgggaactt tagggagact gccggtgata accggagga aggtggggac gacgccaagt   1200
catcatggcc cttacgagta gggctacaca cgtgctacaa tggtcggtac agagggttgc   1260
aaagccgcga ggtggagcta atctcacaaa gccggtcgta gtccggattg gagtctgcaa   1320
ctcgactcca tgaagtcgga atcgctagta atcgtagatc agaatgctac ggtgaatacg   1380
ttcccgggcc ttgtacacac cgcccgtcac accatgggag tgggctgcac cagaagtaga   1440
tagcttaacc ttcgggaggg cgtttaccac ggtgtggttc atgact                  1486

<210> SEQ ID NO 63
```

<211> LENGTH: 1481
<212> TYPE: DNA
<213> ORGANISM: Shewanella piezotolerans

<400> SEQUENCE: 63

| | | | | | |
|---|---|---|---|---|---|
| agagtttgat | cctggctcag | attgaacgct | ggcggcaggc | ctaacacatg | caagtcgagc | 60 |
| ggaaacagga | aggtgcttgc | acctttgctg | tcgagcggcg | gacgggtgag | taatgcctag | 120 |
| ggaactgccc | agtcgagggg | gataacagtt | ggaaacgact | gctaataccg | catacgccct | 180 |
| acggggaaa | ggaggggacc | ttcgggcctt | cgcgattgg | atgtacctag | gtgggattag | 240 |
| ctagttggta | aggtaatggc | ttaccaaggc | aacgatccct | agctggtctg | agaggatgat | 300 |
| cagccacact | ggaactgaga | cacggtccag | actcctacgg | gaggcagcag | tggggaatat | 360 |
| tgcacaatgg | gcgaaagcct | gatgcagcca | tgccgcgtgt | gtgaagaagc | cttcggttg | 420 |
| taaagcactt | ttcaagcgaa | gaggaaagg | ttgtagttta | ataaactata | gctgtgcgtt | 480 |
| actcgcagaa | gaagcaccgg | ctaacttcgt | gccagcagcc | gcggtaatac | gagggtgca | 540 |
| agcgttaatc | ggaattactg | ggcgtaaagc | gtacgcaggc | ggtttgttaa | gcaagatgtg | 600 |
| aaagccccgg | gctcaacctg | ggaattgcat | tttgaactgg | caaactagag | tcttgtagag | 660 |
| gggggtgaa | tttcaggtgt | agcggtgaaa | tgcgtagaga | tctgaaggaa | taccggtggc | 720 |
| gaaggcggcc | ccctggacaa | agactgacgc | tcaggtacga | aagcgtgggg | agcaaacagg | 780 |
| attagatacc | ctggtagtcc | acgccgtaaa | cgatgtctac | tcggaatttg | gtgtcttgaa | 840 |
| cactgggttc | tcaagctaac | gcattaagta | gaccgcctgg | ggagtacggc | cgcaaggtta | 900 |
| aaactcaaat | gaattgacgg | gggcccgcac | aagcggtgga | gcatgtggtt | taattcgatg | 960 |
| caacgcgaag | aaccttacct | actcttgaca | tccacagaac | tttccagaga | tggattggtg | 1020 |
| ccttcgggaa | ctgtgagaca | ggtgctgcat | ggctgtcgtc | aagctcgtgt | tgtaaatgtt | 1080 |
| gggttaagtc | ccgcaacgag | cgcaccctta | tccttatttg | ccagcacgta | atggtgggaa | 1140 |
| ctttaggag | actgccggtg | ataaaccgga | ggaaggtggg | gacgacgtca | agtcatcatg | 1200 |
| gcccttacga | gtagggctac | acacgtgcta | caatggtcgg | tacagagggt | cgcaaagccg | 1260 |
| cgaggtcaag | ctaatcccac | aaagccggtc | gtagtccgga | tcgagtctg | caactcgact | 1320 |
| ccgtgaagtc | ggaatcgcta | gtaatcgtag | atcagaatgc | tacggtgaat | acgttcccgg | 1380 |
| gccttgtaca | caccgcccgt | cacaccatgg | gagtgggctg | caccagaagt | agatagctta | 1440 |
| acctttcggg | gagggcgttt | accacggtgt | ggttcatgac | t | | 1481 |

<210> SEQ ID NO 64
<211> LENGTH: 1334
<212> TYPE: DNA
<213> ORGANISM: Shewanella profunda
<220> FEATURE:
<221> NAME/KEY: misc_feature
<222> LOCATION: (2)..(2)
<223> OTHER INFORMATION: n is a, c, g, or t

<400> SEQUENCE: 64

| | | | | | |
|---|---|---|---|---|---|
| gnggggacct | tcgggccttc | gcgattgga | tgaacctagg | tgggattagc | tagttggtga | 60 |
| ggtaatggct | caccaaggcg | acgatcccta | gctgttctga | gaggatgatc | agccacactg | 120 |
| ggactgagac | acggcccaga | ctcctacggg | aggcagcagt | ggggaatatt | gcacaatggg | 180 |
| ggaaccctg | atgcagccat | gccgcgtgtg | tgaagaaggc | cttcggttg | taaagcactt | 240 |
| tcagtaggga | ggaagggtg | taacttaata | cgttatatct | gtgacgttac | ctacagaaga | 300 |
| aggaccggct | aactccgtgc | cagcagccgc | ggtaatacgg | agggtccgag | cgttaatcgg | 360 |

```
aattactggg cgtaaagcgt gcgcaggcgg tttgttaagc gagatgtgaa agccctgggc    420
tcaacctagg aatagcattt cgaactggcg aactagagtc ttgtagaggg ggggtagaat    480
tccaggtgta gcggtgaaat gcgtagagat ctggaggaat accggtggcg aaggcggccc    540
cctggacaaa gactgacgct catgcacgaa agcgtgggga gcaaacagga ttagatacc    600 tggtagtcca cgccgtaaac gatgtctact cggagtttgg tgtcttgaac actgggctct    660
caaagtaacg cattaagtag accgcctggg gagtacggcc gcaaggttaa aaatcaaatg    720
aattgacggg ggcccgcaca agcggtggag catgtggttt aattcgatgc aacgcgaaga    780
accttaccta ctcttgacat ccacagaact ttccagagat ggattggtgc ttcgggaact    840
gtgagacagg tgctgcatgg ctgtcgtcag ctcgtgttgt gaaatgttgg gttaagtccc    900
gcaacgagcg caacccctat ccttatttgc cagcacgtaa tggtgggaac tctaggagag    960
ctgccggtga taaaccggag gaaggtgggg acgacgtcaa gtcatcatgg cccttacgag    1020
tagggctaca cacgtgctac aatggcgagt acagagggtt gcaaagccgc gaggtggagc    1080
caatctcaca aagctcgtcg tagtccggat cggagtctgc aactcgactc cgtgaagtcg    1140
gaatcgctag taatcgtgga tcagaatgcc acggtgaata cgttcccggg ccttgtacac    1200
accgcccgtc acaccatggg agtgggctgc aaaagaagtg ggtagcttaa ccttcggggg    1260
ggcgctcacc actttgtggt tcatgactgg ggtgaagtcg taacaaggta gccctagggg    1320
aacctggggc tgga    1334
```

<210> SEQ ID NO 65
<211> LENGTH: 1448
<212> TYPE: DNA
<213> ORGANISM: Shewanella decolorationis
<220> FEATURE:
<221> NAME/KEY: misc_feature
<222> LOCATION: (970)..(970)
<223> OTHER INFORMATION: n is a, c, g, or t

<400> SEQUENCE: 65

```
gcaggcctaa cacatgcaag tcgagcggca gcacaagtga gtttactcat gaggtggcga     60
gcggcggacg ggtgagtaat gcctagggat ctgcccagtc gagggggata acagttggaa    120
acgactgcta ataccgcata cgcccctacgg gggaaaggag gggacctttt ggccttccgc    180
gattggatga acctaggtgg gattagctag ttggtgaggt aatggctcac caaggcgacg    240
atccctagct gttctgagag gatgatcagc cacactggga ctgagacacg gcccagactc    300
ctacgggagg cagcagtggg gaatattgca caatggggga aaccctgatg cagccatgcc    360
gcgtgtgtga agaaggcctt cgggttgtaa agcactttca gtagggagga aaggttgtaa    420 gttaataccct tgcagctgtg acgttaccta cagaagaagg accggctaac tccgtgccag    480
cagccgcggt aatacggagg gtccaagcgt taatcggaat tactgggcgt aaagcgtgcg    540
caggcggttt gttaagcgag atgtgaaagc cccgggctca acctgggaat tgcatttcga    600
actggcaaac tagagtcttg tagaggggg tagaattcca ggtgtagcgg tgaaatgcgt    660
agagatctgg aggaataccg gtggcgaagg cggcccctg acaaagact gacgctcagg    720 cacgaaagcg tggggagcaa acaggattag ataccctggt agtccacgcc gtaaacgatg    780
tctactcgga gtttggtgtc ttgaacactg gctctcaag ctaacgcatt aagtagaccg    840
cctggggagt acgccgcaa ggttaaaact caaatgaatt gacggggcc cgcacaagcg    900 gtggagcatg tggtttaatt cgatgcaacg cgaagaacct tacctactct tgacatccag    960
```

```
agaactttcn agagatggat tggtgccttc gggaactctg agacaggtgc tgcatggctg   1020
tcgtcagctc gtgttgtgaa atgttgggtt aagtcccgca acgagcgcaa cccctatcct   1080
tatttgccag cgcgtaatgg cgggaactct agggagactg ccggtgataa accggaggaa   1140
ggtggggacg acgtcaagtc atcatggccc ttacgagtag ggctacacac gtgctacaat   1200
ggcgagtaca gagggttgca aagccgcgag gtggagctaa tctcacaaag ctcgtcgtag   1260
tccggattgg agtctgcaac tcgactccat gaagtcggaa tcgctagtaa tcgtgaatca   1320
gaatgtcacg gtgaatacgt tcccgggcct tgtacacacc gcccgtcaca ccatgggagt   1380
gggctgcaaa agaagtgggt agcttaacct tcgggagggc gctcaccact ttgtggttca   1440
tgactggg                                                            1448
```

<210> SEQ ID NO 66
<211> LENGTH: 1500
<212> TYPE: DNA
<213> ORGANISM: Shewanella marisflavi

<400> SEQUENCE: 66

```
attgaacgct ggcggcaggc ctaacacatg caagtcgagc ggtaacagga agaaagcttg     60
ctttctttgc tgacgagcgg cggacgggtg agtaatgcct agggaactgc ccagtcgagg    120
gggataacag ttggaaacga ctgctaatac cgcatacgcc ctacggggga aagaggggga    180
ccttcgggcc ttctgcgatt ggatgtacct aggtgggatt agctagtagg tgaggtaatg    240
gctcacctag gcgacgatcc ctagctgttc tgagaggatg atcagccaca ctgggactga    300
gacacggccc agactcctac gggaggcagc agtggggaat attgcacaat gggcgcaagc    360
ctgatgcagc catgccgcgt gtgtgaagaa ggccttcggg ttgtaaagca ctttcagcga    420
ggaggaaagg ttaagtgtta atagcgctta gctgtgacgt tactcgcaga agaagcaccg    480
gctaacttcg tgccagcagc cgcggtaata cgaggggtgc aagcgttaat cggaattact    540
gggcgtaaag cgtacgcagg cggttttgtta agcgagatgt gaaagccccg ggctcaacct    600
gggaactgca tttcgaactg caaactagag tcttgtaga gggggtaga atttcaggtg    660 tagcggtgaa atgcgtagag atctgaagga ataccgtgg cgaaggcggc cccctggaca    720
aagactgacg ctcaggtacg aaagcgtggg gagcaaacag gattagatac cctggtagtc    780
cacgccgtaa acgatgtcta ctcggaattt ggtgtcttga acactgggtt ctcaagctaa    840
cgcattaagt agaccgcctg gggagtacgg ccgcaaggtt aaaactcaaa tgaattgacg    900
ggggcccgca caagcggtgg agcatgtggt ttaattcgat gcaacgcgaa gaaccttacc    960
tactcttgac atccagagaa ttcgctagag atagcttagt gccttcggga actctgagac   1020
aggtgctgca tggctgtcgt cagctcgtgt tgtgaaatgt tgggttaagt cccgcaacga   1080
gcgcaaccct tatccttact tgccagcggg tcatgccggg aactttaggg agactgccgg   1140
tgataaaccg gaggaaggtg gggacgacgt caagtcatca tggcccttac gagtagggct   1200
acacacgtgc tacaatggcg agtacagagg gttgcgaagc cgcgaggtgg agctaatctc   1260
agaaagctcg tcgtagtccg gattggagtc tgcaactcga ctccatgaag tcggaatcgc   1320
tagtaatcgt ggatcagaat gccacggtga atacgttccc gggccttgta cacaccgccc   1380
gtcacaccat gggagtgggc tgcaccagaa gtagatagct taaccttcgg gagggcgttt   1440
accacggtgt ggttcatgac tggggtgaag tcgtaacaag gtagccctag ggaacctggg   1500
```

<210> SEQ ID NO 67
<211> LENGTH: 1499

<212> TYPE: DNA
<213> ORGANISM: Shewanella aquimarina

<400> SEQUENCE: 67

```
attgaacgct ggcggcaggc ctaacacatg caagtcgagc ggtaacattt caaaagcttg      60
cttttgaaga tgacgagcgg cggacgggtg agtaatgcct agggaactgc ccagtcgagg     120
gggataacag ttggaaacga ctgctaatac cgcatacgcc ctacggggga aagaggggga     180
tcttcggacc ttctgcgatt ggatgtacct aggtgggatt agctagtagg tgaggtaatg     240
gctcacctag gcgacgatcc ctagctgttc tgagaggatg atcagccaca ctgggactga     300
gacacggccc agactcctac gggaggcagc agtggggaat attgcacaat gggcgcaagc     360
ctgatgcagc catgccgcgt gtgtgaagaa ggccttcggg ttgtaaagca ctttcagcga     420
ggaggaaagg ttaacggtta atacccgtta gctgtgacgt tactcgcaga agaagcaccg     480
gctaacttcg tgccagcagc cgcggtaata cgagggggtgc aagcgttaat cggaattact     540
gggcgtaaag cgtacgcagg cggttgatta agcgagatgt gaaagccccg ggcttaacct     600
gggaactgca tttcgaactg gtcaactaga gtcttgtaga gggggtaga atttcaggtg     660
tagcggtgaa atgcgtagag atctgaagga ataccgtgg cgaaggcggc cccctggaca     720
aagactgacg ctcaggtacg aaagcgtggg gagcaaacag gattagatac cctggtagtc     780
cacgccgtaa acgatgtcta ctcggaattt ggtgtcttga acactgggtt ctcaagctaa     840
cgcattaagt agaccgccgg ggagtacggc cgcaaggtta aaactcaaat gaattgacgg     900
gggcccgcac aagcggtgga gcatgtggtt taattcgatg caacgcgaag aaccttacct     960
actcttgaca tccagagaac tttccagaga tggattggtg ccttcgggaa ctctgagaca    1020
ggtgctgcat ggctgtcgtc agctcgtgtt gtgaaatgtt gggttaagtc cgcaacgag    1080
cgcaaccctt atccttactt gccagcgggt aatgccggga actttaggga gactgccggt    1140
gataaaccgg aggaaggtgg ggacgacgtc aagtcatcat ggcccttacg agtagggcta    1200
cacacgtgct acaatggtcg gtacagaggg ttgcgaagcc gcgaggtgga gctaatctca    1260
caaagccggt cgtagtccgg attggagtct gcaactcgac tccatgaagt cggaatcgct    1320
agtaatcgta gatcagaatg ctacggtgaa tacgttcccg gccttgtac acaccgcccg    1380
tcacaccatg ggagtgggct gcaccagaag tagatagctt aaccttcggg agggcgttta    1440
ccacggtgtg gttcatgact ggggtgaagt cgtaacaagg tagccctagg ggaacctgg    1499
```

<210> SEQ ID NO 68
<211> LENGTH: 1285
<212> TYPE: DNA
<213> ORGANISM: Shewanella canadensis

<400> SEQUENCE: 68

```
ttgctatcag acgtcgagcg gcggacgggt gaagtaatgc ctagatatct gcctagtcgt      60
gggggataac agttggaaac gactgctaat accgcatacg ccctacgggg aaaggaggg     120
gaccttcggg cctttcgcga ttagatgagt ctaggtggga ttagctagta ggtgaggtaa    180
tggctcacct aggcgacgat ccctagctgt tctgagagga tgatcagcca cactgggact    240
gagacacggc ccagactcct acggagggca gcagtgggga atattgcaca atgggcgaaa    300
gcctgatgca gccatgccgc gtgtgtgaag aaggccttcg ggttgtaaag cactttcagc    360
gaggaggaaa ggttggtagt taatagctgc cagctgtgac gttactcgca gaagaagcac    420
cggctaactt cgtgccagca gccgcggtaa tacgaggggt gcaagcgtta atcggaatta    480
```

```
ctgggcgtaa agcgtacgca ggcggttttgt taagccagat gtgaaagccc cgggctcaac    540
ctgggaattg catttggaac tggcaaacta gagtcttgta gagggggggta gaatttcagg    600
tgtagcggtg aaatgcgtag agatctgaag gaataccggt ggcgaaggcg ccccctggga    660
caaagactga cgctcatgta cgaaagcgtg gggagcaaac aggattagat accctggtag    720
tccacgccgt aaacgatgtc tactcggagt ttggtaactt agttactggg ctcccaagct    780
aacgcattaa gtagaccgcc tggggagtac ggccgcaagg ttaaaactca aatgaattga    840
cgggggcccg cacaagcggt ggagcatgtg gtttaattcg atgcaacgcg aagaacctta    900
cctactcttg acatccagag aattcgctag agatagctta gtgccttcgg gagctctgag    960
acaggtgctg catggctgtc gtcagctcgt gttgtgaaat gttgggttaa gtcccgcaac   1020
gagcgcaacc cttatcctta tttgccagca cgtaatggtg gaactttag ggagactgcc    1080
ggtgataaac cggaggaagg tggggacgac gtcaagtcat catggccctt acgagtaggg   1140
ctacacacgt gctacaatgg tcggtacaga gggtcgcaaa ccgcgaggt ggagctaatc    1200
ccacaaagcc ggtcgtagtc cggatcggag tctgcaactc gactccgtga agtcggaatc   1260
gctagtaatc gagatcagaa tgtac                                          1285

<210> SEQ ID NO 69
<211> LENGTH: 1288
<212> TYPE: DNA
<213> ORGANISM: Shewanella sediminis

<400> SEQUENCE: 69
aagatgcttg cttatcaaac gtcgagcggc ggacggggtg agtaatgcct agatatctgc     60
ctagtcgtgg gggataacag ttggaaacga ctgctaatac cgcatacgcc ctacggggga    120
aaggagggga ccttcgggcc tttcgcgatt agatgagtct aggtgggatt agctagtagg    180
tgaggtaatg gctcacctag gcgacgatcc ctagctgttc tgagaggatg atcagccaca    240
ctgggactga gacacggccc agactcctac gggaggcagc agtggggaat attgcacaat    300
gggcgaaagc ctgatgcacc catgccgcgt gtgtgaaaaa ggccttcggg ttgtaaagca    360
ctttcagcga ggaggaaagg taggtagtta ataactgctt gctgtgacgt tactcgcaga    420
agaagcaccg gctaacttcg tgccagcagc cgcggtaata cgagggtgc aagcgttaat     480
cggaattact gggcgtaaag cgtacgcagg cggtttgtta agccagatgt gaaagccccg    540
ggctcaacct gggaattgca tttggaactg gcaaactaga gtcttgtaga gggggtaga    600
atttcaggtg tagcggtgaa atgcgtagag atctgaagga ataccggtgg cgaaggcggc    660
cccctggaca aagactgacg ctcatgtacg aaagcgtggg gagcaaacag gattagatac    720
cctggtagtc cacgccgtaa acgatgtcta ctcggagttt ggtaacttag ttactgggct    780
cccaagctaa cgcattaagt agaccgcctg ggagtacgg ccgcaaggtt aaaactcaaa     840
tgaattgacg ggggcccgca caagcggtgg agcatgtggt ttaattcgat gcaacgcgaa    900
gaaccttacc tactcttgac atccagagaa ttcgctagag atagcttagt gccttcggga    960
gctctgagac aggtgctgca tggctgtcgt cagctcgtgt tgtgaaatgt tgggttaagt   1020
cccgcaacga gcgcaaccct tatccttatt tgccagcacg taatggtggg actttaggg    1080
agactgccgg tgataaaccg gaggaaggtg gggacgacgt caagtcatca tggcccttac   1140
gagtagggct acacacgtgc tacaatggtc ggtacagagg gtcgcaaagc gcgaggtgg    1200
agctaatccc acaaagccgg tcgtagtccg gatcggagtc tgcaactcga ctccgtgaag   1260
tcggaatcgc tagtaatcga gatcagaa                                      1288
```

<210> SEQ ID NO 70
<211> LENGTH: 1293
<212> TYPE: DNA
<213> ORGANISM: Shewanella halifaxensis

<400> SEQUENCE: 70

```
gagcttgctc ctgaggtgac gagcggcgga cgggtgagta atgcctaggt atctgcccag      60
tcgaggggga taacagttgg aaacgactgc taataccgca tacgccctac ggggaaagg     120
aggggacctt cgggccttcc gcgattggat gaacctaggt gggattagct agttggtggg    180
gtaatggctc accaaggcga cgatccctag ctggtctgag aggatgatca gccacactgg    240
aactgagaca cggtccagac tcctacggga ggcagcagtg gggaatattg cacaatgggc    300
gaaagcctga tgcagccatg ccgcgtgtgt gaagaaggcc ttcgggttgt aaagcacttt    360
cagcgaggag gaaagctcaa gcgttaatag cgtttgggtg tgacgttact cgcagaagaa    420
gcaccggcta acttcgtgcc agcagccgcg gtaatacgag gggtgcaagc gttaatcgga    480
attactgggc gtaaagcgta cgcaggcggt ttgttaagca agatgtgaaa gccccgggct    540
caacctggga actgcatttt gaactggcaa actagagtct tgtagagggg ggtagaattt    600
cagtgtagcg gtgaaatgcg tagagatctg aaggaatacc ggtggcgaag gcggcccct    660
ggacaaagac tgacgctcag gtacgaaagc gtggggagca acaggatta gatacctgg     720
tagtccacgc cgtaaacgat gtctactcgg agtttggtgt cttgaacact gggctctcaa    780
gctaacgcat taagtagacc gcctgggag tacggccgca aggttaaaac tcaaatgaat    840
tgacggggc ccgcacaagc ggtggagcat gtggtttaat tcgatgcaac gcgaagaacc    900
ttacctactc ttgacatcca gagaattcgc tagagatagc ttagtgcctt cgggaactct    960
gagacaggtg ctgcatggct gtcgtcagct cgtgttgtga atgttgggt taagtcccgc   1020
aacgagcgca acccttatcc ttatttgcca gcacgtaatg gtgggaactt tagggagact   1080
gccggtgata accggagga aggtggggac gacgtcaagt catcatggcc cttacgagta   1140
gggctacaca cgtgctacaa tggtcggtac agagggttgc gaagccgcga ggtggagcta   1200
atctcacaaa gccggtcgta gtccggatcg gagtctgcaa ctcgactccg tgaagtcgga   1260
atcgctagta atcgagatca gaatgtacgg ata                                1293
```

<210> SEQ ID NO 71
<211> LENGTH: 1295
<212> TYPE: DNA
<213> ORGANISM: Shewanella atlantica
<220> FEATURE:
<221> NAME/KEY: misc_feature
<222> LOCATION: (1290)..(1290)
<223> OTHER INFORMATION: n is a, c, g, or t

<400> SEQUENCE: 71

```
cttgctactt tgctgtcgag cggcggacgg gtgagtaatg cctagatatc tgcctagtcg      60
tgggggataa cagttggaaa cgactgctaa taccgcatac gccctacggg ggaaaggagg    120
ggaccttcgg gccttcgcg attagatgag tctaggtggg attagctagt aggtgaggta    180
atggctcacc taggcgacga tccctagctg ttctgagagg atgatcagcc acactgggac    240
tgagacacgg cccagactcc tacgggaggc agcagtgggg aatattgcac aatgggcgaa    300
agcctgatgc agccatgccg cgtgtgtgaa gaaggcttc gggttgtaaa gcactttcag    360
cgaggaggaa aggttggtag ttaataactg ccagctgtga cgttactcgc agaagaagca    420
```

-continued

```
ccggctaact tcgtgccagc agccgcggta atacgagggg tgcaagcgtt aatcggaatt      480
actgggcgta aagcgtacgc aggcggtttg ttaagccaga tgtgaaagcc ccgggctcaa      540
cctgggaatt gcatttggaa ctggcaaact agagtcttgt agagggggt agaatttcag       600 gtgtagcggt gaaatgcgta gagatctgaa ggaataccgg tggcgaaggc ggccccctgg      660
acaaagactg acgctcaggt acgaaagcgt ggggagcaaa caggattaga taccctggta     720
gtccacgccg taaacgatgt ctactcggaa tttggtgtct tgaacactgg gttctcaagc     780
taacgcatta agtagaccgc ctggggagta cggccgcaag gttaaaactc aaatgaattg     840 acggggccc gcacaagcgg tggagcatgt ggtttaattc gatgcaacgc gaagaacctt      900
acctactctt gacatccaga gaattcgcta gagatagctt agtgccttcg ggagctctga     960
gacaggtgct gcatggctgt cgtcagctcg tgttgtgaaa tgttgggtta agtcccgcaa     1020
cgagcgcaac ccttatcctt atttgccagc acgtaatggt gggaacttta gggagactgc    1080
cggtgataaa ccggaggaag gtggggacga cgtcaagtca tcatggccct tacgagtagg     1140
gctacacacg tgctacaatg gtcggtacag agggttgcga agccgcgagg tgaagctaat    1200
cccagaaagc cggtcgtagt ccggatcgga gtctgcaact cgactccgtg aagtcggaat    1260
cgctagtaat cgtggatcag aatgccacgn aaacg                                1295
```

<210> SEQ ID NO 72
<211> LENGTH: 1462
<212> TYPE: DNA
<213> ORGANISM: Shewanella japonica
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (1456)..(1456)
<223> OTHER INFORMATION: n is a, c, g, or t

<400> SEQUENCE: 72

```
ggcctaacac atgcaagtcg agcggtaaca gaaagtagct tgctactttg ctgacgagcg      60
gnggacgggt gagtaatgcc tagggatctg cccagtcgag ggggataaca gttggaaacg     120
actgctaata ccgcatacgc cctacggggg aaggaggggg accttcgggc ctttcgcgat    180
tggatgaacc taggtgggat tagctagttg gtaaggtaat ggcttaccaa ggcgacgatc     240
cctagctgtt ctgagaggat gatcagccac actgggactg agacacggcc cagantccta     300
cgggaggcag cagtggggaa tattgcacaa tgggggaaac cctgatgcag ccatgccgcg     360
tgtgtgaaga aggccttcgg gttgtaaagc actttcagta gggaggaaag gtagcagctt     420
aatacgttgt tgctgtgacg ttacctacag aagaaggacc ggctaacttc gtgccagcag    480
ccgcggtaat acgagggtc caagcgttaa tcggaattac tgggcgtaaa gcgtacgcag     540
gcggttcatt aagccagatg tgaaatcccc gggctcaacc tgggaattgc atttggaact    600
ggtgaactag agtcttgtag aggggggtag aatttcaggt gtagcggtga atgcgtaga     660 gatctgaagg aataccggtg gcgaaggcgg ccccctggac aaagactgac gctcatgtac    720
gaaagcgtgg ggagcaaaca ggattagata ccctggtagt ccacgccgta aacgatgtct    780
actcggagtt tggtgccttg agcactgggc tccaagcta acgcattaag tagaccgcct    840
ggggagtacg gccgcaaggt taaaactcaa atgaattgac ggggcccgc acaagcggtg     900
```

```
gagcatgtgg tttaattcga tgcaacgcga agaaccttac ctactcttga catccagaga    960
actttccaga gatggattgg tgccttcggg aactctgaga caggtgctgc atggctgtcg   1020
tcagctcgtg ttgtgaaatg ttgggttaag tcccgcaacg agcgcaaccc ctatccttat   1080
ttgccagcgc gtaatggcgg gaactctagg gagactgccg gtgataaacc ggaggaaggt   1140
ggggacgacg tcaagtcatc atggccctta cgagtagggc tacacacgtg ctacaatggc   1200
gagtacagag ggttgcaaag ccgcaaggtc tagctaatct cataaagctc gtcgtagtcc   1260
ggattggagt ctgcaactcg actccatgaa gtcggaatcg ctagtaatcg tagatcagaa   1320
tgctacggtg aatacgttcc cgggccttgt acacaccgcc cgtcacacca tgggagtggg   1380
ctgcaccaga agtagatagt ctaaccttcg gaggacgtt taccacggtg tggttcatga    1440
ctggggtgaa gtcgtnacaa gg                                             1462
```

<210> SEQ ID NO 73
<211> LENGTH: 1498
<212> TYPE: DNA
<213> ORGANISM: Shewanella colwelliana

<400> SEQUENCE: 73

```
attgaacgct ggcggcaggc ctaacacatg caagtcgagc ggtaacagga attagcttgc     60
taatttgctg acgagcggcg gacgggtgag taatgcctag gaactgccc agtcgagggg    120
gataacagtt ggaaacgact gctaataccg catacgccct acggggaaa agaggggacc    180
ttcgggcctt ctgcgattgg atgtacctag gtgggattag ctagttggtg aggtaatggc    240
tcaccaaggc gacgatccct agctgttctg agaggatgat cagccacact gggactgaga    300
cacggcccag actcctacgg gaggcagcag tggggaatat tgcacaatgg gcgcaagcct    360
gatgcagcca tgccgcgtgt gtgaagaagg ccttcgggtt gtaaagcact ttcagcgagg    420
aggaaagctt aagcgttaat agcgtttagg tgtgacgtta ctcgcagaag aaggaccggc    480
taacttcgtg ccagcagccg cggtaatacg agggtccaa gcgttaatcg gaattactgg    540
gcgtaaagcg tacgcaggcg gtttgttaag cgagatgtga agccccggg ctcaacctgg    600
gaactgcatt tcgaactggc aaactagagt cttgtagagg ggggtagaat ttcaggtgta    660
gcggtgaaat gcgtagagat ctgaaggaat accggtggcg aaggcggccc cctggacaaa    720
gactgacgct catgtacgaa agcgtgggga gcaaacagga ttagataccc tggtagtcca    780
cgccgtaaac gatgtctact cggaatttgg tgtcttgaac actgggttct caagctaacg    840
cattaagtag accgcctggg gagtacggcc gcaaggttaa aactcaaatg aattgacggg    900
ggcccgcaca gcggtggag catgtggttt aattcgatgc aacgcgaaga accttaccta    960
ctcttgacat ccagagaatt cgctagagat agcttagtgc cttcgggaac tctgagacag   1020
gtgctgcatg gctgtcgtca gctcgtgttg tgaaatgttg ggttaagtcc cgcaacgagc   1080
gcaacccta tccttatttg ccagcacgta atggtgggaa ctttagggag actgccggtg   1140
ataaaccgga ggaaggtggg gacgacgtca agtcatcatg gcccttacga gtagggctac   1200
acacgtgcta caatgcaag tacagagggt tgcgaagccg cgaggtggag ctaatctcac   1260
aaagcttgtc gtagtccgga ttggagtctg caactcgact ccatgaagtc ggaatcgcta   1320
gtaatcgtgg atcagaatgc cacggtgaat acgttcccgg ccttgtaca caccgcccgt   1380
cacaccatgg gagtgggctg caccagaagt agatagctta accttcggga gggcgtttac   1440
cacggtgtgg ttcatgactg gggtgaagtc gtaacaaggt agcccaggg gaacctgg     1498
```

<210> SEQ ID NO 74
<211> LENGTH: 1487
<212> TYPE: DNA
<213> ORGANISM: Shewanella abyssi

<400> SEQUENCE: 74

| | | | | | |
|---|---|---|---|---|---|
| gatcctggct | cagattgaac | gctggcggca | ggcctaacac | atgcaagtcg | agcggaaaca | 60 |
| ggaaggtagc | ttgctacttt | tgctgtcgag | cggcggacgg | gtgagtaata | cctaggtatc | 120 |
| tgcccagtcg | tgggggataa | cagttggaaa | cgactgctaa | taccgcatac | gccctacggg | 180 |
| ggaaaggagg | ggaccttcgg | gccttccgcg | attggatgaa | cctaggcggg | attagctagt | 240 |
| tggtgaggta | atggctcacc | aaggcgacga | tccctagctg | gtctgagagg | atgatcagcc | 300 |
| acactggaac | tgagacacgg | tccagactcc | tacgggaggc | agcagtgggg | aatattgcac | 360 |
| aatgggcgaa | agcctgatgc | agccatgccg | cgtgtatgaa | gaaggccttc | gggttgtaaa | 420 |
| gtactttcag | cgaggaggaa | agttcaagtg | ttaatagcac | ttggatgtga | cgttactcgc | 480 |
| agaagaagca | ccggctaact | tcgtgccagc | agccgcggta | atacgagggg | tgcaagcgtt | 540 |
| aatcggaatt | actgggcgta | aagcgtacgc | aggcggtttg | ttaagcgaga | tgtgaaagcc | 600 |
| ccgggctcaa | cctgggaact | gcatttcgaa | ctggcaaact | agagtcttgt | agaggggggt | 660 |
| agaatttcag | gtgtagcggt | gaaatgcgta | gagatctgaa | ggaataccgg | tggcgaaggc | 720 |
| ggcccctgg | acaaagactg | acgctcatgt | acgaaagcgt | ggggagcaaa | caggattaga | 780 |
| taccctggta | gtccacgccg | taaacgatgt | ctactcggaa | tttggtgtct | gaacactgg | 840 |
| gttctcaagc | taacgcatta | agtagaccgc | ctggggagta | cggccgcaag | gttaaaactc | 900 |
| aaatgaattg | acgggggccc | gcacaagcgg | tggagcatgt | ggtttaattc | gatgcaacgc | 960 |
| gaagaacctt | acctactctt | gacatccaca | gaattcgcta | gagatagctt | agtgccttcg | 1020 |
| ggaactgtga | gacaggtgct | gcatggctgt | cgtcagctcg | tgttgtgaaa | tgttgggtta | 1080 |
| agtcccgcaa | cgagcgcaac | ccttatcctt | atttgccagc | acgtaatggt | gggaacttta | 1140 |
| gggagactgc | cggtgataaa | ccggaggaag | gtggggacga | cgtcaagtca | tcatggccct | 1200 |
| tacgagtagg | gctacacacg | tgctacaatg | gccggtacag | agggttgcaa | agccgcgagg | 1260 |
| tggagctaat | ctcacaaagc | cggtcgtagt | ccggatcgga | gtctgcaact | cgactccgtg | 1320 |
| aagtcggaat | cgctagtaat | cgtgaatcag | aatgtcacgg | tgaatacgtt | cccgggcctt | 1380 |
| gtacacaccg | cccgtcacac | catgggagtg | ggctgcacca | gaagtagata | gcttaacctt | 1440 |
| cgggagggcg | tttaccacgg | tgtggttcat | gactggggtg | aagtcgt | | 1487 |

<210> SEQ ID NO 75
<211> LENGTH: 1418
<212> TYPE: DNA
<213> ORGANISM: Shewanella hafniensis

<400> SEQUENCE: 75

| | | | | | |
|---|---|---|---|---|---|
| acacatgcaa | gtcgagcggc | agcacaaggg | agtttactcc | tgaggtggcg | agcggcggac | 60 |
| gggtgagtaa | tgcctaggga | tctgcccagt | cgaggggat | aacagttgga | aacgactgct | 120 |
| aataccgcat | acgccctacg | ggggaaagga | ggggaccttc | gggccttccg | cgattggatg | 180 |
| aacctaggtg | ggattagcta | gttggtgagg | taatggctca | ccaaggcgac | gatccctagc | 240 |
| tgttctgaga | ggatgatcag | ccacactggg | actgagacac | ggcccagact | cctacgggag | 300 |
| gcagcagtgg | ggaatattgc | acaatggggg | aaaccctgat | gcagccatgc | cgcgtgtgtg | 360 |
| aagaaggcct | tcgggttgta | aagcactttc | agtagggagg | aaagggtgag | gcttaatacg | 420 |

```
ccttttctgt gacgttacct acagaagaag gaccggctaa ctccgtgcca gcagccgcgg      480
taatacggag ggtccgagcg ttaatcggaa ttactgggcg taaagcgtgc gcaggcggtt      540
tgttaagcga gatgtgaaag ccccgggctc aacctgggaa ttgcatttcg aactggcgaa      600
ctagagtctt gtagagggggg gtagaattcc aggtgtagcg gtgaaatgcg tagagatctg      660
gaggaatacc ggtggcgaag gcggccccct ggacaaagac tgacgctcag gcacgaaagc      720
gtggggagca aacaggatta gataccctgg tagtccacgc cgtaaacgat gtctactcgg      780
agtttggtgt cttgaacact gggctctcaa gctaacgcat aagtagacc gcctggggag       840 tacggccgca aggttaaaac tcaaatgaat tgacggggggc ccgcacaagc ggtggagcat     900
gtggtttaat tcgatgcaac gcgaagaacc ttacctactc ttgacatcca cagaattttc      960
cagagatgga ttggtgcctt cgggaactgt gagacaggtg ctgcatggct gtcgtcagct     1020
cgtgttgtga atgttgggt taagtcccgc aacgagcgca accccttatcc ttatttgcca     1080 gcacgtaatg gtgggaactc tagggagact gccggtgata aaccggagga aggtggggac     1140
gacgtcaagt catcatggcc cttacgagta gggctacaca cgtgctacaa tggcgagtac     1200
agagggttgc aaagccgcga ggtggagcta atctcacaaa gctcgtcgta gtccggattg     1260
gagtctgcaa ctcgactcca tgaagtcgga atcgctagta atcgtggatc agaatgccac     1320
ggtgaatacg ttcccgggcc ttgtacacac cgcccgtcac accatgggag tgggctgcaa     1380
aagaagtggg tagcttaacc ttcgggggggg cgctcacc                            1418

<210> SEQ ID NO 76
<211> LENGTH: 1413
<212> TYPE: DNA
<213> ORGANISM: Shewanella algidipiscicola

<400> SEQUENCE: 76
acacatgcaa gtcgagcggt aacaggaatt agcttgctaa tttgctgacg agcggcggac       60
gggtgagtaa tgcctaggga actgcccagt cgaggggggat aacagttgga aacgactgct     120
aataccgcat acgccctacg ggggaaaaga gggaccttc gggccttctg cgattggatg      180
tacctaggtg ggattagcta gttggtgagg taatggctca ccaaggcgac gatccctagc      240
tgttctgaga ggatgatcag ccacactggg actgagacac ggcccagact cctacgggag      300
gcagcagtgg ggaatattgc acaatgggcg caagcctgat gcagccatgc cgcgtgtgtg      360
aagaaggcct tcgggttgta aagcactttc agcgaggagg aaagcttaag cgttaatagc      420
gtttaggtgt gacgttactc gcagaagaag gaccggctaa cttcgtgcca gcagccgcgg      480
taatacggag ggtccaagcg ttaatcggaa ttactgggcg taaagcgtac gcaggcggtt      540
tgttaagcga gatgtgaaag ccccgggctc aacctgggaa ttgcatttcg aactggcaaa      600
ctagagtctt gtagagggggg gtagaatttc aggtgtagcg gtgaaatgcg tagagatctg      660
aaggaatacc ggtggcgaag gcggccccct ggacaaagac tgacgctcag gtacgaaagc      720
gtggggagca aacaggatta gataccctgg tagtccacgc cgtaaacgat gtctactcgg      780
aatttggtgt cttgaacact gggttcccaa gctaacgcat aagtagacc gcctggggag       840 tacggccgca aggttaaaac tcaaatgaat tgacggggggc ccgcacaagc ggtggagcat     900
gtggtttaat tcgatgcaac gcgaagaacc ttacctactc ttgacatcca gagaattcgc      960
tagagatagc ttagtgcctt cgggagctct gagacaggtg ctgcatggct gtcgtcagct     1020
cgtgttgtga atgttgggt taagtcccgc aacgagcgca acccttatcc ttatttgcca     1080
```

```
gcacgtaatg gtgggaactt tagggagact gccggtgata aaccggagga aggtggggac    1140
gacgtcaagt catcatggcc cttacgagta gggctacaca cgtgctacaa tggcaagtac    1200
agagggttgc aaagccgcga ggtggagcta atctcacaaa gcttgtcgta gtccggattg    1260
gagtctgcaa ctcgactcca tgaagtcgga atcgctagta atcgtggatc agaatgccac    1320
ggtgaatacg ttcccgggcc ttgtacacac cgcccgtcac accatgggag tgggctgcac    1380
cagaagtaga tagcttaacc ttcgggaggg cgt                                 1413
```

<210> SEQ ID NO 77
<211> LENGTH: 1418
<212> TYPE: DNA
<213> ORGANISM: Shewanella glacialipiscicola

<400> SEQUENCE: 77

```
acacatgcaa gtcgagcggc agcgcaaggg agtttactcc tgaggcggcg agcggcggac     60
gggtgagtaa tacctaggga tctgcccagt cgagggggat aacagttgga aacgactgct    120
aataccgcat acgccctacg ggggaaagaa ggggaccttc gggccttttcg cgattggatg    180 aacctaggtg ggattagcta gttggtgagg taatggctca ccaaggcgac gatccctagc    240
tgttctgaga ggatgatcag ccacactggg actgagacac ggcccagact cctacgggag    300
gcagcagtgg ggaatattgg acaatggggg caaccctgat ccagccatgc cgcgtgtgtg    360
aagaaggcct cgggttgta aagcactttc agtaggagg aaaggtaata acttaatacg    420
ttattactgt gacgttacct acagaagaag gaccggctaa ctccgtgcca gcagccgcgg    480 taatacgag ggtccgagcg ttaatcggaa ttactgggcg taaagcgtgc gcaggcggtt    540
tgttaagcaa gatgtgaaag ccccgggctc aacctgggaa ttgcattttg aactggcaaa    600
ctagagtctt gtagaggggg gtagaattcc aggtgtagcg gtgaaatgcg tagagatctg    660
gaggaatacc ggtggcgaag gcggccccct ggacaaagac tgacgctcag gcacgaaagc    720
gtggggagca acaggatta gataccctgg tagtccacgc cgtaaacgat gtctactcgg    780
agtttggtgt cttgaacact gggctctcaa gctaacgcat taagtagacc gcctggggag    840
tacggccgca aggttaaaac tcaaatgaat tgacggggc ccgcacaagc ggtggagcat    900
gtggtttaat tcgatgcaac gcgaagaacc ttacctactc ttgacatcca cagaagccag    960
tagagataca ggtgtgcctt cgggaactgt gagacaggtg ctgcatggct gtcgtcagct    1020
cgtgttgtga atgttgggt taagtcccgc aacgagcgca accctatcc ttatttgcca    1080 gcacgtaatg gtgggaactc tagggagact gccggtgata aaccggagga aggtggggac    1140
gacgtcaagt catcatggcc cttacgagta gggctacaca cgtgctacaa tggcgagtac    1200
agagggttgc aaagccgcga ggtggagcta atctcacaaa gctcgtcgta gtccggattg    1260
gagtctgcaa ctcgactcca tgaagtcgga atcgctagta atcgtgaatc agaatgtcac    1320
ggtgaatacg ttcccgggcc ttgtacacac cgcccgtcac accatgggag tgggctgcaa    1380
aagaagtggg tagcttaacc ttcgggggg cgctcacc                             1418
```

<210> SEQ ID NO 78
<211> LENGTH: 1426
<212> TYPE: DNA
<213> ORGANISM: Shewanella morhuae

<400> SEQUENCE: 78

```
ggctacacat gcaagtcgag cggcagcgca agggagttta ctcctgaggc ggcgagcggc     60
ggacgggtga gtaataccta gggatctgcc cagtcgaggg ggataacagt tggaaacgac    120
```

```
tgctaatacc gcatacgccc tacgggggaa agaagggggac cttcgggcct ttcgcgattg     180
gatgaaccta ggtgggatta gctagttggt gaggtaatgg ctcaccaagg cgacgatccc     240
tagctgttct gagaggatga tcagccacac tgggactgag acacggccca gactcctacg     300
ggaggcagca gtggggaata ttggacaatg ggggcaaccc tgatccagcc atgccgcgtg     360
tgtgaagaag gccttcgggt tgtaaagcac tttcagtagg gaggaaaggt agcgtgttaa     420
tagcacgtta ctgtgacgtt acctacagaa gaaggaccgg ctaactccgt gccagcagcc     480
gcggtaatac ggagggtccg agcgttaatc ggaattactg ggcgtaaagc gtgcgcaggc     540
ggtttgttaa gcaagatgtg aaagccccgg gctcaacctg gaattgcat tttgaactgg      600 cgaactagag tcttgtagag ggggtagaa ttccaggtgt agcggtgaaa tgcgtagaga      660
tctggaggaa taccggtggc gaaggcggcc cctggacaa agactgacgc tcaggcacga      720
aagcgtgggg agcaaacagg attagatacc ctggtagtcc acgccgtaaa cgatgtctac     780
tcggagtttg gtgtcttgaa cactgggctc tcaagctaac gcattaagta gaccgcctgg     840
ggagtacggc cgcaaggtta aaactcaaat gaattgacgg gggcccgcac aagcggtgga     900
gcatgtggtt taattcgatg caacgcgaag aaccttacct actccttgaca tccacagaag    960 agaccagaga tggacttgtg ccttcgggaa ctgtgagaca ggtgctgcat ggctgtcgtc    1020
agctcgtgtt gtgaaatgtt gggttaagtc cgcaacgag cgcaacccct atccttattt    1080
gccagcacgt aatggtggga actctaggga gactgccggt gataaaccgg aggaaggtgg    1140
ggacgacgtc aagtcatcat ggcccttacg agtagggcta cacacgtgct acaatggcga    1200
gtacagaggg ttgcaaagcc gcgaggtgga gctaatctca caaagctcgt cgtagtccgg    1260
attggagtct gcaactcgac tccatgaagt cggaatcgct agtaatcgtg aatcagaatg    1320
tcacggtgaa tacgttcccg ggccttgtac acaccgcccg tcacaccatg ggagtgggct    1380
gcaaaagaag tgggtagctt aaccttcggg ggggcgctca ccactt                   1426
```

<210> SEQ ID NO 79
<211> LENGTH: 1515
<212> TYPE: DNA
<213> ORGANISM: Shewanella pneumatophori

<400> SEQUENCE: 79

```
cgctcagatt gaacgctggc ggcaggccta acacatgcaa gtcgagcggt aacacaaggg     60
agcttgctcc tgaggtgacg agcggcggac gggtgagtaa tgcctaggta tctgcccagt    120 cgaggggggat aacagttgga aacgactgct aataccgcat acgccctacg ggggaaagga    180
ggggaccttc gggccttccg cgattggatg aacctaggtg ggattagcta gttggtgagg    240
taatggctca ccaaggcgac gatccctagc tggtctgaga ggatgatcag ccacactgga    300
actgagacac ggtccagact cctacgggag gcagcagtgg ggaatattgc acaatgggcg    360
aaagcctgat gcagccatgc cgcgtgtgtg aagaaggcct tcgggttgta agcactttc     420 agcgaggagg aaaggttagt gattaatact cactagctgt gacgttactc gcagaagaag    480
caccggctaa cttcgtgcca gcagccgcgg taatacgagg ggtgcaagcg ttaatcggaa    540
ttactgggcg taaagcgtac gcaggcggtt tgttaagcga gatgtgaaag ccccgggctc    600
aacctgggaa ctgcatttcg aactggcaaa ctagagtctt gtagagggg gtagaatttc     660 aggtgtagcg gtgaaatgcg tagagatctg aaggaatacc ggtggcgaag gcggcccct     720 ggacaaagac tgacgctcag gtacgaaagc gtggggagca acaggatta gatacctgg     780
```

```
tagtccacgc cgtaaacgat gtctactcgg agtttggtgt cttgaacact gggctctcaa        840
gctaacgcat taagtagacc gcctggggag tacggccgca aggttaaaac tcaaatgaat        900 tgacggggc ccgcacaagc ggtggagcat gtggtttaat tcgatgcaac gcgaagaacc         960
ttacctactc ttgacatcca gagaattcgc tagagatagc ttagtgcctt cgggaactct       1020
gagacaggtg ctgcatggct gtcgtcagct cgtgttgtga atgttgggt taagtcccgc        1080 aacgagcgca acccttatcc ttatttgcca gcacgtaatg gtgggaactt tagggagact      1140
gccggtgata accggagga aggtggggac gacgtcaagt catcatggcc cttacgagta       1200
gggctacaca cgtgctacaa tggtcggtac agagggttgc gaagccgcga ggtgagcta       1260 atctcacaaa gccggtcgta gtccggatcg gagtctgcaa ctcgactccg tgaagtcgga       1320
atcgctagta atcgtagatc agaatgctac ggtgaatacg ttcccgggcc ttgtacacac       1380
cgcccgtcac accatgggag tgggctgcac cagaagtaga tagcttaacc ttcgggaggg      1440
cgtttaccac ggtgtggttc atgactgggg tgaagtcgta acaaggtagc cctaggggaa      1500
cctggggctg gattc                                                        1515

<210> SEQ ID NO 80
<211> LENGTH: 1474
<212> TYPE: DNA
<213> ORGANISM: Shewanella spongiae

<400> SEQUENCE: 80
ctaccatgca agtctagcgg tacagagagt agcttgctac tctgctgacg agcggcggac         60
gggtgagtaa tgcctgggaa tttgcccagt tgtgggggat aacagttgga aacgactgct       120
aataccgcat aaaccctacg gggaaaagca ggggaccta gggccttgcg caattggata        180
agcccaggtg ggattagcta gtaggtgagg taagagctca cctaggcgac gatccctagc      240
tgttctgaga ggatgatcag ccacactggg actgagacac ggcccagact cctacgggag     300
gcagcagtgg ggaatattgc acaatgggcg aaagcctgat gcagccatgc cgcgtgtgtg     360
aagaaggcct tcgggttgta aagcactttc agtggggagg aaaagttgtt ggttaataac      420
cagcagccgt gacgttaccc acagaagaag gaccggctaa ctccgtgcca gcagccgcgg    480
taatacggag ggtccgagcg ttaatcggaa ttactgggcg taaagcgtgc gcaggcggtc     540
tgttaagtca gatgtgaaag ccccgggctc aacctgggaa tagcatttga aactggcaga    600
ctagagtctt gtagagggggg gtagaatttc aggtgtagcg gtgaaatgcg tagagatctg   660
aaggaatacc ggtggcgaag gcggcccct ggacaaagac tgacgctcat gcacgaaagc      720
gtggggagca acaggatta gataccctgg tagtccacgc cgtaaacgat gtctactcgg      780
aatttggtct cttgaagact gggttctcaa gctaacgcat taagtagacc gcctggggag     840
tacggccgca aggttaaaac tcaaatgaat tgacggggc ccgcacaagc ggtggagcat       900
gtggtttaat tcgatgcaac gcgaagaacc ttacctactc ttgacatcca gagaactttc      960
cagagatgga ttggtgcctt cgggaactct gagacaggtg ctgcatggct gtcgtcagct     1020
cgtgttgtga atgttgggt taagtcccgc aacgagcgca acccttatcc ttatttgcca      1080
gcacttcggg tggaactttt agggagactg ccggtgataa accggaggaa ggtggggacg     1140
acgtcaagtc atcatggccc ttacgagtag gctacacac gtgctacaat gggcaataca    1200
aagggttgcg aagccgcgaa ggtgagcta atctcataaa gttgttcgta gtccggattg     1260
gagtctgcaa ctcgactcca tgaagtcgga atcgctagta atcgtagatc agaatgctac    1320
ggtgaatacg ttcccgggcc ttgtacacac cgcccgtcac accatgggag tgggctgcaa   1380
```

```
aagaagtggg tagtttaacc ttcgggagaa cgctcaccac tttgtggttc atgactgggg    1440
tgaagtcgta acaaggtagc cctagggaa cctg                                 1474
```

<210> SEQ ID NO 81
<211> LENGTH: 1462
<212> TYPE: DNA
<213> ORGANISM: Shewanella irciniae

<400> SEQUENCE: 81

```
gctggcggca ggctaacaca tgcaagtcga gcggtaacag agagtagctt gctactctgc     60
tgacgagcgg cggacgggtg agtaatgcct gggaatttgc ccagttgtgg gggataacag    120
ttggaaacga ctgctaatac cgcataaacc ctacgggaa aagcagggga ccttcgggcc    180 tgcgcaatt ggataagccc aggtgggatt agctagatgg tgaggtaaag gctcaccatg    240
gcgacgatcc ctagctgttc tgagaggatg atcagccaca ctgggactga gacacggccc    300
agactcctac gggaggcagc agtggggaat attgcacaat gggggaaacc ctgatgcagc    360
catgccgcgt gtgtgaagaa ggccctaggg ttgtaaagca ctttcagtca ggaggaaagg    420
ttggtagtta ataactgcta gctgtgacgt tactgacaga agaaggaccg gctaactccg    480
tgccagcagc cgcggtaata cggagggtcc gagcgttaat cggaattact gggcgtaaag    540
cgtgcgcagg cggtttgtta agtcagatgt gaaagccccg ggctcaacct gggaatagca    600
tttgaaactg gcaaactaga gtcttgtaga gggggtaga atttcaggtg tagcggtgaa    660
atgcgtagag atctgaagga ataccagtgg cgaaggcggc ccctggaca aagactgacg    720 ctcaggcacg aaagcgtggg gagcaaacag gattagatac cctggtagtc cacgccgtaa    780
acgatgtcta ctcggaattt ggtctcttga agactgggtt ctcaagctaa cgcattaagt    840
agaccgcctg gggagtacgg ccgcaaggtt aaaactcaaa tgaattgacg ggggcccgca    900
caagcggtgg agcatgtggt ttaattcgat gcaacgcgaa gaaccttacc tactcttgac    960
atccagagaa ctttccagag atggattggt gccttcggga actctgagac aggtgctgca   1020
tggctgtcgt cagctcgtgt tgtgaaatgt tgggttaagt cccgcaacga gcgcaaccct   1080
tatccttatt tgccagcact tcgggtggga actttaggga gactgccggt gataaaccgg   1140
aggaaggtgg ggacgacgtc aagtcatcat ggcccttacg agtagggcta cacacgtgct   1200
acaatgggca ttacagaggg ttgcgaagcc gcgaggtgga gctaatctca gaaaggtgct   1260
cgtagtccgg attggagtct gcaactcgac tccatgaagt cggaatcgct agtaatcgcg   1320
gatcagaatg ccgcggtgaa tacgttcccg ggccttgtac acaccgcccg tcacaccatg   1380
ggagtgggct gcaaaagaag tggctagtct aaccttcggg gggacggtca ccactttgtg   1440
gttcatgact ggggtgaagt cg                                             1462
```

<210> SEQ ID NO 82
<211> LENGTH: 1537
<212> TYPE: DNA
<213> ORGANISM: Shewanella loihica

<400> SEQUENCE: 82

```
agagtttgat catggctcag attgaacgct ggcggcaggc ctaacacatg caagtcgagc     60
ggtaacattt caaaagcttg cttttgaaga tgacgagcgg cggacgggtg agtaatgcct    120
agggaactgc ccagtcgagg gggataacag ttggaaacga ctgctaatac cgcatacgcc    180
ctacggggga aagagggga tcttcggacc ttctgcgatt ggatgtaccct aggtgggatt    240
```

```
agctagtagg tgaggtaatg gctcacctag gcgacgatcc ctagctgttc tgagaggatg    300
atcagccaca ctgggactga gacacggccc agactcctac gggaggcagc agtggggaat    360
attgcacaat gggcgcaagc ctgatgcagc catgccgcgt gtgtgaagaa ggccttcggg    420
ttgtaaagca ctttcagcga ggaggaaagg ttaacggtta atacccgtta gctgtgacgt    480
tactcgcaga agaagcaccg gctaacttcg tgccagcagc cgcggtaata cgagggggtgc   540
aagcgttaat cggaattact gggcgtaaag cgtacgcagg cggttgatta agcgagatgt    600
gaaagccccg gcttaacctg ggaactgcat ttcgaactg tcaactaga gtcttgtaga      660
gggggggtaga atttcaggtg tagcggtgaa atgcgtagag atctgaagga ataccgtgg    720
cgaaggcggc cccctggaca aagactgacg ctcaggtacg aaagcgtggg gagcaaacag    780
gattagatac cctggtagtc cacgccgtaa acgatgtcta ctcggaattt ggtgtcttga    840
acactgggtt ctcaagctaa cgcattaagt agaccgcctg ggagtacgg ccgcaaggtt     900
aaaactcaaa tgaattgacg ggggcccgca caagcggtgg agcatgtggt ttaattcgat    960
gcaacgcgaa gaaccttacc tactcttgac atccagagaa cttttcagag atgaattggt    1020
gccttcggga actctgagac aggtgctgca tggctgtcgt cagctcgtgt tgtgaaatgt    1080
tgggttaagt cccgcaacga gcgcaaccct tatccttact tgccagcggg taatgccggg    1140
aactttaggg agactgccgg tgataaaccg gaggaaggtg gggacgacgt caagtcatca    1200
tggcccttac gagtagggct acacacgtgc tacaatggtc ggtacagagg gttgcgaagc    1260
cgcgaggtgg agctaatctc acaaagccgg tcgtagtccg gattggagtc tgcaactcga    1320
ctccatgaag tcggaatcgc tagtaatcgt ggatcagaat gccacggtga atacgttccc    1380
gggccttgta cacaccgccc gtcacaccat gggagtgggc tgcaccagaa gtagatagct    1440
taaccttcgg gagggcgttt accacggtgt ggttcatgac tggggtgaag tcgtaacaag    1500
gtagccctag ggaacctgg ggctggatca cctcctt                              1537

<210> SEQ ID NO 83
<211> LENGTH: 1459
<212> TYPE: DNA
<213> ORGANISM: Shewanella olleyana

<400> SEQUENCE: 83
ctggcggcag gcctaacaca tgcaagtcga gcggtaacag aaagaaagct tgctttcttt     60
gctgacgagc ggcagacggg tgagtaatgc ctagggatct gcccagtcga gggggataac    120
agttggaaac gactgctaat accgcatacg ccctacgggg gaaaggaggg gaccttcggg    180
cctttcgcga ttggatgaac ctatgtggga ttagctagtt tgtaaggtaa tggcttacca    240
aggccactat ccctagctgt tctgagagga tgatcagcca cactgggact gagacacggc    300
ccagactcct acgggaggca gcagtgggga atattgcaca atgggcgaaa gcctgatgca    360
gccatgccgc gtgtgtgaag aagccctagg gtttgtaaag cactctcagt agggaggaaa    420
ggcagttgtt taatacgctc tcgctgtgac gttacctaca gaagaaagac cggctaactt    480
cgtgccagca gccgcggtaa tacggagggt ccaagcgtta atcagaatta ctgggcgtaa    540
agcgtacgca ggcggttcat taagccagat gtgaaatccc tgggctcaac ctgggaattg    600
cattttgaac tggtgaacta gagtcttgta gagggggta gaatttcagg tgtagcggtg    660
aaatgcgtag atatctgaag gaataccggt ggcgaaggcg ccccctgga caaagactga    720
cgctcatgca cgaaagcgtg gggagcaaac aggattagat accctggtag tccacgccgt    780
aaacgatgtc tactcggagt ttggtgcctt gagcactggg ctcccaagct aacgcattaa    840
```

```
gtagaccgcc tggggagtac ggccgcaagg ttaaaactca aatgaattga cgggggcccg      900
cacaagcggt ggagcatgtg gtttaattcg atgcaacgcg aagaacctta cctactcttg      960
acatccagag aattcgctag agatagctta gtgccttcgg gaactctgag acaggtgctg     1020
catggctgtc gtcagctcgt gttgtgaaat gttgggttaa gtcccgcaac gagcgcaacc     1080
cctatcctta tttgccagcg cgtaatggcg ggaactctag ggagactgcc ggtgataaac     1140
cggaggaagg tggggacgac gtcaagtcat catggccctt acgagtaggg ctacacacgt     1200
gctacaatgg cgtatacaga gggttgcaaa gccgcaaggt ctagctaatc tcacaaagta     1260
cgtcgtagtc cggattggag tctgcaactc gactccatga agtcggaatc gctagtaatc     1320
gtagatcaga atgctacggt gaatacgttc ccgggccttg tacacaccgc ccgtcacacc     1380
atgggagtgg gctgcaccag aagtagatag tctaaccttc gggggacgt ttaccactgt      1440 gtggtttatg gctggggtg                                                  1459

<210> SEQ ID NO 84
<211> LENGTH: 1419
<212> TYPE: DNA
<213> ORGANISM: Shewanella woodyi

<400> SEQUENCE: 84
aggcctaaca catgcaagtc gagcggaaac agaaarttac ttgctacttt tgctgtcgag       60
cggcggacgg gtgagtaatg cctagatatc tgcctagtcg tggggataaa cagttggaaa      120
cgactgctaa taccgcatac gccctacggg ggaaaggagg ggaccttcgg gcctttcgcg      180
attagatgag tctaggtggg attagctagt aggtgaggta atggctcacc taggcgacga      240
tccctagctg ttctgagagg atgatcagcc acactgggac tgagacacgg cccagactcc      300
tacgggaggc agcagtgggg aatattgcac aatgggcgaa agcctgatgc agccatgccg      360
cgtgtgtgaa gaaggccttc gggttgtaaa gcactttcag cgaggaggaa aggttaacgg      420
ttaataaccg ttagctgtga cgttactcgc agaagaagca ccggctaact tcgtgccagc      480
agccgcggta atacgagggg tgcaagcgtt aatcggaatt actgggcgta aagcgtacgc      540
aggcggtttg ttaagccaga tgtgaaagcc ccgggctcaa cctgggaatt gcatttggaa      600
ctggcaaact agagtcttgt agaggggggt agaatttcag gtgtagcggt gaaatgcgta      660
gagatctgaa ggaataccgg tggcgaaggc ggccccctgg acaaagactg acgctcaggt      720
acgaaagcgt ggggagcaaa caggattaga taccctggta gtccacgccg taaacgatgt      780
ctactcggag tttggtaact tagttactgg gctcccaagc taacgcatta agtagaccgc      840
ctggggagta cggccgcaag gttaaaactc aaatgaattg acgggggccc gcacaagcgg      900
tggagcatgt ggtttaattc gatgcaacgc gaagaacctt acctactctt gacatccaca      960
gaactttcca gagatgratt ggtgccttcg gaactgtga caggtgct gcatggctgt      1020 cgtcagctcg tgttgtgaaa tgttgggtta agtcccgcaa cgagcgcaac ccttatcctt      1080
atttgccagc gagttatgtc gggaacttta gggagactgc cggtgataaa ccggaggaag      1140
gtggggacga cgtcaagtca tcatggccct tacgagtagg gctacacacg tgctacaatg      1200
gtcggtacag agggttgcga agccgcgagg tggagctaat cccagaaagc cggtcgtagt      1260
ccggattgga gtctgcaact cgactccatg aagtcggaat cgctagtaat cgtggatcag      1320
aatgccacgt gaatacgttc ccgggccttg tacacaccg cccgtcacac catgggagtg      1380
ggctgcacca gaagtagata gcttaacctt cgggagggc                            1419
```

<210> SEQ ID NO 85
<211> LENGTH: 1542
<212> TYPE: DNA
<213> ORGANISM: Escherichia coli

<400> SEQUENCE: 85

| | | | | | |
|---|---|---|---|---|---|
| aaattgaaga | gtttgatcat | ggctcagatt | gaacgctggc | ggcaggccta | acacatgcaa | 60 |
| gtcgaacggt | aacaggaaga | agcttgcttc | tttgctgacg | agtggcggac | gggtgagtaa | 120 |
| tgtctgggaa | actgcctgat | ggagggggat | aactactgga | aacggtagct | aataccgcat | 180 |
| aacgtcgcaa | gaccaaagag | ggggaccttc | gggcctcttg | ccatcggatg | tgcccagatg | 240 |
| ggattagcta | gtaggtgggg | taacggctca | cctaggcgac | gatccctagc | tggtctgaga | 300 |
| ggatgaccag | ccacactgga | actgagacac | ggtccagact | cctacgggag | gcagcagtgg | 360 |
| ggaatattgc | acaatgggcg | caagcctgat | gcagccatgc | cgcgtgtatg | aagaaggcct | 420 |
| tcgggttgta | aagtactttc | agcggggagg | aagggagtaa | agttaatacc | tttgctcatt | 480 |
| gacgttaccc | gcagaagaag | caccggctaa | ctccgtgcca | gcagccgcgg | taatacggag | 540 |
| ggtgcaagcg | ttaatcggaa | ttactgggcg | taaagcgcac | gcaggcggtt | tgttaagtca | 600 |
| gatgtgaaat | ccccgggctc | aacctggaa | ctgcatctga | tactggcaag | cttgagtctc | 660 |
| gtagaggggg | gtagaattcc | aggtgtagcg | gtgaaatgcg | tagagatctg | gaggaatacc | 720 |
| ggtggcgaag | gcggccccct | ggacgaagac | tgacgctcag | gtgcgaaagc | gtggggagca | 780 |
| aacaggatta | gataccctgg | tagtccacgc | cgtaaacgat | gtcgacttgg | aggttgtgcc | 840 |
| cttgaggcgt | ggcttccgga | gctaacgcgt | taagtcgacc | gcctggggag | tacggccgca | 900 |
| aggttaaaac | tcaaatgaat | tgacggggc | ccgcacaagc | ggtggagcat | gtggtttaat | 960 |
| tcgatgcaac | gcgaagaacc | ttacctggtc | ttgacatcca | cggaagtttt | cagagatgag | 1020 |
| aatgtgcctt | cgggaaccgt | gagacaggtg | ctgcatggct | gtcgtcagct | cgtgttgtga | 1080 |
| aatgttgggt | taagtcccgc | aacgagcgca | acccttatcc | tttgttgcca | gcggtccggc | 1140 |
| cgggaactca | aaggagactg | ccagtgataa | actggaggaa | ggtggggatg | acgtcaagtc | 1200 |
| atcatggccc | ttacgaccag | ggctacacac | gtgctacaat | ggcgcataca | aagagaagcg | 1260 |
| acctcgcgag | agcaagcgga | cctcataaag | tgcgtcgtag | tccggattgg | agtctgcaac | 1320 |
| tcgactccat | gaagtcggaa | tcgctagtaa | tcgtggatca | gaatgccacg | gtgaatacgt | 1380 |
| tcccgggcct | tgtacacacc | gcccgtcaca | ccatgggagt | gggttgcaaa | agaagtaggt | 1440 |
| agcttaacct | tcgggagggc | gcttaccact | ttgtgattca | tgactggggt | gaagtcgtaa | 1500 |
| caaggtaacc | gtaggggaac | ctgcggttgg | atcacctcct | ta | | 1542 |

<210> SEQ ID NO 86
<211> LENGTH: 1532
<212> TYPE: DNA
<213> ORGANISM: Shewanella oneidensis

<400> SEQUENCE: 86

| | | | | | |
|---|---|---|---|---|---|
| agagtttgat | catggctcag | attgaacgct | ggcggcaggc | ctaacacatg | caagtcgagc | 60 |
| ggcagcacaa | gtgagtttac | tcatgaggtg | cgagcggcg | gacgggtgag | taatgcctag | 120 |
| ggatctgccc | agtcgagggg | gataacagtt | ggaaacgact | gctaataccg | catacgccct | 180 |
| acggggaaa | gagggggact | ttcgggcctc | tcgcgattgg | atgaacctag | gtgggattag | 240 |
| ctagttggtg | aggtaatggc | tcaccaaggc | gacgatccct | agctgttctg | agaggatgat | 300 |
| cagccacact | gggactgaga | cacggcccag | actcctacgg | gaggcagcag | tgggaatat | 360 |

```
tgcacaatgg gggaaaccct gatgcagcca tgccgcgtgt gtgaagaagg ccttcgggtt    420
gtaaagcact ttcagtaggg aggaaagggt aagtcctaat acgacttatc tgtgacgtta    480
cctacagaag aaggaccggc taactccgtg ccagcagccg cggtaatacg agggtccga     540 gcgttaatcg gaattactgg gcgtaaagcg tgcgcaggcg gtttgttaag cgagatgtga    600
aagccctggg ctcaacctag gaatcgcatt tcgaactgac caactagagt cttgtagagg    660
ggggtagaat tccaggtgta gcggtgaaat gcgtagagat ctggaggaat accggtggcg    720
aaggcggccc cctggacaaa gactgacgct catgcacgaa agcgtgggga gcaaacagga    780
ttagataccc tggtagtcca cgccgtaaac gatgtctact cggagtttgg tgtcttgaac    840
actgggctct caagctaacg cattaagtag accgcctggg gagtacggcc gcaaggttaa    900
aactcaaatg aattgacggg ggcccgcaca agcggtggag catgtggttt aattcgatgc    960
aacgcgaaga accttaccta ctcttgacat ccacggaaga ctgcagagat gcggttgtgc   1020
cttcgggaac cgtgagacag gtgctgcatg gctgtcgtca gctcgtgttg tgaaatgttg   1080
ggttaagtcc cgcaacgagc gcaaccccta tccttatttg ccagcacgta atggtgggaa   1140
ctctagggag actgccggtg ataaaccgga ggaaggtggg gacgacgtca agtcatcatg   1200
gcccttacga gtagggctac acacgtgcta caatggcgag tacagagggt tgcaaagccg   1260
cgaggtggag ctaatctcac aaagctcgtc gtagtccgga ttggagtctg caactcgact   1320
ccatgaagtc ggaatcgcta gtaatcgtgg atcagaatgc cacggtgaat acgttcccgg   1380
gccttgtaca caccgcccgt cacaccatgg gagtgggctg caaaagaagt gggtagctta   1440
accttcgggg gggcgctcac cactttgtgg ttcatgactg gggtgaagtc gtaacaaggt   1500
agccctaggg gaacctgggg ctggatcacc tt                                 1532
```

<210> SEQ ID NO 87
<211> LENGTH: 1555
<212> TYPE: DNA
<213> ORGANISM: Shewanella putrefaciens

<400> SEQUENCE: 87

```
taattgaaga gtttgatcat ggctcagatt gaacgctggc ggcaggccta acacatgcaa     60
gtcgagcggc agcacaaggg agtttactcc tgaggtggcg agcggcggac gggtgagtaa    120
tgcctaggga tctgcccagt cgaggggggat aacagttgga aacgactgct aataccgcat    180
acgccctacg ggggaaagga ggggaccttc gggccttccg cgattggatg aacctaggtg    240
ggattagcta gttggtgagg taatggctca ccaaggcgac gatccctagc tgttctgaga    300
ggatgatcag ccacactggg actgagacac ggcccagact cctacgggag gcagcagtgg    360
ggaatattgc acaatggggg aaaccctgat gcagccatgc cgcgtgtgtg aagaaggcct    420
tcgggttgta aagcactttc agtagggagg aaagggtaag gtttaatacg ccttatctgt    480
gacgttacct acagaagaag gaccggctaa ctccgtgcca gcagccgcgg taatacggag    540
ggtccgagcg ttaatcggaa ttactgggcg taaagcgtgc gcaggcggtt tgttaagcga    600
gatgtgaaag ccctgggctc aacctaggaa tagcatttcg aactggcgaa ctagagtctt    660
gtagaggggg gtagaattcc aggtgtagcg gtgaaatgcg tagagatctg gaggaatacc    720
ggtggcgaag gcggccccct ggacaaagac tgacgctcat gcacgaaagc gtggggagca    780
aacaggatta gataccctgg tagtccacgc cgtaaacgat gtctactcgg agtttggtgt    840
cttgaacact gggctctcaa gctaacgcat taagtagacc gcctggggag tacggccgca    900
```

```
aggttaaaac tcaaatgaat tgacgggggc ccgcacaagc ggtggagcat gtggtttaat      960
tcgatgcaac gcgaagaacc ttacctactc ttgacatcca cagaactttc cagagatgga     1020
ttggtgcctt cgggaactgt gagacaggtg ctgcatggct gtcgtcagct cgtgttgtga     1080
aatgttgggt taagtcccgc aacgagcgca accoctatcc ttatttgcca gcacgtaatg     1140
gtgggaactc tagggagact gccggtgata aaccggagga aggtggggac gacgtcaagt     1200
catcatggcc cttacgagta gggctacaca cgtgctacaa tggcgagtac agagggttgc     1260
aaagccgcga ggtggagcta atctcacaaa gctcgtcgta gtccggattg gagtctgcaa     1320
ctcgactcca tgaagtcgga atcgctagta atcgtggatc agaatgccac ggtgaatacg     1380
ttcccgggcc ttgtacacac cgcccgtcac accatgggag tgggctgcaa agaagtggg     1440 tagcttaacc ttcgggggggg cgctcaccac tttgtggttc atgactgggg tgaagtcgta     1500
acaaggtagc cctaggggaa cctggggctg atcacctcc ttacctatac gacta           1555
```

<210> SEQ ID NO 88
<211> LENGTH: 1537
<212> TYPE: DNA
<213> ORGANISM: Shewanella baltica

<400> SEQUENCE: 88

```
agagtttgat catggctcag attgaacgct ggcggcaggc ctaacacatg caagtcgagc       60
ggcagcggga agatagttta ctatctttgc cggcgagcgg cggacgggtg agtaatgcct      120
agggatctgc ccagtcgagg gggataacag ttggaaacga ctgctaatac cgcatacgcc      180
ctacggggga aaggagggga ccttcgggcc ttccgcgatt ggatgaacct aggtgggatt      240
agctagttgg tgaggtaatg gctcaccaag gcgacgatcc ctagctgttc tgagaggatg      300
atcagccaca ctgggactga gacacggccc agactcctac ggaggcagc agtggggaat       360 attgcacaat gggggaaacc ctgatgcagc catgccgcgt gtgtgaagaa ggccttcggg      420
ttgtaaagca ctttcagtag ggaggaaagg tagcagctta atacgctgtt gctgtgacgt      480
tacctacaga agaaggaccg gctaactccg tgccagcagc cgcggtaata cggagggtcc      540
gagcgttaat cggaattact gggcgtaaag cgtgcgcagg cggtttgtta agcgagatgt      600
gaaagccccg ggctcaacct gggaattgca tttcgaactg gcgaactaga gtcttgtaga      660 gggggggtaga attccaggtg tagcggtgaa atgcgtagag atctggagga ataccggtgg     720
cgaaggcggc cccctggaca agactgacg ctcaggcacg aaagcgtggg gagcaaacag       780
gattagatac cctggtagtc cacgccgtaa acgatgtcta ctcggagttt ggtgtcttga     840
acactgggct ctcaagctaa cgcattaagt agaccgcctg gggagtacgg ccgcaaggtt    900
aaaactcaaa tgaattgacg ggggcccgca caagcggtgg agcatgtggt ttaattcgat    960
gcaacgcgaa gaaccttacc tactcttgac atccacggaa ttcgctagag atagcttagt    1020
gccttcggga accgtgagac aggtgctgca tggctgtcgt cagctcgtgt tgtgaaatgt    1080
tgggttaagt cccgcaacga gcgcaacccc tatccttatt tgccagcacg taatggtggg    1140
aactctaggg agactgccgg tgataaaccg gaggaaggtg gggacgacgt caagtcatca    1200
tggcccttac gagtagggct acacacgtgc tacaatggcg agtacagagg ttgcaaagc     1260 cgcgaggtgg agctaatctc acaaagctcg tcgtagtccg gattgagtc tgcaactcga     1320 ctccatgaag tcggaatcgc tagtaatcgt ggatcagaat gccacggtga atacgttccc    1380
gggccttgta cacaccgccc gtcacaccat gggagtgggc tgcaaaagaa gtgggtagct    1440
taaccttcgg ggggcgctc accactttgt ggttcatgac tggggtgaag tcgtaacaag    1500
```

```
gtagccctag gggaacctgg ggctggatca cctcctt                                1537
```

<210> SEQ ID NO 89
<211> LENGTH: 1535
<212> TYPE: DNA
<213> ORGANISM: Shewanella sediminis

<400> SEQUENCE: 89

```
agagtttgat catggctcag attgaacgct ggcggcaggc ctaacacatg caagtcgagc     60
ggaaacggag atagcttgct atcagacgtc gagcggcgga cgggtgagta atgcctagat   120
atctgcctag tcgtggggga taacagttgg aaacgactgc taataccgca tacgccctac   180
gggggaaagg aggggacctt cgggcctttc gcgattagat gagtctaggt gggattagct   240
agtaggtgag gtaatggctc acctaggcga cgatccctag ctgttctgag aggatgatca   300
gccacactgg gactgagaca cggcccagac tcctacggga ggcagcagtg gggaatattg   360
cacaatgggc gaaagcctga tgcagccatg ccgcgtgtgt gaagaaggcc ttcgggttgt   420
aaagcacttt cagcgaggag gaaaggtagg tagttaataa ctgcttgctg tgacgttact   480
cgcagaagaa gcaccggcta acttcgtgcc agcagccgcg gtaatacgag gggtgcaagc   540
gttaatcgga attactgggc gtaaagcgta cgcaggcggt ttgttaagcc agatgtgaaa   600
gccccgggct caacctggga attgcatttg gaactggcaa actagagtct tgtagagggg   660
ggtagaattt caggtgtagc ggtgaaatgc gtagagatct gaaggaatac cggtggcgaa   720
ggcggccccc tggacaaaga ctgacgctca tgtacgaaag cgtggggagc aaacaggatt   780
agataccctg gtagtccacg ccgtaaacga tgtctactcg gagtttggta acttagttac   840
tgggctccca agctaacgca ttaagtagac cgcctgggga gtacggccgc aaggttaaaa   900
ctcaaatgaa ttgacggggg cccgcacaag cggtggagca tgtggtttaa ttcgatgcaa   960
cgcgaagaac cttacctact cttgacatcc agagaattcg ctagagatag cttagtgcct  1020
tcgggagctc tgagacaggt gctgcatggc tgtcgtcagc tcgtgttgtg aaatgttggg  1080
ttaagtcccg caacgagcgc aacccttatc cttatttgcc agcacgtaat ggtgggaact  1140
ttagggagac tgccggtgat aaaccggagg aaggtgggga cgacgtcaag tcatcatggc  1200
ccttacgagt agggctacac acgtgctaca atggtcggta cagagggtcg caaagccgcg  1260
aggtggagct aatcccacaa agccggtcgt agtccggatc ggagtctgca actcgactcc  1320
gtgaagtcgg aatcgctagt aatcgtagat cagaatgcta cggtgaatac gttcccgggc  1380
cttgtacaca ccgcccgtca caccatggga gtgggctgca ccagaagtag atagcttaac  1440
ctttcgggga gggcgtttac cacggtgtgg ttcatgactg gggtgaagtc gtaacaaggt  1500
agccctaggg gaacctgggg ctggatcacc tcctt                              1535
```

<210> SEQ ID NO 90
<211> LENGTH: 1538
<212> TYPE: DNA
<213> ORGANISM: Shewanella algae
<220> FEATURE:
<221> NAME/KEY: misc_feature
<222> LOCATION: (11)..(12)
<223> OTHER INFORMATION: n is a, c, g, or t

<400> SEQUENCE: 90

```
agagtttgat nntggctcag attgaacgct ggcggcaggc ctaacacatg caagtcgagc     60
ggtaacattt caaaagcttg cttttgaaga tgacgagcgg cggacgggtg agtaatgcct   120
```

```
gggaatttgc ccatttgtgg gggataacag ttggaaacga ctgctaatac cgcatacgcc    180
ctacggggga aagcagggga ccttcgggcc ttgcgctgat ggataagccc aggtgggatt    240
agctagtagg tgaggtaaag gctcacctag gcgacgatcc ctagctggtc tgagaggatg    300
atcagccaca ctgggactga gacacggccc agactcctac gggaggcagc agtggggaat    360
attgcacaat gggggaaacc ctgatgcagc catgccgcgt gtgtgaagaa ggccttcggg    420
ttgtaaagca ctttcagcga ggaggaaagg ttgtaagtta ataccttaca tctgtgacgt    480
tactcgcaga agaagcaccg gctaactccg tgccagcagc cgcggtaata cggagggtgc    540
gagcgttaat cggaattact gggcgtaaag cgtgcgcagg cggtttgtta agcgagatgt    600
gaaagccccg gctcaacctg ggaaccgca tttcgaactg gcaaactaga gtcttgtaga    660 gggggggtaga attccaggtg tagcggtgaa atgcgtagag atctggagga ataccggtgg    720
cgaaggcggc ccctggaca aagactgacg ctcaggcacg aaagcgtggg gagcaaacag    780
gattagatac cctggtagtc cacgccgtaa acgatgtcta ctcggagttt ggtgtcttga    840
acactgggct ctcaagctaa cgcattaagt agaccgcctg ggagtacgg ccgcaaggtt    900 aaaactcaaa tgaattgacg ggggcccgca caagcggtgg agcatgtggt ttaattcgat    960
gcaacgcgaa gaaccttacc tactcttgac atccacagaa cttttcagag atgaattggt    1020
gccttcggga actgtgagac aggtgctgca tggctgtcgt cagctcgtgt tgtgaaatgt    1080
tgggttaagt cccgcaacga gcgcaacccc tatccttact tgccagcggg taatgccggg    1140
aactttaggg agactgccgg tgataaaccg gaggaaggtg gggacgacgt caagtcatca    1200
tggcccttac gagtagggct acacacgtgc tacaatggtc agtacagagg ttgcgaagc    1260 cgcgaggtgg agctaatccc ataaagctgg tcgtagtccg gattggagtc tgcaactcga    1320
ctccatgaag tcggaatcgc tagtaatcgt ggatcagaat gccacggtga atacgttccc    1380
gggccttgta cacaccgccc gtcacaccat gggagtgggc tgcaccagaa gtagatagct    1440
taaccttcgg gagggcgttt accacggtgt ggttcatgac tggggtgaag tcgtaacaag    1500
gtagccctag gggaacctgg ggctggatca cctccttt                            1538

<210> SEQ ID NO 91
<211> LENGTH: 1459
<212> TYPE: DNA
<213> ORGANISM: Shewanella algae

<400> SEQUENCE: 91
acgctggcgg caggcctaac acatgcaagt cgagcggtaa catttcaaaa gcttgctttt     60
gaagatgacg agcggcggac gggtgagtaa tgcctgggaa tttgcccatt tgtggggat    120 aacagttgga aacgactgct aataccgcat acgccctacg gggaaagca ggggaacttc    180 ggtccttgcg ctgatggata agcccaggtg ggattagcta gtaggtgggg taatggctca    240
cctaggcaac gatccctagc tggtctgaga ggatgatcag ccacactggg actgagacac    300
ggcccagact cctacgggag gcagcagtgg ggaatattgc acaatggggg aaaccctgat    360
gcagccatgc cgcgtgtgtg aagaaggcct tcggttgta aagcactttc agcgaggagg    420
aaagggtgta agttaatacc ttacatctgt gacgttactc gcagaagaag caccggctaa    480
ctccgtgcca gcagccgcgg taatacggag ggtgcgagcg ttaatcggaa ttactgggcg    540
taaagcgtgc gcaggcggtt tgttaagcga gatgtgaaag ccccgggctc aacctgggaa    600
ccgcatttcg aactgcaaa ctagagtctt gtagaggggg gtagaattcc aggtgtagcg    660
gtgaaatgcg tagagatctg gaggaatacc ggtggcgaag gcggcccct ggacaaagac    720
```

```
tgacgctcag gcacgaaagc gtggggagca aacaggatta gatacccctgg tagtccacgc      780
```

```
tgacgctcag gcacgaaagc gtggggagca aacaggatta gatacccctgg tagtccacgc      780
cgtaaacgat gtctactcgg agtttggtgt cttgaacact gggctctcaa gctaacgcat      840
taagtagacc gcctggggag tacggccgca aggttaaaac tcaaatgaat tgacgggggc      900
ccgcacaagc ggtggagcat gtggtttaat tcgatgcaac gcgaagaacc ttacctactc      960
ttgacatcca gagaactttc cagagatgga ttggtgcctt cgggaactct gagacaggtg     1020
ctgcatggct gtcgtcagct cgtgttgtga atgttgggt taagtcccgc aacgagcgca      1080
accccctatcc ttacttgcca gcgggtaatg ccgggaactt tagggagact gccggtgata    1140
aaccggagga aggtggggac gacgtcaagt catcatggcc cttacgagta gggctacaca     1200
cgtgctacaa tggtcggtac agagggttgc gaagccgcga ggtggagcta atctcataaa     1260
gccggtcgta gtccggattg gagtctgcaa ctcgactcca tgaagtcgga atcgctagta     1320
atcgtggatc agaatgccac ggtgaatacg ttcccgggcc ttgtacacac cgcccgtcac     1380
accatgggag tgggctgcac cagaagtaga tagcttaacc ttcgggaggg cgtttaccac     1440
ggtgtggttc atgactggg                                                  1459
```

<210> SEQ ID NO 92
<211> LENGTH: 1459
<212> TYPE: DNA
<213> ORGANISM: Rhodobacter capsulatus

<400> SEQUENCE: 92

```
acgctggcgg caggcctaac acatgcaagt cgagcggtaa catttcaaaa gcttgctttt       60
gaagatgacg agcggcggac gggtgagtaa tgcctgggaa tttgcccatt tgtgggggat      120
aacagttgga aacgactgct aataccgcat acgccctacg ggggaaagca ggggaacttc      180
ggtccttgcg ctgatggata agcccaggtg ggattagcta gtaggtgggg taatggctca      240
cctaggcaac gatccctagc tggtctgaga ggatgatcag ccacactggg actgagacac      300
ggcccagact cctacgggag gcagcagtgg ggaatattgc acaatggggg aaaccctgat      360
gcagccatgc cgcgtgtgtg aagaaggcct tcggggttgta aagcactttc agcgaggagg     420
aaagggtgta agttaatacc ttacatctgt gacgttactc gcagaagaag caccggctaa      480
ctccgtgcca gcagccgcgg taatacggag ggtgcgagcg ttaatcggaa ttactgggcg      540
taaagcgtgc gcaggcggtt tgttaagcga gatgtgaaag ccccgggctc aacctggaa      600
ccgcatttcg aactggcaaa ctagagtctt gtagaggggg gtagaattcc aggtgtagcg     660
gtgaaatgcg tagagatctg gaggaatacc ggtggcgaag gcggcccct ggacaaagac      720
tgacgctcag gcacgaaagc gtggggagca aacaggatta gatacccctgg tagtccacgc    780
cgtaaacgat gtctactcgg agtttggtgt cttgaacact gggctctcaa gctaacgcat      840
taagtagacc gcctggggag tacggccgca aggttaaaac tcaaatgaat tgacgggggc      900
ccgcacaagc ggtggagcat gtggtttaat tcgatgcaac gcgaagaacc ttacctactc      960
ttgacatcca gagaactttc cagagatgga ttggtgcctt cgggaactct gagacaggtg     1020
ctgcatggct gtcgtcagct cgtgttgtga atgttgggt taagtcccgc aacgagcgca      1080
accccctatcc ttacttgcca gcgggtaatg ccgggaactt tagggagact gccggtgata    1140
aaccggagga aggtggggac gacgtcaagt catcatggcc cttacgagta gggctacaca     1200
cgtgctacaa tggtcggtac agagggttgc gaagccgcga ggtggagcta atctcataaa     1260
gccggtcgta gtccggattg gagtctgcaa ctcgactcca tgaagtcgga atcgctagta     1320
```

| | |
|---|---|
| atcgtggatc agaatgccac ggtgaatacg ttcccgggcc ttgtacacac cgcccgtcac | 1380 |
| accatgggag tgggctgcac cagaagtaga tagcttaacc ttcgggaggg cgtttaccac | 1440 |
| ggtgtggttc atgactggg | 1459 |

<210> SEQ ID NO 93
<211> LENGTH: 1459
<212> TYPE: DNA
<213> ORGANISM: Shewanella algae

<400> SEQUENCE: 93

| | |
|---|---|
| acgctggcgg caggcctaac acatgcaagt cgagcggtaa catttcaaaa gcttgctttt | 60 |
| gaagatgacg agcggcggac gggtgagtaa tgcctgggaa tttgcccatt tgtgggggat | 120 |
| aacagttgga aacgactgct aataccgcat acgccctacg ggggaaagca ggggaccttc | 180 |
| gggccttgcg ctgatggata agcccaggtg ggattagcta gtaggtgagg taatggctca | 240 |
| cctaggcaac gatccctagc tggtctgaga ggatgatcag ccacactggg actgagacac | 300 |
| ggcccagact cctacgggag gcagcagtgg ggaatattgc acaatggggg aaaccctgat | 360 |
| gcagccatgc cgcgtgtgtg aagaaggcct tcggggttgta aagcactttc agcgaggagg | 420 |
| aaagggtgta agttaatacc ttacatctgt gacgttactc gcagaagaag caccggctaa | 480 |
| ctccgtgcca gcagccgcgg taatacggag ggtgcgagcg ttaatcggaa ttactgggcg | 540 |
| taaagcgtgc gcaggcggtt tgttaagcga gatgtgaaag ccccgggctc aacctgggaa | 600 |
| ccgcatttcg aactggcaaa ctagagtctt gtagagggggg tagaattcc aggtgtagcg | 660 |
| gtgaaatgcg tagagatctg gaggaatacc ggtggcgaag gcggcccct ggacaaagac | 720 |
| tgacgctcag gcacgaaagc gtggggagca acaggatta gataccctgg tagtccacgc | 780 |
| cgtaaacgat gtctactcgg agtttggtgt cttgaacact gggctctcaa gctaacgcat | 840 |
| taagtagacc gcctggggag tacggccgca aggttaaaac tcaaatgaat tgacggggc | 900 |
| ccgcacaagc ggtggagcat gtggtttaat tcgatgcaac gcgaagaacc ttacctactc | 960 |
| ttgacatcca gagaactttc cagagatgga ttggtgcctt cgggaactct gagacaggtg | 1020 |
| ctgcatggct gtcgtcagct cgtgttgtga atgttgggt taagtcccgc aacgagcgca | 1080 |
| accctatcc ttacttgcca gcgggtaatg ccgggaactt agggagact gccggtgata | 1140 |
| aaccggagga aggtggggac gacgtcaagt catcatggcc cttacgagta gggctacaca | 1200 |
| cgtgctacaa tggtcggtac agagggttgc gaagccgcga ggtggagcta atctcataaa | 1260 |
| gccggtcgta gtccggattg gagtctgcaa ctcgactcca tgaagtcgga atcgctagta | 1320 |
| atcgtggatc agaatgccac ggtgaatacg ttcccgggcc ttgtacacac cgcccgtcac | 1380 |
| accatgggag tgggctgcac cagaagtaga tagcttaacc ttcgggaggg cgtttaccac | 1440 |
| ggtgtggttc atgactggg | 1459 |

<210> SEQ ID NO 94
<211> LENGTH: 1476
<212> TYPE: DNA
<213> ORGANISM: unknown
<220> FEATURE:
<223> OTHER INFORMATION: Shewanella sp EM0501

<400> SEQUENCE: 94

| | |
|---|---|
| tcagattgaa cgctggcggc aggcctaaca catgcaagtc gagcggtaac atttcaaaag | 60 |
| cttgcttttg aagatgacga gcggcggacg ggtgagtaat gcctgggaat ttgcccattt | 120 |
| gtgggggata acagttggaa acgactgcta ataccgcata cgccctacgg gggaaagcag | 180 |

```
gggaacttcg gtccttgcgc tgatggataa gcccaggtgg gattagctag taggtggggt    240
aatggctcac ctaggcaacg atccctagct ggtctgagag gatgatcagc cacactggga    300
ctgagacacg gcccagactc ctacgggagg cagcagtggg gaatattgca caatgggggga   360 aaccctgatg cagccatgcc gcgtgtgtga agaaggcctt cgggttgtaa agcactttca    420
gcgaggagga aagggtgtaa gttaatacct tacatctgtg acgttactcg cagaagaagc    480
accggctaac tccgtgccag cagccgcggt aatacggagg gtgcgagcgt taatcggaat    540
tactgggcgt aaagcgtgcg caggcggttt gttaagcgag atgtgaaagc cccgggctca    600
acctgggaac cgcatttcga actggcaaac tagagtcttg tagagggggg tagaattcca    660
ggtgtagcgg tgaaatgcgt agagatctgg aggaataccg gtggcgaagg cggcccctg    720 gacaaagact gacgctcagg cacgaaagcg tggggagcaa acaggattag ataccctggt    780
agtccacgcc gtaaacgatg tctactcgga gtttggtgtc ttgaacactg gctctcaag    840 ctaacgcatt aagtagaccg cctggggagt acggccgcaa ggttaaaact caaatgaatt    900
gacgggggcc cgcacaagcg gtggagcatg tggtttaatt cgatgcaacg cgaagaacct    960
tacctactct tgacatccag agaactttcc gagatggat tggtgccttc gggaactctg   1020
agacaggtgc tgcatggctg tcgtcagctc gtgttgtgaa atgttgggtt aagtcccgca   1080
acgagcgcaa cccctatcct tacttgccag cgggtaatgc cgggaacttt agggagactg   1140
ccggtgataa accggaggaa ggtggggacg acgtcaagtc atcatggccc ttacgagtag   1200
ggctacacac gtgctacaat ggtcggtaca gagggttgcg aagccgcgag gtggagctaa   1260
tctcataaag ccggtcgtag tccggattgg agtctgcaac tcgactccat gaagtcggaa   1320
tcgctagtaa tcgtggatca gaatgccacg gtgaatacgt tcccgggcct tgtacacacc   1380
gcccgtcaca ccatgggagt gggctgcacc agaagtagat agcttaacct tcgggagggc   1440
gtttaccacg gtgtggttca tgactggggt gaagtc                             1476
```

<210> SEQ ID NO 95
<211> LENGTH: 1500
<212> TYPE: DNA
<213> ORGANISM: unknown
<220> FEATURE:
<223> OTHER INFORMATION: Shewanella sp. KJW27

<400> SEQUENCE: 95

```
ttgatcatgg ctcagattga acgctggcgg caggcctaac acatgcaagt cgagcggtaa     60
catttcaaaa gcttgctttt gaagatgacg agcggcggac gggtgagtaa tgcctggaa    120 tttgcccatt tgtgggggat aacagttgga aacgactgct aataccgcat acgccctacg    180
ggggaaagca ggggaccttc gggccttgcg ctgatggata gcccaggtg ggattagcta    240 gtaggtgagg taatggctca cctaggcaac gatccctagc tggtctgaga ggatgatcag    300
ccacactggg actgagacac ggcccagact cctacgggag gcagcagtgg ggaatattgc    360
acaatggggg aaaccctgat gcagccatgc cgcgtgtgtg aagaaggcct tcgggttgta    420
aagcactttc agcgaggagg aaagggtgta agttaatacc ttacatctgt gacgttactc    480
gcagaagaag caccggctaa ctccgtgcca gcagccgcgg taatacgagg gtgcgagcg    540 ttaatcggaa ttactgggcg taaagcgtgc gcaggcggtt tgttaagcga gatgtgaaag    600 cccgggctc aacctgggaa ccgcatttcg aactggcaaa ctagagtctt gtagaggggg    660
gtagaattcc aggtgtagcg gtgaaatgcg tagagatctg gaggaatacc ggtggcgaag    720
```

-continued

```
gcggcccct  ggacaaagac  tgacgctcag  gcacgaaagc  gtggggagca  acaggatta    780
gataccctgg  tagtccacgc  cgtaaacgat  gtctactcgg  agtttggtgt  cttgaacact   840
gggctctcaa  gctaacgcat  taagtagacc  gcctggggag  tacggccgca  aggttaaaac   900
tcaaatgaat  tgacggggc   ccgcacaagc  ggtggagcat  gtggtttaat  tcgatgcaac   960
gcgaagaacc  ttacctactc  ttgacatcca  gagaactttc  cagagatgga  ttggtgcctt  1020
cgggaactct  gagacaggtg  ctgcatggct  gtcgtcagct  cgtgttgtga  aatgttgggt  1080
taagtcccgc  aacgagcgca  accctatcc   ttacttgcca  gcgggtaatg  ccgggaactt  1140
tagggagact  gccggtgata  aaccggagga  aggtggggac  gacgtcaagt  catcatggcc  1200
cttacgagta  gggctacaca  cgtgctacaa  tggtcggtac  agagggttgc  gaagccgcga  1260
ggtggagcta  atctcataaa  gccgtcgta   gtccggattg  gagtctgcaa  ctcgactcca  1320
tgaagtcgga  atcgctagta  atcgtggatc  agaatgccac  ggtgaatacg  ttcccgggcc  1380
ttgtacacac  cgcccgtcac  accatgggag  tgggctgcac  cagaagtaga  tagcttaacc  1440
ttcgggaggg  cgtttaccac  ggtgtggttc  atgactgggg  tgaagtcgta  acaaggtaac  1500
```

<210> SEQ ID NO 96
<211> LENGTH: 1490
<212> TYPE: DNA
<213> ORGANISM: Alishewanella jeotgali

<400> SEQUENCE: 96

```
tagagtttga  tcatggctca  gattgaacgc  tggcggcagg  cctaacacat  gcaagtcgag     60
cgaggttttc  ggacctagcg  gcggacgggt  gagtaatgcg  taggaagctg  cccgatagag    120
ggggatacca  gttggaaacg  actgttaata  ccgcataatg  tctacggacc  aaagtgtggg    180
accttcgggc  cacatgctat  cggatgcgcc  tacgtgggat  tagctagttg  gtggggtaat    240
ggctcaccaa  ggcgacgatc  cctagctggt  ttgagaggat  gatcagccac  actgggactg    300
agacacggcc  cagactccta  cgggaggcag  cagtggggaa  tattggacaa  tgggcgcaag    360
cctgatccag  ccatgccgcg  tgtgtgaaga  aggccttcgg  gttgtaaagc  actttcagtg    420
gggaggaagg  ggttgtagtt  aatagctgca  attttttgacg  ttacccacag  aagaagcacc   480
ggctaactcc  gtgccagcag  ccgcggtaat  acggagggtg  caagcgttaa  tcggaattac    540
tgggcgtaaa  gcgcacgcag  gcggcttttt  aagtcgatg   tgaaagcccc  gggctcaacc    600
tgggaattgc  atctgatact  gggaagctag  agtatgtgag  agggggtag   aattccaagt    660
gtagcggtga  aatgcgtaga  gatttggagg  aataccagtg  gcgaaggcgg  ccccctggca    720
caatactgac  gctcaggtgc  gaaagcgtgg  ggagcaaaca  ggattagata  ccctggtagt    780
ccacgccgta  aacgatgtct  actagctgtt  cgcggcttg   tgttgtgagt  agcgcagcta    840
acgcattagg  tagaccgcct  ggggagtacg  gtcgcaagat  taaaactcaa  atgaattgac    900
ggggcccgc   acaagcggtg  gagcatgtgg  tttaattcga  cgcaacgcga  agaaccttac    960
ctactcttga  catctacaga  acttggtaga  gataccttgg  tgccttcggg  aactgtaaga   1020
caggtgctgc  atggctgtcg  tcagctcgtg  ttgtgaaatg  ttgggttaag  tcccgcaacg   1080
agcgcaaccc  ttatccttag  ttgccagcga  ttcggtcggg  aactctaggg  agactgccgg   1140
tgataaaccg  gaggaaggtg  gggacgacgt  caagtcatca  tggcccttac  gagtagggct   1200
acacacgtgt  acaatggta   tgtacagagg  gaggcaagct  ggcgacagtg  agcggatctc   1260
ttaaagcata  tcgtagtccg  gattggagtc  tgcaactcga  ctccatgaag  tcggaatcgc   1320
tagtaatcgc  aaatcagaat  gttgcggtga  atacgttccc  gggccttgta  cacaccgccc   1380
```

```
gtcacaccat gggagtgggt tgcaaaagaa gtaggtagct taaccttcgg gagggcgctt      1440
accactttgt gattcatgac tggggtgaag tcgtaacaag gtaaccgtaa                 1490
```

<210> SEQ ID NO 97
<211> LENGTH: 1426
<212> TYPE: DNA
<213> ORGANISM: Pseudoalteromonas rubra
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t

<400> SEQUENCE: 97

```
ttgaacgctg gcggcaggcc taacacatgc aagtcgagcg gtaacatttc tagcttgcta       60
gaagatgacg agcggcggac gggtgagtaa tgcttgggaa catgccttta ggtggggggac     120 aaccattgga aacgatggct aataccgcat aatgtctacg gaccaaaggg ggcttcggct      180 ctcgcccttta gattggccca agtgggatta gctagttggt naggtaacgg ctnaccaagg     240
cnacgatccc tagctggttt gagaggatga tcagccacac tggaactgag acacggtcca     300
gactcctacg ggaggcagca gtggggaata ttgcacaatg ggcgcaagcc tgatgcagcc     360
atgccgcgtg tgtgaagaag gccttcgggt tgtaaagcac tttcagtcag gaggaaaggt     420
tagtagttaa tacctgctag ctgtgacgtt actgacagaa gaagcaccgg ctaactccgt     480
gccagcagcc gcggtaatac ggagggtgcg agcgttaatc ggaattactg ggcgtaaagc     540
gtacgcaggc ggtttgttaa gcgagatgtg aaagccccgg gcttaacctg gaactgcat     600 ttcgaactgg caaactagag tgtgatagag ggtggtagaa tttcaggtgt agcggtgaaa     660
tgcgtagaga tctgaaggaa taccgatggc gaaggcagcc acctgggtca acactgacgc     720
tcatgtacga aagcgtgggg agcaaacagg attagatacc ctggtagtcc acgccgtaaa     780
cgatgtctac taggagctgg ggtccttcgg acaacttttc caaagctaac gcattaagta     840
gaccgcctgg ggagtacggc cgcaaggtta aaactcaaat gaattgacgg gggccgcaca     900
agcggtggag catgtggttt aattcgatgc aacgcgaaga accttaccta cacttgacat     960
acagagaact taccagagat ggtttggtgc cttcgggaac tctgatacag gtgctgcatg    1020
gctgtcgtca gctcgtgttg tgagatgttg ggttaagtcc cgcaacgagc gcaaccctta    1080
tccttagttg ccagcgattc ggtcgggaac tctaaggaga ctgccggtga taaaccggag    1140
gaaggtgggg acgacgtcaa gtcatcatgg cccttacgtg tagggctaca cacgtgctac    1200
aatggcatat acagagtgct gcgaactagc gatagtaagc gaatcactta aagtatgtcg    1260
tagtccggat tggagtctgc aactcgactc catgaagtcg gaatcgctag taatcgcgga    1320
tcagaatgcc gcggtgaata cgttcccggg ccttgtacac accgcccgtc acaccatggg    1380
agtgggttgc tccagaagtg gatagcttaa cttcgggagg gcgttc                    1426
```